United States Patent
Conrad et al.

(10) Patent No.: US 9,802,956 B2
(45) Date of Patent: Oct. 31, 2017

(54) SPIROQUINOXALINE DERIVATIVES AS INHIBITORS OF NON-APOPTOTIC REGULATED CELL-DEATH

(71) Applicant: HELMHOLTZ ZENTRUM MÜNCHEN DEUTSCHES FORSCHUNGSZENTRUM FÜR GESUNDHEIT UND UMWELT (GMBH), Neuherberg (DE)

(72) Inventors: Marcus Conrad, Munich (DE); Joel Schick, Munich (DE); Bettina Proneth, Munich (DE); Peter Sennhenn, Munich (DE)

(73) Assignee: Helmholtz Zentrum Munchen-Deutsches Forschungszentrum fur Gesundheit und Umwelt (GmbH), Neuherberg (DE)

( * ) Notice: Subject to any disclaimer, the term of this patent is extended or adjusted under 35 U.S.C. 154(b) by 0 days.

(21) Appl. No.: 14/904,377

(22) PCT Filed: Jul. 15, 2014

(86) PCT No.: PCT/EP2014/065145
§ 371 (c)(1),
(2) Date: Jan. 11, 2016

(87) PCT Pub. No.: WO2015/007730
PCT Pub. Date: Jan. 22, 2015

(65) Prior Publication Data
US 2016/0222025 A1 Aug. 4, 2016

(30) Foreign Application Priority Data

Jul. 15, 2013 (EP) .................... 13176580
Jul. 15, 2013 (EP) .................... 13176581
Jul. 15, 2013 (EP) .................... 13176582

(51) Int. Cl.
| | | |
|---|---|---|
| *C07D 495/10* | (2006.01) |
| *C07D 471/10* | (2006.01) |
| *C07D 487/10* | (2006.01) |
| *C07D 491/107* | (2006.01) |
| *C07D 403/12* | (2006.01) |
| *A61K 31/498* | (2006.01) |
| *A61K 31/499* | (2006.01) |
| *A61K 31/55* | (2006.01) |
| *A61K 31/5513* | (2006.01) |
| *C07D 241/36* | (2006.01) |
| *C07D 491/06* | (2006.01) |
| *C07D 241/42* | (2006.01) |
| *C07D 413/06* | (2006.01) |

(52) U.S. Cl.
CPC .......... *C07D 495/10* (2013.01); *A61K 31/498* (2013.01); *A61K 31/499* (2013.01); *A61K 31/55* (2013.01); *A61K 31/5513* (2013.01); *C07D 241/36* (2013.01); *C07D 241/42* (2013.01); *C07D 403/12* (2013.01); *C07D 413/06* (2013.01); *C07D 471/10* (2013.01); *C07D 487/10* (2013.01); *C07D 491/06* (2013.01); *C07D 491/107* (2013.01)

(58) Field of Classification Search
IPC .............. C07D 495/10,487/10, 413/06, 241/42, 471/10, 491/107
See application file for complete search history.

(56) References Cited

U.S. PATENT DOCUMENTS 6,369,057 B1 4/2002 Billhardt et al.

FOREIGN PATENT DOCUMENTS

| | | |
|---|---|---|
| CA | 2137605 A1 | 6/1995 |
| EP | 0509398 A1 | 10/1992 |
| EP | 0657166 A1 | 6/1995 |
| KR | 20120105714 A | 9/2012 |
| WO | WO 2007/117180 A1 | 10/2007 |
| WO | WO 2015/007730 A1 | 1/2015 |

OTHER PUBLICATIONS

CAS Registry No. 1172351-24-4, Entered STN: Aug. 4, 2009, 17 pages.
CAS Registry No. 1223830-23-6, Entered STN: May 16, 2010, 18 pages.
CAS Registry No. 1223982-82-8, Entered STN: May 16, 2010, 18 pages.
Chari, Murugulla Adharvana. "Amberlyst-15: an efficient and reusable catalyst for multi-component synthesis of 3, 4-dihydroquinoxalin-2-amine derivatives at room temperature." Tetrahedron Letters (2011); 52.46: 6108-6112.
Database Registry [Online], Chemical Abstracts Service, Accession No. 1223807-41-7, Entered STN: May 16, 2010, XP-002715540, Abstract, 1 page.

(Continued)

*Primary Examiner* — Shirley V Gembeh
(74) *Attorney, Agent, or Firm* — Cooley LLP

(57) ABSTRACT

The present invention relates to compounds which are inhibitors of non-apoptotic regulated cell death, and to pharmaceutical compositions containing such compounds. Furthermore, the present invention relates to the use of such compounds and pharmaceutical compositions in therapy, in particular in the treatment of a condition, disorder or disease that is characterised by non-apoptotic regulated cell-death or where non-apoptotic regulated cell-death is likely to play or plays a substantial role. The compounds and pharmaceutical compositions described herein are also useful in the treatment of a condition, disorder or disease that is characterised by oxidative stress or where oxidative stress is likely to play or plays a substantial role; and/or a condition, disorder or disease that is characterised by activation of (1) one or more components of the necrosome; (2) death domain receptors; and/or (3) Toll-like receptors; and/or (4) players in ferroptotic/ferroptosis signalling, or where activation of any one of (1) to (3) and/or (4) is likely to play or plays a substantial role.

12 Claims, 4 Drawing Sheets

(56) References Cited

OTHER PUBLICATIONS

Database Registry [Online], Chemical Abstracts Service, Accession No. 1223830-23-6, Entered STN: May 16, 2010, XP-002715539, Abstract, 1 page.
Database Registry [Online], Chemical Abstracts Service, Accession No. 1223968-05-5, Entered STN: May 16, 2010, XP-002715538, Abstract, 1 page.
Database Registry [Online], Chemical Abstracts Service, Accession No. 1223984-84-6, Entered STN: May 16, 2010, XP-002715537, Abstract, 1 page.
Database Registry [Online], Chemical Abstracts Service, Accession No. 1223999-27-6, Entered STN: May 16, 2010, XP-002715536, Abstract, 1 page.
Database Registry [Online], Chemical Abstracts Service, Accession No. 1224002-65-6, Entered STN: May 16, 2010, XP-002715529, Abstract, 1 page.
Degterev, Alexei, et al. "Chemical inhibitor of nonapoptotic cell death with therapeutic potential for ischemic brain injury." Nature Chemical Biology (2005); 1.2: 112-119.
Dixon, Scott J., et al. "Ferroptosis: an iron-dependent form of nonapoptotic cell death." Cell (2012); 149.5: 1060-1072.
Feoktistova, Maria, et al. "cIAPs block Ripoptosome formation, a RIP1/caspase-8 containing intracellular cell death complex differentially regulated by cFLIP isoforms." Molecular Cell (2011); 43.3: 449-463.
Frankowski, K.J., et al. "Synthesis and receptor profiling of Stemona alkaloid analogues reveal a potent class of sigma ligands." Proc Natl Acad Sci U S A (2011); 108(17): 6727-6732. doi: 10.1073/pnas.1016558108. Epub Feb. 28, 2011. and Erratum: Proc Natl Acad Sci U S A. (2012);109(38): 15526-15527.
Galluzzi, Lorenzo, and Kroemer, Guido. "Necroptosis: a specialized pathway of programmed necrosis." Cell (2008); 135.7: 1161-1163.
Galluzzi, Lorenzo, et al. "Molecular definitions of cell death subroutines: recommendations of the Nomenclature Committee on Cell Death 2012." Cell Death and Differentiation (2012); 19.1: 107-120.
Hitomi, Junichi, et al. "Identification of a molecular signaling network that regulates a cellular necrotic cell death pathway." Cell (2008); 135.7: 1311-1323.
International Patent Application No. PCT/EP2014/065145, Search Report and Written Opinion mailed Sep. 11, 2014, 10 pages.
International Patent Application No. PCT/EP2014/065145, International Preliminary Report on Patentability mailed Jan. 19, 2016, 6 pages.
Kaiser, William J., et al. "Receptor-interacting protein homotypic interaction motif-dependent control of NF-κB activation via the DNA-dependent activator of IFN regulatory factors." The Journal of Immunology (2008); 181.9: 6427-6434.
Kolla, Srinivasa Rao, and Lee, Yong Rok . "EDTA-catalyzed synthesis of 3, 4-dihydroquinoxalin-2-amine derivatives by a three-component coupling of one-pot condensation reactions in an aqueous medium." Tetrahedron (2010); 66.46: 8938-8944.
Kroemer, G., et al. "Classification of cell death: recommendations of the Nomenclature Committee on Cell Death 2009." Cell Death and Differentiation (2009); 16.1: 3-11.
Kysil, Volodymyr, et al. "General Multicomponent Strategy for the Synthesis of 2-Amino-1, 4-diazaheterocycles: Scope, Limitations, and Utility." European Journal of Organic Chemistry (2010); 2010. 8: 1525-1543.
Lin, Michael T., and Beal, M. Flint. "Mitochondrial dysfunction and oxidative stress in neurodegenerative diseases." Nature (2006); 443.7113: 787-795.
Mack, Claudia, et al. "Inhibition of proinflammatory and innate immune signaling pathways by a cytomegalovirus RIP1-interacting protein." Proceedings of the National Academy of Sciences (2008); 105.8: 3094-3099.
Micheau, Olivier, and Tschopp, Jürg. "Induction of TNF receptor I-mediated apoptosis via two sequential signaling complexes." Cell (2003); 114.2: 181-190.
Sun, Liming, et al. "Mixed lineage kinase domain-like protein mediates necrosis signaling downstream of RIP3 kinase." Cell (2012); 148.1: 213-227.
Tenev, Tencho, et al. "The Ripoptosome, a signaling platform that assembles in response to genotoxic stress and loss of IAPs." Molecular Cell (2011); 43.3: 432-448.
Vandenabeele, Peter, et al. "Molecular mechanisms of necroptosis: an ordered cellular explosion." Nature Reviews Molecular Cell Biology (2010); 11.10: 700-714.
Vanlangenakker, Nele, et al. "cIAP1 and TAK1 protect cells from TNF-induced necrosis by preventing RIP1/RIP3-dependent reactive oxygen species production." Cell Death & Differentiation (2011); 18.4: 656-665.
Wang, Zhigao, et al. "The mitochondrial phosphatase PGAM5 functions at the convergence point of multiple necrotic death pathways." Cell (2012); 148.1: 228-243.

☐ Sham + vehicle
☒ IRI + vehicle
▥ IRI + Cmpd

IRI

| + Compound | + Vehicle |

SPIROQUINOXALINE DERIVATIVES AS INHIBITORS OF NON-APOPTOTIC REGULATED CELL-DEATH

TECHNICAL FIELD OF THE INVENTION

The present invention relates to compounds which are inhibitors of non-apoptotic regulated cell death, and to pharmaceutical compositions containing such compounds. Furthermore, the present invention relates to the use of such compounds and pharmaceutical compositions in therapy, in particular in the treatment of a condition, disorder or disease that is characterised by non-apoptotic regulated cell-death or where non-apoptotic regulated cell-death is likely to play or plays a substantial role. The compounds and pharmaceutical compositions described herein are also useful in the treatment of a condition, disorder or disease that is characterised by oxidative stress or where oxidative stress is likely to play or plays a substantial role; and/or a condition, disorder or disease that is characterised by activation of (1) one or more components of the necrosome; (2) death domain receptors; and/or (3) Toll-like receptors; and/or (4) players in ferroptotic/ferroptosis signalling, or where activation of any one of (1) to (3) and/or (4) is likely to play or plays a substantial role.

BACKGROUND OF THE INVENTION

The incidence of many debilitating conditions, disorders and diseases, especially Alzheimer's disease, Parkinson's disease, cardiac infarction, amyotrophic lateral sclerosis (ALS), organ transplantations, and stroke, is continuously increasing in ageing societies, and thus represents not only a major health problem but also a growing socio-economic burden. Yet, and in particular, treatment strategies to combat these diseases are inadequate or fail to exist entirely. One major underlying factor of many such conditions, disorders and diseases is the role of non-apoptotic regulated cell death, and the associated diversity of aberrant cellular processes, which ultimately lead to cellular demise.

Cell death has been traditionally classified as apoptosis or necrosis. While apoptosis is now known and used as a term to describe a small set of lethal signalling pathways, the mechanisms for which have been extensively studied, necrosis was, until relatively recently, considered an unregulated process of mere accidental cell death. Little effort had been made to study necrosis due to its believed unregulated nature. More recently, support for forms of regulated cell-death mechanism other than apoptosis have since been found, described and standardised nomenclature recommended (Galluzzi et al. (2012); Cell Death Diff. 19:107-20, especially Table 1 thereof), including those termed "regulated necrosis" and "necroptosis"; a specific regulated cellular necrosis mechanisms, discrete from apoptosis as described by Hitomi et al. (Cell 135:1311-23 (2008)) and Degterev and co-workers (Nat. Chem. Biol. 1:112-9 (2005)). Other forms of regulated cell death are described in Galluzzi et al. (2012), including certain tentative new names for very specific signalling pathways that lead to cell death such as "parthanatos", "paraptosis" and several others (see references in Galluzzi et al. 2012). Another form of non-apoptotic regulated cell death includes "ferroptosis", a non-apoptotic, iron-dependent, oxidative form of cell-death recently described by Dixon and co-workers (Cell 149:1060-72 (2012)). While necroptosis and ferroptosis share many features, differences between their phenotypes can be observed, and it is to be expected that additional regulated cell death modalities and lethal signalling pathways exist and may be described and defined separately to necroptosis etc.

However, evidence is mounting that oxidative stress, a state associated with a high level of reactive oxygen species (ROS), is a common denominator of many such non-apoptotic regulated cell-death processes (and also a specific form of apoptosis known as "caspase-independent apoptosis", a pathway of regulated cell-death that operates in parallel to caspase-dependent apoptosis in response to multiple intracellular stress conditions), and in particular most neuronal dysfunction, ultimately resulting in neurodegeneration (Lin, M. T. & Beal, M. F., Nature 443, 787-795 (2006)). Oxidative stress, the imbalance between the generation and clearance of ROS, is a potent inducer of cell death. Increased levels of ROS, impaired ROS regulating systems and oxidatively modified proteins, lipids and DNA are all hallmarks of postmortem brain tissues from Alzheimer's, Parkinson's and ALS patients. ROS are also a major causative factor in the degeneration of neurons in stroke patients. Stroke is one prominent example of tissue damage caused by ROS following ischemia-reperfusion injury. Tissue damage due to ischemia-reperfusion injury is, however, not restricted to the central nervous system, it is also a hallmark of infarction (cardiac infarction being the most prevalent type of infarction) and an important complication in surgery with special emphasis on solid organ transplantation. Oxidative stress and/or non-apoptotic regulated cell death is associated with many other conditions, disorders and diseases, or is a symptom the result of or arising from such a condition, disorder and disease. Of particular importance is cell, tissue, organ or organism intoxication, such as circumstances which are the result of, arise from or are associated with drug treatment (e.g., kidney toxicity from cisplatin), drug overdose (e.g., liver toxicity from paracetamol), acute poisoning (e.g., from alcohol, paraquat or environmental toxins) or exposure to ionizing radiation. Other conditions, disorders and diseases result in a state that is associated with oxidative stress and/or non-apoptotic regulated cell death, and include head trauma, asphyxia, cold or mechanical injury and burns. Oxidative stress and/or non-apoptotic regulated cell death may also be related to aesthetic conditions such as UV-damage/aging in skin and hair loss.

Oxidative stress-dependent cell death occurs frequently in a regulated fashion. Although there is no generalized consensus on the use of the expression 'necroptosis' (Vandenabeele et al. (2010) Nat. Rev. Mol. Cell Biol. 11:700-14), the terms 'regulated necrosis' and necroptosi and 'ferroptosis' (Dixon et al., Cell, 2012) are used herein and known in the art to indicate general and specific forms (respectively) of regulated—as opposed to accidental—necrosis (Galluzzi et al. 2012). As indicated above, for a long time, necrosis was considered merely as an accidental uncontrolled form of cell death, but evidence that the execution of some forms of necrotic cell death is also finely regulated by a set of signal transduction pathways and catabolic mechanisms is further accumulating (Galluzzi and Kroemer, Cell 135 26:1161-1163 (2008); Kroemer et al., Cell Death Differ.; 16(1): 3-11, (2009)). For instance, death domain receptors (e.g., TNFR1, Fas/CD95 and TRAIL-R) and Toll-like receptors (e.g., TLR3 and TLR4) have been shown to elicit necrotic cell death, in particular in the presence of caspase inhibitors—strong evidence of the non-apoptotic nature of regulated necrosis and necroptosis. TNFR1-, Fas/CD95-, TRAILR- and TLR3-mediated cell death seemingly depends on the kinase RIP1, as this has been demonstrated by its knockout/ knockdown and chemical inhibition with necrostatin-1. While little is currently known about the molecular mechanism of ferroptosis, this form of non-apoptotic regulated cell-death is characterised by the overwhelming, iron-dependent accumulation of lethal lipid ROS, and in at least some cells, NOX family enzymes make important contributions to this process, and Dixon et al. postulate that the executioners of death in certain cancer cells undergoing ferroptosis are these ROS themselves.

Although there is no consensus on the biochemical changes that may be used to unequivocally identify oxidative stress-dependent or non-apoptotic regulated cell-death, several mediators, organelles and cellular processes have already been implicated in such cell death (Kroemer et al., Cell Death Differ.; 16(1): 3-11, (2009)). These phenomena include mitochondrial alterations (e.g., uncoupling, production of reactive oxygen species, i.e., ROS, nitrosative stress by nitric oxide or similar compounds and mitochondrial membrane permeabilization, i.e., MMP, often controlled by cyclophilin D), lysosomal changes (ROS production by Fenton reactions, lysosomal membrane permeabilization), nuclear changes (hyperactivation of PARP-1 and concomitant hydrolysis of NAD+), lipid degradation (following the activation of phospholipases, lipoxygenases and sphingomyelinases), increases in the cytosolic concentration of calcium ($Ca^{2+}$) that result in mitochondrial overload and activation of noncaspase proteases (e.g., calpains and cathepsins). It is still unclear, though, how they interrelate with each other.

Notwithstanding, a crucial role for the RIP (receptor interacting protein) kinases, in particular serine/threonine kinases RIP1 and RIP3, has been demonstrated for regulated necrotic cell death (Declerq et al., Cell 138:229-232 (2009)). The multiprotein complex comprising RIP1 and RIP3 is known in the art as "necrosome". RIP1 and RIP3 form the core complex within the necrosome. The necrosome complex further comprises TRADD and FAS-associated protein with a death domain (FADD), caspase 8, the serine/threonine-protein phosphatase (PGAM5)(Micheau et al., Cell 14:1814-190 (2003) and Wang et al. (2012), Cell 148:228-243) and the mixed lineage kinase domain-like protein (MLKL)(Sun et al. (2012), Cell 148:213-227). The necrosome regulates the decision between cell survival and regulated necrosis. In more detail, the phosphorylation of RIP1 and RIP3 engages the effector mechanism of regulated necrosis. In contrast, if caspase 8 is activated, it cleaves RIP1 and RIP3 thereby preventing the effector mechanism of regulated necrosis (Vandenabeele et al., Nature Reviews Mol. Cell Biol., 11:700-714 (2010)). Accordingly, the activation status of caspase 8 appears to be decisive whether a cell undergoes regulated necrosis or apoptosis by the initiation of the pro-apoptotic caspase activation cascade. Whether FADD or TRADD are strictly required for the assembly of the necrosome is presently not clear.

Besides caspase 8, negative regulators of TNR-receptor-family- or Toll like receptor-mediated regulated necrosis include E3 ubiquitin ligases cIAP1 and cIAP2, cFLIP, and TAK1, whereas the deubiquitinating enzymes CYLD and A20 act as positive regulators of regulated necrosis (Vandenlakker et al, Cell Death Differ 18, 656-665, 2011). Remarkably, the long and short isoforms of cFLIP were shown to act antagonistically, the short isoform promoting and the long isoform inhibiting TLR-ligand induced regulated necrosis (Feoktistova et al., Mol. Cell 43, 449-463, 2011). FAB2 and FAB2 are additional components of the signalling complex formed upon TNF receptor-ligation whose precise function in the regulation of regulated necrosis is still unknown. TRIF, an adapter protein with a RIP1 homology interaction motif (RHIM) is coupling the signalling complex formed upon Toll like receptor ligation to TLR3 and TLR4.

A RIP1 and RIP3 containing multiprotein complex promoting apoptosis or regulated necrosis is formed independently from TNF receptor family members in response to DNA damage-mediated depletion of cIAP1 and cIAP2. This complex further comprises FADD and caspase 8, the latter being the decisive determinant for the choice between apoptosis and regulated necrosis (Tenev et al., Mol. Cell 43, 432-448, 2011).

RIP1 is found in several types of complexes mediating an innate immune response to RNA and DNA viruses. A complex comprising TANK, FADD, TRADD, NEMO, and RIP1 is recruited to the outer membrane of mitochondria in response to ligation of pattern recognition receptors RIG-I or MDA5 recognizing viral RNAs through interaction with IPS1 (also called MAVS). RIP1 shares RIP1 homotypic interaction motifs (RIM) for dimerization not only with RIP3, but also with the cytosolic DNA sensor DA and TRIF (the latter being involved in signal transduction through TLR3 and TLR4). As exemplified for the murine cytomegalovirus protein M45, proteins or peptides containing a RHIM sequence may disrupt the RHIM interaction between RIP1 and RIP3 and may thus inhibit regulated necrosis (consensus sequence: I/V-Q-I/L/V-G-x-x-N-x-M/L/I)(Mack et al., PNAS 105, 3094-3099, 2008; Kaiser et al., J. Immunol. 181, 6427-6434, 2008). Although regulated necrosis promoting activities have not been reported so far for the sensors of viral RNA and DNA, these RIP1 containing protein complexes might nevertheless operate as molecular switches for oxidative signals that convert a pro-survival (or an interferon-inducing) signal into a regulated necrosis inducing signal.

In respect of ferroptosis, Dixon and co-workers (2012) cannot exclude the possibility of a death-inducing protein or protein complex that is activated downstream of ROS accumulation as observed for that form of non-apoptotic regulated cell-death.

Accordingly, regulated necrosis (and potentially other related forms of non-apoptotic regulated cell-death such as ferroptosis) may be characterised as a type of cell death that can be avoided by inhibiting—either directly or indirectly—the necrosome or other components of ferroptotic signalling, in particular the activity and/or interaction of components thereof such as RIP1, RIP3 and others such as one or more members of the ferroptotic pathway (either through genetic or pharmacological methods). This represents a convenient means to discriminate between regulated necrosis (e.g., necroptosis) and accidental forms of necrosis (Kromer et al., Cell Death Differ.; 16(1): 3-11, (2009)).

Certain spiroquinoxaline derivatives, and pharmaceutical compositions thereof, are generically disclosed in EP 0 509 398A1 and EP 0 657 166 A1, in particular for use in the treatment of virus infection.

Together with a very large number of other generic structures, certain spiroquinoxaline derivatives are generically disclosed in WO 2007/117180 A1 as formula 2.2, and a small number of specific spiroquinoxaline compounds are disclosed in the expansive Table 12 thereof. WO 2007/117180 A1 relates primarily to the construction and composition of large combinatorial libraries of small molecules having interest as merely potential physiologically active substances and pharmaceutical compositions thereof. Of the huge number of specific compounds disclosed therein, only a small number of compounds (not being spiroquinoxalines)

are tested for and suggested to have anti-cancer properties (example 40 and Table 14 thereof).

Frankowski and co-workers (PNAS 108:6727-32 (2012)) describe the synthesis of a small library of Stemona alkaloid analogues (reported as having antitussive activity) that are fused by a spiro-carbon to quinoxaline derivatives (Scheme 4 therein), and the activity of such alkaloid-quinoxalines spiro-fusions in various receptor-binding assays.

Various organic chemistry methods are disclosed for the synthesis of quinoxaline derivatives and spiro forms thereof. These include, Kysil et al (Eur. J. Org. Chem. 8:1525-43 (2010)), Lee (KR 2012-105714), Adarvana (Tetrahedron Lett. 52:6108-12 (2011)), and Kolla and Lee (Tetrahedron 66:8938-44 (2010)).

Other specific spiroquinoxaline compounds are known and are commercially available, but without indication of synthesis or utility. These include those with CAS registry numbers: 1172351-24-4, 1223830-23-6 and 1223982-82-8.

Accordingly, it is an object of the present invention to provide alternative, improved and/or integrated means or methods that address one or more problems, including those described above such as in the treatment (including prophylactic treatment) of one or more conditions, disorders or diseases (or related conditions or symptoms) and/or agents and pharmaceutical compositions useful for such treatment. Such an object underlying the present invention is solved by the subject matter as disclosed or defined anywhere herein, for example by the subject matter of the attached claims.

SUMMARY OF THE INVENTION

In a first aspect, the present invention provides a compound selected from the group consisting of a spiroquinoxaline derivative having the general formula (I)

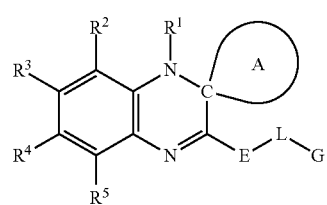

and solvates, salts, complexes, polymorphs, crystalline forms, racemic mixtures, diastereomers, enantiomers, tautomers, isotopically labeled forms, prodrugs, and combinations thereof, wherein $R^1$ to $R^5$, ring A, E, L, and G are as specified in claim 1, for use in a method of treating (i) a condition, disorder or disease that is characterised by non-apoptotic regulated cell-death or where non-apoptotic regulated cell-death is likely to play or plays a substantial role; (ii) a condition, disorder or disease that is characterised by oxidative stress or where oxidative stress is likely to play or plays a substantial role; (iii) a condition, disorder or disease that is characterised by activation of (1) one or more components of the necrosome; (2) death domain receptors; and/or (3) Toll-like receptors; and/or (4) players in ferroptotic/ferroptosis signalling, or where activation of any one of (1) to (3) and/or (4) is likely to play or plays a substantial role; (iv) a condition, disorder or disease selected from the group consisting of a neurodegenerative disease of the central or peripheral nervous system, muscle wasting, muscular dystrophy, ischemia, compartment syndrome, gangrene, pressure sores, sepsis, degenerative arthritis, retinal necrosis, heart disease, liver, gastrointestinal or pancreatic disease, avascular necrosis, diabetes, sickle cell disease, alteration of blood vessels, cancer-chemo/radiation therapy-induced cell-death and intoxication, or is the result of, arises from or is associated with any of the foregoing; and/or (v) a condition, disorder or disease which is the result of, arises from or is associated with a circumstance selected from the group consisting of forms of infection of viruses, bacteria, fungi, or other microorganisms; a reduction in cell-proliferation, an alteration in cell-differentiation or intracellular signalling; an undesirable inflammation; cell death of retinal neuronal cells, cardiac muscle cells, or cells of the immune system or cell death associated with renal failure; neonatal respiratory distress, asphyxia, incarcerated hernia, placental infarct, iron-load complications, endometriosis, congenital disease; head trauma/traumatic brain injury, liver injury; injuries from environmental radiation; burns; cold injuries; mechanical injuries, and decompression sickness.

In a second aspect, the present application provides a method of treating an individual with a need thereof (in particular a human patient), comprising administering a pharmaceutically effective amount of (in particular a therapeutically effective dose of) a compound selected from the group consisting of a spiroquinoxaline derivative having the general formula (I)

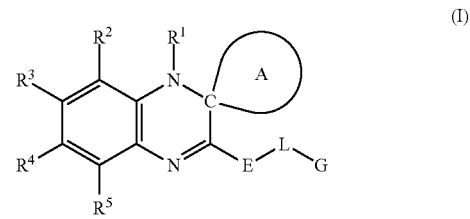

and solvates, salts, complexes, polymorphs, crystalline forms, racemic mixtures, diastereomers, enantiomers, tautomers, isotopically labeled forms, prodrugs, and combinations thereof, wherein $R^1$ to $R^5$, ring A, E, L, and G are as specified in claim 2, with the proviso that when ring A is a monocyclic 4- to 10-membered N-heterocycloalkylene, then the individual is not suffering from a condition, disorder or disease that is cancer, and/or one the result of, arising from or associated with cancer.

In a third aspect, the present application provides a compound selected from the group consisting of a spiroquinoxaline derivative having the general formula (I)

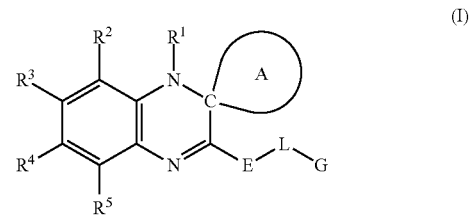

and solvates, salts, complexes, polymorphs, crystalline forms, racemic mixtures, diastereomers, enantiomers, tautomers, isotopically labeled forms, prodrugs, and combinations thereof, wherein $R^1$ to $R^5$, ring A, E, L, and G are as specified in claim 3.

In a fourth aspect, the present application provides a compound selected from the group consisting of a spiroquinoxaline derivative having the general formula (I)

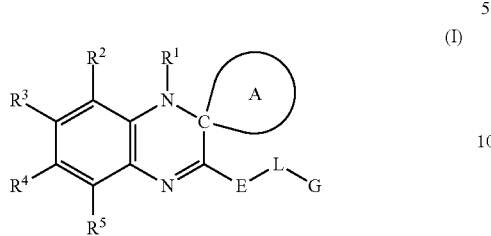

(I)

and solvates, salts, complexes, polymorphs, crystalline forms, racemic mixtures, diastereomers, enantiomers, tautomers, isotopically labeled forms, prodrugs, and combinations thereof, wherein $R^1$ to $R^5$, ring A, E, L, and G are as specified in claim 4 for use as medicament.

In a fifth aspect, the present invention provides a pharmaceutical composition comprising a compound as specified in the first or second aspect and a pharmaceutically acceptable excipient.

Further aspects of the invention are disclosed herein.

DETAILED DESCRIPTION OF THE PRESENT INVENTION

Figure 1A:
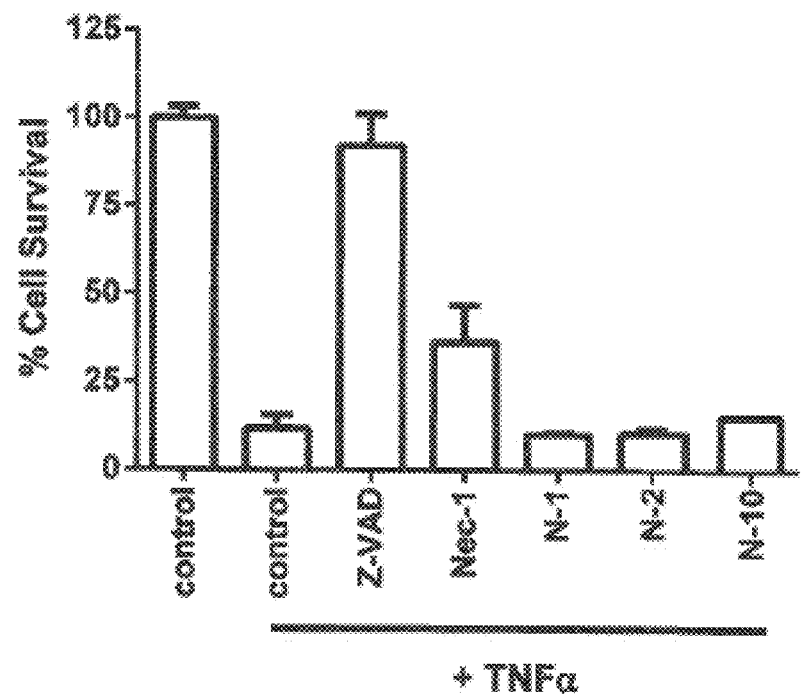
FIG. 1: Non-inhibition of apoptotic cell-death by compounds disclosed herein. SH-SY5Y cells were propagated and seeded in 96-well plates, together with compound N-1, N-2, N-10 of Table 1-N (FIG. 1(a)), compound O/S-6 or O/S-3 of Table 1-O/S (FIG. 1(b)), or compound C-12, C-91, or C-205 of Table 1-C (FIG. 1(c))(each 1 μM) and TNF-alpha was added (final concentration: 10 mg/mL) to induce apoptosis. The apoptosis and pan-caspase inhibitor z-vad (final concentration: 50 μM) and the necroptosis inhibitor Necrostatin-1 (Nec-1; final concentration: 5 μM) were used for comparison. Control wells were established with vehicle only (DMSO), with and without treatment with TNF-alpha to induce apoptosis. Cells were incubated, and cell survival was detected and quantified. Percentage cell survival after TNF-alpha-induced apoptosis is shown (error bars indicate standard deviation (SD)).

Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims and other disclosures herein. Unless defined otherwise, all technical and scientific terms used herein have the same meanings as commonly understood by one of ordinary skill in the art.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in one embodiment $R^8$ of the compound of the invention is halogen (such as Cl) and in another embodiment of the compound of the invention ring A is 4-piperidinylene, then in a preferred embodiment, $R^8$ of the compound of the invention is halogen (such as Cl) and ring A is 4-piperidinylene.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., Molecular Cloning: A Laboratory Manual, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "alkyl" refers to a monoradical of a saturated straight or branched hydrocarbon. Preferably, the alkyl group comprises from 1 to 12 (such as 1 to 10) carbon atoms, i.e., 1, 2, 3, 4, 5, 6, 7, 8, 9, 10, 11, or 12 carbon atoms (such as 1, 2, 3, 4, 5, 6, 7, 8, 9, or 10 carbon atoms), more preferably 1 to 8 carbon atoms, such as 1 to 6 or 1 to 4 carbon atoms. Exemplary alkyl groups include methyl, ethyl, propyl, iso-propyl, butyl, iso-butyl, tert-butyl, n-pentyl, iso-pentyl, sec-pentyl, neo-pentyl, 1,2-dimethyl-propyl, iso-amyl, n-hexyl, iso-hexyl, sec-hexyl, n-heptyl, iso-heptyl, n-octyl, 2-ethyl-hexyl, n-nonyl, n-decyl, n-undecyl, n-dodecyl, and the like.

The term "alkylene" refers to a diradical of a saturated straight or branched hydrocarbon. Preferably, the alkylene comprises from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkylene groups include methylene, ethylene (i.e., 1,1-ethylene, 1,2-ethylene), propylene (i.e., 1,1-propylene, 1,2-propylene (—CH(CH$_3$)CH$_2$—), 2,2-propylene (—C(CH$_3$)$_2$—), and 1,3-propylene), the butylene isomers (e.g., 1,1-butylene, 1,2-butylene, 2,2-butylene, 1,3-butylene, 2,3-butylene (cis or trans or a mixture thereof), 1,4-butylene, 1,1-iso-butylene, 1,2-iso-butylene, and 1,3-iso-butylene), the pentylene isomers (e.g., 1,1-pentylene, 1,2-pentylene, 1,3-pentylene, 1,4-pentylene, 1,5-pentylene, 1,1®iso-pentylene, 1,1-sec-pentyl, 1,1-neo-pentyl), the hexylenisomers (e.g., 1,1-hexylene, 1,2-hexylene, 1,3-hexylene, 1,4-hexylene, 1,5-hexylene, 1,6-hexylene, and 1,1-isohexylene), and the like.

The term "alkenyl" refers to a monoradical of an unsaturated straight or branched hydrocarbon having at least one carbon-carbon double bond. Generally, the maximal number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include vinyl, 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom.

The term "alkenylene" refers to a diradical of an unsaturated straight or branched hydrocarbon having at least one carbon-carbon double bond. Generally, the maximal number of carbon-carbon double bonds in the alkenylene group can be equal to the integer which is calculated by dividing the number of carbon atoms in the alkenylene group by 2 and, if the number of carbon atoms in the alkenylene group is uneven, rounding the result of the division down to the next integer. For example, for an alkenylene group having 9 carbon atoms, the maximum number of carbon-carbon double bonds is 4. Preferably, the alkenylene group has 1 to 4, i.e., 1, 2, 3, or 4, carbon-carbon double bonds. Preferably, the alkenylene group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenylene group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenylene groups include ethen-1,2-diyl, vinyliden, 1-propen-1,2-diyl, 1-propen-1,3-diyl, 1-propen-2,3-diyl, allylidene, 1-buten-1,2-diyl, 1-buten-1,3-diyl, 1-buten-1,4-diyl, 1-buten-2,3-diyl, 1-buten-2,4-diyl, 1-buten-3,4-diyl, 2-buten-1,2-diyl, 2-buten-1,3-diyl, 2-buten-1,4-diyl, 2-buten-2,3-diyl, 2-buten-2,4-diyl, 2-buten-3,4-diyl, and the like. If an alkenylene group is attached to a nitrogen atom, the double bond cannot be alpha to the nitrogen atom.

The term "alkynyl" refers to a monoradical of an unsaturated straight or branched hydrocarbon having at least one carbon-carbon triple bond. Generally, the maximal number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2-octynyl, 3-octynyl, 4-octynyl, 5-octynyl, 6-octynyl, 7-octynyl, 1-nonynyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom.

The term "alkynylene" refers to a diradical of an unsaturated straight or branched hydrocarbon having at least one carbon-carbon triple bond. Generally, the maximal number of carbon-carbon triple bonds in the alkynylene group can be equal to the integer which is calculated by dividing the number of carbon atoms in the alkynylene group by 2 and, if the number of carbon atoms in the alkynylene group is uneven, rounding the result of the division down to the next integer. For example, for an alkynylene group having 9 carbon atoms, the maximum number of carbon-carbon triple bonds is 4. Preferably, the alkynylene group has 1 to 4, i.e., 1, 2, 3, or 4, more preferably 1 or 2 carbon-carbon triple bonds. Preferably, the alkynylene group comprises from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynylene group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynylene groups include ethyl-1,2-diyl, 1-propyn-1,3-diyl, 1-propyn-3,3-diyl, 1-butyn-1,3-diyl, 1-butyn-1,4-diyl, 1-butyn-3,4-diyl, 2-butyn-1,4-diyl and the like. If an alkynylene group is attached to a nitrogen atom, the triple bond cannot be alpha to the nitrogen atom.

The term "aryl" or "aromatic ring" refers to a monoradical of an aromatic cyclic hydrocarbon. Preferably, the aryl group contains 3 to 14 (e.g., 5 to 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl.

The term "heteroaryl" or "heteroaromatic ring" means an aryl group as defined above in which one or more carbon atoms in the aryl group are replaced by heteroatoms of O, S, or N. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. Exemplary heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), tetrazolyl, thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), benzofuranyl (1- and 2-), indolyl, isoindolyl, benzothienyl (1- and 2-), 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl (1,2,3- and 1,2,4-benzotriazinyl), pyridazinyl, phenoxazinyl, thiazolopyridinyl, pyrrolotriazolyl, phenothiazinyl, isobenzofuranyl, chromenyl, xanthenyl, phenoxathiinyl, pyrrolizinyl, indolizinyl, indazolyl, purinyl, quinolizinyl, phthalazinyl, naphthyridinyl (1,5-, 1,6-, 1,7-, 1,8-, and 2,6-), cinnolinyl, pteridinyl, carbazolyl, phenanthridinyl, acridinyl, perimidinyl, phenanthrolinyl (1,7-, 1,8-, 1,10-, 3,8-, and 4,7-), phenazinyl, oxazolopyridinyl, isoxazolopyridinyl, pyrrolooxazolyl, and pyrrolopyrrolyl. Exemplary 5- or 6-membered heteroaryl groups include furanyl, thienyl, oxazolyl, isoxazolyl, oxadiazolyl (1,2,5- and 1,2,3-), pyrrolyl, imidazolyl, pyrazolyl, triazolyl (1,2,3- and 1,2,4-), thiazolyl, isothiazolyl, thiadiazolyl (1,2,3- and 1,2,5-), pyridyl, pyrimidinyl, pyrazinyl, triazinyl (1,2,3-, 1,2,4-, and 1,3,5-), and pyridazinyl.

The term "cycloalkyl" or "cycloaliphatic" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 7 carbon atoms. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cyclodecyl, cyclodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclohexyl, cycloheptyl, cyclooctyl, spiro[3,3]heptyl, spiro[3,4]octyl, spiro[4,3]octyl, bicyclo[4.1.0]heptyl, bicyclo[3.2.0]heptyl, bicyclo[2.2.1]heptyl, bicyclo[2.2.2]octyl, bicyclo[5.1.0]octyl, and bicyclo[4.2.0]octyl.

The term "cyclopropylene" means a cyclopropyl group as defined above in which one hydrogen atom has been removed resulting in a diradical. The cyclopropylene may link two atoms or moieties via the same carbon atom (1,1-cyclopropylene, i.e., a geminal diradical) or via two carbon atoms (1,2-cyclopropylene).

The term "heterocyclyl" or "heterocyclic ring" means a cycloalkyl group as defined above in which from 1, 2, 3, or 4 carbon atoms in the cycloalkyl group are replaced by heteroatoms of O, S, or N. Preferably, in each ring of the heterocyclyl group the maximum number of O atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholino, isochromanyl, chromanyl, pyrrolidinyl, imidazolidinyl, pyrazolidinyl, piperidinyl, piperazinyl, indolinyl, isoindolinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydrothiazolyl (1,2,3- and 1,2,4-), di- and tetrahydrothiazolyl, di- and tetrahydrothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), di- and tetrahydrobenzofuranyl (1- and 2-), di- and tetrahydroindolyl, di- and tetrahydroisoindolyl, di- and tetrahydrobenzothienyl (1- and 2), di- and tetrahydro-1H-indazolyl, di- and tetrahydrobenzimidazolyl, di- and tetrahydrobenzoxazolyl, di- and tetrahydroindoxazinyl, di- and tetrahydrobenzisoxazolyl, di- and tetrahydrobenzothiazolyl, di- and tetrahydrobenzisothiazolyl, di- and tetrahydrobenzotriazolyl, di- and tetrahydroquinolinyl, di- and tetrahydroisoquinolinyl, di- and tetrahydrobenzodiazinyl, di- and tetrahydroquinoxalinyl, di- and tetrahydroquinazolinyl, di- and tetrahydrobenzotriazinyl (1,2,3- and 1,2,4-), di- and tetrahydropyridazinyl, di- and tetrahydrophenoxazinyl, di- and tetrahydrothiazolopyridinyl (such as 4,5,6-7-tetrahydro[1,3]thiazolo[5,4-c]pyridinyl or 4,5,6-7-tetrahydro[1,3]thiazolo[4,5-c]pyridinyl, e.g., 4,5,6-7-tetrahydro[1,3]thiazolo[5,4-c]pyridin-2-yl or 4,5,6-7-tetrahydro[1,3]thiazolo[4,5-c]pyridin-2-yl), di- and tetrahydropyrrolothiazolyl (such as 5,6-dihydro-4H-pyrrolo[3,4-d][1,3]thiazolyl), di- and tetrahydrophenothiazinyl, di- and tetrahydroisobenzofuranyl, di- and tetrahydrocbromenyl, di- and tetrahydroxanthenyl, di- and tetrahydrophenoxathiinyl, di- and tetrahydropyrrolizinyl, di- and tetrahydroindolizinyl, di- and tetrahydroindazolyl, di- and tetrahydropurinyl, di- and tetrahydroquinolizinyl, di- and tetrahydrophthalazinyl, di- and tetrahydronaphthyridinyl (1,5-, 1,6-, 1,7-, 1,8-, and 2,6-), di- and tetrahydrocinnolinyl, di- and tetrahydropteridinyl, di- and tetrahydrocarbazolyl, di- and tetrahydrophenanthridinyl, di- and tetrahydroacridinyl, di- and tetrahydroperimidinyl, di- and tetrahydrophenanthrolinyl (1,7-, 1,8-, 1,10-, 3,8-, and 4,7-), di- and tetrahydrophenazinyl, di- and tetrahydrooxazolopyridinyl, di- and tetrahydroisoxazolopyridinyl, di- and tetrahydropyrrolooxazolyl, and di- and tetrahydropyrrolopyrrolyl. Exemplary 5- or 6-membered heterocyclyl groups include morpholino, pyrrolidinyl, imidazolidinyl, pyrazolidinyl, piperidinyl, piperazinyl, di- and tetrahydrofuranyl, di- and tetrahydrothienyl, di- and tetrahydrooxazolyl, di- and tetrahydroisoxazolyl, di- and tetrahydrooxadiazolyl (1,2,5- and 1,2,3-), dihydropyrrolyl, dihydroimidazolyl, dihydropyrazolyl, di- and tetrahydropyrazolyl (1,2,3- and 1,2,4-), di- and tetrahydrothiazolyl, di- and tetrahydroisothiazolyl, di- and tetrahydrothiadiazolyl (1,2,3- and 1,2,5-), di- and tetrahydropyridyl, di- and tetrahydropyrimidinyl, di- and tetrahydropyrazinyl, di- and tetrahydrotriazinyl (1,2,3-, 1,2,4-, and 1,3,5-), and di- and tetrahydropyridazinyl.

The term "N-heterocycloalkylene" as used herein means a heterocyclyl group as defined above which contains at least one ring nitrogen atom and in which one hydrogen atom has been removed from the same carbon atom resulting in a geminal diradical. In addition to the at least one ring nitrogen atom, the N-heterocycloalkylene may contain 1, 2, or 3 further ring heteroatoms selected from the group consisting of O, S, or N. Preferably, in each ring of the N-heterocycloalkylene group the maximum number of O atoms is 1, the maximum number of S atoms is 1, and the maximum total number of O and S atoms is 2. Preferably, the N-heterocycloalkylene is monocyclic and contains 1, 2 or 3 ring nitrogen atoms and optionally does not contain O or S ring atoms. The term "N-heterocycloalkylene" is also meant to encompass partially or completely hydrogenated forms (such as dihydro, tetrahydro or perhydro forms) of the above-mentioned heteroaryl groups (preferably partially or completely hydrogenated forms of the above-mentioned monocyclic heteroaryl groups) which contain at least one ring nitrogen atom and in which one hydrogen atom has been removed from the same carbon atom resulting in a geminal diradical. Thus, according to the invention, an N-heterocycloalkylene may be saturated or unsaturated (i.e., it may contain one or more double bonds within the ring) but cannot be aromatic. Exemplary N-heterocycloalkylene groups include azetidinylene (N at position 2 or 3 relative to the diradical carbon atom), pyrrolidinylene (N at position 2 or 3), pyrazolidinylene (Ns at positions 2 and 3 or 3 and 4), imidazolidinylene (Ns at positions 2 and 4 or 2 and 5), triazolidinylene (Ns at positions 2, 3, and 4 or 2, 3, and 5), piperidinylene (N at position 2, 3, or 4), piperazinylene (Ns at positions 2 and 5), di-, tetra-, and hexahydropyridazinylene (Ns at position 2 and 3 or 3 and 4), di-, tetra-, and hexahydropyrimidinylene (Ns at positions 2 and 4 or 3 and 5), di- and tetrahydrotriazinylene, azepanylene (N at position 2, 3, or 4), diazepanylene (Ns at positions 2 and 3; 2 and 4; 2 and 5; 2 and 6; 2 and 7; 3 and 4; 3 and 5; 3 and 6; or 4 and 5), triazepanylene (Ns at positions 2, 3, and 4; 2, 3, and 5; 2, 3, and 6; 2, 3, and 7; 2, 4, and 5; 2, 4, and 6; 2, 4, and 7; 2, 5, and 6; 2, 5, and 7; 3, 4, and 5; or 3, 4, and 6), azocanylene (N at position 2, 3, 4, or 5), diazocanylene (Ns at positions 2 and 3; 2 and 4; 2 and 5; 2 and 6; 2 and 7; 2 and 8; 3 and 4; 3 and 5; 3 and 6; 3 and 7; 4 and 5; or 4 and 6), triazocanylene (Ns at position 2, 3, and 4; 2, 3, and 5; 2, 3, and 6; 2, 3, and 7; 2, 3, and 8; 2, 4, and 5; 2, 4, and 6; 2, 4, and 7; 2, 4, and 8; 2, 5, and 6; 2, 5, and 7; 2, 5, and 8; 2, 6, and 7; 3, 4, and 5; 3, 4, and 6; 3, 4, and 7; 3, 5, and 6; 3, 5, and 7; or 4, 5, and 6), and morpholinylene.

The term "monocyclic 4- to 10-membered N-heterocycloalkylene" as used herein means that the 4 to 10 members of the N-heterocycloalkylene are connected in such a manner that they form a single ring (e.g. piperidinylene). Thus, with the exception of the spiro carbon atom of ring A (which belongs to both ring A and the quinoxaline moiety) the remaining 3 to 9 ring atoms of ring A only belong to ring A, i. e, the ring atoms of ring A do not belong to any further ring. Therefore, according to the invention, the term "monocyclic 4- to 10-membered N-heterocycloalkylene" does not encompass polycyclic (e.g., bi- or tricyclic) structures (such as indolinylene), wherein at least two ring atoms belong to more than one ring.

The term "O/S-heterocycloalkylene" as used herein means a heterocyclyl group as defined above which contains at least one ring heteroatom selected from oxygen and sulfur and in which one hydrogen atom has been removed from the same carbon atom resulting in a geminal diradical. Preferably, each of the ring atoms of the O/S-heterocycloalkylene is selected from the group consisting of carbon, oxygen, and sulfur (i.e., the O/S-heterocycloalkylene preferably does not contain heteroatoms other than oxygen or sulfur). Preferably, in each ring of the O/S-heterocycloalkylene group the maximum number of O atoms is 2 or 1, the maximum number of S atoms is 2 or 1, and the maximum total number of O and S atoms is 2. Preferably, the O/S-heterocycloalkylene is monocyclic and contains 1 or 2 ring heteroatoms selected from oxygen and sulfur and optionally does not contain ring heteroatoms other than oxygen or sulfur.

The term "O/S-heterocycloalkylene" is also meant to encompass partially or completely hydrogenated forms (such as dihydro, tetrahydro or perhydro forms) of the above-mentioned heteroaryl groups (preferably partially or completely hydrogenated forms of the above-mentioned monocyclic heteroaryl groups) which contain at least one ring heteroatom selected from oxygen and sulfur and in which one hydrogen atom has been removed from the same carbon atom resulting in a geminal diradical. Thus, according to the invention, an O/S-heterocycloalkylene may be saturated or unsaturated (i.e., it may contain one or more double bonds within the ring) but cannot be aromatic. Exemplary O/S-heterocycloalkylene groups include oxetanylene (O at position 2 or 3), thietanylene (S at position 2 or 3), di- and tetrahydrofuranylene (O at position 2 or 3), di- and tetrahydrothienylene (S at position 2 or 3), di- and tetrahydropyranylene (O at position 2, 3, or 4), di- and tetrahydrothiopyranylene (S at position 2, 3, or 4), oxepanylene (O at position 2, 3, or 4), thiepanylene (S at position 2, 3, or 4), oxocanylene (O at position 2, 3, 4, or 5), thiocanylene (S at position 2, 3, 4, or 5), dioxolanylene (Os at positions 2 and 4 or 2 and 5), dithiolanylene (Ss at positions 2 and 3; 2 and 4; 2 and 5; or 3 and 4), oxathiolanylene (O at position 2 and S at position 3 or 4; O at position 4 and S at position 2; or O at position 2 and S at position 5), dioxanylene (Os at positions 2 and 4; 2 and 5; 2 and 6; or 3 and 5), dithianylene (Ss at positions 2 and 3; 2 and 4; 2 and 5; 2 and 6; 3 and 4; or 3 and 5), oxathianylene (O at position 2 and S at position 4, 5, or 6; O at position 3 and S at position 5 or 6; or S at position 2 and O at position 4), dioxepanylene (Os at positions 2 and 4; 2 and 5; 2 and 6; 2 and 7; 3 and 5; or 3 and 6), dithiepanylene (Ss at positions 2 and 3; 2 and 4; 2 and 5; 2 and 6; 2 and 7; 3 and 4; 3 and 5; 3 and 6; or 4 and 5), oxathiepanylene (O at position 2 and S at position 4, 5, 6, or 7; 0 at position 3 and S at position 5, 6, or 7; 0 at position 4 and S at position 6 or 7; or S at position 2 and O at position 4), dioxocanylene (Os at positions 2 and 4; 2 and 5; 2 and 6; 2 and 7; 2 and 8; 3 and 5; 3 and 6; 3 and 7; or 4 and 6), dithiocanylene (Ss at positions 2 and 3; 2 and 4; 2 and 5; 2 and 6; 2 and 7; 2 and 8; 3 and 4; 3 and 5; 3 and 6; 3 and 7; 4 and 5; or 4 and 6), and oxathiocanylene (O at position 2 and S at position 2, 3, 4, 5, 6, or 7; O at position 3 and S at position 5, 6, 7, or 8; O at position 4 and S at position 6, 7, or 8; S at position 2 and O at position 4 or 5; S at position 3 and 0 at position 5).

The term "monocyclic 4- to 10-membered O/S-heterocycloalkylene" as used herein means that the 4 to 10 members of the O/S-heterocycloalkylene are connected in such a manner that they form a single ring (e.g. tetrahydropyranylene). Thus, with the exception of the spiro carbon atom of ring A (which belongs to both ring A and the quinoxaline moiety) the remaining 3 to 9 ring atoms of ring A only belong to ring A, i.e, the ring atoms of ring A do not belong to any further ring. Therefore, according to the invention, the term "monocyclic 4- to 10-membered O/S-heterocycloalkylene" does not encompass polycyclic (e.g., bi- or tricyclic) structures (such as 3,4-dihydro-2H-chromenylene), wherein at least two ring atoms belong to more than one ring.

The term "cycloalkylene" as used herein means a cycloalkyl group as defined above in which one hydrogen atom has been removed from the same carbon atom resulting in a geminal diradical. Preferably, the cycloalkylene is monocyclic. The term "cycloalkylene" is also meant to encompass partially or completely hydrogenated forms (such as dihydro, tetrahydro or perhydro forms) of the above-mentioned aryl groups (preferably partially or completely hydrogenated forms of the above-mentioned monocyclic aryl groups) in which one hydrogen atom has been removed from the same carbon atom resulting in a geminal diradical. Thus, according to the invention, a cycloalkylene may be saturated or unsaturated (i.e., it may contain one or more double bonds within the ring) but cannot be aromatic. Exemplary cycloalkylene groups include cyclohexylene, cycloheptylene, cyclopropylene, cyclobutylene, cyclopentylene, cyclooctylene, cyclohexenylene, cycloheptenylene, cyclopropenylene, cyclobutenylene, cyclopentenylene, and cyclooctenylene.

The term "monocyclic 3- to 10-membered cycloalkylene" as used herein means that the 3 to 10 ring carbon atoms of the cycloalkylene are connected in such a manner that they form a single ring (e.g. cyclohexylene). Thus, with the exception of the spiro carbon atom of ring A (which belongs to both ring A and the quinoxaline moiety) the remaining 2 to 9 ring carbon atoms of ring A only belong to ring A, i.e, the ring carbon atoms of ring A do not belong to any further ring. Therefore, according to the invention, the term "monocyclic 3- to 10-membered cycloalkylene" does not encompass polycyclic (e.g., bi- or tricyclic) structures (such as indenylene), wherein at least two ring atoms belong to more than one ring.

The term "halogen" or "halo" means fluoro, chloro, bromo, or iodo.

The term "azido" means $N_3$.

The term "any two $R^9$ which are bound to the same carbon atom of ring A may join together to form =X" as used herein means that two monoradicals (i.e., $R^9$) when substituting in total 2 hydrogen atoms bound to only one ring carbon atom of ring A can form the diradical =X. For example, according to the invention, ring A being

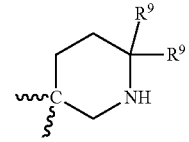

encompasses not only (1) the possibility that both $R^9$ groups are monoradicals independently selected from the particular moieties specified herein (e.g., methyl, —Cl, —OH, or —C(O)CH$_3$)) but also (2) the possibility that the two $R^9$ groups join together to form the diradical =X resulting in a ring A having the following formula:

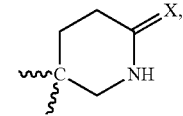

wherein X is O, S, or N(R$^{14}$). Similar terms such as "any two $R^{30}$ which are bound to the same carbon atom of a cycloalkyl or heterocyclyl group may join together to form =X$^1$" as used herein are to be interpreted in an analogous manner.

The term "optionally substituted" indicates that one or more (such as 1 to the maximum number of hydrogen atoms bound to a group, e.g., 1, 2, 3, 4, 5, 6, 7, 8, 9, or up to 10, such as between 1 to 5, 1 to 4, or 1 to 3, or 1 or 2) hydrogen atom(s) may be replaced with a group (i.e., a $1^{st}$ level substituent) different from hydrogen such as alkyl (preferably, $C_{1-6}$alkyl), alkenyl (preferably, $C_{2-6}$ alkenyl), alkynyl (preferably, $C_{2-6}$ alkynyl), aryl (preferably, 3- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, azido, —NO$_2$, —OR$^{71}$, —N(R$^{72}$)(R$^{73}$), —ON(R$^{72}$)(R$^{73}$), —N$^+$(—O$^-$)(R$^{72}$)(R$^{73}$), —S(O)$_{0-2}$R$^{71}$, —S(O)$_{0-2}$R$^{71}$, —OS(O)$_{0-2}$R$^{71}$, —OS(O)$_{0-2}$R$^{71}$, —S(O)$_{0-2}$N(R$^{72}$)(R$^{73}$), —OS(O)$_{0-2}$N(R$^{72}$)(R$^{73}$), —N(R$^{71}$)S(O)$_{0-2}$R$^{71}$, —NR$^{71}$S(O)$_{0-2}$OR$^{71}$, —NR$^{71}$S(O)$_{0-2}$N(R$^{72}$)(R$^{73}$), —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, and/or any two 1$^{st}$ level substituents which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups of the 1$^{st}$ level substituent may themselves be substituted by one, two or three substituents (i.e., a 2$^{nd}$ level substituent) selected from the group consisting of C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —ON(R$^{82}$)(R$^{83}$), —N$^+$(O$^-$)(R$^{82}$)(R$^{83}$), —S(O)$_{0-2}$R$^{81}$, —S(O)$_{0-2}$OR$^{81}$, —OS(O)$_{0-2}$R$^{81}$, —OS(O)$_{0-2}$OR$^{81}$, —S(O)$_{0-2}$N(R$^{82}$)(R$^{83}$), —OS(O)$_{0-2}$N(R$^{82}$)(R$^{83}$), —N(R$^{81}$)S(O)$_{0-2}$R$^{81}$, —NR$^{81}$S(O)$_{0-2}$OR$^{81}$, —NR$^{81}$S(O)$_{0-2}$N(R$^{82}$)(R$^{83}$), —C(=X$^2$)R$^{81}$, —C(=X$^2$)X$^2$R$^{81}$, —X$^2$C(=X$^2$)R$^{81}$, and —X$^2$C(=X$^2$)X$^2$R$^{81}$, and/or any two 2$^{nd}$ level substituents which are bound to the same carbon atom of a cycloalkyl or heterocyclyl group may join together to form =X$^2$, wherein each of the C$_{1-6}$alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl groups of the 2$^{nd}$ level substituent is optionally substituted with one, two or three substituents (i.e., a 3$^{rd}$ level substituent) independently selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —(C$_{1-3}$ alkyl), —N(C$_{1-3}$ alkyl)$_2$, —NHS(O)$_2$(C$_{1-3}$ alkyl), —S(O)$_2$N$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, and/or any two 3$^{rd}$ level substituents which are bound to the same carbon atom of a cycloalkyl or heterocyclyl group may join together to form =O, =S, =NH, or =N(C$_{1-3}$ alkyl);

wherein

R$^{71}$, R$^{72}$, and R$^{73}$ are independently selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, or R$^{72}$ and R$^{73}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

R$^{81}$, R$^{82}$, and R$^{83}$ are independently selected from the group consisting of —H, C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, or R$^{82}$ and R$^{83}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=N)NH$_{2-z}$(C$_{1-3}$ alkyl)$_z$, and —N(C$_{1-3}$alkyl)C(=NH)N$_{2-z}$(C$_{1-3}$ alkyl)$_z$, wherein z is 0, 1, or 2 and C$_{1-3}$ alkyl is methyl, ethyl, propyl or isopropyl;

X$^1$ and X$^2$ are independently selected from O, S, and NR$^{84}$, wherein R$^{84}$ is —H or C$_{1-3}$ alkyl.

Typical 1$^{st}$ level substituents are preferably selected from the group consisting of C$_{1-6}$ alkyl, C$_{2-6}$ alkenyl, C$_{2-6}$ alkynyl, 3- to 14-membered (such as 5- or 6-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, halogen, —CN, azido, —NO$_2$, —OR$^{71}$, —N(R$^{72}$)(R$^{73}$), —S(O)$_{0-2}$R$^{71}$, —S(O)$_{0-2}$OR$^{71}$, —OS(O)$_{0-2}$R$^{71}$, —OS(O)$_{0-2}$OR$^{71}$, —S(O)$_{0-2}$N(R$^{72}$)(R$^{73}$), —OS(O)$_{0-2}$N(R$^{72}$)(R$^{73}$), —N(R$^{71}$)S(O)$_{0-2}$R$^{71}$, —NR$^{71}$S(O)$_{0-2}$OR$^{71}$, —C(=X$^1$)R$^{71}$, —C(=X$^1$)X$^1$R$^{71}$, —X$^1$C(=X$^1$)R$^{71}$, and —X$^1$C(=X$^1$)X$^1$R$^{71}$, such as C$_{1-4}$ alkyl, C$_{2-4}$ alkenyl, C$_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)N$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl; X$^1$ is independently selected from O, S, NH and N(CH$_3$); and R$^{71}$, R$^{72}$, and R$^{73}$ are as defined above or, preferably, are independently selected from the group consisting of —H, C$_{1-4}$ alkyl, C$_{2-4}$ alkenyl, C$_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of C$_{1-3}$ alkyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)OH, —C(=O)O(C$_{1-3}$ alkyl), —C(=O)NH$_{2-z}$(C$_{1-3}$ alkyl)$_z$, —NHC(=O)(C$_{1-3}$ alkyl), —NHC(=NH)NH$_{2-z}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and $C_{1-3}$ alkyl is methyl, ethyl, propyl or isopropyl; or $R^{72}$ and $R^{73}$ may join together with the nitrogen atom to which they are attached to form a 5- or 6-membered ring, which is optionally substituted with one, two or three substituents selected from the group consisting of $C_{1-3}$ alkyl, halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl.

Typical $2^{nd}$ level substituents are preferably selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5- or 6-membered heterocyclyl, halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl), —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl. Particularly preferred $2^{nd}$ level substituents include 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —$CH_2CH_2OCH_3$, —$OCH_2CH_2OCH_3$, —$CH_2CH_2NH_{2-z}(CH_3)_z$, —$OCH_2CH_2NH_{2-z}(CH_3)_z$, —$CF_3$, and —$OCF_3$.

Typical $3^{rd}$ level substituents are preferably selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$SCH_3$, —$NH_{2-z}(CH_3)_z$, —C(=O)OH, and —C(=O)OCH$_3$, wherein z is 0, 1, or 2.

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The phrase "partially hydrogenated form" of an unsaturated compound or group as used herein means that part of the unsaturation has been removed by formally adding hydrogen to the initially unsaturated compound or group without removing all unsaturated moieties. The phrase "completely hydrogenated form" of an unsaturated compound or group is used herein interchangeably with the term "perhydro" and means that all unsaturation has been removed by formally adding hydrogen to the initially unsaturated compound or group. For example, partially hydrogenated forms of a 5-membered heteroaryl group (containing 2 double bonds in the ring, such as furan) include dihydro forms of said 5-membered heteroaryl group (such as 2,3-dihydrofuran or 2,5-dihydrofuran), whereas the tetrahydro form of said 5-membered heteroaryl group (e.g., tetrahydrofuran, i.e., THF) is a completely hydrogenated (or perhydro) form of said 5-membered heteroaryl group. Likewise, for a 6-membered heteroaryl group having 3 double bonds in the ring (such as pyridyl), partially hydrogenated forms include di- and tetrahydro forms (such as di- and tetrahydropyridyl), whereas the hexahydro form (such as piperidinyl in case of the heteroaryl pyridyl) is the completely hydrogenated (or perhydro) derivative of said 6-membered heteroaryl group. Consequently, a hexahydro form of an aryl or heteroaryl can only be considered a partially hydrogenated form according to the present invention if the aryl or heteroaryl contains at least 4 unsaturated moieties consisting of double and triple bonds between ring atoms.

The term "optional" or "optionally" as used herein means that the subsequently described event, circumstance or condition may or may not occur, and that the description includes instances where said event, circumstance, or condition occurs and instances in which it does not occur. "Isomers" are compounds having the same molecular formula but differ in structure ("structural isomers") or in the geometrical positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are non-superimposable mirror-images of each other. "Tautomers" are structural isomers of the same chemical substance that spontaneously interconvert with each other, even when pure.

In case a structural formula shown in the present application can be interpreted to encompass more than one isomer, said structural formula, unless explicitly stated otherwise, encompasses all possible isomers, and hence each individual such isomer. For example, a compound of formula (I), wherein ring A is

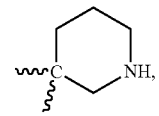

encompasses both isomers, i.e., the isomer having the following formula (B1) and the isomer having the following formula (B2):

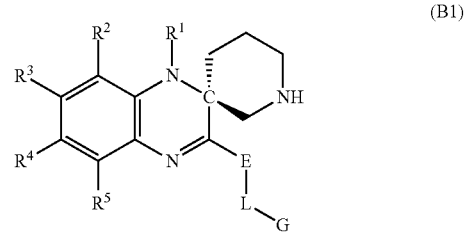

(B1)

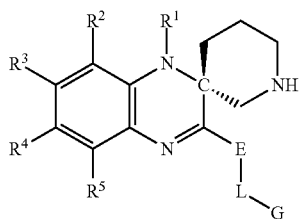
(B2)

"Polymorphism" as referred to herein means that a solid material (such as a compound) is able to exist in more than one form or crystalline structure, i.e., "polymorphic modifications" or "polymorphic forms". The terms "polymorphic modifications", "polymorphic forms", and "polymorphs" are used interchangeable in the present invention. According to the present invention, these "polymorphic modifications" include crystalline forms, amorphous forms, solvates, and hydrates. Mainly, the reason for the existence of different polymorphic forms lies in the use of different conditions during the crystallization process, such as the following:
  solvent effects (the packing of crystal may be different in polar and nonpolar solvents);
  certain impurities inhibiting growth pattern and favor the growth of a metastable polymorphs;
  the level of supersaturation from which material is crystallized (in which generally the higher the concentration above the solubility, the more likelihood of metastable formation);
  temperature at which crystallization is carried out;
  geometry of covalent bonds (differences leading to conformational polymorphism);
  change in stirring conditions.

Polymorphic forms may have different chemical, physical, and/or pharmacological properties, including but not limited to, melting point, X-ray crystal and diffraction pattern, chemical reactivity, solubility, dissolution rate, vapor pressure, density, hygroscopicity, flowability, stability, compactability, and bioavailability. Polymorphic forms may spontaneously convert from a metastable form (unstable form) to the stable form at a particular temperature. According to Ostwald's rule, in general it is not the most stable but the least stable polymorph that crystallizes first. Thus, quality, efficacy, safety, processability and/or manufacture of a chemical compound, such as a compound of the present invention, can be affected by polymorphism. Often, the most stable polymorph of a compound (such as a compound of the present invention) is chosen due to the minimal potential for conversion to another polymorph. However, a polymorphic form which is not the most stable polymorphic form may be chosen due to reasons other than stability, e.g. solubility, dissolution rate, and/or bioavailability.

The term "crystalline form" of a material as used herein means that the smallest components (i.e., atoms, molecule or ions) of said material form crystal structures. A "crystal structure" as referred to herein means a unique three-dimensional arrangement of atoms or molecules in a crystalline liquid or solid and is characterized by a pattern, a set of atoms arranged in a particular manner, and a lattice exhibiting long-range order and symmetry. A lattice is an array of points repeating periodically in three dimensions and patterns are located upon the points of a lattice. The subunit of the lattice is the unit cell. The lattice parameters are the lengths of the edges of a unit cell and the angles between them. The symmetry properties of the crystal are embodied in its space group. In order to describe a crystal structure the following parameters are required: chemical formula, lattice parameters, space group, the coordinates of the atoms and occupation number of the point positions.

The term "amorphous form" of a material as used herein means that the smallest components (i.e., atoms, molecule or ions) of said material are not arranged in a lattice but are arranged randomly. Thus, unlike crystals in which a short-range order (constant distances to the next neighbor atoms) and a long-range order (periodical repetition of a basic lattice) exist, only a short-range order exists in an amorphous form.

The term "complex of a compound" as used herein refers to a compound of higher order which is generated by association of the compound with other one or more other molecules. Exemplary complexes of a compound include, but are not limited to, solvates, clusters, and chelates of said compound.

The term "solvate" as used herein refers to an addition complex of a dissolved material in a solvent (such as an organic solvent (e.g., an aliphatic alcohol (such as methanol, ethanol, n-propanol, isopropanol), acetone, acetonitrile, ether, and the like), water or a mixture of two or more of these liquids), wherein the addition complex exists in the form of a crystal or mixed crystal. The amount of solvent contained in the addition complex may be stoichiometric or non-stoichiometric. A "hydrate" is a solvate wherein the solvent is water.

In isotopically labeled compounds one or more atoms are replaced by a corresponding atom having the same number of protons but differing in the number of neutrons. For example, a hydrogen atom may be replaced by a deuterium atom. Exemplary isotopes which can be used in the compounds of the present invention include deuterium, $^{11}$C, $^{13}$C, $^{14}$C, $^{15}$N, $^{18}$F, $^{32}$S, $^{36}$Cl, and $^{125}$I.

The term "half-life" relates to the period of time which is needed to eliminate half of the activity, amount, or number of molecules. In the context of the present invention, the half-life of a compound of formula (I) is indicative for the stability of said compound.

The terms "patient", "individual", or "animal" relate to multicellular animals, such as vertebrates. For example, vertebrates in the context of the present invention are mammals, birds (e.g., poultry), reptiles, amphibians, bony fishes, and cartilaginous fishes, in particular domesticated animals of any of the foregoing as well as animals (in particular vertebrates) in captivity such as animals particular vertebrates) of zoos. Mammals in the context of the present invention include, but are not limited to, humans, non-human primates, domesticated mammals, such as dogs, cats, sheep, cattle, goats, pigs, horses etc., laboratory mammals such as mice, rats, rabbits, guinea pigs, etc. as well as mammals in captivity such as mammals of zoos. The term "animal" as used herein also includes humans. Particular non-limiting examples of birds include domesticated poultry, and include birds such as chickens, turkeys, ducks, geese, guinea fowl, pigeons, pheasants etc; while particular non-limiting examples of bony or cartilaginous fish include those suitable for cultivation by aquiculture, and include bony fish such as salmon, trout, perch, carp, cat-fish, etc.

Compounds

In one aspect, the present invention provides a compound selected from the group consisting of a spiroquinoxaline derivative having the general formula (I)

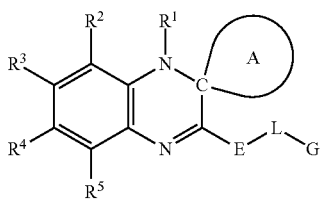

(I)

and solvates, salts, complexes, polymorphs, crystalline forms, racemic mixtures, diastereomers, enantiomers, tautomers, isotopically labeled forms, prodrugs, and combinations thereof, wherein E is —N($R^6$)—;

L is selected from the group consisting of $C_{1-10}$ alkylene, $C_{2-10}$ alkenylene, $C_{2-10}$ alkynylene, 1,1-$(CH_2)_a$-cyclopropylene-$(CH_2)_b$—, wherein each of a and b is independently selected from an integer between 0 and 3, and —$(CH_2)_m$—[Y—$(CH_2)_n]_o$—, wherein m is an integer between 1 and 6, n is an integer between 0 and 3, o is an integer between 1 and 3, wherein if n is 0 then o is 1; Y is independently selected from O, S, and —N($R^7$)—; and each of the $C_{1-10}$ alkylene, $C_{2-10}$ alkenylene, $C_{2-10}$ alkynylene, 1,1-cyclopropylene, —$(CH_2)_m$—, and —$(CH_2)_n$— groups is optionally substituted with one or more (such as 1 to the maximum number of hydrogen atoms bound to the $C_{1-10}$ alkylene, $C_{2-10}$ alkenylene, $C_{2-10}$ alkynylene, 1,1-cyclopropylene, —$(CH_2)_m$—, or —$(CH_2)_n$— group, e.g., 1, 2, 3, 4, 5, 6, 7, 8, 9, or up to 10, such as between 1 to 5, 1 to 4, or 1 to 3, or 1 or 2) independently selected $R^{30}$;

G is phenyl, optionally substituted with 1, 2, 3, 4 or 5 independently selected $R^8$;

ring A is a monocyclic 4- to 10-membered N-heterocycloalkylene, a monocyclic 4- to 10-membered O/S-heterocycloalkylene, or a monocyclic 3- to 10-membered cycloalkylene, wherein each of the N-heterocycloalkylene, O/S-heterocycloalkylene, and cycloalkylene groups is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$;

$R^1$ is H;

$R^2$, $R^3$, $R^4$, and $R^5$ are independently selected from the group consisting of —H, alkyl, alkenyl, alkynyl, aryl, heteroaryl, cycloalkyl, heterocyclyl, halogen, —CN, azido, —$NO_2$, —$OR^{11}$, —N($R^{12}$)($R^{13}$), —N($R^{11}$)($OR^{11}$), —S(O)$_{0-2}$$R^{11}$, —S(O)$_{1-2}$$OR^{11}$, —OS(O)$_{1-2}$$R^{11}$, —OS(O)$_{1-2}$$OR^{11}$, —S(O)$_{1-2}$N($R^{12}$)($R^{13}$), —OS(O)$_{1-2}$N($R^{12}$)($R^{13}$), —N($R^{11}$)S(O)$_{1-2}$$R^{11}$, —$NR^{11}$S(O)$_{1-2}$$OR^{11}$, —$NR^{11}$S(O)$_{1-2}$N($R^{12}$)($R^{13}$), —C(=X)$R^{11}$, —C(=X)X$R^{11}$, —XC(=X)$R^{11}$, and —XC(=X)X$R^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

or $R^2$ and $R^3$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; $R^3$ and $R^4$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; and/or $R^4$ and $R^5$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$;

$R^6$ is H;

$R^7$ is selected from the group consisting of —H, alkyl, alkenyl, alkynyl, cycloalkyl, aryl, heteroaryl, heterocyclyl, —$OR^{11}$, and —$NHR^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^8$ is, in each case, selected from the group consisting of alkyl, alkenyl, alkynyl, aryl, heteroaryl, cycloalkyl, heterocyclyl, halogen, —CN, azido, —$NO_2$, —$OR^{11}$, —N($R^{12}$)($R^{13}$), —N($R^{11}$)($OR^{11}$), —S(O)$_{0-2}$$R^{11}$, —S(O)$_{1-2}$$OR^{11}$, —OS(O)$_{1-2}$$R^{11}$, —OS(O)$_{1-2}$$OR^{11}$, —S(O)$_{1-2}$N($R^{12}$)($R^{13}$), —OS(O)$_{1-2}$N ($R^{12}$)($R^{13}$), —N($R^{11}$)S(O)$_{1-2}$$R^{11}$, —$NR^{11}$S(O)$_{1-2}$$OR^{11}$, —$NR^{11}$S(O)$_{1-2}$N($R^{12}$)($R^{13}$), —C(=X)X$R^{11}$, —XC(=X)$R^{11}$, and —XC(=X)X$R^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^9$ is, when substituting a hydrogen atom bound to a ring carbon atom, independently selected from the group consisting of alkyl, alkenyl, alkynyl, aryl, heteroaryl, cycloalkyl, heterocyclyl, halogen, —CN, azido, —$NO_2$, —$OR^{11}$, —N($R^{12}$)($R^{13}$), —S(O)$_{0-2}$$R^{11}$, —S(O)$_{1-2}$$OR^{11}$, —OS(O)$_{1-2}$$R^{11}$, —OS(O)$_{1-2}$$OR^{11}$, —S(O)$_{1-2}$N($R^{12}$)($R^{13}$), —OS(O)$_{1-2}$N($R^{12}$)($R^{13}$), —N($R^{11}$)S(O)$_{1-2}$R, —$NR^{11}$S(O)$_{1-2}$ $OR^{11}$, —$NR^{11}$S(O)$_{1-2}$N($R^{12}$)($R^{13}$), —C(=X)$R^{11}$, —C(=X)X$R^{11}$, —XC(=X)$R^{11}$, and —XC(=X)X$R^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, and/or any two $R^9$ which are bound to the same carbon atom of ring A may join together to form =X; or $R^9$ is, when substituting a hydrogen atom bound to a ring nitrogen atom, independently selected from the group consisting of alkyl, alkenyl, alkynyl, aryl, heteroaryl, cycloalkyl, heterocyclyl, —$OR^{11}$, —N($R^{12}$)($R^{13}$), —S(O)$_{1-2}$$R^{11}$, —S(O)$_{1-2}$$OR^{11}$, —S(O)$_{1-2}$N($R^{12}$)($R^{13}$), —N($R^{11}$)S(O)$_{1-2}$$R^{11}$, —$NR^{11}$ S(O)$_{1-2}$ $OR^{11}$, —$NR^{11}$S(O)$_{1-2}$N($R^{12}$)($R^{13}$), —C(=X)$R^{11}$, —C(=X)X$R^{11}$, —N($R^{14}$)C(=X)$R^{11}$, and —N($R^{14}$)C(=X)X$R^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; or $R^9$ is, when bound to a ring sulfur atom of ring A, independently selected from the group consisting of alkyl, alkenyl, alkynyl, aryl, heteroaryl, cycloalkyl, heterocyclyl, —$OR^{11}$, and =O, wherein each of the alkyl, alkenyl, alkynyl, aryl, heteroaryl, cycloalkyl, and heterocyclyl groups is optionally substituted with one or more independently selected $R^{30}$;

X is independently selected from O, S, and $N(R^{14})$;

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=$CR^{15}R^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{14}$ is independently selected from the group consisting of —H, alkyl alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —$NH_yR^{20}{}_{2-y}$, or $R^{15}$ and $R^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2} N(R^{72})(R^{73})$, —$OS(O)_{1-2}N(R^{72})(R^{73})$, —$N(R^{71})S(O)_{1-2} R^{71}$, —$NR^{71}S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more (such as 1 to the maximum number of hydrogen atoms bound to the alkyl, alkenyl, alkynyl, aryl, heteroaryl, cycloalkyl, or heterocyclyl group being a $1^{st}$ level substituent, e.g., 1, 2, 3, 4, 5, 6, 7, 8, 9, or up to 10, such as between 1 to 5, 1 to 4, or 1 to 3, or 1 or 2) $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, and 3- to 14-membered heterocyclyl groups being a $2^{nd}$ level substituent is optionally substituted with one or more (such as 1 to the maximum number of hydrogen atoms bound to the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, or 3- to 14-membered heterocyclyl group being a $2^{nd}$ level substituent, e.g., 1, 2, 3, 4, 5, 6, 7, 8, 9, or up to 10, such as between 1 to 5, 1 to 4, or 1 to 3, or 1 or 2) $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —$O(C_{1-3}$ alkyl), —$OCF_3$, —$S(C_{1-3}$ alkyl), —$NH_2$, —$N(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =$N(C_{1-3}$ alkyl);

wherein $R^{71}$, $R^{72}$, and $R^{73}$ are independently selected from the group consisting of —H, $C_{1-6}$alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_{2-z}$—$(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}$ $(C_{1-3}$ alkyl)$_z$, —$NHC(=O)(C_{1-3}$ alkyl), —$NHC(=NH)$ $NH_{z-2}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkenyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}$ $(C_{1-3}$ alkyl)$_z$, —$NHC(=O)(C_{1-3}$ alkyl), —$NHC(=NH)$ $NH_{z-2}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and $N(R^{84})$, wherein $R^{84}$ is —H or $C_{1-3}$ alkyl.

In one embodiment, the spiroquinoxaline derivative has the general formula (II)

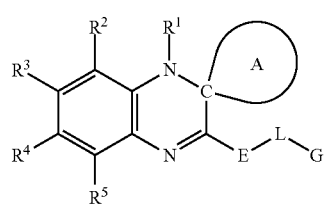

(II)

wherein $R^1$ to $R^5$, E, L and G are as defined above or below and ring A (i) is a N-heterocycloalkylene which contains 1 ring nitrogen atom and is 4- to 8-membered (preferably 5-, 6- or 7-membered, more preferably 6- or 7-membered) or which contains 2 or 3 ring nitrogen atoms and is 5- to 8-membered, preferably 5-, 6- or 7-membered, more preferably 6- or 7-membered; (ii) is a O/S-heterocycloalkylene which contains 1 ring oxygen or sulfur atom and is 4- to 8-membered (preferably 5-, 6- or 7-membered, more preferably 6- or 7-membered) or which contains 2 ring heteroatoms selected from oxygen and sulfur and is 5- to 8-membered, preferably 5-, 6- or 7-membered, more preferably 6- or 7-membered; or (iii) is a cycloalkylene which is 3- to 8-membered, preferably 4-, 5-, 6- or 7-membered, more preferably 6- or 7-membered. In one embodiment of the spiroquinoxaline derivative of formula (II), ring A as such is unsaturated (i.e., the members of ring A constitute 1, 2, or 3 (preferably 1 or 2, most preferably 1) double bonds within the ring) but is not aromatic. In an alternative embodiment of the spiroquinoxaline derivative of formula (II), ring A is saturated (i.e., ring A as such is free of unsaturation within the ring); however, if ring A is substituted by one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) $R^9$, $R^9$ may be unsaturated (i.e., may contain double and/or triple bonds and/or one or more (e.g., 1, 2. or 3) aromatic ring(s)). In any of the above embodiments of the spiroquinoxaline derivative of formula (II), the ring nitrogen, oxygen, and/or sulfur atoms of ring A (preferably all ring heteroatoms of ring A) are not at position alpha to the spiro carbon atom (i.e., in this embodiment, preferably the two atoms of ring A positioned alpha to the spiro carbon atom are carbon atoms). In any of the above embodiments of the spiroquinoxaline derivative of formula (II), ring A may be selected from the group consisting of piperidinylene, azepanylene (e.g., homopiperidinylene), azetidinylene, pyrrolidinylene, azocanylene, pyrazolidinylene, hexahydropyridazinylene, hexahydropyrimidinylene, diazepanylene (e.g., homopiperazinylene), diazocanylene, triazepanylene, triazocanylene, di- and tetrahydropyranylene, di- and tetrahydrothiopyranylene, oxepanylene, thiepanylene, oxetanylene, thietanylene, di- and tetrahydrofuranylene, di- and tetrahydrothienylene, oxocanylene, thiocanylene, dithiolanylene, oxathiolanylene, dioxanylene, dithianylene, oxathianylene, dioxepanylene, dithiepanylene, oxathiepanylene, dioxocanylene, dithiocanylene, oxathiocanylene, cyclohexylene, cycloheptylene, cyclopropylene, cyclobutylene, cyclopentylene, cyclooctylene, cyclohexenylene, cycloheptenylene, cyclopentenylene, cyclooctenylene, and their regioisomers, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$. In one embodiment of the spiroquinoxaline derivative of formula (II), ring A is selected from the group consisting of 3- and 4-piperidinylene (N at position 3 or 4 relative to the spiro carbon atom); 3- and 4-azepanylene, 3-azetidinylene, 3-pyrrolidinylene, 3-, 4-, and 5-azocanylene, 3,4-pyrazolidinylene, 3,4-hexahydropyridazinylene, 3,5-hexahydropyrimidinylene, 3,4-, 3,5-, 3,6-, and 4,5-diazepanylene, 3,4-, 3,5-, 3,6-, 3,7-, 4,5-, 4,6-diazocanylene, 3- and 4-tetrahydropyranylene (O at position 3 or 4 relative to the spiro carbon atom); 3- and 4-tetrahydrothiopyranylene; 3- and 4-oxepanylene; 3- and 4-thiepanylene; 3-oxetanylene; 3-thietanylene; 3-tetrahydrofuranylene; 3-tetrahydrothienylene; 3-, 4-, and 5-oxocanylene; 3-, 4-, and 5-thiocanylene; 3,4-dithiolanylene; 3,4-oxathiolanylene; 3,5-dioxanylene; 3,4- and 3,5-dithianylene; 3,4-, 3,5-, and 4,3-oxathianylene; 3,5- and 3,6-dioxepanylene; 3,4-, 3,5-, 3,6-, and 4,5-dithiepanylene; 3,4-, 3,5-, 3,6-, 4,5-, 4,3-, and 4,2-oxathiepanylene; 3,5-, 3,6-, 3,7-, and 4,6-dioxocanylene; 3,3-, 3,4-, 3,5-, 3,6, 3,7-, 4,5-, and 4,6-dithiocanylene; and 3,4-, 3,5-, 3,6-, 3,7-, 4,5-, 4,6, 4,7-, 4-3-, 5,4-, and 5,3-oxathiocanylene, cyclohexylene, cycloheptylene, cyclopropylene, cyclobutylene, cyclopentylene, and cyclooctylene, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected R. In one embodiment of the spiroquinoxaline derivative of formula (II), ring A is selected from the group consisting of 4-piperidinylene, 3-piperidinylene, 3-azetidinylene, 3-pyrrolidinylene, 4-azepanylene, 3-azepanylene, 5-azocanylene, 4-azocanylene, 3-azocanylene, 3,6-diazocanylene (such as 4-piperidinylene, 3-piperidinylene, 4-azepanylene, and 3-azepanylene), 44-tetrahydropyranylene, 4-tetrahydrothiopyranylene, 3-tetrahydropyranylene, 3-tetrahydrothiopvranylene, 4-oxepanylene, 4-thiepanylene, 3-oxepanylene, 3-thiepanylene, 3-oxetanylene, 3-thietanylene, 3-tetrahydrofuranylene, 3-tetrahydrothienylene, 5-oxocanylene, 5-thiocanylene, 4-oxocanylene, 4-thiocanylene (such as-tetrahydropyranylene, 4-tetrahydrothiopyranylene, 3-tetrahydropyranylene, 3-tetrahydrothiopyranylene, 4-oxepanylene, 4-thiepanylene, 3-oxepanylene, and 3-thiepanylene), cyclohexylene, cycloheptylene, cyclopentylene, and cyclooctylene, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$.

In any of the above embodiments of the spiroquinoxaline derivative of formula (II), ring A may be unsubstituted.

In any of the above embodiments of the spiroquinoxaline derivative of formula (II), wherein ring A is substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$, either (i) only one or more (preferably, 1, 2, or 3) ring heteroatoms of ring A (selected from nitrogen, oxygen, and sulfur, wherein the maximum number of oxygen and sulfur atoms in ring A is preferably 2) are substituted with independently selected $R^9$, or (ii) only one or more (preferably, 1, 2, or 3) ring carbon atoms of ring A are substituted with independently selected $R^9$, or (iii) one or more (preferably, 1, 2, or 3) ring heteroatoms (selected from nitrogen, oxygen, and sulfur, wherein the maximum number of oxygen and sulfur atoms in ring A is preferably 2) and one or more (preferably, 1, 2, or 3) ring carbon atoms of ring A (e.g., 1 or 2 ring heteroatoms and 1 or 2 ring carbon atoms) are substituted with independently selected R. For example, if ring A contains 1 ring heteroatom (selected from nitrogen, oxygen, and sulfur), ring A may be substituted (i) only at the ring heteroatom atom with B (preferably, the ring heteroatom is at position 3 if ring A is 4- or 5-membered; at position 3 or 4 (preferably 4) if ring A is 6- or 7-membered; or at position 3, 4, or 5 (preferably 4 or 5) if ring A is 8-membered); (ii) only at 1 or 2 ring carbon atoms of ring A each with 1 or 2 independently selected $R^9$; or (iii) at the ring heteroatom with $R^9$ (preferably, the ring heteroatom is at position 3 if ring A is 4- or 5-membered; at position 3 or 4 (preferably 4) if ring A is 6- or 7-membered; or at position 3, 4, or 5 (preferably 4 or 5) if ring A is 8-membered) and at 1 or 2 ring carbon atoms of ring A each with 1 or 2 independently selected $R^9$.

In any of the above embodiments of the spiroquinoxaline derivative of formula (II), wherein $R^9$ substitutes a hydrogen atom bound to a ring carbon atom of ring A, each such $R^9$ may be independently selected from the group consisting of $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^3$, and/or any two $R^9$ which are bound to the same carbon atom of ring A may join together to form =X. In any of the above embodiments of the spiroquinoxaline derivative of formula (II), wherein $R^9$ substitutes a hydrogen atom bound to a ring carbon atom of ring A, each such $R^9$ may be independently selected from the group consisting of $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=O)R^{11}$, —$C(=O)OR^{11}$, —$C(=O)SR^{11}$, —$C(=O)N(R^{14})(R^{11})$, —$C(=S)OR^{11}$, —$N(R^{14})C(O)R^{11}$, —$OC(=O)R^{11}$, —$OC(=S)R^{11}$, —$(R^{14})C(=O)N(R^{14})(R^{11})$, and —$N(R^{14})C(=N(R^{14}))N(R^{14})(R^{11})$, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$, and/or any two $R^9$ which are bound to the same carbon atom of ring A may join together to form =O or =S. In one embodiment, each $R^9$ when substituting a hydrogen atom bound to a ring carbon atom of ring A is independently selected from the group consisting of $C_{1-4}$ alkyl; $C_{1-4}$ alkyl substituted with 1 substituent selected from the group consisting of —OH, —$O(C_{1-3}$ alkyl), —$NH_{2-z}(CH_3)_z$, morpholinyl (e.g., 4-morpholinyl), piperazinyl (e.g., 1-piperazinyl), and N-methylpiperazinyl (e.g., 4-methylpiperazin-1-yl); $C_{1-4}$ alkyl substituted with 1, 2, or 3 halogen (preferably F), such as —$CF_3$, —$CH_2CF_3$, —$CH_2CHF_2$, or —$CH_2CH_2F$; —$O(C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; cyclopropyl; 4-morpholinyl; homomorpholinyl; 4-piperidinyl; homopiperidinyl; 4-piperazinyl; homopiperazinyl; homopiperazinyl; 4-methyl-piperazin-1-yl; N-methyl-homopiperazinyl; halogen; —CN; —OH; =O; —$O(C_{1-3}$ alkyl optionally substituted with —$NH_{2-z}(CH_2)_z$); —$NH_2$; —$NH(C_{1-3}$ alkyl); —$N(C_{1-3}$ alkyl)$_2$; —$S(C_{1-3}$ alkyl); —$S(O)_2(C_{1-3}$ alkyl optionally substituted with —$NH_{2-z}(CH_3)_z$); —$S(O)_2N_{2-z}(C_{1-3}$ alkyl); —$NHS(O)_2(C_{1-3}$ alkyl optionally substituted with —$NH_{2-z}(CH_2)_z$); —$C(=O)(C_{1-3}$ alkyl optionally substituted with —$NH_{2-z}(CH_3)_z$); —$C(=O)OH$; —$C(=O)O(C_{1-3}$ alkyl); —$C(=O)NH_{2-z}(C_{1-3}$ alkyl)$_z$; —$NHC(=O)(C_{1-3}$ alkyl optionally substituted with —$NH_{2-z}(CH_3)_z$); —$NHC(=O)NH_{2-z}(CH_3)_z$; —$NHC(=NH)NH_{2-z}(C_{1-3}$ alkyl)$_z$; and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; tert-butyl; cyclopropyl; —$(CH_2)_d$—$NH_{2-z}(CH_3)_z$; —$O(CH_2)_d$—$NH_{2-z}(CH_3)_z$; —$(CH_2)_d$—$O(CH_3)$; —$CF_3$; —$CH_2CF_3$; —$CH_2CF_2$; —$CH_2CH_2F$; —$(CH_2)_d$-(4-morpholinyl); —$(CH_2)_d$-(1-piperazinyl); —$(CH_2)_d$-(4-methylpiperazin-1-yl); 4-morpholinyl; 4-piperazinyl; 4-methyl-piperazin-1-yl; halogen (in particular, —F, —Cl, —Br); —$NHC(=O)(C_{1-3}$ alkyl optionally substituted with —$NH_{2-z}(CH_3)_z$); —$NHC(=O)NH_{2-z}(CH_3)_z$; —$NS(O)_2(C_{1-3}$ alkyl optionally substituted with —$NH_{2-z}(CH_3)_z$); —$C(=O)CH_3$; —$C(=O)CH_2NH_{2-z}(CH_3)_z$; $C(=O)NH_{2-z}(C_{1-3}$ alkyl); —$S(O)_2(C_{1-3}$ alkyl); —$S(O)_2(CH_2)_dNH_2$—$(CH_3)_z$; —OH; and —$O(C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; cyclopropyl; —$(CH_2)_d$—$NH_{2-z}(CH_3)_z$, —(CH$_2$)$_d$—O(CH$_3$); —CF$_3$; —CH$_2$CF$_3$; —CH$_2$CH$_2$, —CH$_2$CH$_2$F; —NH$_2$; —NH(C$_{1-3}$ alkyl); —N(C$_{1-3}$ alkyl)$_2$; halogen (in particular, —F, —Cl, —Br); —C(=O)CH$_3$; —C(=O)CH$_2$NH$_{2-z}$(CH$_3$)$_z$; —C(=O)NH$_{2-z}$(C$_{1-3}$ alkyl)$_z$; —S(O)$_2$(C$_{1-3}$ alkyl); —S(O)$_2$(CH$_2$)$_d$NH$_{2-z}$(CH$_3$)$_z$; —OH; and —O(C$_{1-3}$ alkyl), wherein z is 0, 1, or 2; d is 1, 2, or 3; and C$_{1-3}$ alkyl is methyl, ethyl, propyl or isopropyl. In one embodiment, each R$^9$ when substituting a hydrogen atom bound to a ring carbon atom of ring A is independently selected from the group consisting of methyl; ethyl; isopropyl; cyclopropyl; —(CH$_2$)$_d$—NH—(CH$_3$)$_z$; —(CH$_2$)$_d$—O(CH$_3$); —CF$_3$; —CH$_2$CF$_3$; —CH$_2$CHF$_2$; —CH$_2$CH$_2$F; halogen (in particular, —F, —Cl, —Br); —C(=O)CH$_3$; —C(=O)CH$_2$NH$_{2-z}$(CH$_3$)$_z$; —C(=O)NH$_{2-z}$(C$_{1-3}$ alkyl)$_z$; —S(O)$_2$(C$_{1-3}$ alkyl); —S(O)$_2$(CH$_2$)$_d$NH$_{2-z}$(CH$_3$)$_z$; —OH; and —O(C$_{1-3}$ alkyl), wherein z is 0, 1, or 2; d is 1, 2, or 3; and C$_{1-3}$ alkyl is methyl, ethyl, propyl or isopropyl. In one embodiment, the ring carbon atoms of ring A are unsubstituted or each R$^9$ substituting a hydrogen atom bound to a ring carbon atom is independently selected from the group consisting of C$_{1-4}$ alkyl (in particular methyl), —N(R$^{12}$)(R$^{13}$)(in particular NH$_2$), and —N(R$^{14}$)C(=O)R$^{11}$ (in particular NHC(O)CH$_3$). In one embodiment, the ring carbon atoms of ring A are unsubstituted or one ring carbon atom of ring A is substituted with one R$^9$ being NH$_2$ or CH$_3$, or with two R$^9$ being CH$_3$.

In any of the above embodiments of the spiroquinoxaline derivative of formula (II), wherein R$^9$ substitutes a hydrogen atom bound to a ring nitrogen atom of ring A, each such R$^9$ may be independently selected from the group consisting of C$_{1-12}$ alkyl (such as C$_{1-8}$ alkyl or C$_{1-6}$ alkyl), C$_{2-6}$ alkenyl, C$_{2-6}$alkynyl, 5- or 6-membered aryl, 5- or 6-membered heteroaryl, 3- to 7-membered cycloalkyl, 3- to 7-membered heterocyclyl, —OR$^{11}$, —N(R$^{12}$)(R$^{13}$), —S(O)$_{1-2}$R, —S(O)$_{1-2}$N(R$^{12}$)(R$^{13}$), —N(R$^{11}$)S(O)$_{1-2}$R$^{11}$, —NR$^{11}$S(O)$_{1-2}$ N(R$^{12}$)(R$^{13}$), —C(=X)R$^{11}$, —C(=X)XR$^{11}$, —N(R$^4$)C(=X)R$^{11}$, and —N(R$^{14}$)C(=X)XR$^{11}$, wherein each of the C$_{1-12}$ alkyl (such as C$_{1-8}$ alkyl or C$_{1-6}$ alkyl), C$_{2-6}$ alkenyl, C$_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the C$_{1-12}$ alkyl (such as C$_{1-8}$ alkyl or C$_{1-6}$ alkyl), C$_{2-6}$ alkenyl, C$_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$. In any of the above embodiments of the spiroquinoxaline derivative of formula (II), wherein R$^9$ substitutes a hydrogen atom bound to a ring nitrogen atom of ring A, each such R$^9$ may be independently selected from the group consisting of C$_{1-12}$ alkyl (such as C$_{1-8}$ alkyl, C$_{1-6}$ alkyl or C$_{1-4}$alkyl), C$_{2-4}$ alkenyl, C$_{2-4}$ alkynyl, 6-membered aryl, 5- or 6-membered heteroaryl, 3-, 5-, 6- or 7-membered cycloalkyl, 3-, 5-, 6- or 7-membered heterocyclyl, —OR$^{11}$, —N(R$^{12}$)(R$^{13}$), —S(O)$_{1-2}$R$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$N(R$^{12}$)(R$^{13}$), —C(=O)R$^{11}$, —C(=O)OR$^{11}$, —C(=O)SR$^{11}$, —C(=O)N(R$^{14}$)(R$^{11}$), —C(=S)OR$^{11}$, —N(R$^{14}$)C(=O)R$^{11}$, —N(R$^{14}$)C(=O)N(R$^{14}$)(R$^{11}$) and —N(R$^{14}$)C(=N(R$^{14}$))N(R$^{14}$)(R$^{11}$), wherein each of the C$_{1-12}$ alkyl (such as C$_{1-8}$ alkyl, C$_{1-6}$ alkyl, or C$_{1-4}$ alkyl), C$_{2-4}$ alkenyl, C$_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected R$^{30}$. In one embodiment, each R$^9$ when substituting a hydrogen atom bound to a ring nitrogen atom of ring A is independently selected from the group consisting of C$_{1-12}$ alkyl (such as C$_{1-8}$ alkyl, C$_{1-6}$ alkyl, or C$_{1-4}$ alkyl); C$_{1-2}$ alkyl (such as C$_{1-8}$ alkyl, C$_{1-6}$ alkyl, or C$_{1-4}$ alkyl) substituted with 1 substituent selected from the group consisting of —OH, —O(C$_{1-3}$ alkyl), and —NH$_{2-z}$(CH$_3$)$_z$; C$_{1-4}$ alkyl substituted with 1, 2, or 3 halogen (preferably F), such as —CF$_3$, —CH$_2$CF$_3$, —CH$_2$CHF$_2$, or —CH$_2$CH$_2$F; cyclopropyl; 4-morpholinyl; homomorpholinyl; 4-piperidinyl; homopiperidinyl; 4-piperazinyl; homopiperazinyl; N-methyl-piperazin-4-yl; N-methyl-homopiperazinyl; —OH; —O(C$_{1-3}$ alkyl); —NH$_2$; —NH(C$_{1-3}$ alkyl); —N(C$_{1-3}$ alkyl)$_z$; —S(C$_{1-3}$ alkyl); —S(O)$_2$(C$_{1-3}$ alkyl optionally substituted with —NH$_{2-z}$(CH$_3$)$_z$); —S(O)$_2$NH$_{2-z}$(C$_{1-3}$ alkyl); —NHS(O)$_2$(C$_{1-3}$ alkyl); —C(=O)(C$_{1-3}$ alkyl optionally substituted with —NH$_{2-z}$(CH$_3$)$_z$); —C(=O)OH; —C(=O)O(C$_{1-3}$ alkyl); —C(=O)NH$_{2-z}$(C$_{1-3}$ alkyl)$_z$; —NHC(=O)(C$_{1-3}$ alkyl); —NHC(=NH)NH$_{z-2}$(C$_{1-3}$ alkyl)$_z$; and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl. In one embodiment, each R$^9$ when substituting a hydrogen atom bound to a ring nitrogen atom of ring A is independently selected from the group consisting of methyl; ethyl; isopropyl; n-octyl; n-dodecyl; cyclopropyl; —(CH$_2$)$_d$—NH$_{2-z}$(CH$_3$)$_z$; —(CH$_2$)$_d$—O(CH$_3$); —CH$_2$CF$_3$; —CH$_2$CHF$_2$; —CH$_2$CH$_2$F; —C(=O)CH$_3$, —C(=O)CH$_2$NH$_{2-z}$(CH$_3$)$_z$; —C(=O)NH$_{2-z}$(C$_{1-3}$ alkyl)$_z$; —S(O)$_2$(C$_{1-3}$ alkyl); —S(O)$_2$(CH$_2$)$_d$NH$_{2-z}$(CH$_3$)$_z$; —OH; and —O(C$_{1-3}$ alkyl), wherein z is 0, 1, or 2; d is 1, 2, or 3; and C$_{1-3}$ alkyl is methyl, ethyl, propyl or isopropyl. In one embodiment, each R$^9$ when substituting a hydrogen atom bound to a ring nitrogen atom of ring A is independently selected from the group consisting of methyl; ethyl; isopropyl; cyclopropyl; —(CH$_2$)$_d$—NH$_{2-z}$(CH$_3$)$_z$; —(CH$_2$)$_d$—O(CH$_3$); —CH$_2$CF$_3$; —CH$_2$CHF$_2$; —CH$_2$CH$_2$F; —C(=O)CH$_3$; —C(=O)CH$_2$NH$_{2-z}$(CH$_3$)$_z$; —C(=O)NH$_{2-z}$(C$_{1-3}$ alkyl)$_z$; —S(O)$_2$(C$_{1-3}$ alkyl); —S(O)$_2$(CH$_2$)$_d$NH$_{2-z}$(CH$_3$)$_z$; —OH; and —O(C$_{1-3}$ alkyl), wherein z is 0, 1, or 2; d is 1, 2, or 3; and C$_{1-3}$ alkyl is methyl, ethyl, propyl or isopropyl. In one embodiment, the ring nitrogen atom of ring A is unsubstituted or each R$^9$ substituting a hydrogen atom bound to a ring nitrogen atom is independently selected from the group consisting of C$_{1-12}$ alkyl (in particular methyl, n-octyl, or n-dodecyl) and —C(=O)R$^{11}$ (in particular —C(=O)CH$_3$ or —C(=O)(CH$_2$)$_6$CH$_3$). In one embodiment, the ring nitrogen atom of ring A is unsubstituted or is substituted with one R$^9$ being methyl.

In any of the above embodiments of the spiroquinoxaline derivative of formula (II), wherein R$^9$ is bound to a ring sulfur atom of ring A, each such R$^9$ may be independently selected from the group consisting of C$_{1-6}$ alkyl, C$_{2-6}$ alkenyl, C$_{2-6}$ alkynyl, 5- or 6-membered aryl, 5- or 6-membered heteroaryl, 3- to 7-membered cycloalkyl, 3- to 7-membered heterocyclyl, —OR$^{11}$, and =O, wherein each of the C$_{1-6}$alkyl, C$_{2-6}$ alkenyl, C$_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the C$_{1-6}$ alkyl, C$_{2-6}$alkenyl, C$_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$. In any of the above embodiments of the spiroquinoxaline derivative of formula (II), wherein R$^9$ is bound to a ring sulfur atom of ring A, each such R$^9$ may be independently selected from the group consisting of C$_{1-4}$ alkyl, C$_{2-4}$ alkenyl, C$_{2-4}$ alkynyl, 6-membered aryl, 5- or 6-membered heteroaryl, 3-, 5-, 6- or 7-membered cycloalkyl, 3-, 5-, 6- or 7-membered heterocyclyl, —OR$^{11}$, and =O, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment, each $R^9$ when bound to a ring sulfur atom of ring A is independently selected from the group consisting of methyl, ethyl, $C_{1-3}$ alkyl, $C_4$ alkyl, —OR$^{11'}$, and =O, wherein $R^{11'}$ is selected from the group consisting of —H, $C_{1-6}$ alkyl, $C_{2-6}$ alkenyl, $C_{2-6}$ alkynyl, 3- to 7-membered cycloalkyl, 5- or 6-membered aryl (e.g., phenyl), 5- or 6-membered heteroaryl, and 3- to 7-membered heterocyclyl, wherein each of the methyl, ethyl, $C_3$ alkyl, $C_4$ alkyl, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with 1, 2, or 3 independently selected $R^{30'}$ ($R^{30'}$ is a $1^{st}$, $2^{nd}$, or $3^{rd}$ level substituent as specified above (in particular one of the typical $1^{st}$, $2^{nd}$, or $3^{rd}$ level substituents as specified above) and, in each case, may be selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —CF$_3$, —OH, —OCH$_3$, —SCH$_3$, —NH$_{2-z}$(CH$_3$)$_z$, —C(=O)OH, and —C(=O)OCH$_3$, wherein z is 0, 1, or 2). In one embodiment, each $R^9$ when bound to a ring sulfur atom of ring A is independently selected from the group consisting of methyl; ethyl; isopropyl; benzyl; —OH; =O; and —O(C$_{1-3}$ alkyl), wherein C$_{1-3}$ alkyl is methyl, ethyl, propyl or isopropyl. In one embodiment, the ring sulfur atom of ring A is unsubstituted or substituted with two =O groups. In one embodiment, the ring sulfur atom of ring A is unsubstituted or ring A contains one sulfur atom which is substituted with two =O groups (i.e., ring A contains the group —S(=O)$_2$—).

In one embodiment, the spiroquinoxaline derivative has the general formula (III)

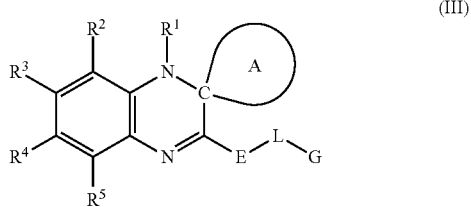

(III)

wherein $R^1$ to $R^5$, ring A, E, and G are as defined above (in particular with respect to formulas (I) and (II)) or below and L is selected from the group consisting of $C_{1-6}$ alkylene, $C_{2-6}$ alkenylene, $C_{2-6}$ alkynylene, —(CH$_2$)$_a$-cyclopropylene-(CH$_2$)$_b$—, wherein each of a and b is independently selected from an integer between 0 and 3, and —(CH$_2$)$_m$—[Y—(CH$_2$)$_n$]$_o$—, wherein m is 1, 2, or 3, n is 0, 1, or 2, o is 1, 2, or 3, wherein if n is 0 then o is 1; Y is independently selected from O, S, and —N(R$^{7'}$)—, wherein R$^{7'}$ is selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, 3- to 7-membered heterocyclyl, —OR$^{11}$, and —NHR$^{20}$, wherein each of the C$_{1-6}$ alkylene, C$_{2-6}$ alkenylene, C$_{2-6}$ alkynylene, 1,1-cyclopropylene, —(CH$_2$)$_m$—, —(CH$_2$)$_n$—, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl groups is optionally substituted with one or more (such as 1 to the maximum number of hydrogen atoms bound to the C$_{1-6}$ alkylene, C$_{2-6}$ alkenylene, C$_{2-6}$ alkynylene, 1,1-cyclopropylene, —(CH$_2$)$_m$—, —(CH$_2$)$_n$—, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment of the spiroquinoxaline derivative of formula (III), $R^1$ to $R^5$, ring A, E, and G are as defined above (in particular with respect to formulas (I) and (II)) or below and L is selected from the group consisting of C$_{1-4}$ alkylene, C$_{2-4}$ alkenylene, C$_{2-4}$ alkynylene, —(CH$_2$)$_a$-1,1-cyclopropylene-(CH$_2$)$_b$—, wherein each of a and b is independently selected from 0, 1, and 2, and —(CH$_2$)$_m$—[Y—(CH$_2$)$_n$]$_o$—, wherein m is 1, 2, or 3, n is 0, 1, or 2, o is 1, 2, or 3, wherein if n is 0 then o is 1; Y is independently selected from O, S, and —N(R$^{7'}$)—, wherein R$^{7'}$ is selected from the group consisting of —H, C$_{1-3}$ alkyl, 3-, 5-, 6- or 7-membered cycloalkyl, 6-membered aryl, 5- or 6-membered heteroaryl, 3-, 5-, 6- or 7-membered heterocyclyl, —O(C$_{1-3}$ alkyl), and —NHR$^{20}$, wherein each of the C$_{1-4}$ alkylene, C$_{2-4}$ alkenylene, C$_{2-4}$ alkynylene, 1,1-cyclopropylene, —(CH$_2$)$_m$—, —(CH$_2$)$_n$—, C$_{1-3}$ alkyl, 3-, 5-, 6- or 7-membered cycloalkyl, 6-membered aryl, 5- or 6-membered heteroaryl, and 3-, 5-, 6- or 7-membered heterocyclyl groups is optionally substituted with 1, 2, or 3 independently selected $R^{30}$. In one embodiment of the spiroquinoxaline derivative of formula (III), $R^1$ to $R^5$, ring A, E, and G are as defined above (in particular with respect to formulas (I) and (II)) or below and L is selected from the group consisting of C$_{1-3}$ alkylene, —(CH$_2$)$_a$-1,1-cyclopropylene-(CH$_2$)$_b$—, wherein each of a and b is independently selected from 0 and 1, and —(CH$_2$)$_m$—[Y—(CH$_2$)$_n$]$_o$—, wherein m is 1 or 2, n is 0, 1, or 2, o is 1 or 2, wherein if n is 0 then o is 1; Y is O, wherein each of the C$_{1-3}$ alkylene, 1,1-cyclopropylene, —(CH$_2$)$_m$—, and —(CH$_2$)$_n$— groups is optionally substituted with 1, 2, or 3 independently selected $R^{30}$. In one embodiment of the spiroquinoxaline derivative of formula (III), $R^1$ to $R^5$, ring A, E, and G are as defined above (in particular with respect to formulas (I) and (II)) or below and L is selected from the group consisting of methylene; 1,1-ethylene; 1,2-ethylene (optionally substituted with one $R^{30}$ (such as phenyl) at position 2); trimethylene (—(CH$_2$)$_3$—); 2,2-propylene (—C(CH$_3$)$_2$—); 2,4-butandiol; -1,1-cyclopropylene-; —(CH$_2$)—, 1-cyclopropylene; -1,1-cyclopropylene-(CH$_2$)—; —(CH$_2$)-1,1-cyclopropylene-(CH$_2$)—; —CH$_2$O—; —(CH$_2$)$_2$—; and —(CH$_2$)$_3$O— (such as methylene; 1,1-ethylene; 1,2-ethylene; trimethylene (—(CH$_2$)$_3$—); 2,2-propylene (—C(CH$_3$)$_2$—); 1,1-cyclopropylene; and —(CH$_2$)$_2$O—, in particular, methylene). In one embodiment of the spiroquinoxaline derivative of formula (III), $R^1$ to $R^5$, ring A, E, and G are as defined above (in particular with respect to formulas (I) and (II)) or below and L is selected from the group consisting of methylene; 1,1-ethylene; 1,2-ethylene; trimethylene (—(CH$_2$)$_3$—); 2,2-propylene (—C(CH$_3$)$_2$—); -1,-cyclopropylene-; —(CH$_2$)-1,1-cyclopropylene; -1,1-cyclopropylene-(CH$_2$)—; —(CH$_2$)-1,1-cyclopropylene-(CH$_2$)—; —CH$_2$O—; —(CH$_2$)$_2$O—; and —(CH$_2$)$_3$O— (such as methylene; 1,1-ethylene; 1,2-ethylene; triethylene (—(CH$_2$)$_3$—); 2,2-propylene (—C(CH$_3$)$_2$—); 1,1-cyclopropylene; and —(CH$_2$)$_2$O—, in particular, methylene). In one embodiment of the spiroquinoxaline derivative of formula (III), $R^1$ to $R^5$, ring A, E, and G are as defined above (in particular with respect to formulas (I) and (II)) or below and L is selected from the group consisting of $C_1$ alkylene, $C_2$ alkylene (in particular 1,2-ethylene or 1,1-ethylene), $C_{1-3}$ alkylene (in particular trimethylene), and $C_4$ alkylene (in particular tetramethylene or 2,4-butanediyl), each of which being optionally substituted with one $R^{30}$. In one embodiment of the spiroquinoxaline derivative of formula (III), $R^1$ to $R^5$, ring A, E, and G are as defined above (in particular with respect to formulas (I) and (II)) or below and L is selected from the group consisting of methylene, 1,1-ethylene, 1,2-ethylene, trimethylene, tetramethylene, 2,4-butanediyl, and 2-phenyl-1,2-ethylene (—$CH_2$—CH($C_6H_5$)—) In one embodiment of the spiroquinoxaline derivative of formula (II), $R^1$ to $R^5$, ring A, E, and G are as defined above (in particular with respect to formulas (I) and (II)) or below and L is selected from the group consisting of methylene and 2-phenyl-1,2-ethylene (—$CH_2$—CH($C_6H_5$)—).

In one embodiment, the spiroquinoxaline derivative has the general formula (IV)

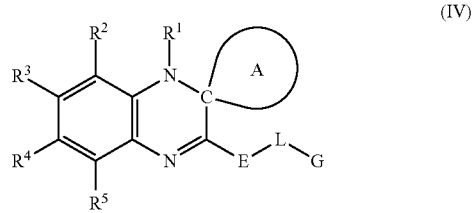

(IV)

wherein $R^1$ to $R^5$, ring A, E, and L are as defined above (in particular with respect to formulas (I), (II) and (III)) or below and G is phenyl which is either unsubstituted or substituted with 1, 2, 3, 4 or 5 (such as between 1 to 4, or 1 to 3, or 1 or 2) independently selected $R^8$. In any of the above embodiments (including those of formulas (I) to (III)), wherein G is substituted, $R^8$ may be, in each case, selected from the group consisting of $C_{1-6}$alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —C(=X)$R^{11}$, —C(=X)$XR^{11}$, —XC(=X)$R^{11}$, and —XC(=X)$XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment of the spiroquinoxaline derivative of formula (IV), $R^1$ to $R^5$, ring A, E, and L are as defined above (in particular with respect to formulas (I), (II) and (III)) or below and $R^8$ is, in each case, selected from the group consisting of $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —C(=O)$R^{11}$, —C(=O)O$R^{11}$, —C(=O)S, —C(=O)N($R^{14}$)($R^{11}$), —C(=S)O$R^{11}$, —N($R^{14}$)C(=O)$R^{11}$, —OC(=O)$R^{11}$, —OC(=S)$R^{11}$, —N($R^{14}$)C(=O)N($R^{14}$)($R^{11}$) and —N($R^{14}$)C(=N($R^{14}$))N($R^{14}$)($R^{11}$), wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment of the spiroquinoxaline derivative of formula (IV), $R^1$ to $R^5$, ring A, E, and L are as defined above (in particular with respect to formulas (I), (II) and (III)) or below and $R^8$ is, in each case, selected from the group consisting of $C_{1-4}$ alkyl; $C_{1-4}$ alkyl substituted with 1 substituent selected from the group consisting of —OH, —O($C_{1-3}$ alkyl), and —$NH_{2-z}(CH_3)_z$; $C_{1-4}$ alkyl substituted with 1, 2, or 3 halogen (preferably F), such as —$CF_3$, —$CH_2CF_3$, —$CH_2CH_2$, or —$CH_2CH_2F$; phenyl; cyclopropyl; 5-membered heterocyclyl (such as pyrrolidinyl); 4-morpholinyl; homomorpholinyl; 4-piperidinyl; homopiperidyl; 4-piperazinyl; homopiperazinyl; N-methyl-piperazin-4-yl; N-methyl-homopiperazinyl; halogen; —CN; —OH; —O($C_{1-3}$ alkyl); —O($C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; —O-phenyl; —$NH_2$; —NH($C_{1-3}$ alkyl); —N($C_{1-3}$ alkyl)$_2$; —S($C_{1-3}$ alkyl); —$S(O)_2(C_{1-3}$ alkyl optionally substituted with —$NH_{2-z}$($CH_3)_z$); —$S(O)_2NH_{2-z}(C_{1-3}$ alkyl)$_z$; —$NHS(O)_2(C_{1-3}$ alkyl); —C(=O)($C_{1-3}$ alkyl optionally substituted with —$NH_{2-z}(CH_3)_z$); —C(=O)OH; —C(=O)O($C_{1-3}$ alkyl); —C(=O)$NH_{2-z}(C_{1-3}$ alkyl)$_z$; —NHC(=O)($C_{1-3}$ alkyl); —NHC(=NH)$NH_{1-2}(C_{1-3}$ alkyl); and —N($C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl and each of the phenyl, cyclopropyl, 5-membered heterocyclyl (such as pyrrolidinyl), 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of $C_{1-3}$ alkyl, halogen, —$CF_3$, —$OCF_3$, —OH, —$OCH_3$, —$SCH_3$, —$NH_{2-z}(CH_3)_z$, —C(=O)OH, and —C(=O)$OCH_3$, wherein z is 0, 1, or 2. In one embodiment, each $R^8$ is independently selected from the group consisting of methyl; ethyl; isopropyl; tert-butyl; phenyl; cyclopropyl; pyrrolidinyl (such as 4-pyrrolidinyl); —$(CH_2)_d$—$NH_{2-z}(CH_3)_z$; —$(CH_2)_d$—O($CH_3$); —$CF_3$; —$OCF_3$; —O-phenyl; —$CH_2CF_3$; —$CH_2CHF_2$; —$CH_2CH_2F$; halogen (in particular, —F, —Cl, —Br); —CN; —$NH_2$; —NH($C_{1-3}$ alkyl), —N($C_{1-3}$ alkyl)$_2$; —C(=O)$CH_3$; —C(=O)$CH_2NH_{2-z}(CH_3)_z$; —C(=O)OH; —C(=O)O($C_{1-3}$ alkyl); —C(=O)$NH_{2-z}(C_{1-3}$ alkyl)$_z$; —NHC(=O)($C_{1-3}$ alkyl); —$S(O)_2(C_{1-3}$ alkyl); —$S(O)_2(CH_2)_dNH_{2-z}(CH_3)_z$; —OH; and —O($C_{1-3}$ alkyl), wherein z is 0, 1, or 2, d is 1, 2, or 3, and $C_{1-3}$ alkyl is methyl, ethyl, propyl or isopropyl. In one embodiment, each $R^8$ is independently selected from the group consisting of methyl; ethyl; isopropyl; phenyl; cyclopropyl; pyrrolidinyl (such as 4-pyrrolidinyl); —$(CH_2)_d$—$NH_{2-z}(CH_3)_z$; —$(CH_2)_d$—O($CH_3$); —$CF_3$; —$OCF_3$; —O-phenyl; —$CH_2CF_3$; —$CH_2CHF_2$; —$CH_2CH_2F$ halogen (in particular, —F, —Cl, —Br); —CN; —$NH_2$; —NH($C_{1-3}$ alkyl); —N($C_{1-3}$ alkyl)$_2$; —C(=O)$CH_3$; —C(=O)$CH_2NH_{2-z}(CH_3)_z$; —C(=O)OH; —C(=O)O($C_{1-3}$ alkyl); —C(=O)$NH_{2-z}(C_{1-3}$ alkyl)$_z$; —NHC(=O)($C_{1-3}$ alkyl); —$S(O)_2(C_{1-3}$ alkyl); —$S(O)_2(CH_2)_dNH_{2-z}(CH_3)_z$; —OH; and —O($C_{1-3}$ alkyl), wherein z is 0, 1, or 2, d is 1, 2, or 3, and $C_{1-3}$ alkyl is methyl, ethyl, propyl or isopropyl. In one embodiment of the spiroquinoxaline derivative of formula (IV), $R^1$ to $R^5$, ring A, E, and L are as defined above (in particular with respect to formulas (I), (II) and (III)) or below and G is either unsubstituted or substituted with 1, 2, or 3 $R^8$, wherein $R^8$ is, in each case, selected from the group consisting of $C_{1-4}$ alkyl (in particular methyl or tert-butyl); halogen (in particular F or Cl); —$OR^{11}$ (in particular —$OCH_3$); and $C_{1-4}$ alkyl substituted with 1, 2, or 3 independently selected $R^{30}$ (in particular —$CF_3$). In one embodiment of the spiroquinoxaline derivative of formula (IV), $R^1$ to $R^5$, ring A, E, and L are as defined above (in particular with respect to formulas (I), (II) and (III)) or below and G is either unsubstituted or substituted with 1 or 2 $R^8$ each independently selected from the group consisting of methyl, F, Cl, —$OCH_3$, and —$CF_3$. In one embodiment of the spiroquinoxaline derivative of formula (IV), $R^1$ to $R^5$, ring A, E, and L are as defined above (in particular with respect to formulas (I), (II) and (III)) or below and G is selected from the group consisting of unsubstituted phenyl, fluorophenyl (in particular 3-fluorophenyl), chlorophenyl (in particular 2-, 3- or 4-chlorophenyl), methylphenyl (in particular 2- or 3-methylphenyl), tert-butylphenyl (in particular 4-tert-butylphenyl), methoxyphenyl (in particular 3-methoxyphenyl), (trifluoromethyl) phenyl (in particular 3- or 4-(trifluoromethyl)phenyl), difluorophenyl (in particular 2,4- or 2,6-difluorophenyl), dichlorophenyl (in particular 2,4- or 3,4-dichlorophenyl), chlorofluorophenyl (in particular 4-chloro-2-fluorophenyl), and dimethylphenyl (in particular 3,5-dimethylphenyl). In one embodiment of the spiroquinoxaline derivative of formula (IV), $R^1$ to $R^5$, ring A, E, and L are as defined above (in particular with respect to formulas (I), (II) and (III)) or below and G is selected from the group consisting of unsubstituted phenyl, 2-chlorophenyl, 3-chlorophenyl, 4-chlorophenyl, 3-methylphenyl, 3-(trifluoromethyl)phenyl, 2,6-difluorophenyl, 3,4-dichlorophenyl, 4-chloro-2-fluorophenyl, and 3,5-dimethylphenyl.

In one embodiment, the spiroquinoxaline derivative has the general formula (V)

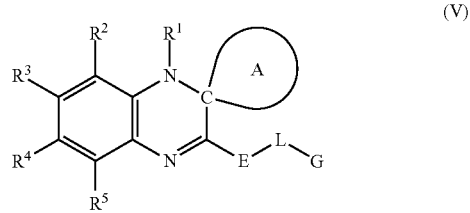

(V)

wherein $R^1$, ring A, E, L and G are as defined above (in particular with respect to formulas (I), (II), (III) and (IV)) or below and each of $R^2$, $R^3$, $R^4$, and $R^5$ is H. In one embodiment of the spiroquinoxaline derivative of formula (V), $R^1$, ring A, E, L and G are as defined above (in particular with respect to formulas (I), (II), (III) and (IV)) or below and at least one of $R^2$, $R^3$, $R^4$, and $R^5$ is different from H. For example, in one embodiment $R^2$ is different from H and each of $R^3$, $R^4$, and $R^5$ is H; or $R^3$ is different from H and each of $R^2$, $R^4$, and $R^5$ is H; or $R^4$ is different from H and each of $R^2$, $R^3$, and $R^5$ is H; or $R^5$ is different from H and each of $R^2$, $R^3$, and $R^4$ is H; or both of $R^2$ and R are different from H and both of $R^4$ and $R^5$ are H; or both of $R^2$ and $R^4$ are different from H and both of $R^3$ and $R^5$ are H; or both of R and R are different from H (preferably in this embodiment $R^2$ and $R^5$ are the same) and both of R and $R^4$ are H; or both of $R^3$ and $R^4$ are different from H (preferably in this embodiment $R^3$ and $R^4$ are the same) and both of $R^2$ and $R^5$ are H; or each of $R^2$, $R^3$, and $R^4$ is different from H and $R^5$ is H; or each of $R^2$, $R^3$, and $R^5$ is different from H and $R^4$ is H; or each of $R^2$, $R^4$, and $R^5$ is different from H and $R^3$ is H; or each of $R^3$, $R^4$, and $R^5$ is different from H and $R^2$ is H; or each of $R^2$, $R^3$, $R^4$, and $R^6$ is different from H. In any of the above embodiments, it is preferred that $R^2$ and $R^5$ are the same and/or $R^3$ and $R^4$ are the same.

In any of the above embodiments (in particular with respect to formulas (I), (II), (III), (IV), and (V)), each of $R^2$ to $R^5$, if it does not join together with another of $R^2$ to $R^5$ to form a ring, is independently selected from the group consisting of —H, $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{11})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment, each of $R^2$, $R^3$, $R^4$, and $R^5$, if it does not join together with another of $R^2$ to $R^5$ to form a ring, may be independently selected from the group consisting of —H, $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=O)R^{11}$, —$C(=O)OR^{11}$, —$C(=O)SR^{11}$, —$C(=O)N(R^{14})(R^{11})$, —$C(=S)OR^{11}$, —$N(R^{14})C(=O)R^{11}$, —$OC(=O)R^{11}$, —$OC(=S)R^{11}$, —$N(R^{14})C(=O)N(R^{14})(R^{11})$ and —$N(R^{14})C(=N(R^{14}))N(R^{14})(R^{11})$, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment of the spiroquinoxaline derivative of formula (V), $R^1$, ring A, E, L and G are as defined above (in particular with respect to formulas (I), (II), (III), and (IV)) or below and each of $R^2$, $R^3$, $R^4$, and $R^5$, if it does not join together with another of $R^2$ to $R^5$ to form a ring, is independently selected from the group consisting of H; $C_{1-4}$ alkyl, $C_{1-4}$ alkyl substituted with 1 substituent selected from the group consisting of —OH, —$O(C_{1-3}$ alkyl), and —$NH_{2-z}(CH_3)_z$; $C_{1-4}$ alkyl substituted with 1, 2, or 3 halogen (preferably F), such as —$CF_3$, —$CH_2CF_3$, —$CH_2CHF_2$, or —$CH_2CH_2F$; phenyl; cyclopropyl; 5-membered heterocyclyl; 4-morpholinyl; homomorpholinyl; 4-piperidinyl; homopiperidinyl; 4-piperazinyl; homopiperazinyl; N-methyl-piperazin-4-yl; N-methyl-homopiperazinyl; halogen; —CN; —OH; —$O(C_{1-3}$ alkyl); —$O(C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; —O-phenyl; —$NH_2$; —$N(C_{1-3}$ alkyl); —$N(C_{1-3}$ alkyl$)_2$; —$S(C_{1-3}$ alkyl); —$S(O)_2(C_{1-3}$ alkyl optionally substituted with —$NH_{2-z}(CH_3)_z$); —$S(O)_{2-z}(C_{1-3}$ alkyl$)_z$; —$NHS(O)_2(C_{1-3}$ alkyl); —$C(=O)(C_{1-3}$ alkyl optionally substituted with —$NH_{2-z}(CH_3)_z$); —$C(=O)OH$; —$C(=O)O(C_{1-3}$ alkyl); —$C(=O)NH_{2-z}(C_{1-3}$ alkyl); —$NHC(=O)(C_{1-3}$ alkyl); —$NHC(=NH_2)NH_2(C_{1-3}$ alkyl$)_z$; and —$N(C_{1-3}$ alkyl)$C(=NH)NH_{2-z}(C_{1-3}$ alkyl$)_z$, wherein z is 0, 1, or 2 and $C_{1-3}$ alkyl is methyl, ethyl, propyl or isopropyl and each of the phenyl, cyclopropyl, 5-membered heterocyclyl, 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of $C_{1-3}$ alkyl, halogen, —CF$_3$, —OCF$_3$, —OH, —OCH$_3$, —SCH$_3$, —NH$_{2-z}$(CH$_3$)$_z$, —C(=O)OH, and —C(=O)OCH$_3$, wherein z is 0, 1, or 2. In one embodiment, each of $R^2$, $R^3$, $R^4$, and $R^5$, if it does not join together with another of $R^2$ to $R^5$ to form a ring, is independently selected from the group consisting of H; methyl; ethyl; isopropyl; phenyl; cyclopropyl; —(CH$_2$)$_d$—NH$_{2-z}$(CH$_3$)$_z$; —(CH$_2$)$_d$—O(CH$_3$); —CF$_3$; —OCF$_3$; —CH$_2$CF$_3$; —CH$_2$CHF$_2$; —CH$_2$CH$_2$F; halogen (in particular, —F, —Cl, —Br); —CN; —NH$_2$; —NH(C$_{1-3}$ alkyl); —N(C$_{1-3}$ alkyl)$_2$; —C(=O)CH$_3$; —C(=O)CH$_2$NH$_{2-z}$(CH$_3$)$_z$; —C(=O)O(C$_{1-3}$ alkyl); —C(=O)$_{2-z}$(C$_{1-3}$ alkyl)$_z$; —NHC(=O)(C$_{1-3}$ alkyl); —S(O)$_2$(C$_{1-3}$ alkyl); —S(O)$_2$(CH$_2$)$_d$N$_{2-z}$(CH$_3$)$_z$; —OH, and —O(C$_{1-3}$ alkyl), wherein z is 0, 1, or 2, d is 1, 2, or 3, and $C_{1-3}$ alkyl is methyl, ethyl, propyl or isopropyl. In one embodiment of the spiroquinoxaline derivative of formula (V), $R^1$, ring A, E, L and G are as defined above (in particular with respect to formulas (I), (II), (III), and (IV)) or below and $R^2$, $R^3$, $R^4$, and $R^5$ are independently selected from the group consisting of —H, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H). In one embodiment of the spiroquinoxaline derivative of formula (V), $R^1$, ring A, E, L and G are as defined above (in particular with respect to formulas (I), (II), (III), and (IV)) or below and $R^2$, $R^3$, $R^4$, and $R^5$ are independently selected from the group consisting of —H, methyl, F, Cl, and CF$_3$ (in particular wherein $R^2$ and $R^5$ are each —H). In one embodiment of the spiroquinoxaline derivative of formula (V), $R^1$, ring A, E, L and G are as defined above (in particular with respect to formulas (I), (II), (III), and (IV)) or below and $R^2$ and $R^5$ are each —H; $R^3$ is selected from the group consisting of —H, methyl, F, and Cl; and $R^4$ is selected from the group consisting of —H, methyl, F, and Cl. In one embodiment of the spiroquinoxaline derivative of formula (V), $R^1$, ring A, E, L and C are as defined above (in particular with respect to formulas (I), (II), (III), and (IV)) or below and (i) $R^2$ to $R^5$ are each —H; or (ii) $R^2$ and $R^5$ are each —H, and both of $R^3$ and $R^4$ are F, Cl, or methyl.

In any of the above embodiments, wherein a ring is formed by (i) $R^2$ and $R^3$, (ii) $R^3$ and $R^4$, and/or (iii) $R^4$ and $R^5$, said ring preferably is a 3- to 7-membered ring (e.g., a ring having 5 or 6 members) which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$. The ring may be an aromatic, cycloaliphatic heteroaromatic, or heterocyclic ring, wherein the heteroaromatic/heterocyclic ring contains 1 or 2 heteroatoms selected from the group consisting of O, S, and N(R$^{40}$), wherein $R^{40}$ is selected from the group consisting of R$^{11}$, —OR$^{11}$, —NH$_y$R$^{20}_{2-y}$, and —S(O)$_{1-2}$R$^{11}$, wherein $R^{11}$, $R^{20}$, and y are as defined above. In one embodiment, the ring formed by (i) $R^2$ and $R^3$, (ii) $R^3$ and $R^4$, and/or (iii) $R^4$ and $R^5$ is a 5- or 6-membered aromatic, cycloaliphatic, heteroaromatic, or heterocyclic ring, wherein the heteroaromatic/heterocyclic ring contains 1 or 2 heteroatoms selected from the group consisting of O, S, and N, wherein at least one heteroatom is N. In one embodiment, the ring formed by (i) $R^2$ and $R^3$, (ii) $R^3$ and $R^4$, and/or (iii) $R^4$ and $R^5$ is selected from the group consisting of cyclopentadiene, furan, pyrrole, thiophene, imidazole, pyrazole, oxazole, isoxazole, thiazole, dioxole (e.g., 1,3-dioxole), benzene, pyridine, pyrazine, pyrimidine, pyridazine, dioxine (e.g., 1,4-dioxine), 1,2,3-triazine, 1,2,4-triazine, and di- or tetrahydro forms of each of the foregoing. In one embodiment, the ring formed by (i) $R^2$ and $R^3$, (ii) $R^3$ and $R^4$, and/or (iii) $R^4$ and $R^5$ is selected from the group consisting of cyclopentadiene, furan, pyrrole, thiophene, imidazole, pyrazole, oxazole, isoxazole, thiazole, benzene, pyridine, pyrazine, pyrimidine, pyridazine, 1,2,3-triazine, 1,2,4-triazine, and di- or tetrahydro forms of each of the foregoing. In one embodiment, the ring formed (i) $R^2$ and $R^3$, (ii) $R^3$ and $R^4$, and/or (iii) $R^4$ and $R^5$ is cyclopentene (such as 2,3-dihydrocyclopentadiene), dioxole (such as 1,3-dioxole, optionally substituted at position 2 with one or two halogen atoms (such as F)), or dioxine (such as 2,3-dihydro-[1,4]-dioxine). In one embodiment, the total number of rings formed by (i) $R^2$ and $R^3$, (ii) $R^3$ and $R^4$, and/or (iii) $R^4$ and $R^5$ is 0 or 1. Thus, in the embodiment, wherein the total number of rings formed by (i) $R^2$ and $R^3$, (ii) $R^3$ and $R^4$, and/or (iii) $R^4$ and $R^5$ is 1, only two adjacent substituents (i.e., either (i) $R^2$ and $R^3$, (ii) $R^3$ and $R^4$, or (iii) $R^4$ and $R^5$) join together with the atoms to which they are attached to form a ring, wherein the ring is as defined in any of the above embodiments and the remaining of $R^2$ to $R^5$ are selected from the particular groups of moieties specified above for the situation that they do not join together to form a ring. For example, the remaining $R^2$ to $R^5$ which do not join together to form a ring may be selected from —H, $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —OR$^{11}$, —N(R$^{12}$)(R$^{13}$), —S(O)$_{0-2}$R$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In an alternative embodiment, $R^2$ to $R^5$ do not join together to form a ring.

In any of the above embodiments, $R^2$ and $R^5$ may be the same and/or $R^3$ and $R^4$ may be the same.

In one embodiment of the spiroquinoxaline derivative of formula (V), $R^1$, ring A, E, L and G are as defined above (in particular with respect to formulas (I), (II), (III), and (IV)) or below and $R^2$, $R^3$, $R^4$, and $R^5$ are independently selected from the group consisting of —H, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H), or $R^3$ and $R^4$ may join together with the atoms to which they are attached to form a 5- or 6-membered ring which is optionally substituted with one or two independently selected $R^{30}$. In one embodiment of the spiroquinoxaline derivative of formula (V), $R^1$, ring A, E, L and G are as defined above (in particular with respect to formulas (I), (II), (III), and (IV)) or below and $R^2$, $R^3$, $R^4$, and $R^5$ are independently selected from the group consisting of —H, methyl, F, Cl, and CF$_3$ (in particular wherein $R^2$ and $R^5$ are each —H), or $R^3$ and $R^4$ may join together with the atoms to which they are attached to form a dioxole or dioxine ring which is optionally substituted with one or two independently selected halogens (in particular F). In one embodiment of the spiroquinoxaline derivative of formula (V), $R^1$, ring A, E, L and G are as defined above (in particular with respect to formulas (I), (II), (III), and (IV) or below and $R^2$ and $R^5$ are each —H; $R^3$ is selected from the group consisting of —H, methyl, F, and Cl; and $R^4$ is selected from the group consisting of —H, methyl, F, and Cl; or $R^3$ and $R^4$ may join together with the atoms to which they are attached to form a dioxole (in particular 1,3-dioxole) or dioxine (in particular 2,3-dihydro-[1,4]-dioxine) ring, wherein the dioxole ring is optionally substituted with two F. In one embodiment of the spiroquinoxaline derivative of formula (V), $R^1$, ring A, E, L and G are as defined above (in particular with respect to formulas (I), (II), (III), and (IV)) or below and (i) $R^2$ to $R^5$ are each —H; (ii) $R^2$ and $R^5$ are each —H, and both of $R^3$ and $R^4$ are F, Cl, or methyl, or (iii) $R^2$ and $R^5$ are each —H, and $R^3$ and $R^4$ join together with the atoms to which they are attached to form a 2,2-difluoro-1,3-dioxole ring or a 2,3-dihydro-[1,4]-dioxine ring.

In any of the above embodiments (in particular with respect to formulas (I), (II), (III), (IV), and (V)), $R^{30}$, in each case, may be a typical $1^{st}$, $2^{nd}$, or $3^{rd}$ level substituent as specified above and may be independently selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5-, 6-, or 7-membered heterocyclyl, halogen, —CF$_3$, —CN, azido, —NO$_2$, —OH, —O(C$_{1-3}$ alkyl), —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$N$_{2-z}$(C$_{1-3}$ alkyl)$_z$, —C(=O)OH, —C(=O)O(C$_{1-3}$ alkyl), —C(=O)NH$_{2-z}$ (C$_{1-3}$ alkyl)$_z$, —NHC(=O)(C$_{1-3}$ alkyl), —NHC(=NH)NH$_{z-2}$ (C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_L$-3 alkyl is methyl, ethyl, propyl or isopropyl, such as 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —CH$_2$CH$_2$OCH$_3$, —OCH$_2$CH$_2$OCH$_3$, —CH$_2$CH$_2$NH$_{2-z}$(CH$_3$)$_z$, —OCH$_2$CH$_2$NH$_{2-z}$(CH$_3$)$_z$, —CF$_3$, —OCF$_3$. Alternatively, $R^{30}$ may be selected from the group consisting of phenyl, furanyl, pyrrolyl, thienyl, imidazolyl, oxazolyl, isoxazolyl, thiazolyl, pyridyl, pyrazinyl, pyrindinyl, pyridazinyl, partially and completely hydrogenated forms of the forgoing groups, morpholino, $C_{1-3}$ alkyl, halogen, —CF$_3$, —OH, —OCH$_3$, —OCF$_3$, —SCH$_3$, —NH$_{2-z}$(CH$_3$)$_z$, —C(=O)OH, and —C(=O)OCH$_3$, wherein z is 0, 1, or 2.

In one embodiment, the spiroquinoxaline derivative has the general formula (N-I)

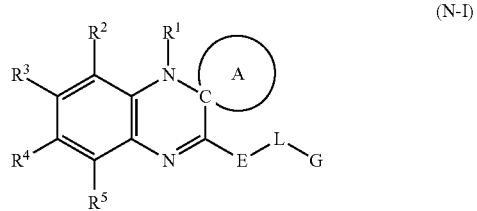

(N-I)

and solvates, salts, complexes, polymorphs, crystalline forms, racemic mixtures, diastereomers, enantiomers, tautomers, isotopically labeled forms, prodrugs, and combinations thereof, wherein
E is —N(R$^6$)—;
L is selected from the group consisting of $C_{1-10}$ alkylene, $C_{2-10}$ alkenylene, $C_{2-10}$ alkynylene, 1,1-(CH$_2$)$_a$-cylopropylene-(CH$_2$)$_b$—, wherein each of a and b is independently selected from an integer between 0 and 3, and —(CH$_2$)$_m$—[Y—(CH$_2$)$_n$]$_o$—, wherein m is an integer between 1 and 6, n is an integer between 0 and 3, o is an integer between 1 and 3, wherein if n is 0 then o is 1; Y is independently selected from O, S, and —N(R$^7$)—; and each of the $C_{1-10}$ alkylene, $C_{2-10}$ alkenylene, $C_{2-10}$ alkynylene, 1,1-cyclopropylene, —(CH$_2$)$_m$—, and —(CH$_2$)$_n$— groups is optionally substituted with one or more (such as 1 to the maximum number of hydrogen atoms bound to the $C_{1-10}$ alkylene, $C_{2-10}$ alkylene, $C_{2-10}$ alkenylene, 1,1-cyclopropylene, —(CH$_2$)$_m$—, or —(CH$_2$)$_n$— group, e.g., 1, 2, 3, 4, 5, 6, 7, 8, 9, or up to 10, such as between 1 to 5, 1 to 4, or 1 to 3, or 1 or 2) independently selected $R^{30}$;

G is phenyl, optionally substituted with 1, 2, 3, 4 or 5 independently selected $R^8$;

ring A is a monocyclic 4- to 10-membered N-heterocycloalkylene, optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected R;

$R^1$ is H;
$R^2$, $R^3$, $R^4$, and $R^5$ are independently selected from the group consisting of —H, alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{12}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

or $R^2$ and $R^3$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; $R^3$ and $R^4$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; and/or $R^4$ and $R^5$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$;

$R^6$ is H;
$R^7$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^8$ is, in each case, selected from the group consisting of alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^9$ is, when substituting a hydrogen atom bound to a ring carbon atom, independently selected from the group consisting of alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, and/or any two $R^9$ which are bound to the same carbon atom of ring A may join together to form =X; or $R^9$ is, when substituting a hydrogen atom bound to a ring nitrogen atom, independently selected from the group consisting of alkyl, alkenyl, alkynyl, aryl, heteroaryl, cycloalkyl, heterocyclyl, —OR$^{11}$, —N(R$^{12}$)(R$^{13}$), —S(O)$_{1-2}$R$^{11}$, —S(O)$_{1-2}$OR$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$R$^{11}$, —NR$^{11}$S(O)$_{1-2}$N(R$^{12}$)(R$^{13}$), —C(=X)R$^{11}$, —C(=X)XR$^{11}$, —N(R$^{14}$)C(=X)R$^{11}$, and —N(R$^{14}$)C(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

X is independently selected from O, S, and N(R$^{14}$);

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{14}$ is independently selected from the group consisting of —H, alkyl, alkenyl, alkynyl, cycloalkyl, aryl, heteroaryl, heterocyclyl, and —OR$^{11}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —NH$_x$R$^{20}{}_{2-y}$, or $R^{15}$ and $R^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; and $R^{30}$ is a 1$^{st}$ level substituent and is, in each case, independently selected from the group consisting of alkyl, alkenyl, alkynyl, aryl, heteroaryl, cycloalkyl, heterocyclyl, halogen, —CN, azido, —NO$_2$, —OR$^7$, —N(R$^{72}$)(R$^{73}$), —S(O)$_{0-2}$R$^{71}$, —S(O)$_{1-2}$OR$^{71}$, —OS(O)$_{1-2}$R$^{71}$, —OS(O)$_{1-2}$OR$^{71}$, —S(O)$_{1-2}$N(R$^{72}$)(R$^{73}$), —OS(O)$_{1-2}$N(R$^{72}$)(R$^{73}$), —N(R$^{71}$)S(O)$_{1-2}$R$^{71}$, —NR$^{71}$S(O)$_{1-2}$OR$^{71}$, —NR$^{71}$S(O)$_{1-2}$N(R$^{72}$)(R$^{73}$), —C(=X$^1$)R$^{71}$, —C(=X$^1$)X$^1$R$^{71}$, —X$^1$C(=X$^1$)R$^7$, and —X$^1$C(=X$^1$)X$^1$R$^{71}$, and/or any two $R^{30}$ which are bound to the same carbon atom of a cycloalkyl or heterocyclyl group may join together to form =X$^1$, wherein each of the alkyl, alkenyl, alkynyl, aryl, heteroaryl, cycloalkyl, and heterocyclyl groups being a 1$^{st}$ level substituent is optionally substituted by one or more (such as 1 to the maximum number of hydrogen atoms bound to the alkyl, alkenyl, alkynyl, aryl, heteroaryl, cycloalkyl, or heterocyclyl group being a 1$^{st}$ level substituent, e.g., 1, 2, 3, 4, 5, 6, 7, 8, 9, or up to 10, such as between 1 to 5, 1 to 4, or 1 to 3, or 1 or 2) 2$^{nd}$ level substituents, wherein said 2$^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —OR$^{81}$, —N(R$^{82}$)(R$^{83}$), —S(O)$_{0-2}$R$^{81}$, —S(O)$_{1-2}$OR$^{81}$, —OS(O)$_{1-2}$R$^{81}$, —OS (O)₁₋₂OR⁸¹, —S(O)₁₋₂N(R⁸²)(R⁸³), —OS(O)₁₋₂N(R⁸²) (R⁸³), —N(R⁸¹)S(O)₁₋₂R⁸¹, —NR⁸¹S(O)₁₋₂R, —NR⁸¹ S(O)₁₋₂N(R⁸²)(R⁸³), —C(=X²)R⁸¹, —C(=X²)X²R⁸¹, —X²C(=X²)R⁸¹, and —X²C(=X²)X²X²R⁸¹, and/or any two 2ⁿᵈ level substituents which are bound to the same carbon atom of a cycloalkyl or heterocyclyl group being a 1ˢᵗ level substituent may join together to form =X², wherein each of the C₁₋₆ alkyl, C₂₋₆ alkenyl, C₂₋₆ alkynyl, 3- to 14-membered aryl, 3- to 14-membered heteroaryl, 3- to 14-membered cycloalkyl, and 3- to 14-membered heterocyclyl groups being a 2ⁿᵈ level substituent is optionally substituted with one or more (such as 1 to the maximum number of hydrogen atoms bound to the C₁₋₆alkyl, C₂₋₆ alkenyl, C₂₋₆ alkynyl, 3- to 14-membered aryl, 3- to 14-membered heteroaryl, 3- to 14-membered cycloalkyl, or 3- to 14-membered heterocyclyl group being a 2ⁿᵈ level substituent, e.g., 1, 2, 3, 4, 5, 6, 7, 8, 9, or up to 10, such as between 1 to 5, 1 to 4, or 1 to 3, or 1 or 2) 3ʳᵈ level substituents, wherein said 3ʳᵈ level substituent is, in each case, independently selected from the group consisting of C₁₋₃ alkyl, halogen, —CF₃, —CN, azido, —NO₂, —OH, —O(C₁₋₃ alkyl), —OCF₃, —S(C₁₋₃ alkyl), —NH₂, —NH(C₁₋₃ alkyl), —N(C₁₋₃ alkyl)₂, —N(C₁₋₃ alkyl)₂, —NHS(O)₂(C₁₋₃ alkyl), —S(O)₂ NH$_{z-2}$(C₁₋₃ alkyl)$_z$, —C(=O)OH, —C(=O)O(C₁₋₃ alkyl), —C(=O)NH$_{2-z}$(C₁₋₃ alkyl)$_z$, —NHC(=O)(C₁₋₃ alkyl), —NHC(=NH)NH$_{2-z}$(C₁₋₃ alkyl)$_z$, and —N(C₁₋₃ alkyl)C (=NH)NH$_{2-z}$(C₁₋₃ alkyl)$_z$, wherein z is 0, 1, or 2 and C₁₋₃ alkyl is methyl, ethyl, propyl or isopropyl, and/or any two 3ʳᵈ level substituents which are bound to the same carbon atom of a 3- to 14-membered cycloalkyl or heterocyclyl group being a 2ⁿᵈ level substituent may join together to form =O, =S, =NH, or =N(C₁₋₃ alkyl);

wherein

R⁷¹, R⁷², and R⁷³ are independently selected from the group consisting of —H, C₁₋₆ alkyl, C₂₋₆ alkenyl, C₂₋₆ alkynyl, 3- to 7-membered cycloalkyl, 5- or 6-membered aryl, 5- or 6-membered heteroaryl, and 3- to 7-membered heterocyclyl, wherein each of the C₁₋₆ alkyl, C₂₋₆ alkenyl, C₂₋₆ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of C₁₋₃ alkyl, halogen, —CF₃, —CN, azido, —NO₂, —OH, —O(C₁₋₃ alkyl), —OCF₃, =O, —S(C₁₋₃ alkyl), —NH₂, —NH(C₁₋₃ alkyl), —N(C₁₋₃ alkyl)₂, —NHS(O)₂(C₁₋₃ alkyl), —S(O)₂NH$_{2-z}$(C₁₋₃ alkyl)$_z$, —C(=O)(C₁₋₃ alkyl), —C(=O)OH, —C(=O)O(C₁₋₃ alkyl), —C(=O)NH$_{2-z}$ (C₁₋₃ alkyl)$_z$, —NHC(=O)(C₁₋₃ alkyl), —NHC(=NH) NH$_{z-2}$ (C₁₋₃ alkyl)$_z$, and —N(C₁₋₃ alkyl)C(=NH)NH$_{2-z}$(C₁₋₃ alkyl)$_z$, wherein z is 0, 1, or 2 and C₁₋₃ alkyl is methyl, ethyl, propyl or isopropyl;

R⁸¹, R⁸², and R⁹² are independently selected from the group consisting of —H, C₁₋₄alkyl, C₂₋₄ alkenyl, C₂₋₄ alkynyl, 3- to 6-membered cycloalkyl, 5- or 6-membered aryl, 5- or 6-membered heteroaryl, and 3- to 6-membered heterocyclyl, wherein each of the C₁₋₄ alkyl, C₂₋₄ alkenyl, C₂₋₄ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of C₁₋₃ alkyl, halogen, —CF₃, —CN, azido, —NO₂, —OH, —O(C₁₋₃ alkyl), —OCF₃, =O, —S(C₁₋₃ alkyl), —NH₂, —NH(C₁₋₃ alkyl), —N(C₁₋₃ alkyl)₂, —NHS(O)₂(C₁₋₃ alkyl), —S(O)₂NH$_{2-z}$(C₁₋₃ alkyl)$_z$, —C(=O)(C₁₋₃ alkyl), —C(=O)OH, —C(=O)O(C₁₋₃ alkyl), —C(=O)NH$_{2-z}$ (C₁₋₃ alkyl)$_z$, —NHC(=O)(C₁₋₃ alkyl), —NHC(=NH) NH$_{z-2}$ (C₁₋₃ alkyl)$_z$, and —N(C₁₋₃ alkyl)C(=NH)NH$_{2-z}$(C₁₋₃ alkyl)$_z$, wherein z is 0, 1, or 2 and C₁₋₃ alkyl is methyl, ethyl, propyl or isopropyl; and X¹ and X² are independently selected from O, S, and N(R⁸⁴), wherein R⁸⁴ is —H or C₁₋₃ alkyl.

In one embodiment, the spiroquinoxaline derivative has the general formula (N-II)

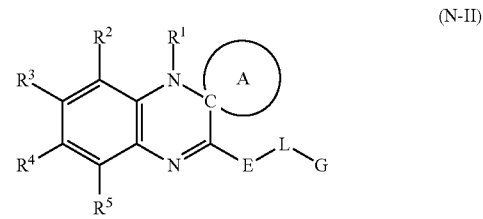

(N-II)

wherein R¹ to R⁵, E, L and G are as defined above or below and the optionally substituted monocyclic 4- to 10-membered N-heterocycloalkylene ring A contains 1 ring nitrogen atom and is 4- to 8-membered (preferably 5-, 6- or 7-membered, more preferably 6- or 7-membered) or said ring A contains 2 or 3 ring nitrogen atoms and is 5- to 8-membered, preferably 5-, 6- or 7-membered, more preferably 6- or 7-membered. In one embodiment of the spiroquinoxaline derivative of formula (N-II), ring A as such is unsaturated (i.e., the 4 to 10 members of ring A constitute 1, 2, or 3 (preferably 1 or 2, most preferably 1) double bonds within the ring) but is not aromatic. In an alternative embodiment of the spiroquinoxaline derivative of formula (N-II), ring A is saturated (i.e., ring A as such is free of unsaturation within the ring); however, if ring A is substituted by one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) R⁹, R⁹ may be unsaturated (i.e., may contain double and/or triple bonds and/or one or more (e.g., 1, 2. or 3) aromatic ring(s)). In any of the above embodiments of the spiroquinoxaline derivative of formula (N-II), the ring nitrogen atoms of ring A (preferably all ring heteroatoms of ring A) are not at position alpha to the spiro carbon atom (i.e., in this embodiment, preferably the two atoms of ring A positioned alpha to the spiro carbon atom are carbon atoms). In any of the above embodiments of the spiroquinoxaline derivative of formula (N-II), ring A may be selected from the group consisting of piperidinylene, azepanylene (e.g., homopiperidinylene), azetidinylene, pyrrolidinylene, azocanylene, pyrazolidinylene, hexahydropyridazinylene, hexahydropyrimidinylene, diazepanylene (e.g., homopiperazinylene), diazocanylene, triazepanylene, triazocanylene and their regioisomers, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected R. In one embodiment of the spiroquinoxaline derivative of formula (N-II), ring A is selected from the group consisting of 3- and 4-piperidinylene (N at position 3 or 4 relative to the spiro carbon atom); 3- and 4-azepanylene, 3-azetidinylene, 3-pyrrolidinylene, 3-, 4-, and 5-azocanylene, 3,4-pyrazolidinylene, 3,4-hexahydropyridazinylene, 3,5-hexahydropyrimidinylene, 3,4-, 3,5-, 3,6-, and 4,5-diazepanylene, 3,4-, 3,5-, 3,6-, 3,7-, 4,5-, and 4,6-diazocanylene, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$. In one embodiment of the spiroquinoxaline derivative of formula (N-II), ring A is selected from the group consisting of 4-piperidinylene, 3-piperidinylene, 3-azetidinylene, 3-pyrrolidiaylene, 4-azepanylene, 3-azepanylene, 5-azocanylene, 4-azocanylene, 3-azocanylene, and 3,6-diazepanylene (such as 4-piperidinylene, 3-piperidinylene, 4-azepanylene, and 3-azepanylene), each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$.

In any of the above embodiments of the spiroquinoxaline derivative of formula (N-II), ring A may be unsubstituted.

In any of the above embodiments of the spiroquinoxaline derivative of formula (N-II), wherein ring A is substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$, either (i) only one or more (preferably, 1, 2, or 3) ring nitrogen atoms of ring A are substituted with independently selected $R^9$, or (ii) only one or more (preferably, 1, 2, or 3) ring carbon atoms of ring A are substituted with independently selected $R^9$, or (iii) one or more (preferably, 1, 2, or 3) ring nitrogen atoms and one or more (preferably, 1, 2, or 3) ring carbon atoms of ring A (e.g., 1 or 2 ring nitrogen atoms and 1 or 2 ring carbon atoms) are substituted with independently selected $R^9$. For example, if ring A contains 1 ring nitrogen atom, ring A may be substituted (i) only at the ring nitrogen atom with $R^9$ (preferably, the ring nitrogen atom is at position 3 if ring A is 4- or 5-membered; at position 3 or 4 (preferably 4) if ring A is 6- or 7-membered; or at position 3, 4, or 5 (preferably 4 or 5) if ring A is 8-membered); (ii) only at 1 or 2 ring carbon atoms of ring A each with 1 or 2 independently selected $R^9$; or (iii) at the ring nitrogen atom with $R^9$ (preferably, the ring nitrogen atom is at position 3 if ring A is 4- or 5-membered; at position 3 or 4 (preferably 4) if ring A is 6- or 7-membered; or at position 3, 4, or 5 (preferably 4 or 5) if ring A is 8-membered) and at 1 or 2 ring carbon atoms of ring A each with 1 or 2 independently selected $R^9$.

In any of the above embodiments of the spiroquinoxaline derivative of formula (N-II), wherein $R^9$ substitutes a hydrogen atom bound to a ring carbon atom of ring A, each such R may be independently selected from the group consisting of $C_{1-6}$alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —C(=X)$R^{11}$, —C(=X)X$R^{11}$, —XC(=X)$R^{11}$, and —XC(=X)X$R^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or to 3, or 1 or 2) independently selected $R^{30}$, and/or any two $R^9$ which are bound to the same carbon atom of ring A may join together to form =X. In any of the above embodiments of the spiroquinoxaline derivative of formula (N-II), wherein $R^9$ substitutes a hydrogen atom bound to a ring carbon atom of ring A, each such $R^9$ may be independently selected from the group consisting of $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{13})$, —$N(R^{11})S(O)_{1-2}R^{11}$, —$NR^{11}S(O)_{1-2}N(R^{12})(R^{13})$, —C(=O)$R^{11}$, —C(=O)O$R^{11}$, —C(=O)S$R^{11}$, —C(=O)N($R^{14}$)($R^{11}$), —C(=S)O$R^{11}$, —$N(R^{14})C(=O)R^{11}$, —OC(=O)$R^{11}$, —OC(=S)$R^{11}$, —$N(R^{14})C(=O)N(R^{14})(R^{11})$, and —$N(R^{14})C(=N(R^{14}))N(R^{14})(R^{11})$, wherein each of the $C_{1-4}$ alkyl, $C_{2-4}$alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$, and/or any two $R^4$ which are bound to the same carbon atom of ring A may join together to form =O or =S. In one embodiment, each $R^9$ when substituting a hydrogen atom bound to a ring carbon atom of ring A is independently selected from the group consisting of $C_{1-4}$ alkyl; $C_{1-4}$alkyl substituted with 1 substituent selected from the group consisting of —OH, —O($C_{1-3}$ alkyl), —$NH_{2-z}$ $(CH_3)Z$, morpholinyl (e.g., 4-morpholinyl), piperazinyl (e.g., 1-piperazinyl), and N-methylpiperazinyl (e.g., 4-methylpiperazin-1-yl); $C_{1-4}$ alkyl substituted with 1, 2, or 3 halogen (preferably F), such as —$CF_3$, —$CH_2CF_3$, —$CH_2CHF_2$, or —$CH_2CH_2F$; —O($C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; cyclopropyl; 4-morpholinyl; homomorpholinyl; 4-piperidinyl; homopiperidinyl; 4-piperazinyl; homopiperazinyl; 4-methyl-piperazin-1-yl; N-methyl-homopiperazinyl; halogen; —CN; —OH; =O; —O($C_{1-3}$ alkyl optionally substituted with —$NH_{2-z}$ $(CH_3)_z$); —NH; —NH($C_{1-3}$ alkyl); —N($C_{1-3}$ alkyl)$_2$; —S($C_{1-3}$ alkyl); —$S(O)_2(C_{1-3}$ alkyl optionally substituted with —$NH_{2-z}$ $(CH_3)_z$); —$S(O)_2NH_{2-z}(C_{1-3}$ alkyl); —$NHS(O)_2(C_{1-3}$ alkyl optionally substituted with —$NH_2$—$(CH_3)_z$); —C(=O)($C_3$ alkyl optionally substituted with —$NH_2(CH_3)_z$); —C; —C(=O)OH; —(O)O($C_{1-3}$ alkyl); —C(=O)$NH_{2-z}(C_{1-3}$ alkyl)$_z$; —NHC(=O)($C_{1-3}$ alkyl optionally substituted with —$NH_{2-z}(CH_3)_z$); —NHC(=O)$NH_{2-z}$ $(CH_3)_z$; —NHC(=NH)$NH_{2-z}(C_{1-3}$ alkyl)$_z$; and —N($C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; tert-butyl; cyclopropyl; —$(CH_2)_d$—$NH_{2-z}(CH_3)_z$; —O$(CH_2)_d$—$NH_{2-z}(CH_3)_z$; —$(CH_2)_d$—O($CH_3$); —$CF_3$; —$CH_2CF_3$; —$CH_2CHF_2$; —$CH_2CH_2F$; —$(CH_2)_d$-(4-morpholinyl); —$(CH_2)_d$-(1-piperazinyl); —$(CH_2)_d$-(4-methylpiperazin-1-yl); 4-morpholinyl; 4-piperazinyl; 4-methyl-piperazin-1-yl; halogen (in particular, —F, —Cl, —Br); —NHC(=O)($C_{1-3}$ alkyl optionally substituted with —$NH_{2-z}(CH_3)_z$); —NHC(=O)$NH_{2-z}(CH_3)_z$; —$NHS(O)_2(C_{1-3}$ alkyl optionally substituted with —$NH_{2-z}(CH_3)_z$); —C(=O)$CH_3$; —C(=O)$CH_2NH_{2-z}(CH_3)_z$; —C(=O)$NH_{2-z}(C_{1-3}$ alkyl)$_z$; —$S(O)_2$ ($C_{1-3}$ alkyl); —$S(O)_2(CH_2)_dNH_2(CH_3)_z$; —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; cyclopropyl; —$(CH_2)_d$—$NH_{2-z}(CH_3)_z$; —$(CH_2)_d$—O ($CH_3$); —$CF_3$; —$CH_2CF_3$; —$CH_2CHF_2$; —$CH_2CH_2F$; —$NH_2$; —NH($C_{1-3}$ alkyl); —N($C_{1-3}$ alkyl)$_2$; halogen (in particular, —F, —Cl, —Br); —C(=O)$CH_3$; —C(=O) $CH_2NH_{2-z}(CH_2)_z$; —C(=O)$NH_{2-z}(C_{1-3}$ alkyl)$_z$; —$S(O)_2$ ($C_{1-3}$ alkyl); —$S(O)_2(CH_2)_dNH_{2-z}(CH_3)_z$; —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; cyclopropyl; —$(CH_2)_d$—$N_2$—$(CH_3)_z$; —$(CH_2)_d$—O($CH_3$); —$CF_3$; —$CH_2CF_3$; —$CH_2CHF_2$; —$CH_2CH_2F$; halogen (in particular, —F, —Cl, —Br); —C(=O)$CH_3$; —C(=O)$CH_2N_2$—$(CH_3)_z$; —C(=O)$NH_{2-z}(C_{1-3}$ alkyl)$_z$; —$S(O)_2(C_{1-3}$ alkyl); —$S(O)_2(CH_2)_dN_{2-z}(CH_3)_z$, —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, the ring carbon atoms of ring A are unsubstituted or each $R^9$ substituting a hydrogen atom bound to a ring carbon atom is independently selected from the group consisting of $C_{1-4}$alkyl (in particular methyl), —N($R^{12}$)($R^{13}$)(in particular $NH_2$), and —N($R^{14}$)C(=O)$R^{11}$ (in particular $NHC(O)CH_3$). In one embodiment, the ring carbon atoms of ring A are unsubstituted or one ring carbon atom of ring A is substituted with one $R^9$ being $NH_2$ or $CH_3$, or with two $R^9$ being $CH_3$.

In any of the above embodiments of the spiroquinoxaline derivative of formula (N-II), wherein $R^9$ substitutes a hydrogen atom bound to a ring nitrogen atom of ring A, each such $R^9$ may be independently selected from the group consisting of $C_{1-2}$ alkyl (such as $C_{1-8}$ alkyl or $C_{1-6}$ alkyl), $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, —$OR^{11}$, —N($R^{12}$)($R^{13}$), —$S(O)_{1-2}R^{11}$, —$S(O)_{1-2}N(R^{12})(R^{13})$, —N($R^{11}$)$S(O)_{1-2}R^{11}$, —$NR^{11}S(O)_{1-2}$ N($R^{12}$)($R^{13}$), —C(=X)$R^{11}$, —C(=X)$XR^{11}$, —N($R^{14}$)C(=X)$R^{11}$, and —N($R^{14}$)C(=X)$XR^{11}$, wherein each of the $C_{1-12}$ alkyl (such as $C_{1-8}$ alkyl or $C_{1-6}$alkyl), $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-12}$ alkyl (such as $C_{1-8}$ alkyl or $C_{1-6}$ alkyl), $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In any of the above embodiments of the spiroquinoxaline derivative of formula (N-II), wherein $R^9$ substitutes a hydrogen atom bound to a ring nitrogen atom of ring A, each such $R^9$ may be independently selected from the group consisting of $C_{1-12}$ alkyl (such as $C_{1-8}$ alkyl, $C_{1-6}$ alkyl or $C_{1-4}$ alkyl), $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, —$OR^{11}$, —N($R^{12}$)($R^{13}$), —$S(O)_{1-2}R^{11}$, —$S(O)_{1-2}N(R^{12})(R13)$, —N(R)$S(O)_{1-2}R^{11}$, —$NR^{11}S(O)_{1-2}N(R^{12})(R^{13})$, —C(=O)$R^{11}$, —C(=O)$OR^{11}$, —C(=O)$SR^{11}$, —C(=O)N($R^{14}$)($R^{11}$), —C(=S)$OR^{11}$, —N($R^{14}$)C(=O)$R^{11}$, —N($R^{14}$)C(=O)N($R^{14}$)($R^{11}$), and —N($R^{14}$)C(=N($R^{14}$))N($R^{14}$)($R^{11}$), wherein each of the $C_{1-12}$ alkyl (such as $C_{1-8}$ alkyl, $C_{1-6}$ alkyl or $C_{1-4}$ alkyl), $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment, each $R^9$ when substituting a hydrogen atom bound to a ring nitrogen atom of ring A is independently selected from the group consisting of $C_{1-12}$ alkyl (such as $C_{1-8}$ alkyl, $C_{1-6}$ alkyl or $C_{1-4}$ alkyl); $CH_{1-2}$ alkyl (such as $C_{1-8}$ alkyl, $C_{1-6}$ alkyl or $C_{1-4}$ alkyl) substituted with 1 substituent selected from the group consisting of —OH, —O($C_{1-3}$ alkyl), and —$NH_{2-z}(CH_3)_z$; $C_{1-4}$ alkyl substituted with 1, 2, or 3 halogen (preferably F), such as —$CF_3$, —$CH_2CF_3$, —$CH_2CH_2$, or —$CH_2CH_2F$; cyclopropyl; 4-morpholinyl; homomorpholinyl; 4-piperidinyl; homopiperidinyl; 4-piperazinyl; homopiperazinyl; N-methyl-piperazin-4-yl; N-methyl-homopiperazinyl; —OH; —O($C_{1-3}$ alkyl); —$NH_2$; —N($C_{1-3}$ alkyl); —N($C_{1-3}$ alkyl)$_2$; —S($C_{1-3}$ alkyl); —$S(O)_2(C_{1-3}$ alkyl optionally substituted with —$NH_{2-z}(CH_3)_z$); —$S(O)_2NH_{2-z}(C_{1-3}$ alkyl); —$NHS(O)_2(C_{1-3}$ alkyl); —C(=O)($C_{1-3}$ alkyl optionally substituted with —$NH_{2-z}(CH_3)_z$); —C(=O)OH; —C(=O)O($C_{1-3}$ alkyl); —C(=O)$NH_{2-z}(C_{1-3}$ alkyl)$_z$; —NHC(=O)($C_{1-3}$ alkyl); —NHC(=NH)$NH_{z-2}(C_{1-3}$ alkyl)$_z$; and —N($C_{1-3}$ alkyl)C(=NH)$NH_{z-z}(C_{1-3}$ alkyl)$_z$, wherein z is 0, 1, or 2 and $C_{1-3}$ alkyl is methyl, ethyl, propyl or isopropyl. In one embodiment, each $R^9$ when substituting a hydrogen atom bound to a ring nitrogen atom of ring A is independently selected from the group consisting of methyl; ethyl; isopropyl; n-octyl; n-dodecyl; cyclopropyl; —$(CH_2)_d$—$NH_{2-z}(CH_3)_z$; —$(CH_2)_d$—O($CH_3$); —$CH_2CF_3$; —$CH_2CHF_2$; —$CH_2CH_2F$; —C(=O)$CH_3$; —C(=O)$CH_2N_{2-z}(CH_3)_z$; —C(=O)$NH_{2-z}(C_{1-3}$ alkyl)$_z$; —$S(O)_2(C_{1-3}$ alkyl); —$S(O)_2(CH_2)_dNH_2-2(C_3)_z$; —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring nitrogen atom of ring A is independently selected from the group consisting of methyl; ethyl; isopropyl; cyclopropyl; —$(CH_2)_d$—$NH_{2-z}(CH_3)_z$; —$(CH_2)_d$—O($CH_3$); —$CH_2CF_3$; —$CH_2CHF_2$; —$CH_2CH_2F$; —C(=O)$CH_3$; —C(=O)$CH_2NH_{2-z}(CH_3)_z$; —C(=O)$NH_{2-z}(C_{1-3}$ alkyl)$_z$; —$S(O)_2(C_{1-3}$ alkyl); —$S(O)_2(CH_2)_dNH_2NH_2(CH_3)_z$; —OH; and —O($C_{1-3}$ alkyl), wherein z is 0, 1, or 2; d is 1, 2, or 3; and $CH_{1-3}$ alkyl is methyl, ethyl, propyl or isopropyl. In one embodiment, the ring nitrogen atom of ring A is unsubstituted or each $R^9$ substituting a hydrogen atom bound to a ring nitrogen atom is independently selected from the group consisting of $C_{1-12}$ alkyl (in particular methyl, n-octyl, or n-dodecyl) and —C(=O)$R^{11}$ (in particular —C(=O)$CH_3$ or —C(=O)($CH_2)_6CH_3$). In one embodiment, the ring nitrogen atom of ring A is unsubstituted or is substituted with one $R^9$ being methyl.

In one embodiment, the spiroquinoxaline derivative has the general formula (N-III)

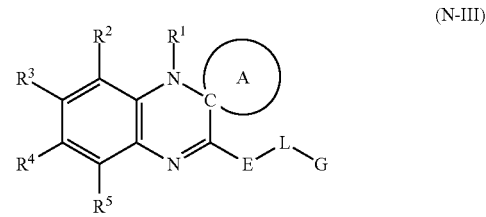

(N-III)

wherein $R^1$ to $R^5$, ring A, E, and G are as defined above (in particular with respect to formulas (N-I) and (N-II)) or below and L is selected from the group consisting of $C_{1-6}$ alkylene, $C_{2-6}$ alkenylene, $C_{2-6}$ alkynylene, —$(CH_2)_a$-cyclopropylene-$(CH_2)_b$—, wherein each of a and b is independently selected from an integer between 0 and 3, and —$(CH_2)_m$—[Y—$(CH_2)_n]_o$—, wherein m is 1, 2, or 3, n is 0, 1, or 2, o is 1, 2, or 3, wherein if n is 0 then o is 1; Y is independently selected from O, S, and —N($R^{7'}$)—, wherein $R^{7'}$ is selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, 3- to 7-membered heterocyclyl, —$OR^{11}$, and —$NHR^{20}$, wherein each of the $C_{1-6}$ alkylene, $C_{2-6}$ alkenylene, $C_{2-6}$ alkynylene, 1,1-cyclopropylene, —$(CH_2)_m$—, —$(CH_2)_n$—, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one or more (such as 1 to the maximum number of hydrogen atoms bound to the $C_{1-6}$ alkylene, $C_{2-6}$ alkenylene, $C_{2-6}$ alkynylene, 1,1-cyclopropylene, —$(CH_2)_m$—, —$(CH_2)_n$—, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment of the spiroquinoxaline derivative of formula (N-III), $R^1$ to $R^5$, ring A, E, and G are as defined above (in particular with respect to formulas (N-I) and (N-II)) or below and L is selected from the group consisting of $C_{1-4}$ alkylene, $C_{2-4}$ alkenylene, $C_{2-4}$ alkynylene, —$(CH_2)_a$-1,1-cyclopropylene-$(CH_2)_b$—, wherein each of a and b is independently selected from 0, 1, and 2, and —$(CH_2)_m$—[Y—$(CH_2)_n]_o$—, wherein m is 1, 2, or 3, n is 0, 1, or 2, o is 1, 2, or 3, wherein if n is 0 then o is 1; Y is independently selected from O, S, and —N(R')—, wherein $R^1$ is selected from the group consisting of —H, $C_{1-3}$ alkyl, 3-, 5-, 6- or 7-membered cycloalkyl, 6-membered aryl, 5- or 6-membered heteroaryl, 3-, 5-, 6- or 7-membered heterocyclyl, —O($C_{1-3}$ alkyl), and —$NHR^2$, wherein each of the $C_{1-4}$ alkylene, $C_{2-4}$ alkenylene, $C_{2-4}$ alkynylene, 1,1-cyclopropylene, —$(CH_2)_m$—, —$(CH_2)_n$—, $C_{1-3}$ alkyl, 3-, 5-, 6- or 7-membered cycloalkyl, 6-membered aryl, 5- or 6-membered heteroaryl, and 3-, 5-, 6- or 7-membered heterocyclyl groups is optionally substituted with 1, 2, or 3 independently selected $R^{30}$. In one embodiment of the spiroquinoxaline derivative of formula (N-III), $R^1$ to $R^5$, ring A, E, and G are as defined above (in particular with respect to formulas (N-I) and (N-II)) or below and L is selected from the group consisting of $C_{1-3}$ alkylene, —$(CH_2)_a$-1,1-cyclopropylene-$(CH_2)_b$—, wherein each of a and b is independently selected from 0 and 1, and —$(CH_2)_m$—[Y—$(CH_2)_n]_o$—, wherein m is 1 or 2, n is 0, 1, or 2, o is 1 or 2, wherein if n is 0 then o is 1; Y is O, wherein each of the $C_{1-3}$ alkylene, 1,1-cyclopropylene, —$(CH_2)_m$—, and —$(CH_2)_n$— groups is optionally substituted with 1, 2, or 3 independently selected $R^{30}$. In one embodiment of the spiroquinoxaline derivative of formula (N-m), $R^1$ to $R^5$, ring A, E, and G are as defined above (in particular with respect to formulas (N-I) and (N-II)) or below and L is selected from the group consisting of methylene; 1,1-ethylene; 1,2-ethylene (optionally substituted with one $R^{30}$ (such as phenyl) at position 2); trimethylene (—$(CH_2)_3$—); 2,2-propylene (—C$(CH_3)_2$—); 2,4-butanediyl; -1,1-cyclopropylene-; —$(CH_2)$-1,1-cyclopropylene; -1,1-cyclopropylene-$(CH_2)$—; —$(CH_2)$-1,1-cyclopropylene-$(CH_2)$—; —$CH_2O$—; —$(CH_2)_2O$—; and —$(CH_2)_3O$— (such as methylene; 1,1-ethylene; 1,2-ethylene; trimethylene (—$(CH_2)_3$—); 2,2-propylene (—C$(CH_3)_2$—); 1,1-cyclopropylene; and —$(CH_2)_2O$—, in particular, methylene). In one embodiment of the spiroquinoxaline derivative of formula (N-III), $R^1$ to $R^5$, ring A, E, and G are as defined above (in particular with respect to formulas (N-I) and (N-II)) or below and L is selected from the group consisting of methylene; 1,1-ethylene; 1,2-ethylene; trimethylene (—$(CH_2)_3$—); 2,2-propylene (—C$(CH_3)_2$—); -1,1-cyclopropylene-; —$(CH_2)$-1,1-cyclopropylene-$(CH_2)$—; —$(CH_2)$-1,1-cyclopropylene-$(CH_2)$—; —$CH_2O$—; —$(CH_2)_2O$—; and —$(CH_2)_3O$— (such as methylene; 1,1-ethylene; 1,2-ethylene; trimethylene (—$(CH_2)_3$—); 2,2-propylene (—$C(CH_3)_2$—); 1,1-cyclopropylene; and —$(CH_2)_2O$—, in particular, methylene). In one embodiment of the spiroquinoxaline derivative of formula (N-III), $R^1$ to $R^5$, ring A, E, and G are as defined above (in particular with respect to formulas (N-I) and (N-II)) or below and L is selected from the group consisting of $C_1$ alkylene, $C_2$ alkylene (in particular 1,2-ethylene or 1,1-ethylene), $C_{1-3}$ alkylene (in particular trimethylene), and $C_4$ alkylene (in particular tetramethylene or 2,4-butanediyl), each of which being optionally substituted with one $R^{30}$. In one embodiment of the spiroquinoxaline derivative of formula (N-II), $R^1$ to $R^5$, ring A, E, and G are as defined above (in particular with respect to formulas (N-I) and (N-II)) or below and L is selected from the group consisting of methylene, 1,1-ethylene, 1,2-ethylene, trimethylene, tetramethylene, 2,4-butanediyl, and 2-phenyl-1,2-ethylene (—$CH_2$—$CH(C_6H_5)$—). In one embodiment of the spiroquinoxaline derivative of formula (N-I), $R^1$ to $R^5$, ring A, E, and G are as defined above (in particular with respect to formulas (N-I) and (N-II)) or below and L is selected from the group consisting of methylene and 2-phenyl-1,2-ethylene (—$CH_2$—$CH(C_6H_5)$—).

In one embodiment, the spiroquinoxaline derivative has the general formula (N-IV)

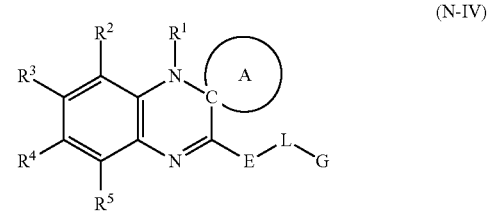

(N-IV)

wherein $R^1$ to $R^5$, ring A, E, and L are as defined above (in particular with respect to formulas (N-I), (N-II) and (N-II)) or below and G is phenyl which is either unsubstituted or substituted with 1, 2, 3, 4 or 5 (such as between 1 to 4, or 1 to 3, or 1 or 2) independently selected $R^8$. In any of the above embodiments (including those of formulas (N-I) to (N-III)), wherein G is substituted, $R^8$ may be, in each case, selected from the group consisting of $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment of the spiroquinoxaline derivative of formula (N-IV), $R^1$ to $R^5$, ring A, E, and L are as defined above (in particular with respect to formulas (N-I), (N-II) and (N-III)) or below and $R^8$ is, in each case, selected from the group consisting of $C_4$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —OR$^{11}$, —N(R$^{12}$)(R$^{13}$), —S(O)$_{0-2}$R$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$N(R$^{12}$)(R$^{13}$), —C(=O)R$^{11}$, —C(=O)OR$^{11}$, —C(=O)SR$^{11}$, —C(=O)N (R$^{14}$)(R$^{11}$), —C(=S)OR$^{11}$, —N(R$^{14}$)C(=O)R$^{11}$, —OC (=O)R$^{11}$, —OC(=S)R$^{11}$, —N(R$^{14}$)C(=O)N(R$^{14}$)(R$^{11}$) and —N(R$^{14}$)C(=N(R$^{14}$))N(R$^{14}$)(R$^{11}$), wherein each of the C$_{1-4}$ alkyl, C$_{2-4}$ alkenyl, C$_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected R$^{30}$. In one embodiment of the spiroquinoxaline derivative of formula (N-IV), R$^1$ to R$^5$, ring A, E, and L are as defined above (in particular with respect to formulas (N-I), (N-II) and (N-II)) or below and R$^8$ is, in each case, selected from the group consisting of C$_{1-4}$ alkyl; C$_{1-4}$ alkyl substituted with 1 substituent selected from the group consisting of —OH, —O(C$_{1-3}$ alkyl), and —NH$_{2-z}$(CH$_3$)$_z$; C$_{1-4}$ alkyl substituted with 1, 2, or 3 halogen (preferably F), such as —CF$_3$, —CH$_2$CF$_3$, —CH$_2$CHF$_2$, or —CH$_2$CH$_2$F; phenyl; cyclopropyl; 5-membered heterocyclyl (such as pyrrolidinyl); 4-morpholinyl; homomorpholinyl; 4-piperidinyl; homopiperidinyl; 4-piperazinyl; homopiperazinyl; N-methyl-piperazin-4-yl; N-methyl-homopiperazinyl; halogen; —CN; —OH; —O(C$_{1-3}$ alkyl); —O(C$_{1-4}$ alkyl substituted with 1, 2, or 3 halogen (preferably F)), such as —OCF$_3$, —OCH$_2$CF$_3$, —OCH$_2$CHF$_2$, or —OCH$_2$CH$_2$F; —O-phenyl; —NH$_2$; —(C$_{1-3}$ alkyl); —N(C$_{1-3}$ alkyl)$_2$; —S(C$_{1-3}$ alkyl); —S(O)$_2$(C$_{1-3}$ alkyl optionally substituted with —NH$_{2-z}$(CH$_3$)$_z$); —S(O)$_2$NH$_{2-z}$(C$_{1-3}$ alkyl)$_z$; —S(O)$_2$ (C$_{1-3}$ alkyl); —C(=O)(C$_{1-3}$ alkyl optionally substituted with —NH$_{2-z}$(CH$_3$)$_z$); —C(=O)OH; —C(=O)O(C$_{1-3}$ alkyl); —C(=O)NH$_{2-z}$(C$_{1-3}$ alkyl)$_z$; —C(=O)(C$_{1-3}$ alkyl); C(=NH)NH$_{2-2}$(C$_{1-3}$ alkyl)$_z$; and —N(C$_{1-3}$ alkyl) C(=NH)$_{2-z}$(C$_{1-3}$ alkyl)$_z$, wherein z is 0, 1, or 2 and C$_{1-3}$ alkyl is methyl, ethyl, propyl or isopropyl and each of the phenyl, cyclopropyl, 5-membered heterocyclyl (such as pyrrolidinyl), 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of C$_{1-3}$ alkyl, halogen, —OCF$_3$, —OCH$_3$, —SCH$_3$, —NH$_{2-z}$(CH$_3$)$_z$, —C(=O)OH, and —C(=O) OCH$_3$, wherein z is 0, 1, or 2. In one embodiment, each R$^8$ is independently selected from the group consisting of methyl; ethyl; isopropyl; tert-butyl; phenyl; cyclopropyl; pyrrolidinyl (such as 4-pyrrolidinyl); —(CH$_2$)$_d$—NH$_{2-z}$ (CH$_3$)$_z$; —(CH$_2$)$_d$—O(CH$_3$); —CF$_3$; —OCF$_3$; —O-phenyl; —CH$_2$CF$_3$; —CH$_2$CHF$_2$; —CH$_2$CH$_2$F; halogen (in particular, —F, —Cl, —Br); —CN; —NH$_2$; NH(C$_{1-3}$ alkyl); —N(C$_{1-3}$ alkyl)$_2$; —C(=O)CH$_3$; —C(=O)CH$_{2-z}$(CH$_3$)$_z$; —C(=O)OH; —C(=O)O(C$_{1-3}$ alkyl); —C(=O)NH$_{2-z}$ (C$_{1-3}$ alkyl); —NHC(=O)(C$_{1-3}$ alkyl); —S(O)$_2$(C$_{1-3}$ alkyl); —S(O)$_2$(CH$_2$)$_d$NH$_{2-z}$(CH$_3$); —OH; and —O(C$_{1-3}$ alkyl), wherein z is 0, 1, or 2, d is 1, 2, or 3, and C$_{1-3}$ alkyl is methyl, ethyl, propyl or isopropyl. In one embodiment of the spiroquinoxaline derivative of formula (N-TV), R$^1$ to R$^5$, ring A, E, and L are as defined above (in particular with respect to formulas (N-I), (N-II) and (N-III)) or below and G is either unsubstituted or substituted with 1, 2, or 3 R$^8$, wherein R$^8$ is, in each case, selected from the group consisting of C$_{1-4}$ alkyl (in particular methyl or tert-butyl); halogen (in particular F or Cl); —OR$^{11}$ (in particular —OCH$_3$); and C$_{1-4}$ alkyl substituted with 1, 2, or 3 independently selected R$^{30}$ (in particular —CF$_3$). In one embodiment of the spiroquinoxaline derivative of formula (N-V), R$^1$ to R$^5$, ring A, E, and L are as defined above (in particular with respect to formulas (N-I), (N-I) and (N-II)) or below and G is either unsubstituted or substituted with 1 or 2 R$^8$ each independently selected from the group consisting of methyl, F, Cl, —OCH$_3$, and —CF$_3$. In one embodiment of the spiroquinoxaline derivative of formula (N-IV), R$^1$ to R$^5$, ring A, E, and L are as defined above (in particular with respect to formulas (N-I), (N-II) and (N-III)) or below and G is selected from the group consisting of unsubstituted phenyl, fluorophenyl (in particular 3-fluorophenyl), chlorophenyl (in particular 2-, 3- or 4-chlorophenyl), methylphenyl (in particular 2- or 3-methylphenyl), tert-butylphenyl (in particular 4-tert-butylphenyl), methoxyphenyl (in particular 3-methoxyphenyl), (trifluoromethyl)phenyl (in particular 3- or 4-(trifluoromethyl)phenyl), difluorophenyl (in particular 2,4- or 2,6-difluorophenyl), dichlorophenyl (in particular 2,4- or 3,4-dichlorophenyl), chlorofluorophenyl (in particular 4-chloro-2-fluorophenyl), and dimethylphenyl (in particular 3,5-dimethylphenyl). In one embodiment of the spiroquinoxaline derivative of formula (N-V), R$^1$ to R$^5$, ring A, E, and L are as defined above (in particular with respect to formulas (N-I), (N-II) and (N-III)) or below and G is selected from the group consisting of unsubstituted phenyl, 2-chlorophenyl, 3-chlorophenyl, 4-chlorophenyl, 3-methylphenyl, 3-(trifluoromethyl)phenyl, 2,6-difluorophenyl, 3,4-dichlorophenyl, 4-chloro-2-fluorophenyl, and 3,5-dimethylphenyl.

In one embodiment, the spiroquinoxaline derivative has the general formula (N-V)

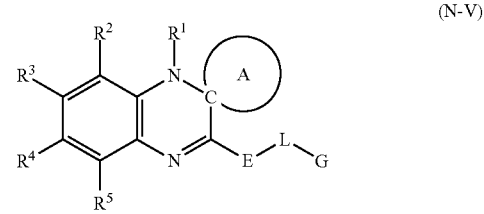

(N-V)

wherein R$^1$, ring A, E, L and G are as defined above (in particular with respect to formulas (N-I), (N-II), (N-III) and (N-IV)) or below and each of R$^2$, R$^3$, R$^4$, and R$^5$ is H. In one embodiment of the spiroquinoxaline derivative of formula (N-V), R$^1$, ring A, E, L and G are as defined above (in particular with respect to formulas (N-I), (N-II), (N-III) and (N-IV)) or below and at least one of R$^2$, R$^3$, R$^4$, and R$^5$ is different from H. For example, in one embodiment R$^2$ is different from H and each of R$^3$, R$^4$, and R$^5$ is H; or R$^3$ is different from H and each of R$^2$, R$^4$, and R$^5$ is H; or R$^4$ is different from H and each of R$^2$, R$^3$, and R$^5$ is H; or R$^5$ is different from H and each of R$^2$, R$^3$, and R$^4$ is H; or both of R$^2$ and R$^3$ are different from H and both of R$^4$ and R$^5$ are H;

or both of $R^2$ and $R^4$ are different from H and both of $R^3$ and $R^5$ are H; or both of $R^2$ and $R^5$ are different from H (preferably in this embodiment $R^2$ and $R^5$ are the same) and both of $R^3$ and $R^4$ are H; or both of $R^3$ and $R^4$ are different from H (preferably in this embodiment $R^3$ and $R^4$ are the same) and both of $R^2$ and $R^5$ are H; or each of $R^2$, $R^3$, and $R^4$ is different from H and $R^5$ is H; or each of $R^2$, $R^3$, and $R^5$ is different from H and $R^4$ is H; or each of $R^2$, $R^4$, and $R^5$ is different from H and $R^3$ is H; or each of $R^3$, $R^4$, and $R^5$ is different from H and $R^2$ is H; or each of $R^2$, R, $R^4$, and $R^1$ is different from H. In any of the above embodiments, it is preferred that $R^2$ and $R^5$ are the same and/or $R^3$ and $R^4$ are the same.

In any of the above embodiments (in particular with respect to formulas (N-I), (N-II), (N-III), (N-IV), and (N-V)), each of $R^2$ to $R^5$, if it does not join together with another of $R^2$ to $R^5$ to form a ring, is independently selected from the group consisting of —H, $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$alkyl, $C_{2-6}$ alkenyl, $C_{2-6}$alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment, each of $R^2$, $R^3$, $R^4$, and $R^5$, if it does not join together with another of $R^2$ to $R^5$ to form a ring, may be independently selected from the group consisting of —H, $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=O)R^{11}$, —$C(=O)OR^{11}$, —$C(=O)SR^{11}$, —$C(=O)N(R^{14})(R^{11})$, —$C(=S)OR^{11}$, —$N(R^{14})C(=O)R^{11}$, —$OC(=O)R^{11}$, —$OC(=S)R^{11}$, —$N(R^{14})C(=O)N(R^{14})(R^{11})$ and —$N(R^{14})C(=N(R^{14})N(R^{14})(R^{11})$, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment of the spiroquinoxaline derivative of formula (N-V), $R^1$, ring A, E, L and G are as defined above (in particular with respect to formulas (N-I), (N-II), (N-III), and (N-IV)) or below and each of $R^2$, $R^3$, $R^4$, and $R^1$, if it does not join together with another of $R^2$ to $R^5$ to form a ring, is independently selected from the group consisting of H; $C_{1-4}$ alkyl; $C_{1-4}$ alkyl substituted with 1 substituent selected from the group consisting of —OH, —$O(C_{1-3}$ alkyl), and —$NH_{2-z}(CH_3)_z$; $C_{1-4}$ alkyl substituted with 1, 2, or 3 halogen (preferably F), such as —$CF_3$, —$CH_2CF_3$, —$CH_2CHF_2$, or —$CH_2CH_2F$; phenyl; cyclopropyl; 5-membered heterocyclyl; 4-morpholinyl; homomorpholinyl; 4-piperidinyl; homopiperidinyl; 4-piperazinyl; homopiperazinyl; N-methyl-piperazin-4-yl; N-methyl-homopiperazinyl; halogen; —CN; —OH; —$O(C_{1-3}$ alkyl); —$O(C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; —O-phenyl; —$NH_2$; —$NH(C_{1-3}$ alkyl); —$N(C_{1-3}$ alkyl)$_2$; —$S(C_{1-3}$ alkyl); —$S(O)_2(C_{1-3}$ alkyl optionally substituted with —$NH_{2-z}(CH_3)_z$); —$S(O)_2N_{2-z}(C_{1-3}$ alkyl)$_z$; —$NHS(O)_2(C_{1-3}$ alkyl); —$C(=O)(C_{1-3}$ alkyl optionally substituted with —$NH_{2-z}(CH_3)_z$); —$C(=O)OH$; —$C(=O)O(C_{1-3}$ alkyl); —$C(=O)NH_{2-z}(C_{1-3}$ alkyl)$_z$; —$NHC(=O)(C_{1-3}$ alkyl); —$NHC(=NH)NH_{2-z}(C_{1-3}$ alkyl)$_z$; and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl and each of the phenyl, cyclopropyl, 5-membered heterocyclyl, 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of $C_{1-3}$ alkyl, halogen, —$CF_3$, —$OCF_3$, —OH, —$OCH_3$, —$SCH_3$, —$NH_{2-1}(CH_3)_z$, —$C(=O)OH$, and —$C(=O)OCH_3$, wherein z is 0, 1, or 2. In one embodiment, each of $R^2$, $R^3$, $R^4$, and $R^5$, if it does not join together with another of $R^2$ to $R^5$ to form a ring, is independently selected from the group consisting of H; methyl ethyl; isopropyl; phenyl; cyclopropyl; —$(CH_2)_d$—$NH_{2-z}(CH_3)_z$; —$(CH_2)_d$—$O(CH_3)$; —$CF_3$; —$OCF_3$; —$CH_2CF_3$; —$CH_2CHF_2$; —$CH_2CH_2F$; halogen (in particular, —F, —Cl, —Br); —CN; —$NH_2$; —$NH(C_{1-3}$ alkyl); —$N(C_{1-3}$ alkyl)$_2$; —$C(=O)CH_3$; —$C(=O)CH_2NH_{2-z}(CH_3)_z$; —$C(=O)O(C_{1-3}$ alkyl); —$C(=O)NH_{2-z}(C_{1-3}$ alkyl)$_z$; —$NHC(=O)(C_{1-3}$ alkyl); —$S(O)_2(C_{1-3}$ alkyl); —$S(O)_2(CH_2)_dNH_{2-z}(CH_3)_z$; —OH, and —$O(C_{1-3}$ alkyl), wherein z is 0, 1, or 2, d is 1, 2, or 3, and $C_{1-3}$ alkyl is methyl, ethyl, propyl or isopropyl. In one embodiment of the spiroquinoxaline derivative of formula (N-V), $R^1$, ring A, E, L and G are as defined above (in particular with respect to formulas (N-I), (N-II), (N-III), and (N-IV)) or below and $R^2$, $R^3$, $R^4$, and $R^5$ are independently selected from the group consisting of —H, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H). In one embodiment of the spiroquinoxalne derivative of formula (N-V), $R^1$, ring A, E, L and G are as defined above (in particular with respect to formulas (N-I), (N-II), (N-III), and (N-IV)) or below and $R^2$, $R^3$, $R^4$, and $R^5$ are independently selected from the group consisting of —H, methyl, F, Cl, and $CF_3$ (in particular wherein $R^2$ and $R^5$ are each —H). In one embodiment of the spiroquinoxaline derivative of formula (N-V), $R^1$, ring A, E, L and G are as defined above (in particular with respect to formulas (N-I), (N-II), (N-III), and (N-IV)) or below and $R^2$ and $R^5$ are each —H; $R^3$ is selected from the group consisting of —H, methyl, F, and Cl; and $R^4$ is selected from the group consisting of —H, methyl, F, and Cl. In one embodiment of the spiroquinoxaline derivative of formula (N-V), $R^1$, ring A, E, L and G are as defined above (in particular with respect to formulas (N-I), (N-II), (N-III), and (N-IV)) or below and (i) $R^2$ to $R^5$ are each —H; or (ii) $R^2$ and $R^5$ are each —H, and both of $R^3$ and $R^4$ are F, Cl, or methyl.

In any of the above embodiments, wherein a ring is formed by (i) $R^2$ and $R^3$, (ii) $R^3$ and $R^4$, and/or (iii) $R^4$ and $R^5$, said ring preferably is a 3- to 7-membered ring (e.g., a ring having 5 or 6 members) which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$. The ring may be an aromatic, cycloaliphatic, heteroaromatic, or heterocyclic ring, wherein the heteroaromatic/heterocyclic ring contains 1 or 2 heteroatoms selected from the group consisting of O, S, and $N(R^{40})$, wherein $R^{40}$ is selected from the group consisting of $R^{11}$, —$OR^{11}$, —$NH_yR^{20}_{2-y}$, and —$S(O)_{1-2}R^{11}$, wherein $R^{11}$, $R^{20}$, and y are as defined above. In one embodiment, the ring formed by (i) $R^2$ and $R^3$, (ii) $R^3$ and $R^4$, and/or (iii) $R^4$ and $R^5$ is a 5- or 6-membered aromatic, cycloaliphatic, heteroaromatic, or heterocyclic ring, wherein the heteroaromatic/heterocyclic ring contains 1 or 2 heteroatoms selected from the group consisting of O, S, and N, wherein at least one heteroatom is N. In one embodiment, the ring formed by (i) $R^2$ and $R^3$, (ii) $R^3$ and $R^4$, and/or (iii) $R^4$ and $R^5$ is selected from the group consisting of cyclopentadiene, furan, pyrrole, thiophene, imidazole, pyrazole, oxazole, isoxazole, thiazole, dioxole (e.g., 1,3-dioxole), benzene, pyridine, pyrazine, pyrimidine, pyridazine, dioxine (e.g., 1,4-dioxine), 1,2,3-triazine, 1,2,4-triazine, and di- or tetrahydro forms of each of the foregoing. In one embodiment, the ring formed (i) $R^2$ and $R^3$, (ii) $R^3$ and $R^4$, and/or (iii) $R^4$ and $R^5$ is cyclopentene (such as 2,3-dihydrocyclopentadiene), dioxole (such as 1,3dioxole, optionally substituted at position 2 with one or two halogen atoms (such as F)), or dioxine (such as 2,3-dihydro-[1,4]-dioxine). In one embodiment, the total number of rings formed by (i) $R^2$ and $R^3$, (ii) $R^3$ and $R^4$, and/or (iii) $R^4$ and $R^5$ is 0 or 1. Thus, in the embodiment, wherein the total number of rings formed by (i) $R^2$ and $R^3$, (ii) $R^3$ and $R^4$, and/or (iii) $R^4$ and $R^5$ is 1, only two adjacent substituents (i.e., either (i) $R^2$ and $R^3$, (ii) $R^3$ and $R^4$, or (iii) $R^4$ and $R^5$) join together with the atoms to which they are attached to form a ring, wherein the ring is as defined in any of the above embodiments and the remaining of $R^2$ to $R^5$ are selected from the particular groups of moieties specified above for the situation that they do not join together to form a ring. For example, the remaining $R^2$ to $R^5$ which do not join together to form a ring may be selected from —H, $C_{1-6}$ alkyl, $C_{2-6}$ alkenyl, $C_{2-6}$alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In an alternative embodiment, $R^2$ to $R^5$ do not join together to form a ring.

In any of the above embodiments, $R^2$ and $R^5$ may be the same and/or $R^3$ and $R^4$ may be the same.

In one embodiment of the spiroquinoxaline derivative of formula (N-V), $R^1$, ring A, E, L and G are as defined above (in particular with respect to formulas (N-I), (N-II), (N-III), and (N-IV)) or below and $R^2$, $R^3$, $R^4$, and $R^5$ are independently selected from the group consisting of —H, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H), or $R^3$ and $R^4$ may join together with the atoms to which they are attached to form a 5- or 6-membered ring which is optionally substituted with one or two independently selected $R^{30}$. In one embodiment of the spiroquinoxaline derivative of formula (N-V), $R^1$, ring A, E, L and G are as defined above (in particular with respect to formulas (N-I), (N-II), (N-III), and (N-IV)) or below and $R^2$, $R^3$, $R^4$, and $R^5$ are independently selected from the group consisting of —H, methyl, F, Cl, and $CF_3$ (in particular wherein $R^2$ and $R^5$ are each —H), or $R^3$ and $R^4$ may join together with the atoms to which they are attached to form a dioxole or dioxine ring which is optionally substituted with one or two independently selected halogens (in particular F). In one embodiment of the spiroquinoxaline derivative of formula (N-V), $R^1$, ring A, E, L and G are as defied above (in particular with respect to formulas (N-I), (N-II), (N-III), and (N-IV)) or below and $R^2$ and $R^5$ are each —H; $R^3$ is selected from the group consisting of —H, methyl, F, and Cl; and $R^4$ is selected from the group consisting of —H, methyl, F, and Cl; or R and $R^4$ may join together with the atoms to which they are attached to form a dioxole (in particular 1,3-dioxole) or dioxine (in particular 2,3-dihydro-[1,4]-dioxine) ring, wherein the dioxole ring is optionally substituted with two F. In one embodiment of the spiroquinoxaline derivative of formula (N-V), $R^1$, ring A, E, L and G are as defined above (in particular with respect to formulas (N-I), (N-II), (N-III), and (N-IV)) or below and (i) $R^2$ to $R^5$ are each —H; (ii) $R^2$ and $R^5$ are each —H, and both of $R^3$ and $R^4$ are F, Cl, or methyl, or (iii) $R^2$ and $R^5$ are each —H, and $R^3$ and $R^4$ join together with the atoms to which they are attached to form a 2,2-difluoro-1,3-dioxole ring or a 2,3-dihydro-[1,4]-dioxine ring.

In any of the above embodiments (in particular with respect to formulas (N-I), (N-II), (N-III), (N-IV), and (N-V)), $R^{30}$, in each case, may be a typical $1^{st}$, $2^{nd}$, or $3^{rd}$ level substituent as specified above and may be independently selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5-, 6-, or 7-membered heterocyclyl, halogen, —$CF_3$, —CN, azido, —$NO_2$, —OH, —$O(C_{1-3}$ alkyl), —$S(C_{1-3}$ alkyl), —$NH_2$, —$N(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, such as 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —$CH_2CH_2OCH_3$, —$OCH_2CH_2CH_3$, —$CH_2CH_2N_{2-z}(CH_3)_z$, —$OCH_{2-z}NH_{2-z}(CH_3)_z$, —$CF_3$, —$OCF_3$. Alternatively, $R^{30}$ may be selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$OCF_3$, —$SCH_3$, —$NH_{2-z}(CH_3)_z$, —$C(=O)OH$, and —$C(=O)OCH_3$, wherein z is 0, 1, or 2.

In one embodiment, the spiroquinoxaline derivative has the general formula (O/S-I)

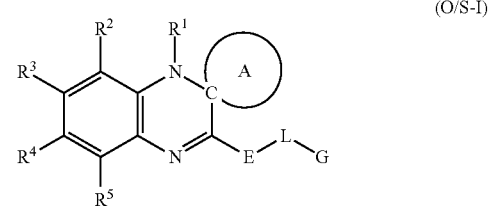

(O/S-I)

and solvates, salts, complexes, polymorphs, crystalline forms, racemic mixtures, diastereomers, enantiomers, tautomers, isotopically labeled forms, prodrugs, and combinations thereof,
wherein E is —N($R^6$)—;

L is selected from the group consisting of $C_{1-10}$ alkylene, $C_{2-10}$ alkenylene, $C_{2-10}$ alkynylene, 1,1-$(CH_2)_a$-cyclopropylene-$(CH_2)_b$—, wherein each of a and b is independently selected from an integer between 0 and 3, and —$(CH_2)_m$—[Y—$(CH_2)_n]_o$—, wherein m is an integer between 1 and 6, n is an integer between 0 and 3, o is an integer between 1 and 3, wherein if n is 0 then o is 1; Y is independently selected from O, S, and —N($R^7$)—; and each of the $C_{1-10}$ alkylene, $C_{2-10}$ alkenylene, $C_{2-10}$ alkynylene, 1,1-cyclopropylene, —$(CH_2)_m$—, and —$(CH_2)_n$— groups is optionally substituted with one or more (such as 1 to the maximum number of hydrogen atoms bound to the $C_{1-10}$ alkylene, $C_{2-10}$ alkenylene, $C_{2-10}$ alkynylene, 1,1-cyclopropylene, —$(CH_2)_m$—, or —$(CH_2)_n$— group, e.g., 1, 2, 3, 4, 5, 6, 7, 8, 9, or up to 10, such as between 1 to 5, 1 to 4, or 1 to 3, or 1 or 2) independently selected $R^{30}$;

G is phenyl, optionally substituted with 1, 2, 3, 4 or 5 independently selected $R^8$;

ring A is a monocyclic 4- to 10-membered O/S-heterocycloalkylene, optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$;

$R^1$ is H;

$R^2$, $R^3$, $R^4$, and $R^5$ are independently selected from the group consisting of —H, alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

or $R^2$ and $R^3$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; $R^3$ and $R^4$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; and/or $R^4$ and $R^5$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$;

$R^6$ is H;

$R^7$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^8$ is, in each case, selected from the group consisting of alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)R$^{11}$, —XC(=X)R$^{11}$, and —XC(=X)XR$^{11}$, wherein each of the alkyl, alkenyl, alkyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^9$ is, when substituting a hydrogen atom bound to a ring carbon atom, independently selected from the group consisting of alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^1$, and —XC(=X)XR$^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, and/or any two $R^9$ which are bound to the same carbon atom of ring A may join together to form =X; or $R^9$ is, when bound to a ring sulfur atom of ring A, independently selected from the group consisting of alkyl, alkenyl, alkynyl, aryl, heteroaryl, cycloalkyl, heterocyclyl, —OR$^{11}$, and =O, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

X is independently selected from O, S, and N(R$^{14}$);

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{14}$ is independently selected from the group consisting of —H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 2, 3, 4, 5, 6, 7, 8, 9, or up to 10, such as between 1 to 5, 1 to 4, or 1 to 3, or 1 or 2) independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$C(=X^1)R^{71}$, —$C(=X)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more (such as 1 to the maximum number of hydrogen atoms bound to the alkyl, alkenyl, alkynyl, aryl, heteroaryl, cycloalkyl, or heterocyclyl group being a $1^{st}$ level substituent, e.g., 1, 2, 3, 4, 5, 6, 7, 8, 9, or up to 10, such as between 1 to 5, 1 to 4, or 1 to 3, or 1 or 2) $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})$ $(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, and 3- to 14-membered heterocyclyl groups being a $2^{nd}$ level substituent is optionally substituted with one or more (such as 1 to the maximum number of hydrogen atoms bound to the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, or 3- to 14-membered heterocyclyl group being a $2^{nd}$ level substituent, e.g., 1, 2, 3, 4, 5, 6, 7, 8, 9, or up to 10, such as between 1 to 5, 1 to 4, or 1 to 3, or 1 or 2) $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)OH$, —$C(=O)O(C_{1-3}$ alkyl), —$C(=O)NH_{2-z}(C_{1-3}$ alkyl)$_z$, —$NHC(=O)(C_{1-3}$ alkyl), —$NHC(=NH)NH_{2-z}(C_{1-3}$ alkyl)$_z$, and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, —NH, or =$N(C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}$ $(C_{1-3}$ alkyl)$_z$, —$NHC(=O)(C_{1-3}$ alkyl), —$NHC(=NH)$ $NH_{z-2}(C_{1-3}$ alkyl)$_z$, and —$N(C_{1-3}$ alkyl)$C(=NH)NH_{2-z}$ $(C_{1-3}$ alkyl), wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —$C(=O)(C_{1-3}$ alkyl), —$C(=O)OH$, —$C(=O)O(C_{1-3}$ alkyl), —$C(=O)NH_{2-z}$ ($C_{1-3}$ alkyl)$_z$, —NHC(=O)($C_{1-3}$ alkyl), —NHC(=NH)NH$_{z-2}$ ($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and N($R^{84}$), wherein $R^{84}$ is —H or $C_{1-3}$ alkyl.

In one embodiment, the spiroquinoxaline derivative has the general formula (O/S-II)

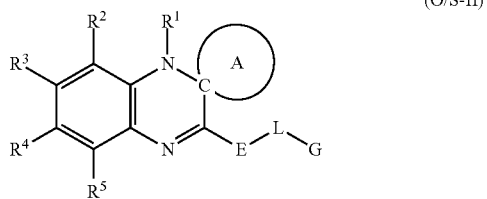

(O/S-II)

wherein $R^1$ to $R^5$, E, L and G are as defined above or below and the optionally substituted monocyclic 4- to 10-membered O/S-heterocycloalkylene ring A contains 1 ring oxygen or sulfur atom and is 4- to 8-membered (preferably 5-, 6- or 7-membered, more preferably 6- or 7-membered) or said ring A contains 2 ring heteroatoms selected from oxygen and sulfur and is 5- to 8-membered, preferably 5-, 6- or 7-membered, more preferably 6- or 7-membered. In one embodiment of the spiroquinoxaline derivative of formula (O/S-II), ring A as such is unsaturated (i.e., the 4 to 10 members of ring A constitute 1, 2, or 3 (preferably 1 or 2, most preferably 1) double bonds within the ring) but is not aromatic. In an alternative embodiment of the spiroquinoxaline derivative of formula (O/S-II), ring A is saturated (i.e., ring A as such is free of unsaturation within the ring); however, if ring A is substituted by one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) $R^9$, $R^9$ may be unsaturated (i.e., may contain double and/or triple bonds and/or one or more (e.g., 1, 2, or 3) aromatic ring(s)). In any of the above embodiments of the spiroquinoxaline derivative of formula (O/S-II), the ring oxygen or sulfur atoms of ring A (preferably all ring heteroatoms of ring A) are not at position alpha to the spiro carbon atom (i.e., in this embodiment, preferably the two atoms of ring A positioned alpha to the spiro carbon atom are carbon atoms). In any of the above embodiments of the spiroquinoxaline derivative of formula (0/S-II), ring A may be selected from the group consisting of di- and tetrahydropyranylene, di- and tetrahydrothiopyranylene, oxepanylene, thiepanylene, oxetanylene, thietanylene, di- and tetrahydrofuranylene, di- and tetrahydrothienylene, oxocanylene, thiocanylene, dithiolanylene, oxathiolanylene, dioxanylene, dithianylene, oxathianylene, dioxepanylene, dithiepanylene, oxathiepanylene, dioxocanylene, dithiocanylene, oxathiocanylene, and their regioisomers, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$. In one embodiment of the spiroquinoxaline derivative of formula (O/S-II), ring A is selected from the group consisting of 3- and 4-tetrahydropyranylene (O at position 3 or 4 relative to the spiro carbon atom); 3- and 4-tetrahydrothiopyranylene; 3- and 4-oxepanylene; 3- and 4-thiepanylene; 3-oxetanylene; 3-thietanylene; 3-tetrahydrofuranylene; 3-tetrahydrothienylene; 3-, 4-, and 5-oxocanylene; 3-, 4-, and 5-thiocanylene; 3,4-dithiolanylene; 3,4-oxathiolanylene; 3,5-dioxanylene; 3,4- and 3,5-dithianylene; 3,4-, 3,5-, and 4,3-oxathianylene; 3,5- and 3,6-dioxepanylene; 3,4-, 3,5-, 3,6-, and 4,5-dithiepanylene; 3,4-, 3,5-, 3,6-, 4,5-, 4,3-, and 4,2-oxathiepanylene; 3,5-, 3,6-, 3,7-, and 4,6-dioxocanylene; 3,3-, 3,4-, 3,5-, 3,6, 3,7-, 4,5-, and 4,6-dithiocanylene; and 3,4-, 3,5-, 3,6-, 3,7-, 4,5-, 4,6, 4,7-, 4-3-, 5,4-, and 5,3-oxathiocanylene, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$. In one embodiment of the spiroquinoxaline derivative of formula (O/S-I), ring A is selected from the group consisting of 4-tetrahydropyranylene, 4-tetrahydrothiopyranylene, 3-tetrahydropyranylene, 3-tetrahydrothiopyranylene, 4-oxepanylene, 4-thiepanylene, 3-oxepanylene, 3-thiepanylene, 3-oxetanylene, 3-thietanylene, 3-tetrahydrofuranylene, 3-tetrahydrothienylene, 5-oxocanylene, 5-thiocanylene, 4-oxocanylene, and 4-thiocanylene (such as -tetrahydropyranylene, 4-tetrahydrothiopyranylene, 3-tetrahydropyranylene, 3-tetrahydrothiopyranylene, 4-oxepanylene, 4-thiepanylene, 3-oxepanylene, and 3-thiepanylene), each of which is optionally substituted with one or more (such as 1 to the maximum number of hydrogen atoms bound to ring A, e.g., 1, 2, 3, 4, 5, 6, 7, 8, 9, or up to 10, such as between 1 to 1 to, to 4, or 1 to 3, or 1 or 2) independently selected $R^9$.

In any of the above embodiments of the spiroquinoxaline derivative of formula (O/S-II), ring A may be unsubstituted.

In any of the above embodiments of the spiroquinoxaline derivative of formula (O/S-1), wherein ring A is substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$, either (i) only one or more (preferably, 1 or 2) ring sulfur atoms of ring A are substituted with independently selected $R^4$, or (ii) only one or more (preferably, 1, 2, or 3) ring carbon atoms of ring A are substituted with independently selected $R^9$, or (iii) one or more (preferably, 1 or 2) ring sulfur atoms and one or more (preferably, 1, 2, or 3) ring carbon atoms of ring A (e.g., 1 or 2 ring sulfur atoms and 1 or 2 ring carbon atoms) are substituted with independently selected $R^9$. For example, if ring A contains 1 ring sulfur atom, ring A may be substituted (i) only at the ring sulfur atom with $R^9$ (preferably, the ring sulfur atom is at position 3 if ring A is 4- or 5-membered; at position 3 or 4 (preferably 4) if ring A is 6- or 7-membered; or at position 3, 4, or 5 (preferably 4 or 5) if ring A is 8-membered); (ii) only at 1 or 2 ring carbon atoms of ring A each with 1 or 2 independently selected $R^9$; or (iii) at the ring sulfur atom with R (preferably, the ring sulfur atom is at position 3 if ring A is 4- or 5-membered; at position 3 or 4 (preferably 4) if ring A is 6- or 7-membered; or at position 3, 4, or 5 (preferably 4 or 5) if ring A is 8-membered) and at 1 or 2 ring carbon atoms of ring A each with 1 or 2 independently selected $R^9$.

In any of the above embodiments of the spiroquinoxaline derivative of formula (O/S-II), wherein $R^9$ substitutes a hydrogen atom bound to a ring carbon atom of ring A, each such $R^9$ may be independently selected from the group consisting of $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —OR$^{11}$, —N(R$^{12}$)(R$^{13}$), —S(O)$_{1-2}$R$^{11}$, —S(O)$_{1-2}$N(R$^{12}$)(R$^{13}$), —N(R$^{11}$)S(O)$_{1-2}$R$^{11}$, —NR$^{11}$ S(O)$_{1-2}$ (R$^{12}$)(R$^{13}$), —C(=X)R$^{11}$, —C(=X)XR$^{11}$, —XC(=X)R$^{11}$, and —XC(=X)XR$^{11}$, wherein each of the $C_{1-6}$ alkyl, $C_{2-6}$ alkenyl, $C_{2-6}$alkyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, and/or any two $R^9$ which are bound to the same carbon atom of ring A may join together to form =X. In any of the above embodiments of the spiroquinoxaline derivative of formula (O/S-I), wherein $R^9$ substitutes a hydrogen atom bound to a ring carbon atom of ring A, each such $R^9$ may be independently selected from the group consisting of $C_{1-4}$alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=O)R^{11}$, —$C(=O)OR^{11}$, —$C(=O)SR^{11}$, —$C(=O)N(R^{14})(R^{11})$, —$C(=S)OR^{11}$, —$N(R^{14})C(=O)R^{11}$, —$OC(=O)R^{11}$, —$OC(=S)R^{11}$, —$N(R^{14})C(=O)N(R^{14})(R^{11})$, and —$N(R^{14})C(=N(R^{14}))N(R^{14})(R^{11})$, wherein each of the $C_{1-4}$alkyl, $C_{2-4}$ alkylenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$, and/or any two $R^9$ which are bound to the same carbon atom of ring A may join together to form =O or =S. In one embodiment, each $R^9$ when substituting a hydrogen atom bound to a ring carbon atom of ring A is independently selected from the group consisting of $C_{1-4}$ alkyl; $C_{1-4}$ alkyl substituted with 1 substituent selected from the group consisting of —OH, —$O(C_{1-3}$ alkyl), —$NH_{2-z}(CH_3)_z$, morpholinyl (e.g., 4-morpholinyl), piperazinyl (e.g., 1-piperazinyl), and N-methylpiperazinyl (e.g., 4-methylpiperazin-1-yl); $C_{1-4}$alkyl substituted with 1, 2, or 3 halogen (preferably F), such as —$CF_3$, —$CH_2CF_3$, —$CH_2CHF_2$, or —$CH_2CH_2F$; —$O(C_{1-4}$alkyl substituted with 1, 2, or 3 halogen (preferably F)), such as —$OCF_3$, —$OCH_2CF_3$, —$OCH_2CHF_2$, or —$OCH_2CH_2F$; cyclopropyl; 4-morpholinyl; hornomorpholinyl; 4-piperidinyl; homopiperidinyl; 4-piperazinyl; homopiperazinyl; 4-methyl-piperazin-1-yl; N-methyl-homopiperazinyl; halogen; —CN; —OH; =O; —$O(C_{1-3}$ alkyl optionally substituted with —$NH_{2-z}(C_3)$); —$N_2$; —$(C_{1-3}$ alkyl); —$N(C_{1-3}$ alkyl)$_2$; —$S(C_{1-3}$ alkyl); —$S(O)_2(C_{1-3}$ alkyl optionally substituted with —$NH_{2-z}(CH_3)_z$); —$S(O)_{2-z}(C_{1-3}$ alkyl)$_z$; —$NHS(O)_2CH_3$ alkyl optionally substituted with —$NH_{2-z}(CH_3)_z$); —$C(=O)(C_{1-3}$ alkyl optionally substituted with —$NH_{2-z}(CH_3)_z$); —$C(=O)OH$; —$C(=O)O(C_{1-3}$ alkyl); —$C(=O)NH_{2-z}(C_{1-3}$ alkyl)$_z$; —$NHC(=O)(C_{1-3}$ alkyl optionally substituted with —$NH_{2-z}(CH_3)_z$); —$NHC(=O)NH_{2-z}(CH_3)$; —$NHC(=NH)NH_{2-2}(C_{1-3}$ alkyl)$_z$; and —$N(C_{1-3}$ alkyl)$C(=NH)NH_{2-z}(C_{1-3}$ alkyl)$_z$, wherein z is 0, 1, or 2 and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; tert-butyl; cyclopropyl; —$(CH_2)_d$—$NH_{2-z}(CH_3)_z$; —$O(CH_2)_d$—$NH_{2-z}(CH_3)_z$; —$(CH_2)_d$—$O(CH_3)$; —$CF_3$; —$CH_2CF_3$; —$CH_2CHF_2$; —$CH_2CH_2F$; —$(CH_2)_d$-(4-morpholinyl); —$(CH_2)_d$-(1-piperazinyl); —$(CH_2)_d$-(4-methyl-piperazin-1-yl); 4-morpholinyl; 4-piperazinyl; 4-methyl-piperazin-1-yl; halogen (in particular, —F, —Cl, —Br); —$NHC(=O)(C_{1-3}$ alkyl optionally substituted with —$NH_{2-z}(C_3)_z$); —$NHC(=O)NH_{2-z}(CH_3)_z$; —$NHS(O)_2(C_{1-3}$ alkyl optionally substituted with —$NH_{2-z}(CH_3)_z$), —$C(=O)CH_3$; —$C(=O)CH_2NH_{2-z}(C_3)_z$; —$C(=O)NH_{2-z}(C_{1-3}$ alkyl)$_z$; —$S(O)_2(C_{1-3}$ alkyl); —$S(O)_2(CH_2)_dNH_{2-z}(CH_3)_z$; —OH; and —$O(C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; cyclopropyl; —$(CH_2)_d$—$NH_{2-z}(CH_3)_z$; —$(CH_2)_d$—$O(CH_3)$; —$CF_3$; —$CH_2CF_3$; —$CH_2CH_2$; —$CH_2CH_2F$; —$N_2$; —$N(C_{1-3}$ alkyl); —$N(C_{1-3}$ alkyl)$_2$; halogen (in particular, —F, —Cl, —Br); —$C(=O)CH_3$; —$C(=O)CH_{2-z}(C_3)_z$; —$C(=O)NH_{2-z}(C_{1-3}$ alkyl)$_z$; —$S(O)_2(C_{1-3}$ alkyl); —$S(O)_2(CH_2)_dNH_{2-z}(CH_3)_z$; —OH; and —$O(C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; cyclopropyl; —$(CH_2)_d$—$NH_{2-z}(CH_3)_z$; —$(CH_2)_d$—$O(CH_3)$; —$CF_3$; —$CH_2CF_3$; —$CH_2CHF_2$; —$CH_2CH_2F$; halogen (in particular, —F, —Cl, —Br); —$C(=O)CH_3$; —$C(=O)CH_2NH_2°(C_3)_z$; —$C(=O)NH_{2-z}(C_{1-3}$ alkyl); —$S(O)_2(C_{1-3}$ alkyl); —$S(O)_2(CH_2)_dNH_{2-z}(CH_3)_z$; —OH; and —$O(C_{1-3}$ alkyl), wherein z is 0, 1, or 2; d is 1, 2, or 3; and $C_{1-3}$ alkyl is methyl, ethyl, propyl or isopropyl. In one embodiment, the ring carbon atoms of ring A are unsubstituted or each $R^9$ substituting a hydrogen atom bound to a ring carbon atom is independently selected from the group consisting of $C_{1-4}$ alkyl (in particular methyl), —$N(R^{12})(R^{13})$(in particular $NH_2$), and —$N(R^{14})C(=O)R^{11}$ (in particular $NHC(O)CH_3$). In one embodiment, the ring carbon atoms of ring A are unsubstituted or one ring carbon atom of ring A is substituted with one $R^9$ being $NH_2$ or $CH_3$, or with two $R^9$ being $CH_3$.

In any of the above embodiments of the spiroquinoxaline derivative of formula (O/S-II), wherein $R^9$ is bound to a ring sulfur atom of ring A, each such $R^9$ may be independently selected from the group consisting of $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, —$OR^{11}$, and =O, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{31}$. In any of the above embodiments of the spiroquinoxaline derivative of formula (O/S-II), wherein $R^9$ is bound to a ring sulfur atom of ring A, each such $R^9$ may be independently selected from the group consisting of $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, —$OR^{11}$, and =O, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment, each $R^9$ when bound to a ring sulfur atom of ring A is independently selected from the group consisting of methyl, ethyl, $C_{1-3}$ alkyl, $C_4$ alkyl, —$OR^{11'}$, and =O, wherein $R^{11'}$ is selected from the group consisting of —H, $C_{1-6}$ alkyl, $C_{2-6}$ alkenyl, $C_{2-6}$ alkynyl, 3- to 7-membered cycloalkyl, 5- or 6-membered aryl (e.g., phenyl), 5- or 6-membered heteroaryl, and 3- to 7-membered heterocyclyl, wherein each of the methyl, ethyl, $C_{1-3}$ alkyl, $C_{1-4}$ alkyl, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with 1, 2, or 3 independently selected $R^{30'}$ ($R^{30'}$ is a $1^{st}, 2^{nd}$, or $3^{rd}$ level substituent as specified above (in particular one of the typical $1^{st}, 2^{nd}$, or $3^{rd}$ level substituents as specified above) and, in each case, may be selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$SCH_3$, —$NH_{2-z}(CH_3)_z$, —C(=O)OH, and —C(=O)OCH_3, wherein z is 0, 1, or 2). In one embodiment, each $R^9$ when bound to a ring sulfur atom of ring A is independently selected from the group consisting of methyl; ethyl; isopropyl; benzyl; —OH; =O; and —O($C_{1-3}$ alkyl), wherein $C_{1-3}$ alkyl is methyl, ethyl, propyl or isopropyl. In one embodiment, the ring sulfur atom of ring A is unsubstituted or substituted with two =O groups. In one embodiment, the ring sulfur atom of ring A is unsubstituted or ring A contains one sulfur atom which is substituted with two =O groups (i.e., ring A contains the group —S(=O)$_2$—).

In one embodiment, the spiroquinoxaline derivative has the general formula (O/S-III)

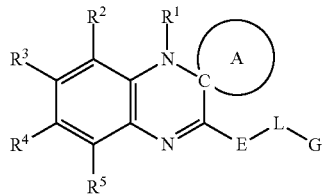

(O/S-III)

wherein $R^1$ to $R^5$, ring A, E, and G are as defined above (in particular with respect to formulas (O/S-I) and (O/S-II)) or below and L is selected from the group consisting of $C_{1-6}$ alkylene, $C_{2-6}$ alkenylene, $C_{2-6}$ alkynylene, —$(CH_2)_a$-cyclopropylene-$(CH_2)_b$—, wherein each of a and b is independently selected from an integer between 0 and 3, and —$(CH_2)_m$—[Y—$(CH_2)_n]_o$—, wherein m is 1, 2, or 3, n is 0, 1, or 2, o is 1, 2, or 3, wherein if n is 0 then o is 1; Y is independently selected from O, S, and —N($R^{7'}$)—, wherein $R^{7'}$ is selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, 3- to 7-membered heterocyclyl, —$OR^{11}$, and —$NHR^{20}$ wherein each of the $C_{1-6}$ alkylene, $C_{2-6}$ alkenylene, $C_{2-6}$ alkynylene, 1,1-cyclopropylene, —$(CH_2)_m$—, —$(CH_2)_n$—, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one or more (such as 1 to the maximum number of hydrogen atoms bound to the $C_{1-6}$ alkylene, $C_{2-6}$ alkenylene, $C_{2-6}$ alkynylene, 1,1-cyclopropylene, —$(CH_2)_m$—, —$(CH_2)_n$—, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment of the spiroquinoxaline derivative of formula (O/S-III), $R^1$ to $R^5$, ring A, E, and G are as defined above (in particular with respect to formulas (O/S-I) and (O/S-II)) or below and L is selected from the group consisting of $C_{1-4}$ alkylene, $C_{2-4}$ alkenylene, $C_{2-4}$ alkynylene, —$(CH_2)_a$-1,1-cyclopropylene-$(CH_2)_b$—, wherein each of a and b is independently selected from 0, 1, and 2, and —$(CH_2)_m$—[Y—$(CH_2)_n]_o$—, wherein m is 1, 2, or 3, n is 0, 1, or 2, o is 1, 2, or 3, wherein if n is 0 then o is 1; Y is independently selected from O, S, and —N($R^7$)—, wherein $R^7$ is selected from the group consisting of —H, $C_{1-3}$ alkyl, 3-, 5-, 6- or 7-membered cycloalkyl, 6-membered aryl, 5- or 6-membered heteroaryl, 3-, 5-, 6- or 7-membered heterocyclyl, —O($C_{1-3}$ alkyl), and —$NHR^{20}$, wherein each of the $C_{1-4}$alkylene, $C_{2-4}$ alkenylene, $C_{2-4}$ alkynylene, 1,1-cyclopropylene, —$(CH_2)_m$—, —$(CH_2)_n$—, $C_{1-3}$ alkyl, 3-, 5-, 6- or 7-membered cycloalkyl, 6-membered aryl, 5- or 6-membered heteroaryl, and 3-, 5-, 6- or 7-membered heterocyclyl groups is optionally substituted with 1, 2, or 3 independently selected $R^{30}$. In one embodiment of the spiroquinoxaline derivative of formula (O/S-III), $R^1$ to $R^5$, ring A, E, and G are as defined above (in particular with respect to formulas (O/S-I) and (O/S-II)) or below and L is selected from the group consisting of $C_{1-3}$ alkylene, —$(CH_2)_a$-1,1-cyclopropylene-$(CH_2)_b$—, wherein each of a and b is independently selected from 0 and 1, and —$(CH_2)_m$—[Y—$(CH_2)_n]_o$—, wherein m is 1 or 2, n is 0, 1, or 2, o is 1 or 2, wherein if n is 0 then o is 1; Y is O, wherein each of the $C_{1-3}$ alkylene, 1,1-cyclopropylene, —$(CH_2)_m$—, and —$(CH_2)_n$— groups is optionally substituted with 1, 2, or 3 independently selected $R^{30}$. In one embodiment of the spiroquinoxaline derivative of formula (O/S-I), $R^1$ to $R^5$, ring A, E, and G are as defined above (in particular with respect to formulas (O/S-I) and (O/S-II)) or below and L is selected from the group consisting of methylene; 1,1-ethylene; 1,2-ethylene (optionally substituted with one $R^{30}$ (such as phenyl) at position 2); trimethylene (—$(CH_2)_3$—); 2,2-propylene (—$C(CH_3)_2$—); 2,4-butanediyl; -1,1-cyclopropylene-; —$(CH_2)$-1,1-cyclopropylene; -1,1-cyclopropylene-$(C_2)$—; —$(CH_2)$-1,1-cyclopropylene-$(CH_2)$—; —$CH_2O$—; —$(CH_2)_2O$—; and —$(CH_2)_3O$— (such as methylene; 1,1-ethylene; 1,2-ethylene; trimethylene (—$(CH_2)_3$—); 2,2-propylene (—$C(CH_3)_2$—); 1,1-cyclopropylene; and —$(CH_2)_2O$—, in particular, methylene). In one embodiment of the spiroquinoxaline derivative of formula (O/S-I), $R^1$ to $R^5$, ring A, E, and G are as defined above (in particular with respect to formulas (O/S-I) and (O/S-II)) or below and L is selected from the group consisting of methylene; 1,1-ethylene; 1,2-ethylene; trimethylene (—$(CH_2)_3$—); 2,2-propylene (—$C(CH_3)_2$—); -1,1-cyclopropylene-; —$(CH_2)$-1,1-cyclopropylene;-1,1-cyclopropylene-$(CH_2)$—; —$(CH_2)$-1,1-cyclopropylene-$(CH_2)$—; —$CH_2O$—; —$(CH_2)_2O$—; and —$(CH_2)_3O$— (such as methylene; 1,1-ethylene; 1,1-ethylene; 1,2-ethylene; trimethylene (—$(CH_2)_3$—): 2,2-propylene (—$C(CH_3)_2$—); 1,1-cyclopropylene; and —$(CH_2)_2O$—, in particular, methylene). In one embodiment of the spiroquinoxalne derivative of formula (O/S-III), $R^1$ to $R^5$, ring A, E, and G are as defined above (in particular with respect to formulas (O/S-I) and (O/S-1)) or below and L is selected from the group consisting of $C_1$ alkylene, $C_2$ alkylene (in particular 1,2-ethylene or 1,1-ethylene), $C_{1-3}$ alkylene (in particular trimethylene), and $C_4$ alkylene (in particular tetramethylene or 2,4-butanediyl), each of which being optionally substituted with one $R^{30}$. In one embodiment of the spiroquinoxaline derivative of formula (O/S-III), $R^1$ to $R^5$ ring A, E, and G are as defined above (in particular with respect to formulas (O/S-I) and (O/S-II)) or below and L is selected from the group consisting of methylene, 1,1-ethylene, 1,2-ethylene, trimethylene, tetramethylene, 2,4-butanediyl, and 2-phenyl-1,2-ethylene (—CH$_2$—C(C$_6$H$_5$)—). In one embodiment of the spiroquinoxaline derivative of formula (O/S-III), R$^1$ to R$^5$, ring A, E, and G are as defined above (in particular with respect to formulas (O/S-I) and (O/S-II)) or below and L is selected from the group consisting of methylene and 2-phenyl-1,2-ethylene (—CH$_2$—CH(C$_6$H$_5$)—).

In one embodiment, the spiroquinoxaline derivative has the general formula (O/S-IV)

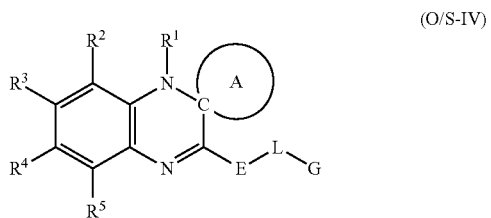

(O/S-IV)

wherein R$^1$ to R$^5$, ring A, E, and L are as defined above (in particular with respect to formulas (O/S-I), (O/S-II) and (O/S-III)) or below and G is phenyl which is either unsubstituted or substituted with 1, 2, 3, 4 or 5 (such as between 1 to 4, or 1 to 3, or 1 or 2) independently selected R$^8$. In any of the above embodiments (including those of formulas (O/S-I) to (O/S-II)), wherein G is substituted, R$^8$ may be, in each case, selected from the group consisting of C$_{1-6}$ alkyl, C$_{2-6}$ alkenyl, C$_{2-6}$alkynyl, 5- or 6-membered aryl, 5- or 6-membered heteroaryl, 3- to 7-membered cycloalkyl, 3- to 7-membered heterocyclyl, halogen, —CN, —OR$^{11}$, —N(R$^{12}$)(R$^{13}$), —S(O)$_{0-2}$R$^{11}$, —S(O)$_{0-2}$N(R$^{12}$)(R$^{13}$), —N(R$^{11}$)S(O)$_{1-2}$R$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the C$_{1-6}$ alkyl, C$_{2-6}$ alkenyl, C$_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the C$_{1-6}$ alkyl, C$_{2-6}$ alkenyl, C$_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected R$^{30}$. In one embodiment of the spiroquinoxaline derivative of formula (O/S-IV), R$^1$ to R$^5$, ring A, E, and L are as defined above (in particular with respect to formulas (O/S-I), (O/S-II) and (O/S-II)) or below and R$^8$ is, in each case, selected from the group consisting of C$_{1-4}$ alkyl, C$_{2-4}$ alkenyl, C$_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —OR$^{11}$, —N(R$^{12}$)(R$^{13}$), —S(O)$_{0-2}$R$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$N(R$^{12}$)(R$^{13}$), —C(=O)R$^{11}$, —C(=O)OR$^{11}$, —C(=O)SR$^{11}$, —C(=O)N(R$^{14}$)(R$^{11}$), —C(=S)OR$^{11}$, —N(R$^{14}$)C(=O)R$^{11}$, —OC(=O)R$^{11}$, —OC(=S)R$^{11}$, —N(R$^{14}$)C(=O)N(R$^{14}$)(R$^{11}$) and —N(R$^{14}$)C(=N(R$^{14}$))N(R$^{14}$)(R$^{11}$), wherein each of the C$_{1-4}$ alkyl, C$_{2-4}$ alkenyl, C$_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2 or 3 independently selected R$^{30}$. In one embodiment of the spiroquinoxaline derivative of formula (O/S-IV), R$^1$ to R$^5$, ring A, E, and L are as defined above (in particular with respect to formulas (O/S-I), (O/S-II) and (O/S-III)) or below and R$^8$ is, in each case, selected from the group consisting of C$_{1-4}$ alkyl; C$_{1-4}$ alkyl substituted with 1 substituent selected from the group consisting of —OH, —O(C$_{1-3}$ alkyl), and NH$_{2-z}$(CH$_3$); C$_{1-4}$ alkyl substituted with 1, 2, or 3 halogen (preferably F), such as —CF$_3$, —CH$_2$CF$_3$, —CH$_2$CF$_2$, or —CH$_2$CH$_2$F; phenyl; cyclopropyl; 5-membered heterocyclyl (such as pyrrolidinyl); 4-morpholinyl; homomorpholinyl; 4-piperidinyl; homopiperidinyl; 4-piperazinyl; homopiperazinyl; N-methyl-piperazin-4-yl; N-methyl-homopiperazinyl; halogen; —CN; —OH; —O(C$_{1-3}$ alkyl); —O(C$_{1-4}$ alkyl substituted with 1, 2, or 3 halogen (preferably F)), such as —OCF$_3$, —OCH$_2$CF$_3$, —OCH$_2$CHF$_2$, or —OCH$_2$CH$_2$F; —O-phenyl; —NH$_2$; —NH(C$_{1-3}$ alkyl); N(C$_{1-3}$ alkyl)$_2$; —S(C$_{1-3}$ alkyl); —S(O)$_2$(C$_{1-3}$ alkyl optionally substituted with —NH$_{2-z}$(CH$_3$)$_z$); —S(O)$_2$NH$_{2-z}$(C$_{1-3}$ alkyl)$_z$; —NHS(O)$_2$(C$_{1-3}$ alkyl); —C(=O)(C$_{1-3}$ alkyl optionally substituted with —NH$_{2-z}$(CH$_3$)$_z$); —C(=O)OH; —C(=O)O(C$_{1-3}$ alkyl); —C(=O)NH$_{2-z}$(C$_{1-3}$ alkyl)$_z$; —NHC(=O)(C$_{1-3}$ alkyl); —NHC(=NH)NH$_{2-z}$(C$_{1-3}$ alkyl)$_z$; and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl and each of the phenyl, cyclopropyl, 5-membered heterocyclyl (such as pyrrolidinyl), 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of C$_{1-3}$ alkyl, halogen, —CF$_3$, —OCF$_3$, —OH, —OCH$_3$, —SCH$_3$, —NH$_{2-z}$(CH$_{1-3}$), —C(=O)OH, and —C(=O)OCH$_3$, wherein z is 0, 1, or 2. In one embodiment, each R$^8$ is independently selected from the group consisting of methyl; ethyl; isopropyl; tert-butyl; phenyl; cyclopropyl; pyrrolidinyl (such as 4-pyrrolidinyl); —(CH$_2$)$_d$—NH$_{2-z}$(CH$_3$)$_z$; —(CH$_2$)$_d$—O(CH$_3$); —CF$_3$; —OCF$_3$; —O-phenyl; —CH$_2$CF$_3$; —CH$_2$CHF$_2$; —CH$_2$CH$_2$F; halogen (in particular, —F, —Cl, —Br); —CN; —NH$_2$; —NH(C$_{1-3}$ alkyl); —N(C$_{1-3}$ alkyl)$_2$; —C(=O)CH$_3$; —C(=O)CH$_2$NH$_{2-z}$(CH$_3$)$_z$; —C(=O)OH; —C(=O)O(C$_{1-3}$ alkyl); —C(=O)NH$_{2-z}$(C$_{1-3}$ alkyl)$_z$; —NHC(=O)(C$_{1-3}$ alkyl); —S(O)$_2$(C$_{1-3}$ alkyl); —S(O)$_2$(CH$_2$)$_d$NH$_{2-z}$(CH$_3$)$_z$; —OH; and —O(C$_{1-3}$ alkyl), wherein z is 0, 1, or 2, d is 1, 2, or 3, and C$_{1-3}$ alkyl is methyl, ethyl, propyl or isopropyl.

In one embodiment, each R$^8$ is independently selected from the group consisting of methyl; ethyl; isopropyl; phenyl; cyclopropyl; pyrrolidinyl (such as 4-pyrrolidinyl); —(CH$_2$)$_d$—NH$_{2-z}$(CH$_3$)$_z$; —(CH$_2$)$_d$—O(CH$_3$); —CF$_3$; —OCF$_3$; —O-phenyl; —CH$_2$CF$_3$; —CH$_2$CHF$_2$; —CH$_2$CH$_2$F; halogen (in particular, —F, —Cl, —Br); —CN; —NH$_2$; —(C$_{1-3}$ alkyl); —N(C$_{1-3}$ alkyl)$_2$; —C(=O)CH$_3$; —C(=O)CH$_2$NH$_{2-z}$(CH$_3$)$_z$; —C(=O)OH; —C(=O)O(C$_{1-3}$ alkyl); —C(=O)NH$_{2-z}$(C$_{1-3}$ alkyl)$_z$.; —NHC(=O)(C$_{1-3}$ alkyl); —S(O)$_2$(C$_{1-3}$ alkyl); —S(O)$_2$(CH$_2$)$_d$NH$_{2-z}$(CH$_3$)$_z$; —OH; and —O(C$_{1-3}$ alkyl), wherein z is 0, 1, or 2, d is 1, 2, or 3, and C$_{1-3}$ alkyl is methyl, ethyl, propyl or isopropyl. In one embodiment of the spiroquinoxaline derivative of formula (O/S-IV), R$^1$ to R$^5$, ring A, E, and L are as defined above (in particular with respect to formulas (O/S-I), (O/S-II) and (O/S-II)) or below and G is either unsubstituted or substituted with 1, 2, or 3 R$^8$, wherein R$^8$ is, in each case, selected from the group consisting of C$_{1-4}$ alkyl (in particular methyl or tert-butyl); halogen (in particular F or Cl); —OR$^{11}$ (in particular —OCH$_3$); and C$_{1-4}$ alkyl substituted with 1, 2, or 3 independently selected R$^{30}$ (in particular —CF$_3$). In one embodiment of the spiroquinoxaline derivative of formula (O/S-IV), $R^1$ to $R^5$, ring A, E, and L are as defined above (in particular with respect to formulas (O/S-I), (O/S-n) and (O/S-II)) or below and G is either unsubstituted or substituted with 1 or 2 $R^8$ each independently selected from the group consisting of methyl, F, Cl, —OCH$_3$, and —CF$_3$. In one embodiment of the spiroquinoxaline derivative of formula (O/S-IV), $R^1$ to $R^5$, ring A, E, and L are as defined above (in particular with respect to formulas (O/S-I), (O/S-II) and (O/S-II)) or below and G is selected from the group consisting of unsubstituted phenyl, fluorophenyl (in particular 3-fluorophenyl), chlorophenyl (in particular 2-, 3- or 4-chlorophenyl), methylphenyl (in particular 2- or 3-methylphenyl), tert-butylphenyl (in particular 4-tert-butylphenyl), methoxyphenyl (in particular 3-methoxyphenyl), (trifluoromethyl)phenyl (in particular 3- or 4-(trifluoromethyl)phenyl), difluorophenyl (in particular 2,4- or 2,6-difluorophenyl), dichlorophenyl (in particular 2,4- or 3,4-dichlorophenyl), chlorofluorophenyl (in particular 4-chloro-2-fluorophenyl), and dimethylphenyl (in particular 3,5-dimethylphenyl). In one embodiment of the spiroquinoxaline derivative of formula (O/S-IV), $R^1$ to $R^5$, ring A, E, and L are as defined above (in particular with respect to formulas (O/S-I), (O/S-II) and (O/S-UI)) or below and G is selected from the group consisting of unsubstituted phenyl, 2-chlorophenyl, 3-chlorophenyl, 4-chlorophenyl, 3-methylphenyl, 3-(trifluoromethyl)phenyl, 2,6-difluorophenyl, 3,4-dichlorophenyl, 4-chloro-2-fluorophenyl, and 3,5-dimethylphenyl.

In one embodiment, the spiroquinoxaline derivative has the general formula (O/S-V)

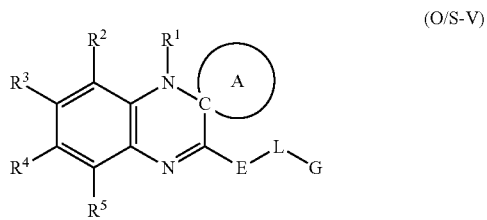

(O/S-V)

wherein $R^1$, ring A, E, L and G are as defined above (in particular with respect to formulas (O/S-I), (O/S-II), (O/S-III) and (O/S-V)) or below and each of $R^2$, $R^3$, $R^4$, and $R^5$ is H. In one embodiment of the spiroquinoxaline derivative of formula (O/S-V), $R^1$, ring A, E, L and G are as defined above (in particular with respect to formulas (O/S-I), (O/S-II), (O/S-III) and (O/S-IV)) or below and at least one of $R^2$, $R^3$, $R^4$, and $R^5$ is different from H. For example, in one embodiment $R^2$ is different from H and each of $R^3$, $R^4$, and $R^5$ is H; or $R^3$ is different from H and each of $R^2$, $R^1$, and $R^5$ is H; or $R^4$ is different from H and each of $R^2$, $R^3$, and $R^1$ is H; or $R^3$ is different from H and each of $R^2$, $R^3$, and $R^4$ is H; or both of $R^2$ and $R^5$ are different from H and both of $R^4$ and $R^5$ are H; or both of $R^2$ and R are different from H and both of $R^3$ and $R^5$ are H; or both of $R^2$ and $R^5$ are different from H (preferably in this embodiment $R^2$ and R are the same) and both of $R^3$ and $R^4$ are H; or both of $R^3$ and $R^4$ are different from H (preferably in this embodiment $R^3$ and $R^4$ are the same) and both of $R^2$ and $R^5$ are H; or each of $R^1$, $R^3$, and $R^4$ is different from H and $R^5$ is H; or each of $R^2$, $R^3$, and $R^5$ is different from H and $R^4$ is H; or each of $R^2$, $R^4$, and $R^5$ is different from H and R is H; or each of R, R, and $R^5$ is different from H and $R^2$ is H; or each of $R^2$, $R^3$, $R^4$, and R is different from H. In any of the above embodiments, it is preferred that $R^2$ and $R^1$ are the same and/or $R^1$ and $R^4$ are the same.

In any of the above embodiments (in particular with respect to formulas (O/S-I), (O/S-II), (O/S-III), (O/S-IV), and (O/S-V)), each of $R^2$ to $R^1$, if it does not join together with another of $R^2$ to $R^5$ to form a ring, is independently selected from the group consisting of —H, $C_{1-6}$alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —OR$^{11}$, —N(R$^{12}$)(R$^{13}$), —S(O)$_{0-2}$R$^{11}$, —S(O)$_{1-2}$N(R$^{12}$)(R$^{13}$), —N(R$^{11}$)S(O)$_{1-2}$ R$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 2, 3, 4, 5, 6, 7, 8, 9, or up to 10, such as between 1 to 5, 1 to 4, or 1 to 3, or 1 or 2) independently selected R$^{30}$. In one embodiment, each of $R^2$, $R^3$, $R^4$, and $R^5$, if it does not join together with another of $R^2$ to $R^5$ to form a ring, may be independently selected from the group consisting of —H, $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —OR$^{11}$, —N(R$^{12}$)(R$^{13}$), —S(O)$_{0-2}$R$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$N(R$^{12}$)(R$^{13}$), —C(=O)R, —C(=O)OR$^{11}$, —C(=O)SR$^{11}$, —C(=O)N(R$^{14}$)(R$^{11}$), —C(=S)OR$^{11}$, —N(R$^{14}$)C(=O)R, —OC(=O) R, —OC(=S)R$^{11}$, —N(R$^{14}$)C(=O)N(R$^{14}$)(R$^{11}$) and —N(R$^{14}$)C(=N(R$^{14}$))N(R$^{14}$)(R$^{11}$), wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected R$^{30}$. In one embodiment of the spiroquinoxaline derivative of formula (O/S-V), $R^1$, ring A, E, L and G are as defined above (in particular with respect to formulas (O/S-I), (O/S-II), (O/S-III), and (O/S-V)) or below and each of $R^2$, $R^3$, $R^4$, and $R^5$, if it does not join together with another of $R^2$ to $R^5$ to form a ring, is independently selected from the group consisting of H; $C_{1-4}$ alkyl; $C_{1-4}$alkyl substituted with 1 substituent selected from the group consisting of —OH, —O($C_{1-3}$ alkyl), and —NH$_{2-z}$(CH$_3$)$_z$; $C_{1-4}$ alkyl substituted with 1, 2, or 3 halogen (preferably F), such as —CF$_3$, —CH$_2$CF$_3$, —CH$_2$CHF$_2$, or —CH$_2$CH$_2$F; phenyl; cyclopropyl; 5-membered heterocyclyl; 4-morpholinyl; homomorpholinyl; 4-piperidinyl; homopiperidinyl; 4-piperazinyl; homopiperazinyl; N-methyl-piperazin-4-yl, N methyl-homopiperazinyl; halogen; —CN; —OH; —O($C_{1-3}$ alkyl); —O($C_{1-4}$alkyl substituted with 1, 2, or 3 halogen (preferably F)), such as —OCF$_3$, —OCH$_2$CF$_3$, —OCH$_2$CHF$_2$, or —OCH$_2$CH$_2$F; —O-phenyl; —NH$_2$; —N($C_{1-3}$ alkyl); —N($C_{1-3}$ alkyl)$_2$; —S($C_{1-3}$ alkyl); —S(O)$_2$($C_{1-3}$ alkyl optionally substituted with —NH$_{2-z}$(CH$_3$)$_z$); —S(O)$_2$NH$_{z-2}$($C_{1-3}$ alkyl)$_z$; —NHS(O)$_2$($C_{1-3}$ alkyl); —C(=O)($C_{1-3}$ alkyl optionally substituted with —NH$_{2-z}$(CH$_3$)$_z$); —C(=O)OH; —C(=O)O($C_{1-3}$ alkyl); —C(=O)NH$_2$ ($C_{1-3}$ alkyl); NHC (=O)($C_{1-3}$ alkyl); —NHC(=N$_z$)NH-2($C_{1-3}$ alkyl)$_z$; and —N($C_{1-3}$ alkyl)C(=NH)NH$_{z-2}$($C_{1-3}$ alkyl)$_z$, wherein z is 0, 1, or 2 and $C_{1-3}$ alkyl is methyl, ethyl, propyl or isopropyl and each of the phenyl, cyclopropyl, 5-membered heterocyclyl, 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of $C_{1-3}$ alkyl, halogen, —$CF_3$, —$OCF_3$, —OH, —$OCH_3$, —$SCH_3$, —$NH_{2-z}(CH_3)_z$, —C(=O)OH, and —C(=O)$OCH_3$, wherein z is 0, 1, or 2. In one embodiment, each of $R^2$, $R^3$, $R^4$, and $R^5$, if it does not join together with another of $R^2$ to $R^5$ to form a ring, is independently selected from the group consisting of H; methyl; ethyl; isopropyl; phenyl; cyclopropyl; —$(CH_2)_d$—$NH_{2-z}(CH_3)_z$; —$(CH_2)_d$—$O(CH_3)$; —$CF_3$; —$OCF_3$; —$CH_2CF_3$; —$CH_2CHF_2$; —$CH_2CH_2F$; halogen (in particular, —F, —Cl, —Br); —CN; —$NH_2$; —$NH(C_{1-3}$ alkyl); —$N(C_{1-3}$ alkyl$)_2$; —C(=O)$CH_3$; —C(=O)$CH_2NH_{2-z}(CH_3)_z$; —C(=O)($C_{1-3}$ alkyl); —C(=O)$NH_{2-z}(C_{1-3}$ alkyl$)_z$; —NHC(=O)($C_{1-3}$ alkyl); —S(O)$_2$($C_{1-3}$ alkyl); —S(O)$_2$$(CH_2)_d NH_{2-z}(CH_3)_z$; —OH, and —O($C_{1-3}$ alkyl), wherein z is 0, 1, or 2, d is 1, 2, or 3, and $C_{1-3}$ alkyl is methyl, ethyl, propyl or isopropyl. In one embodiment of the spiroquinoxaline derivative of formula (O/S-V), $R^1$, ring A, E, L and G are as defined above (in particular with respect to formulas (O/S-I), (O/S-II), (O/S-II), and (O/S-IV)) or below and $R^2$, $R^3$, $R^4$, and $R^5$ are independently selected from the group consisting of —H—, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H) In one embodiment of the spiroquinoxaline derivative of formula (O/S-V), $R^1$, ring A, E, L and G are as defined above (in particular with respect to formulas (O/S-I), (O/S-II), (O/S-III), and (O/S-IV)) or below and $R^2$, $R^3$, $R^4$, and $R^5$ are independently selected from the group consisting of —H, methyl, F, Cl, and $CF_3$ (in particular wherein $R^2$ and $R^5$ are each —H). In one embodiment of the spiroquinoxaline derivative of formula (O/S-V), $R^1$, ring A, E, L and G are as defined above (in particular with respect to formulas (O/S-I), (O/S-II), (O/S-III), and (O/S-IV)) or below and $R^2$ and $R^5$ are each —H; $R^3$ is selected from the group consisting of —H, methyl, F, and Cl; and $R^4$ is selected from the group consisting of —H, methyl, F, and Cl. In one embodiment of the spiroquinoxaline derivative of formula (O/S-V), $R^1$, ring A, E, L and G are as defined above (in particular with respect to formulas (O/S-I), (O/S-II), (O/S-III), and (O/S-IV)) or below and (i) $R^2$ to $R^5$ are each —H; or (ii) $R^2$ and $R^5$ are each —H, and both of $R^3$ and $R^4$ are F, Cl, or methyl.

In any of the above embodiments, wherein a ring is formed by (i) $R^2$ and $R^3$, (ii) $R^3$ and $R^4$, and/or (iii) $R^4$ and $R^5$, said ring preferably is a 3- to 7-membered ring (e.g., a ring having 5 or 6 members) which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$. The ring may be an aromatic, cycloaliphatic, heteroaromatic, or heterocyclic ring, wherein the heteroaromatic/heterocyclic ring contains 1 or 2 heteroatoms selected from the group consisting of O, S, and N($R^{40}$), wherein $R^{40}$ is selected from the group consisting of $R^{11}$, —$OR^{11}$, —$NH_yR^{20}_{2-y}$, and —S(O)$_{1-2}R^{11}$, wherein $R^{11}$, $R^{20}$, and y are as defined above. In one embodiment, the ring formed by (i) $R^2$ and $R^3$, (ii) $R^3$ and $R^4$, and/or (iii) $R^4$ and $R^5$ is a 5- or 6-membered aromatic, cycloaliphatic, heteroaromatic, or heterocyclic ring, wherein the heteroaromatic/heterocyclic ring contains 1 or 2 heteroatoms selected from the group consisting of O, S, and N, wherein at least one heteroatom is N. In one embodiment, the ring formed by (i) $R^2$ and $R^3$, (ii) $R^3$ and $R^4$, and/or (iii) $R^4$ and $R^5$ is selected from the group consisting of cyclopentadiene, furan, pyrrole, thiophene, imidazole, pyrazole, oxazole, isoxazole, thiazole, dioxole (e.g., 1,3-dioxole), benzene, pyridine, pyrazine, pyrimidine, pyridazine, dioxine (e.g., 1,4-dioxine), 1,2,3-triazine, 1,2,4-triazine, and di- or tetrahydro forms of each of the foregoing. In one embodiment, the ring formed (i) $R^2$ and $R^3$, (ii) $R^3$ and $R^4$, and/or (iii) $R^4$ and $R^5$ is cyclopentene (such as 2,3-dihydrocyclopentadiene), dioxole (such as 1,3-dioxole, optionally substituted at position 2 with one or two halogen atoms (such as F)), or dioxine (such as 2,3-dihydro-[1,4]-dioxine). In one embodiment, the total number of rings formed by (i) $R^2$ and $R^3$, (ii) $R^3$ and $R^4$, and/or (iii) $R^4$ and $R^5$ is 0 or 1. Thus, in the embodiment, wherein the total number of rings formed by (i) $R^2$ and $R^3$, (ii) $R^3$ and $R^4$, and/or (iii) $R^4$ and $R^1$ is 1, only two adjacent substituents (i.e., either (i) $R^2$ and $R^3$, (ii) $R^3$ and $R^4$, or (iii) $R^4$ and $R^5$) join together with the atoms to which they are attached to form a ring, wherein the ring is as defined in any of the above embodiments and the remaining of $R^2$ to $R^5$ are selected from the particular groups of moieties specified above for the situation that they do not join together to form a ring. For example, the remaining $R^2$ to $R^5$ which do not join together to form a ring may be selected from —H, $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —S(O)$_{0-2}R^{11}$, —S(O)$_{1-2}N(R^{12})(R^{13})$, —$N(R^{11})S(O)_{1-2}R^{11}$, —$NR^{11}$ S(O)$_{1-2}$ $N(R^{12})(R^{13})$, —C(=X)$R^{11}$, —C(=X)$XR^{11}$, —XC(=X)$R^{11}$, and —XC(=X)$XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In an alternative embodiment, $R^2$ to $R^5$ do not join together to form a ring.

In any of the above embodiments, $R^2$ and $R^5$ may be the same and/or $R^3$ and $R^4$ may be the same.

In one embodiment of the spiroquinoxaline derivative of formula (O/S-V), $R^1$, ring A, E, L and G are as defined above (in particular with respect to formulas (O/S-I), (O/S-II), (O/S-III), and (O/S-IV)) or below and $R^2$, $R^3$, $R^4$, and $R^5$ are independently selected from the group consisting of —H, $C_{1-4}$ alkyl, and halogen, wherein the $C_{1-4}$ alkyl is optionally substituted with 1, 2, or 3 independently selected $R^{10}$ (in particular wherein $R^2$ and $R^5$ are each —H), or $R^3$ and $R^4$ may join together with the atoms to which they are attached to form a 5- or 6-membered ring which is optionally substituted with one or two independently selected $R^{30}$. In one embodiment of the spiroquinoxaline derivative of formula (O/S-V), $R^1$, ring A, E, L and G are as defined above (in particular with respect to formulas (O/S-I), (O/S-II), (O/S-II), and (O/S-IV)) or below and $R^2$, $R^3$, $R^4$, and R are independently selected from the group consisting of —H, methyl, F, Cl, and $CF_3$ (in particular wherein $R^2$ and $R^5$ are each —H), or $R^3$ and $R^4$ may join together with the atoms to which they are attached to form a dioxole or dioxine ring which is optionally substituted with one or two independently selected halogens (in particular F). In one embodiment of the spiroquinoxaline derivative of formula (O/S-V), $R^1$, ring A, E, L and G are as defined above (in particular with respect to formulas (O/S-I), (O/S-II), (O/S-III), and (O/S-IV)) or below and $R^2$ and $R^5$ are each —H; $R^3$ is selected from the group consisting of —H, methyl, F, and Cl; and $R^4$ is selected from the group consisting of —H, methyl, F, and Cl; or $R^3$ and $R^4$ may join together with the atoms to which they are attached to form a dioxole (in particular 1,3-dioxole) or dioxine (in particular 2,3-dihydro-[1,4]-dioxine) ring, wherein the dioxole ring is optionally substituted with two F. In one embodiment of the spiroquinoxaline derivative of formula (O/S-V)R, ring A, E, L and G are as defined above (in particular with respect to formulas (O/S-I), (O/S-II), (O/S-III), and (O/S-IV)) or below and (i) R to $R^1$ are each —H; (ii) $R^2$ and $R^5$ are each —H, and both of R and $R^4$ are F, Cl, or methyl, or (iii) $R^2$ and $R^5$ are each —H, and $R^3$ and $R^4$ join together with the atoms to which they are attached to form a 2,2-difluoro-1,3-dioxole ring or a 2,3-dihydro-[1,4]-dioxine ring.

In any of the above embodiments (in particular with respect to formulas (O/S-I), (O/S-II), (O/S-III), (O/S-IV), and (O/S-V)), $R^{30}$, in each case, may be a typical $1^{st}$, $2^{nd}$, or $3^{rd}$ level substituent as specified above and may be independently selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5-, 6-, or 7-membered heterocyclyl, halogen, —$CF_3$, —CN, azido, —$NO_2$, —OH, —O($C_{1-3}$ alkyl), —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl, such as 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —$CH_2CH_2OCH_3$, —$OCH_2CH_2OCH_3$, —$CH_2CH_2NH_{2-z}(CH_3)_z$, —$OCH_2CH_2N_{2-z}(CH_3)_z$, —$CF_3$, —$OCF_3$. Alternatively, $R^{30}$ may be selected from the group consisting of phenyl, firanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$OCF_3$, —$SCH_3$, —$NH_{2-z}(CH_3)_z$, —C(=O)OH, and —C(=O)$OCH_3$, wherein z is 0, 1, or 2.

In one embodiment, the spiroquinoxaline derivative has the general formula (C-I)

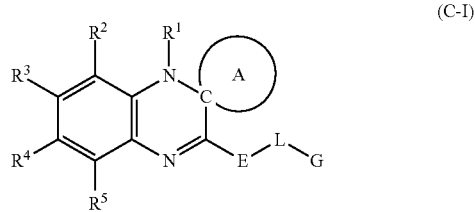

(C-I)

and solvates, salts, complexes, polymorphs, crystalline forms, racemic mixtures, diastereomers, enantiomers, tautomers, isotopically labeled forms, prodrugs, and combinations thereof, wherein E is —N($R^6$)—;

L is selected from the group consisting of $C_{1-10}$ alkylene, $C_{2-10}$ alkenylene, $C_{2-10}$ alkynylene, 1,1-($CH_2$)$_a$-cyclopropylene-($CH_2$)$_b$—, wherein each of a and b is independently selected from an integer between 0 and 3, and —($CH_2$)$_n$—[Y—($CH_2$)$_n$]$_o$-, wherein m is an integer between 1 and 6, n is an integer between 0 and 3, o is an integer between 1 and 3, wherein if n is 0 then o is 1; Y is independently selected from O, S, and —N($R^7$)—; and each of the $C_{1-10}$ alkylene, $C_{2-10}$ alkenylene, $C_{2-10}$ alkynylene, 1,1-cyclopropylene, —($CH_2$)$_m$—, and —($CH_2$)$_n$— groups is optionally substituted with one or more (such as 1 to the maximum number of hydrogen atoms bound to the $C_{1-10}$ alkylene, $C_{2-10}$ alkenylene, $C_{2-10}$ alkynylene, 1,1-cyclopropylene, —($CH_2$)$_m$—, or —($CH_2$)$_n$— group, e.g., 1, 2, 3, 4, 5, 6, 7, 8, 9, or up to 10, such as between 1 to 5, 1 to 4, or 1 to 3, or 1 or 2) independently selected $R^{30}$;

G is phenyl, optionally substituted with 1, 2, 3, 4 or 5 independently selected $R^8$;

ring A is a monocyclic 3- to 10-membered cycloalkylene, optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$;

$R^1$ is H;

$R^2$, $R^3$, $R^4$, and $R^5$ are independently selected from the group consisting of —H, alkyl, alkenyl, alkynyl, aryl, heteroaryl, cycloalkyl, heterocyclyl, halogen, —CN, azido, —$NO_2$, —$OR^{11}$, —N($R^{12}$)($R^{13}$), —N($R^{11}$)($OR^{11}$), —S(O)$_{0-2}R^{11}$, —S(O)$_{1-2}R^{11}$, —OS(O)$_{1-2}R^{11}$, —OS(O)$_{1-2}OR^{11}$, —S(O)$_{1-2}$N($R^{12}$)($R^{13}$), —OS(O)$_{1-2}$N($R^{12}$)($R^{13}$), —N($R^{11}$)S(O)$_{1-2}R^{11}$, —$NR^{11}$S(O)$_{1-2}OR^{11}$, —$NR^{11}$S(O)$_{0-2}$N($R^{12}$)($R^{13}$), —C(=X)$R^{11}$, —C(=X)$XR^{11}$, —XC(=X)R, and —XC(=X)$XR^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

or $R^2$ and $R^3$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; $R^3$ and $R^4$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$; and/or $R^4$ and $R^5$ may join together with the atoms to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$;

$R^6$ is H;

$R^7$ is selected from the group consisting of —H, alkyl, alkenyl, alkynyl, cycloalkyl, aryl, heteroaryl, heterocyclyl, —$OR^{11}$, and —$NHR^{20}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^8$ is, in each case, selected from the group consisting of alkyl, alkenyl, alkynyl, aryl, heteroaryl, cycloalkyl, heterocyclyl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, $N^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^9$ is independently selected from the group consisting of alkyl, alkenyl, alkynyl, aryl, heteroaryl, cycloalkyl, heterocyclyl, halogen, —CN, azido, —$NO_2$, —$OR^{11}$, —$N(R^{12})(R^{13})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, aryl, heteroaryl, cycloalkyl, and heterocyclyl groups is optionally substituted with one or more (such as 1 to the maximum number of hydrogen atoms bound to the alkyl, alkenyl, alkynyl, aryl, heteroaryl, cycloalkyl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, and/or any two $R^9$ which are bound to the same carbon atom of ring A may join together to form =X;

X is independently selected from O, S, and $N(R^{14})$;

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —$N=CR^{15}R^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; $R^{14}$ is independently selected from the group consisting of —H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, azido, —$NO_2$, —$OR^{71}$, —$N(R^{72})(R^{73})$, —$S(O)_{0-2}R^{11}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more (such as 1 to the maximum number of hydrogen atoms bound to the alkyl, alkenyl, alkynyl, aryl, heteroaryl, cycloalkyl, or heterocyclyl group being a $1^{st}$ level substituent, e.g., 1, 2, 3, 4, 5, 6, 7, 8, 9, or up to 10, such as between 1 to 5, 1 to 4, or 1 to 3, or 1 or 2) $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, and 3- to 14-membered heterocyclyl groups being and level substituent is optionally substituted with one or more (such as 1 to the maximum number of hydrogen atoms bound to the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, or 3- to 14-membered heterocyclyl group being a $2^{nd}$ level substituent, e.g., 1, 2, 3, 4, 5, 6, 7, 8, 9, or up to 10, such as between 1 to 5, 1 to 4, or 1 to 3, or 1 or 2) $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —O($C_{1-3}$ alkyl), —$OCF_3$, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$;($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N($C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$ ($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and N($R^{84}$), wherein $R^{84}$ is —H or $C_{1-3}$ alkyl, In one embodiment, the spiroquinoxaline derivative has the general formula (C-II)

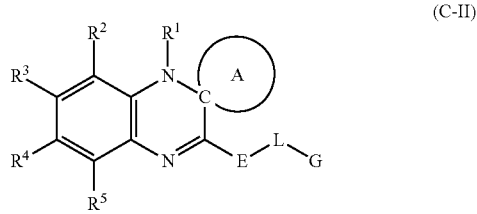

(C-II)

wherein $R^1$ to $R^5$, E, L and G are as defined above or below and the optionally substituted monocyclic ring A is 3- to 8-membered, preferably 4-, 5-, 6- or 7-membered, more preferably 6- or 7-membered. In one embodiment of the spiroquinoxaline derivative of formula (C-II), ring A as such is unsaturated (i.e., the 3 to 10 members of ring A constitute 1, 2, or 3 (preferably 1 or 2, most preferably 1) double bonds within the ring) but is not aromatic. In an alternative embodiment of the spiroquinoxaline derivative of formula (C-II), ring A is saturated (i.e., ring A as such is free of unsaturation within the ring); however, if ring A is substituted by one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) $R^9$, $R^9$ may be unsaturated (i.e., may contain double and/or triple bonds and or one or more (e.g., 1, 2. or 3) aromatic ring(s)). In any of the above embodiments of the spiroquinoxaline derivative of formula (C-I), ring A may be selected from the group consisting of cyclohexylene, cycloheptylene, cyclopropylene, cyclobutylene, cyclopentylene, cyclooctylene, cyclohexenylene, cycloheptenylene, cyclopentenylene, cyclooctenylene and their regioisomers, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$. In one embodiment of the spiroquinoxaline derivative of formula (C-II), ring A is selected from the group consisting of cyclohexylene, cycloheptylene, cyclopropylene, cyclobutylene, cyclopentylene, and cyclooctylene, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$. In one embodiment of the spiroquinoxaline derivative of formula (C-II), ring A is selected from the group consisting of cyclohexylene, cycloheptylene, cyclopentylene, and cyclooctylene, each of which is optionally substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$.

In any of the above embodiments of the spiroquinoxaline derivative of formula (C-II), ring A may be unsubstituted.

In any of the above embodiments of the spiroquinoxaline derivative of formula (C-II), wherein ring A is substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$, each such $R^9$ may be independently selected from the group consisting of $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —N($R^{12}$)($R^{13}$), —S(O)$_{0-2}R^{11}$, —S(O)$_{1-2}$N($R^{12}$)($R^{13}$), —N($R^{11}$)S(O)$_{1-2}R^{11}$, —NR$^{11}$S(O)$_{1-2}$N($R^{12}$)($R^{13}$), —C(=X)$R^{11}$, —C(=X)X$R^{11}$, —XC(=X)$R^{11}$, and —XC(=X)X$R^{11}$ wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-3}$ alkyl, $C_{2-6}$ alkenyl, $C_{2-6}$ alkanyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$, and/or any two $R^9$ which are bound to the same carbon atom of ring A may join together to form =X. In any of the above embodiments of the spiroquinoxaline derivative of formula (C-II), each $R^9$ may be independently selected from the group consisting of $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R)S(O)_{1-2}R^{11}$, —$NR^{11}S(O)_{1-2}N(R^{12})(R^{13})$, —C(=O)$R^{11}$, —C(=O)$OR^{11}$, —C(=O)$SR^{11}$, —C(=O)N($R^{14}$)($R^{11}$), —C(=S)$OR^{11}$, —$N(R^{14})C(=O)R^{11}$, —OC(O)$R^{11}$, —OC(=S)$R^{11}$, —$N(R^{14})C('O)N(R^{14})(R^{11})$, and —$N(R^{14})C(=N(R^{14}))N(R^{14})R^{11})$, wherein each of the $C_{1-4}$ alkyl, $C_{2-4}$ alkenyl, $C_{2-4}$ alkyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$, and/or any two $R^9$ which are bound to the same carbon atom of ring A may join together to form =O or =S. In one embodiment, each $R^1$ is independently selected from the group consisting of $C_{1-4}$ alkyl; $C_{1-4}$ alkyl substituted with 1 substituent selected from the group consisting of —OH, —O($C_{1-3}$ alkyl), —$NH_{2-z}$($CH_3$)$_z$, morpholinyl (e.g., 4-morpholinyl), piperazinyl (e.g., 1-piperazinyl), and N-methylpiperazinyl (e.g., 4-methylpiperazin-1-yl); $C_{1-4}$ alkyl substituted with 1, 2, or 3 halogen (preferably F), such as —$CF_3$, —$CH_2CF_3$, —$CH_2CHF_2$, or —$CH_2CH_2F$; —O($C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; cyclopropyl; 4-morpholinyl; homomorpholinyl; 4-piperidinyl; homopiperidinyl; 4-piperazinyl; homopiperazinyl; 4-methyl-piperazin-1-yl; N-methyl-homopiperazinyl; halogen; —CN; —OH; =O; —O($C_{1-3}$ alkyl optionally substituted with —$NH_{2-z}(CH_3)_z$); —$NH_2$; —NH($C_{1-3}$ alkyl); —N($C_{1-3}$ alkyl)$_2$; —S($C_{1-3}$ alkyl); —S(O)$_2$($C_{2-3}$ alkyl optionally substituted with —$NH_{2-z}(CH_3)_z$); —S(O)$_2N_{2-z}(C_{1-3}$ alkyl); —NHS(O)$_2$($C_{1-3}$ alkyl optionally substituted with —$NH_{2-z}(CH_3)_z$); —C(=O)($C_{1-3}$ alkyl optionally substituted with —$NH_{2-z}(CH_3)_z$); —C(=O)OH; —C(=O)O($C_{1-3}$ alkyl); —C(=O)$NH_{2-z}$($C_{1-3}$ alkyl)$_z$; —NHC(=O)($C_{1-3}$ alkyl optionally substituted with —$NH_{2-z}(CH_3)_z$); —NHC(=O)$NH_{2-z}(CH_3)$; —NC(=N)$NH_{z-2}(C_{1-3}$ alkyl)$_z$; and —N($C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl. In one embodiment, each $R^9$ is independently selected from the group consisting of methyl; ethyl; isopropyl; tert-butyl; cyclopropyl; —$(CH_2)_d$—$NH_{2-z}(CH_3)_z$; —O($CH_2)_d$—$N_{2-z}(CH_3)_z$; —$(CH_2)_d$—O($CH_3$); —$CF_3$; —$CH_2CF_3$; —$CH_2CHF_2$; —$CH_2CH_2F$; —$(CH_2)_d$-(4-morpholinyl); —$(CH_2)_d$-(1-piperazinyl); —$(CH_2)_d$-(4-methylpiperazin-1-yl); 4-morpholinyl; 4-piperazinyl; 4-methyl-piperazin-1-yl; halogen (in particular, —F, —Cl, —Br); —NHC(=O)($C_{1-3}$ alkyl optionally substituted with —$NH_2$—($CH_3$)$_z$); —NHC(O)$NH_{2-z}(CH_2)_z$; —NHS(O)$_2$($C_{1-3}$ alkyl optionally substituted with —$NH_{2-z}$($CH_3$)$_z$); —C(=O)$CH_3$; —C(=O)$NH_{2-z}(C_{1-3})$; —C(=O)$NH_{2-z}(C_{1-3}$ alkyl)$_z$; —S(O)$_2$($C_{1-3}$ alkyl); —S(O)$_2$($CH_2)_d NH_{2-z}(CH_3)_z$; —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, each R is independently selected from the group consisting of methyl; ethyl; isopropyl; cyclopropyl; —$(CH_2)_d$—$NH_{2-z}(CH_3)_z$; —$(CH_2)_d$—O($CH_3$); —$CF_3$; —$CH_2CF_3$; —$CH_2CHF_2$; —$CH_2CH_2F$; —$NH_2$; —N($C_{1-3}$ alkyl); —N($C_{1-3}$ alkyl)$_2$; halogen (in particular, —F, —Cl, —Br); —C(=O)$CH_3$; —C(=O)$CH_2NH_{2-z}(CH_3)_z$; —C(=O)$NH_{2-z}(C_{1-3}$ alkyl)$_z$; —S(O)$_2$($C_{1-3}$ alkyl); —S(O)$_2$($CH_2)_d NH_{2-z}(CH_3)_z$; —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, each $R^9$ when substituting a hydrogen atom bound to a ring carbon atom of ring A is independently selected from the group consisting of methyl; ethyl; isopropyl; cyclopropyl; —$(CH_2)_d$—$NH_{2-z}(CH_3)_z$; —$(CH_2)_d$—O($CH_3$); —$CF_3$; —$CH_2CF_3$; —$CH_2CHF_2$; —$CH_2CH_2F$; halogen (in particular, —F, —Cl, —Br); —C(=O)CH; —C(=O)$CH_2NH_{2-z}(CH_3)_z$; —C(=O)$NH_{2-z}(C_{1-3}$ alkyl)$_z$; —S(O)$_2$($C_{1-3}$ alkyl); —S(O)$_2$($CH_2)_d NH_{2-z}(CH_3)_z$; —OH; and —O($C_{1-3}$ alkyl), wherein z is 0, 1, or 2; d is 1, 2, or 3; and $C_{1-3}$ alkyl is methyl, ethyl, propyl or isopropyl. In one embodiment, the ring carbon atoms of ring A are unsubstituted or each $R^9$ substituting a hydrogen atom bound to a ring carbon atom of ring A is independently selected from the group consisting of $C_{1-4}$ alkyl (in particular methyl), —$N(R^{12})(R^{13})$(in particular $NH_2$), and —$N(R^{14})C(=O)R^{11}$ (in particular $NHC(O)CH_3$). In one embodiment, the ring carbon atoms of ring A are unsubstituted or one ring carbon atom of ring A is substituted with one $R^9$ being $NH_2$ or $CH_3$, or with two R being $CH_3$.

In any of the above embodiments of the spiroquinoxaline derivative of formula (C-II), wherein ring A is substituted with one or more (such as 1 to the maximum number of hydrogen atoms bound to ring A, e.g., 1, 2, 3, 4, 5, 6, 7, 8, 9, or up to 10, such as between 1 to 5, 1 to 4, or 1 to 3, or 1 or 2) independently selected $R^9$, preferably $R^9$ is bound to ring A at position 3 if ring A is 4-membered; at position 3 or 4 if ring A is 5-membered; at position 3, 4, or 5 if ring A is 6-membered; at position 3, 4, 5, or 6 if ring A is 7-membered; or at position 3, 4, 5, 6, or 7 if ring A is 8-membered. In one embodiment, in particular if ring A is substituted with 1 or 2 independently selected $R^9$, $R^1$ is bound to ring A at position 3 if ring A is 4- or 5-membered; at position 3 or 4 (preferably 4) if ring A is 6- or 7-membered; or at position 3, 4, or 5 if ring A is 8-membered.

In one embodiment, the spiroquinoxaline derivative has the general formula (C-III)

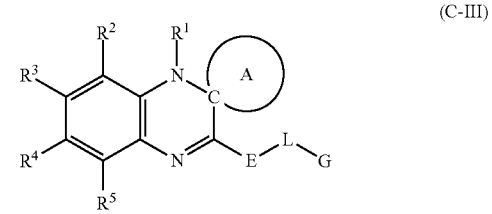

(C-III)

wherein $R^1$ to $R^5$, ring A, E, and G are as defined above (in particular with respect to formulas (C-I) and (C-II)) or below and L is selected from the group consisting of $C_{1-6}$ alkylene, $C_{2-6}$ alkenylene, $C_{2-6}$ alkynylene, —$(CH_2)_a$-cyclopropylene-$(CH_2)_b$—, wherein each of a and b is independently selected from an integer between 0 and 3, and —$(CH_2)_z$-[Y—$(CH_2)_m$]$_o$-, wherein m is 1, 2, or 3, n is 0, 1, or 2, o is 1, 2, or 3, wherein if n is 0 then o is 1; Y is independently selected from O, S, and —N($R^7$)—, wherein $R^7$ is selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, 3- to 7-membered heterocyclyl, —$OR^{11}$, and —$NHR^{20}$, wherein each of the $C_{1-6}$ alkylene, $C_{2-6}$ alkenylene, $C_{2-6}$ alkynylene, 1,1-cyclopropylene, —$(CH_2)_m$—, —$(CH_2)$—, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one or more (such as 1 to the maximum number of hydrogen atoms bound to the $C_{1-6}$ alkylene, $C_{2-6}$ alkenylene, $C_{2-6}$ alkynylene, 1,1-cyclopropylene, —$(CH_2)_m$—, —$(CH_2)_n$—, $C_{1-6}$ alkyl, $C_{2-6}$ alkyl, $C_{2-6}$ alkenyl, $C_{2-6}$ alkynyl, 3- to 7-membered cycloalkyl, 5- or 6-membered aryl, 5- or 6-membered heteroaryl, or 3- to 7-membered heterocyclyl group, e.g., 1, 2, 3, 4, 5, 6, 7, 8, 9, or up to 10, such as between 1 to 5, 1 to 4, or to 3, or or 2) independently selected $R^{30}$. In one embodiment of the spiroquinoxaline derivative of formula (C-III), $R^1$ to $R^5$, ring A, E, and G are as defined above (in particular with respect to formulas (C-I) and (C-II)) or below and L is selected from the group consisting of $C_{1-4}$ alkylene, $C_{2-4}$ alkenylene, $C_{2-4}$ alkynylene, —$(CH_2)_a$-1,1-cyclopropylene-$(CH_2)_b$-, wherein each of a and b is independently selected from 0, 1, and 2, and —$(CH_2)_m$—$[Y—(CH_2)_n]_o$-, wherein m is 1, 2, or 3, n is 0, 1, or 2, o is 1, 2, or 3, wherein if n is 0 then o is 1; Y is independently selected from O, S, and —$N(R^{7'})$—, wherein $R^{7'}$ is selected from the group consisting of —H, $C_{1-3}$ alkyl, 3-, 5-, 6- or 7-membered cycloalkyl, 6-membered aryl, 5- or 6-membered heteroaryl, 3-, 5-, 6- or 7-membered heterocyclyl, —$O(C_{1-3}$ alkyl), and —$NHR^{20}$, wherein each of the $C_{1-4}$ alkylene, $C_{2-4}$ alkenylene, $C_{2-4}$ alkynylene, 1,1-cyclopropylene, —$(CH_2)_m$—, —$(CH_2)$—, $C_{1-3}$ alkyl, 3-, 5-, 6- or 7-membered cycloalkyl, 6-membered aryl, 5- or 6-membered heteroaryl, and 3-, 5-, 6- or 7-membered heterocyclyl groups is optionally substituted with 1, 2, or 3 independently selected $R^{30}$. In one embodiment of the spiroquinoxaline derivative of formula (C-II), $R^1$ to $R^5$, ring A, E, and G are as defined above (in particular with respect to formulas (C-I) and (C-II)) or below and L is selected from the group consisting of $C_{1-3}$ alkylene, —$(CH_2)_a$-1,1-cyclopropylene-$(CH_2)_b$—, wherein each of a and b is independently selected from 0 and 1, and —$(CH_2)_m$—$[Y—(CH_2)_n]_o$—, wherein m is 1 or 2, n is 0, 1, or 2, o is 1 or 2, wherein if n is 0 then o is 1; Y is O, wherein each of the $C_{1-3}$ alkylene, 1,1-cyclopropylene, —$(CH_2)_m$—, and —$(CH_2)_n$-groups is optionally substituted with 1, 2, or 3 independently selected $R^{30}$. In one embodiment of the spiroquinoxaline derivative of formula (C-II), $R^1$ to $R^5$, ring A, E, and G are as defined above (in particular with respect to formulas (C-I) and (C-II)) or below and L is selected from the group consisting of methylene; 1,1-ethylene; 1,2-ethylene (optionally substituted with one $R^{30}$ (such as phenyl) at position 2); trimethylene (—$(CH_2)_3$—); 2,2-propylene (—$C(CH_3)_2$—); 2,4-butanediyl; -1,1-cyclopropylene-; —$(CH_2)$-1,1-cyclopropylene; -1,1-cyclopropylene-$(CH_2)_3$; —$(CH_2)$-1,1-cyclopropylene-$(CH_2)$—; —$CH_2O$—; —$(CH_2)_2O$—; and —$(CH_2)_3O$— (such as methylene; 1,1-ethylene; 1,2-ethylene; trimethylene (—$(CH_2)_3$—); 2,2-propylene (—$C(CH_3)_2$—); 1,1-cyclopropylene; and —$(CH_2)_2O$—, in particular, methylene). In one embodiment of the spiroquinoxaline derivative of formula (C-III), $R^1$ to $R^5$, ring A, E, and G are as defined above (in particular with respect to formulas (C-I) and (C-II)) or below and L is selected from the group consisting of methylene; 1,1-ethylene; 1,2-ethylene; trimethylene (—$(CH_2)_3$—); 2,2-propylene (—$C(CH_3)_2$—); -1,1-cyclopropylene-; —$(CH_2)$-1,1-cyclopropylene;-1,1-cyclopropylene-$(CH_2)$—; —$(CH_2)$-1,1-cyclopropylene-$(CH_2)$—; —$CH_2O$—; —$(CH_2)_2O$—; and —$(CH_2)_3O$— (such as methylene; 1,1-ethylene; 1,2-ethylene; trimethylene (—$(CH_2)_3$—); 2,2-propylene (—$C(CH_3)_2$—); 1,1-cyclopropylene; and —$(CH_2)_2O$—, in particular, methylene). In one embodiment of the spiroquinoxaline derivative of formula (C-III), $R^1$ to $R^5$, ring A, E, and G are as defined above (in particular with respect to formulas (C-I) and (C-II)) or below and L is selected from the group consisting of $C_1$ alkylene, $C_2$ alkylene (in particular 1,2-ethylene or 1,1-ethylene), $C_{1-3}$ alkylene (in particular trimethylene), and $C_4$ alkylene (in particular tetramethylene or 2,4-butanediyl), each of which being optionally substituted with one $R^{30}$. In one embodiment of the spiroquinoxaline derivative of formula (C-III), $R^1$ to $R^5$, ring A, E, and G are as defined above (in particular with respect to formulas (C-I) and (C-II)) or below and L is selected from the group consisting of methyl-ethylene, 1,2-ethylene, trimethylene, tetramethylene, 2,4-butanediyl, and 2-phenyl-1,2-ethylene (—$CH_2$—$CH(C_6H_5)$—) In one embodiment of the spiroquinoxaline derivative of formula (C-III), $R^1$ to $R^5$, ring A, E, and G are as defined above (in particular with respect to formulas (C-I) and (C-II)) or below and L is selected from the group consisting of methylene and 2-phenyl-1,2-ethylene (—$CH_2$—$CH(C_6H_5)$—).

In one embodiment, the spiroquinoxaline derivative has the general formula (C-IV)

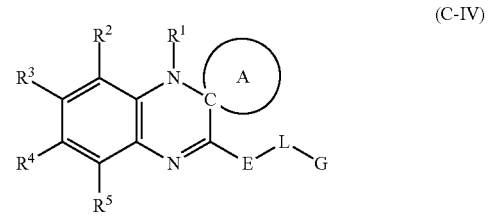

(C-IV)

wherein $R^1$ to $R^5$, ring A, E, and L are as defined above (in particular with respect to formulas (C-I), (C-II) and (C-III)) or below and G is phenyl which is either unsubstituted or substituted with 1, 2, 3, 4 or 5 (such as between 1 to 4, or 1 to 3, or 1 or 2) independently selected $R^8$. In any of the above embodiments (including those of formulas (C-I) to (C-III)), wherein G is substituted, $R^8$ may be, in each case, selected from the group consisting of $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment of the spiroquinoxaline derivative of formula (C-IV), $R^1$ to $R^5$, ring A, E, and L are as defined above (in particular with respect to formulas (C-I), (C-II) and (C-III)) or below and $R^8$ is, in each case, selected from the group consisting of $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N(R^{12})(R^{11})$, —$C(=O)R^{11}$, —$C(=O)OR^{11}$, —$C(=O)SR^{11}$, —$C(=O)N(R^{14})(R^{11})$, —$C(=S)OR^{11}$, —$N(R^{14})C(=O)R^{11}$, —$OC(=O)R^{11}$, —$OC(=S)R^{11}$, —$N(R^{14})C(=O)N(R^{14})(R^{11})$ and —$N(R^{14})C(=N(R^{14}))N(R^{14})(R^{11})$, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment of the spiroquinoxaline derivative of formula (C-IV), $R^1$ to $R^5$, ring A, E, and L are as defined above (in particular with respect to formulas (C-I), (C-II) and (C-III)) or below and $R^8$ is, in each case, selected from the group consisting of $C_{1-4}$ alkyl; $C_{1-4}$ alkyl substituted with 1 substituent selected from the group consisting of —OH, —O($C_{1-3}$ alkyl), and —$NH_2$— $(CH_3)_z$; $C_{1-4}$ alkyl substituted with 1, 2, or 3 halogen (preferably F), such as —$CF_3$, —$CH_2CF_3$, —$CH_2CHF_2$, or —$CH_2CH_2F$; phenyl; cyclopropyl; 5-membered heterocyclyl (such as pyrrolidinyl); 4-morpholinyl; homomorpholinyl; 4-piperidinyl; homopiperidyl; 4-piperazinyl; homopiperazinyl; N-methyl-piperazin-4-yl; N-methyl-homopiperazinyl; halogen; —CN; —OH; —O($C_{1-3}$ alkyl); —O($C_{1-4}$ alkyl substituted with 1, 2, or 3 halogen (preferably F)), such as —$OCF_3$, —$OCH_2CF_3$, —$OCH_2CHF_2$, or —$OCH_2CH_2F$; —O-phenyl; —$NH_2$; —NH($C_{1-3}$ alkyl); —N($C_{1-3}$ alkyl)$_2$; —S($C_{1-3}$ alkyl); —S(O)$_2$($C_{1-3}$ alkyl optionally substituted with —$NH_{2-z}(C_{1-3})$), —S(O)$_2NH_{2-z}$($C_{1-3}$ alkyl).; —NHS(O)$_2$($C_{1-3}$ alkyl); —C(=O)($C_{1-3}$ alkyl optionally substituted with —$NH_{2-z}(CH_3)_z$); —C(=O)OH; —C(=O)O($C_{1-3}$ alkyl); —C(=O)$NH_{2-z}$($C_{1-3}$ alkyl)$_z$; —NHC(=O)($C_{1-3}$ alkyl); —NHC(=NH)$NH_{z-2}$($C_{1-3}$ alkyl); and —N($C_{1-3}$ alkyl)C(=NH)$NH_{2-z}$($C_{1-3}$ alkyl)$_z$, wherein z is 0, 1, or 2 and $C_{1-3}$ alkyl is methyl, ethyl, propyl or isopropyl and each of the phenyl, cyclopropyl, 5-membered heterocyclyl (such as pyrrolidinyl), 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of $C_{1-3}$ alkyl, halogen, —$CF_3$, —$OCF_3$, —OH, —$OCH_3$, —$SCH_3$, —$NH_{2-z}(CH_3)_z$, —C(=O)OH, and —C(=O)$OCH_3$, wherein z is 0, 1, or 2. In one embodiment, each $R^5$ is independently selected from the group consisting of methyl; ethyl; isopropyl; tert-butyl; phenyl; cyclopropyl; pyrrolidinyl (such as 4-pyrrolidinyl); —$(CH_2)_d$—$NH_{2-z}(CH_3)_z$; —$(CH_2)_d$—O($CH_3$), —$CF_3$; —$OCF_3$; —O-phenyl; —$CH_2CF_3$; —$CH_2CHF_2$; —$CH_2CH_2F$; halogen (in particular, —F, —Cl, —Br); —CN; —$NH_2$; —$NH_{2-z}$($C_{1-3}$ alkyl); —N($C_{1-3}$ alkyl)$_2$; —C(=O)$CH_3$; —C(=O) $CH_2H_{2-z}(CH_3)_z$; —C(=O)OH; —C(=O)O($C_{1-3}$ alkyl); —C(=O)$NH_{2-z}$($C_{1-3}$ alkyl); —NHC(=O)($C_{1-3}$ alkyl); —S(O)$_2$($C_{1-3}$ alkyl); —S(O)$_2$($CH_2$)$_d$$NH_{2-z}(CH_3)_z$; —OH; and —O($C_{1-3}$ alkyl), wherein z is 0, 1, or 2, d is 1, 2, or 3, and $C_{1-3}$ alkyl is methyl, ethyl, propyl or isopropyl. In one embodiment, each $R^8$ is independently selected from the group consisting of methyl; ethyl; isopropyl; phenyl; cyclopropyl; pyrrolidinyl (such as 4-pyrrolidinyl); —$(CH_2)_d$—$NH_{2-z}(CH_3)_z$; —$(CH_2)_d$—O($CH_3$); —$CF_3$; —$OCF_3$; —O-phenyl; —$CH_2CF_3$; —$CH_2CHF_2$; —$CH_2CH_2F$; halogen (in particular, —F, —Cl, —Br); —CN; —$NH_2$; NH($C_{1-3}$ alkyl); —N($C_{1-3}$ alkyl)$_2$; —C(=O)$CH_3$; —C(=O)$CH_2NH_{2-z}$ $(CH_3)_z$; —C(=O)OH; —C(=O)O($C_{1-3}$ alkyl); —C(=O)$NH_{2-z}$($C_{1-3}$ alkyl)$_z$; —NHC(=O)($C_{1-3}$ alkyl); —S(O)$_2$($C_{1-6}$ alkyl); —S(O)$_2$($CH_2$)$_d$$NH_{2-z}(CH_3)_z$, —OH; and —O($C_{1-3}$ alkyl), wherein z is 0, 1, or 2, d is 1, 2, or 3, and $C_{1-3}$ alkyl is methyl, ethyl, propyl or isopropyl.

In one embodiment of the spiroquinoxaline derivative of formula (C-IV), $R^1$ to $R^5$, ring A, E, and L are as defined above (in particular with respect to formulas (C-I), (C-I) and (C-III)) or below and G is either unsubstituted or substituted with 1, 2, or 3 $R^5$, wherein $R^5$ is, in each case, selected from the group consisting of $C_{1-4}$ alkyl (in particular methyl or tert-butyl); halogen (in particular F or Cl); —$OR^{11}$ (in particular —$OCH_3$); and $C_{1-4}$ alkyl substituted with 1, 2, or 3 independently selected $R^{30}$ (in particular —$CF_3$). In one embodiment of the spiroquinoxaline derivative of formula (C-IV), $R^1$ to $R^5$, ring A, E, and L are as defined above (in particular with respect to formulas (C-I), (C-II) and (C-III)) or below and G is either unsubstituted or substituted with 1 or 2 $R^8$ each independently selected from the group consisting of methyl, F, Cl, —$OCH_3$, and —$CF_3$. In one embodiment of the spiroqu noxaline derivative of formula (C-IV), $R^1$ to $R^5$, ring A, E, and L are as defined above (in particular with respect to formulas (C-I), (C-II) and (C-III)) or below and G is selected from the group consisting of unsubstituted phenyl, fluorophenyl (in particular 3-fluorophenyl), chlorophenyl (in particular 2-, 3- or 4-chlorophenyl), methylphenyl (in particular 2- or 3-methylphenyl), tert-butylphenyl (in particular 4-tert-butylphenyl), methoxyphenyl (in particular 3-methoxyphenyl), (trifluoromethyl)phenyl (in particular 3- or 4-(trifluoromethyl)phenyl), difluorophenyl (in particular 2,4- or 2,6-difluorophenyl), dichlorophenyl (in particular 2,4- or 3,4-dichlorophenyl), chlorofluorophenyl (in particular 4-chloro-2-fluorophenyl), and dimethylphenyl (in particular 3,5-dimethyl). In one embodiment of the spiroquinoxaline derivative of formula (C-IV), $R^1$ to $R^5$, ring A, E, and L are as defined above (in particular with respect to formulas (C-I), (C-II) and (C-III)) or below and G is selected from the group consisting of unsubstituted phenyl, 2-chlorophenyl, 3-chlorophenyl, 4-chlorophenyl, 3-methylphenyl, 3-(trifluoromethyl)phenyl, 2,6-difluorophenyl, 3,4-dichlorophenyl, 4-chloro-2-fluorophenyl, and 3,5-dimethylphenyl.

In one embodiment, the spiroquinoxaline derivative has the general formula (C-V)

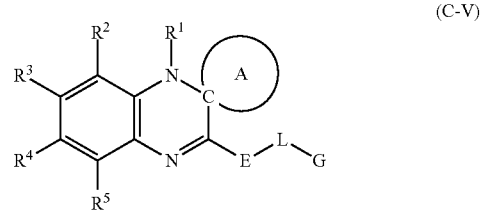

(C-V)

wherein $R^{11}$, ring A, E, L and G are as defined above (in particular with respect to formulas (C-I), (C-II), (C-III) and (C-IV)) or below and each of $R^2$, $R^3$, $R^4$, and R is H. In one embodiment of the spiroquinoxaline derivative of formula (C-V), $R^1$, ring A, E, L and G are as defined above (in particular with respect to formulas (C-I), (C-II), (C-III) and (C-IV)) or below and at least one of $R^2$, $R^3$, $R^4$, and $R^5$ is different from H. For example, in one embodiment $R^2$ is different from H and each of $R^3$, $R^4$, and $R^5$ is H; or $R^3$ is different from H and each of $R^2$, $R^4$, and $R^5$ is H; or $R^4$ is different from H and each of $R^2$, $R^3$, and $R^5$ is H; or $R^5$ is different from H and each of $R^2$, $R^3$, and $R^4$ is H; or both of $R^2$ and $R^3$ are different from H and both of $R^4$ and $R^5$ are H; or both of $R^2$ and $R^4$ are different from H and both of $R^3$ and $R^5$ are H; or both of $R^2$ and $R^5$ are different from H (preferably in this embodiment $R^2$ and $R^5$ are the same) and both of $R^3$ and $R^4$ are H; or both of PR and $R^4$ are different from H (preferably in this embodiment $R^3$ and $R^4$ are the same) and both of $R^2$ and $R^5$ are H; or each of $R^2$, $R^3$, and $R^4$ is different from H and $R^5$ is H; or each of $R^2$, $R^3$ and $R^5$ is different from H and RP is H; or each of $R^2$, $R^4$, and R is different from H and $R^3$ is H; or each of $R^3$, $R^4$, and $R^5$ is different from H and R is H; or each of $R^2$, $R^3$, $R^4$, and $R^5$ is different from H. In any of the above embodiments, it is preferred that $R^2$ and $R^5$ are the same and/or $R^3$ and $R^4$ are the same.

In any of the above embodiments (in particular with respect to formulas (C-I), (C-I), (C-III), (C-IV), and (C-V)), each of $R^2$ to $R^5$, if it does not join together with another of $R^2$ to $R^5$ to form a ring, is independently selected from the group consisting of —H, $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{12})S(O)_{1-2}R^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In one embodiment, each of $R^2$, $R^3$, $R^4$, and $R^5$, if it does not join together with another of $R^2$ to $R^5$ to form a ring, may be independently selected from the group consisting of —H, $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, 3-, 5-, 6- or 7-membered heterocyclyl, halogen, —CN, —$OR^{11}$, —$N(R^{12})(R^{13})$, —$S(O)_{0-2}R^{11}$, —$S(O)_{1-2}N(R^{12})(R^{13})$, —$N(R^{11})S(O)_{1-2}R$, —$NR^{11}S(O)_{1-2}N(R^{12})(R^{13})$, —$C(=O)R^{11}$, —$C(=O)OR^{11}$, —$C(=O)SR^{11}$, —$C(=O)N(R^{14})(R^{11})$, —$C(=S)OR^{11}$, —$N(R^{14})C(=O)R^{11}$, —$OC(=O)R^{11}$, —$OC(=S)R^{11}$, —$N(R^{14})C(=O)N(R^{14})(R^{11})$ and —$N(R^{14})C(=N(R^{14}))N(R^{14})(R^{11})$, wherein each of the $C_{1-4}$ alkyl, $C_{2-4}$ alkenyl, $C_{2-4}$ alkynyl, 6-membered aryl, 5- or 6-membered heteroaryl, 3-, 5-, 6- or 7-membered cycloalkyl, and 3-, 5-, 6- or 7-membered heterocyclyl groups is optionally substituted with 1, 2, or 3 independently selected $R^{30}$. In one embodiment of the spiroquinoxaline derivative of formula (C-V), $R^{11}$, ring A, E, L and G are as defined above (in particular with respect to formulas (C-I), (C-II), (C-III), and (C-IV)) or below and each of $R^2$, $R^3$, $R^4$, and $R^5$, if it does not join together with another of $R^2$ to $R^3$ to form a ring, is independently selected from the group consisting of H; $C_{1-4}$ alkyl; $C_{1-4}$ alkyl substituted with 1 substituent selected from the group consisting of —OH, —$O(C_{1-3}$ alkyl), and —$NH_{2-z}(CH_3)_z$; $C_{1-4}$ alkyl substituted with 1, 2, or 3 halogen (preferably F), such as —$CF_3$, —$CH_2CF_3$, —$CH_2CHF_2$, or —$CH_2CH_2F$; phenyl; cyclopropyl; 5-memberedheterocyclyl; 4-morpholinyl; homomorpholinyl; 4-piperidinyl; homopiperidinyl; 4-piperazinyl; homopiperazinyl; N-methyl-piperazin-4-yl; N-methyl-homopiperazyl; halogen; —CN; —OH; —$O(C_{1-3}$ alkyl); —$O(C_{1-4}$ alkyl substituted with 1, 2, or 3 halogen (preferably F)), such as —$OCF_3$, —$OCH_2CF_3$, —$OCH_2CH_2F$, or —$OCH_2CH_2F$; —O-phenyl; —$NH_2$; —$NH(C_{1-3}$ alkyl); —$N(C_{1-3}$ alkyl)$_2$; —$S(C_{1-3}$ alkyl); —$S(O)_2(C_{1-3}$ alkyl optionally substituted with —$NH_{2-z}(CH_3)_z)$; —$S(O)NH_{z-2}(C_{6-3}$ alkyl)$_z$; —$NHS(O)_2(C_{1-3}$ alkyl); —$C(=O)(C_{1-3}$ alkyl optionally substituted with —$NH_2$-z $(CH_3)_z$); —$C(=O)OH$; —$C(=O)O(C_{1-3}$ alkyl); —$C(=O)NH_{2-z}(C_{1-3}$ alkyl)$_z$; —$NHC(=O)(C_{1-3}$ alkyl); —$NHC(=NH)NH_{z-2}$ ($C_{1-3}$ alkyl)$_z$; and —$N(C_{1-3}$ alkyl)$C(=N)NH_{2-z}(C_{1-3}$ alkyl)$_z$, wherein z is 0, 1, or 2 and $C_{1-3}$ alkyl is methyl, ethyl, propyl or isopropyl and each of the phenyl, cyclopropyl, 5-membered heterocyclyl, 4-morpholinyl, homomorpholinyl, 4-piperidinyl, homopiperidinyl, 4-piperazinyl, homopiperazinyl, N-methyl-piperazin-4-yl, N-methyl-homopiperazinyl, and —O-phenyl groups is optionally substituted with 1, 2, or 3 substituents independently selected from the group consisting of $C_{1-3}$ alkyl, halogen, —$CF_3$, —$OCF_3$, —OH, —$OCH_3$, —$SCH_3$, —$NH_{2-z}(CH_3)_z$, —$C(=O)OH$, and —$C(=O)OCH_3$, wherein z is 0, 1, or 2. In one embodiment, each of $R^2$, $R^3$, $R^4$, and $R^5$, if it does not join together with another of $R^2$ to $R^5$ to form a ring, is independently selected from the group consisting of H; methyl; ethyl; isopropyl; phenyl; cyclopropyl; —$(CH_2)_d$—$NH_{2-z}(CH_3)_z$; —$(CH_2)_d$—$O(CH_3)$; —$CF_3$; —$OCF_3$; —$CH_2CF_3$; —$CH_2CHF_2$; —$CH_2CH_2F$; halogen (in particular, —F, —Cl, —Br); —CN; —$NH_2$; —$N(C_{1-3}$ alkyl); —$N(C_{1-3}$ alkyl)$_2$; —$C(=O)CH_3$; —$C(=O)CH_2NH_{2-z}(CH_3)_z$; —$C(=O)O(C_{1-3}$ alkyl); —$C(=O)NH_{2-z}(C_{1-3}$ alkyl)$_z$; —$NHC(=O)(C_{1-3}$ alkyl); —$S(O)_2(C_{1-3}$ alkyl); —$S(O)_2(CH_2)_dNH_{2-z}(CH_3)$; —OH, and —$O(C_{1-3}$ alkyl), wherein z is 0, 1, or 2, d is 1, 2, or 3, and $C_{1-3}$ alkyl is methyl, ethyl, propyl or isopropyl. In one embodiment of the spiroquioxaline derivative of formula (C-V), $R^{11}$, ring A, E, L and G are as defined above (in particular with respect to formulas (C-I), (C-II), (C-III), and (C-IV)) or below and $R^2$, $R^3$, $R^4$, and Rare independently selected from the group consisting of —H, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H). In one embodiment of the spiroquinoxaline derivative of formula (C-V), R, ring A, E, L and G are as defined above (in particular with respect to formulas (C-I), (C-II), (C-II), and (C-IV)) or below and $R^2$, $R^3$, $R^4$, and $R^5$ are independently selected from the group consisting of —H, methyl, F, Cl, and $CF_3$ (in particular wherein $R^2$ and $R^5$ are each —H). In one embodiment of the spiroquinoxaline derivative of formula (C-V), $R^{11}$, ring A, E, L and G are as defined above (in particular with respect to formulas (C-I), (C-I), (C-II), and (C-IV)) or below and $R^2$ and $R^5$ are each —H; R is selected from the group consisting of —H, methyl, F, and Cl; and $R^4$ is selected from the group consisting of —H, methyl, F, and Cl. In one embodiment of the spiroquinoxaline derivative of formula (C-V), $R^{11}$, ring A, E, L and G are as defined above (in particular with respect to formulas (C-I), (C-II), (C-III), and (C-IV)) or below and (i) $R^2$ to $R^5$ are each —H; or (ii) $R^2$ and $R^5$ are each —H, and both of $R^3$ and $R^4$ are F, Cl, or methyl. In any of the above embodiments, wherein a ring is formed by (i) $R^2$ and $R^3$, (ii) $R^3$ and $R^4$, and/or (iii) $R^4$ and $R^5$, said ring preferably is a 3- to 7-membered ring (e.g., a ring having 5 or 6 members) which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$. The ring may be an aromatic, cycloaliphatic, heteroaromatic, or heterocyclic ring, wherein the heteroaromatic/heterocyclic ring contains 1 or 2 heteroatoms selected from the group consisting of O, S, and $N(R^{40})$, wherein $R^{40}$ is selected from the group consisting of $R^{11}$, —$OR^{11}$, —$NH_yR^{20}_{2-y}$, and —$S(O)_{1-2}R^{11}$, wherein $R^{11}$, $R^{21}$, and y are as defined above. In one embodiment, the ring formed by (i) $R^2$ and $R^3$, (ii) $R^3$ and $R^4$, and/or (iii) $R^4$ and $R^5$ is a 5- or 6-membered aromatic, cycloaliphatic, heteroaromatic, or heterocyclic ring, wherein the heteroaromatic/heterocyclic ring contains 1 or 2 heteroatoms selected from the group consisting of O, S, and N, wherein at least one heteroatom is N. In one embodiment, the ring formed by (i) $R^2$ and $R^3$, (ii) $R^3$ and $R^4$, and/or (iii) $R^4$ and $R^5$ is selected from the group consisting of cyclopentadiene, furan, pyrrole, thiophene, imidazole, pyrazole, oxazole, isoxazole, thiazole, dioxole (e.g., 1,3-dioxole), benzene, pyridine, pyrazine, pyrimidine, pyridazine, dioxine (e.g., 1,4-dioxine), 1,2,3-triazine, 1,2,4-triazine, and di- or tetrahydro forms of each of the foregoing. In one embodiment, the ring formed (i) $R^2$ and $R^3$, (ii) $R^3$ and $R^4$, and/or (iii) $R^4$ and R is cyclopentene (such as 2,3-dihydrocyclopentadiene), dioxole (such as 1,3-dioxole, optionally substituted at position 2 with one or two halogen atoms (such as F)), or dioxine (such as 2,3-dihydro-[1,4]-dioxine). In one embodiment, the total number of rings formed by (i) $R^2$ and $R^3$, (ii) $R^3$ and $R^4$, and/or (iii) $R^4$ and $R^1$ is 0 or 1. Thus, in the embodiment, wherein the total number of rings formed by (i) $R^2$ and $R^3$, (ii) $R^3$ and $R^2$, and/or (iii) $R^4$ and $R^1$ is 1, only two adjacent substituents (i.e., either (i) $R^2$ and $R^3$, (ii) $R^3$ and $R^4$, or (iii) $R^4$ and $R^5$) join together with the atoms to which they are attached to form a ring, wherein the ring is as defined in any of the above embodiments and the remaining of $R^2$ to $R^5$ are selected from the particular groups of moieties specified above for the situation that they do not join together to form a ring. For example, the remaining $R^2$ to R which do not join together to form a ring may be selected from —H, $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, 3- to 7-membered heterocyclyl, halogen, —CN, —$OR^{11}$, —$N(R^{12})(R^{11})$, —$S(O)_{0-2}R^{11}$, —$S(O)_{1-2}N(R^{12})(R^{13})$, —$N(R^{11})S(O)_{1-2}R^{11}$, —$NR^{11}S(O)_{1-2}N)(R^{12})(R^{13})$, —$C(=X)R^{11}$, —$C(=X)XR^{11}$, —$XC(=X)R$, and —$XC(=X)XR^{11}$, wherein each of the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, and 3- to 7-membered heterocyclyl groups is optionally substituted with one or more (such as 1 to the maximum number of hydrogen atoms bound to the $C_{1-6}$ alkyl, $C_{2-6}$ alkenyl, $C_{2-6}$ alkynyl, 5- or 6-membered aryl, 5- or 6-membered heteroaryl, 3- to 7-membered cycloalkyl, or 3- to 7-membered heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$. In an alternative embodiment, $R^2$ to $R^5$ do not join together to form a ring.

In any of the above embodiments, $R^2$ and R may be the same and/or RP and $R^4$ may be the same.

In one embodiment of the spiroquinoxaline derivative of formula (C-V), R, ring A, E, L and G are as defined above (in particular with respect to formulas (C-I), (C-II), (C-III), and (C-V)) or below and $R^2$, $R^3$, $R^4$, and $R^5$ are independently selected from the group consisting of —H, $C_{1-4}$ alkyl, and halogen, wherein the $C_{1-4}$ alkyl is optionally substituted with 1, 2, or 3 independently selected $R^{30}$ (in particular wherein $R^2$ and $R^5$ are each —H), or $R^3$ and $R^4$ may join together with the atoms to which they are attached to form a 5- or 6-membered ring which is optionally substituted with one or two independently selected $R^{30}$. In one embodiment of the spiroquinoxaline derivative of formula (C-V), $R^{11}$, ring A, E, L and G are as defined above (in particular with respect to formulas (C-I), (C-II), (C-III), and (C-IV)) or below and $R^2$, $R^3$, $R^4$, and $R^5$ are independently selected from the group consisting of —H, methyl, F, Cl, and $CF_3$ (in particular wherein $R^2$ and $R^5$ are each —H), or $R^3$ and $R^4$ may join together with the atoms to which they are attached to form a dioxole or dioxine ring which is optionally substituted with one or two independently selected halogens (in particular F). In one embodiment of the spiroquinoxaline derivative of formula (V), $R^{11}$, ring A, E, L and G are as defined above (in particular with respect to formulas (C-I), (C-II), (C-II), and (C-IV)) or below and $R^2$ and $R^5$ are each —H; $R^3$ is selected from the group consisting of —H, methyl, F, and Cl; and $R^4$ is selected from the group consisting of —H, methyl, F, and Cl; or $R^3$ and $R^4$ may join together with the atoms to which they are attached to form a dioxole (in particular, 3-dioxole) or dioxine (in particular 2,3-dihydro-[1,4]-dioxine) ring, wherein the dioxole ring is optionally substituted with two F. In one embodiment of the spiroquinoxaline derivative of formula (C-V), $R^{11}$, ring A, E, L and G are as defined above (in particular with respect to formulas (C-I), (C-II), (C-III), and (C-IV)) or below and (i) $R^2$ to $R^5$ are each —H; (ii) $R^2$ and $R^5$ are each —H, and both of $R^3$ and $R^4$ are F, Cl, or methyl, or (iii) $R^2$ and $R^5$ are each —H, and $R^3$ and $R^4$ join together with the atoms to which they are attached to form a 2,2-difluoro-1,3-dioxole ring or a 2,3-dihydro-[1,4]-dioxine ring.

In any of the above embodiments (in particular with respect to formulas (C-I), (C-II), (C-III), (C-IV), and (C-V)), $R^{30}$, in each case, may be a typical $1^{st}$, $2^{nd}$, or $3^{rd}$ level substituent as specified above and may be independently selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5-, 6-, or 7-membered heterocyclyl, halogen, —$CF_3$, —CN, azido, —$NO_2$, —OH, —O($C_{1-3}$ alkyl), —S($C_{1-3}$ alkyl), —$NH_2$, —N($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{2-z}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl, such as 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —$CH_2CH_2OCH_3$, —$OCH_2CH_2OCH_3$, —$CH_2CH_2N_{2-z}$($CH_3$)$_z$, —$OCH_2CH_2NH_{2-z}$($CH_3$)$_z$, —$CF_3$, —$OCF_3$. Alternatively, $R^{30}$ may be selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —$CF_3$, —OH, —$OCH_3$, —$OCF_3$, —$SCH_3$, —$NH_{2-z}$($CH_3$)$_z$, —C(=O)OH, and —C(=O)$OCH_3$, wherein z is 0, 1, or 2.

In one embodiment, the compound of the invention is selected from the compounds shown in Tables 1-N, 1-O/S, and 1-C.

It is intended that the compounds of the present invention (in particular, the compounds of any one of formulas (I), (N-I), (O/S-I), (C-I), (II), (N-II), (O/S-II), (C-II), (III), (N-III), (O/S-III), (C-III), (IV), (N-IV), (O/S-IV), (C-IV), (V), (N-V), (O/S-V), and (C-V), such as those depicted in Tables 1-N, 1-O/S, and 1-C, below) encompass not only the compounds as depicted but also their solvates (e.g., hydrates), salts (in particular, pharmaceutically acceptable salts), complexes, polymorphs, crystalline forms, non-crystalline forms, amorphous forms, racemic mixtures, non-racemic mixtures, diastereomers, enantiomers, tautomers, unlabeled forms, isotopically labeled forms, prodrugs, and any combinations thereof.

A selection of compounds within the scope of, or for use within the methods of, the present invention is listed in the following Tables 1-N, 1-O/S, and 1-C.

TABLE 1-N
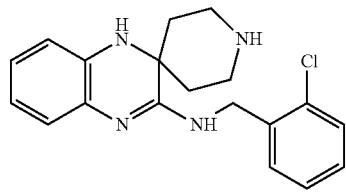 [SMILES: Clc1ccccc1CNC1=Nc2ccccc2NC12CCNCC2] N-1
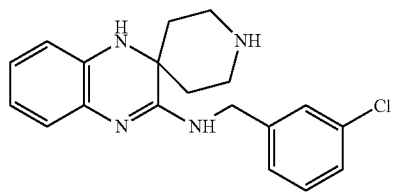 [SMILES: Clc1cccc(CNC2=Nc3ccccc3NC23CCNCC3)c1] N-2
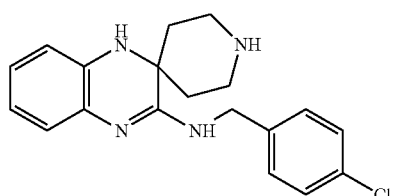 N-3
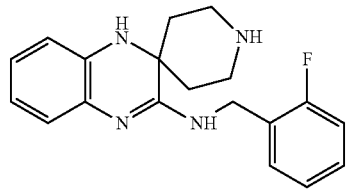 [SMILES: Fc1ccccc1CNC1=Nc2ccccc2NC12CCNCC2] N-4
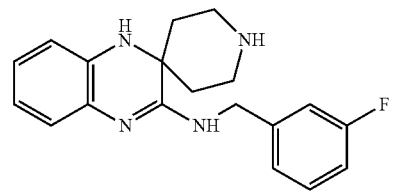 [SMILES: Fc1cccc(CNC2=Nc3ccccc3NC23CCNCC3)c1] N-5
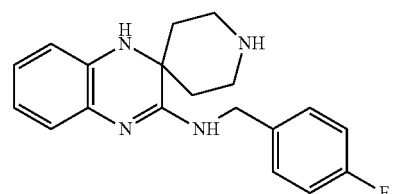 N-6
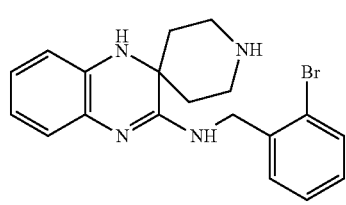 [SMILES: Brc1ccccc1CNC1=Nc2ccccc2NC12CCNCC2] N-7
TABLE 1-N-continued
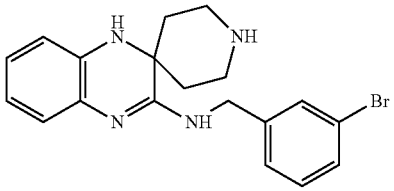 [SMILES: Brc1cccc(CNC2=Nc3ccccc3NC23CCNCC3)c1] N-8
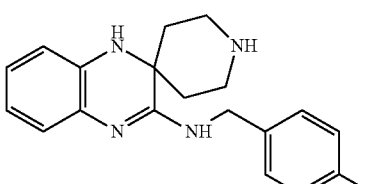 N-9
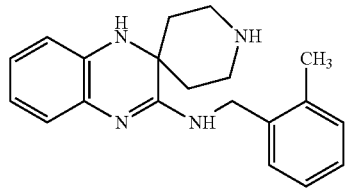 N-10
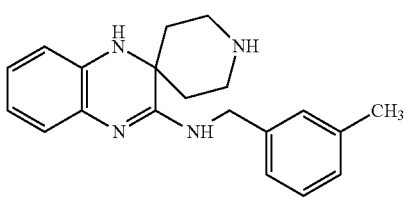 [SMILES: Cc1cccc(CNC2=Nc3ccccc3NC23CCNCC3)c1] N-11
 N-12
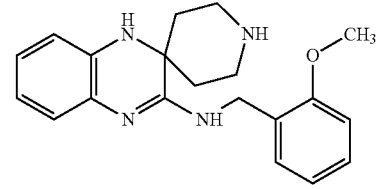 [SMILES: COc1ccccc1CNC1=Nc2ccccc2NC12CCNCC2] N-13
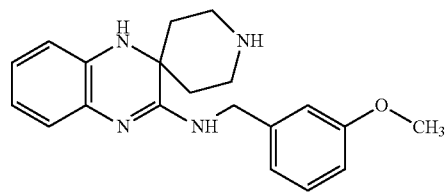 [SMILES: COc1cccc(CNC2=Nc3ccccc3NC23CCNCC3)c1] N-14

TABLE 1-N-continued
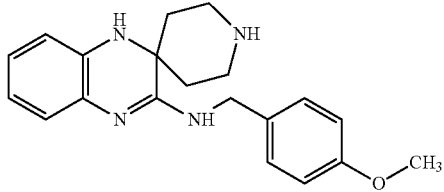 [SMILES: COc1ccc(CNC2=Nc3ccccc3NC23CCNCC3)cc1] N-15
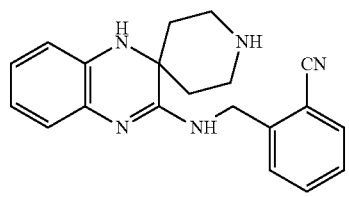 [SMILES: N#Cc1ccccc1CNC1=Nc2ccccc2NC12CCNCC2] N-16
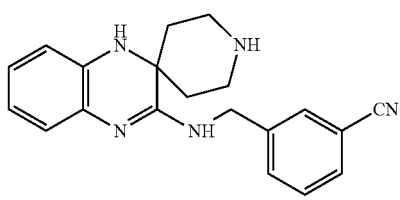 [SMILES: N#Cc1cccc(CNC2=Nc3ccccc3NC23CCNCC3)c1] N-17
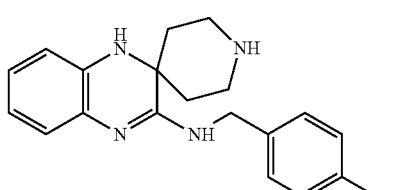 N-18
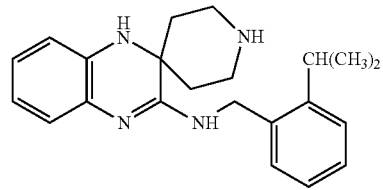 N-19
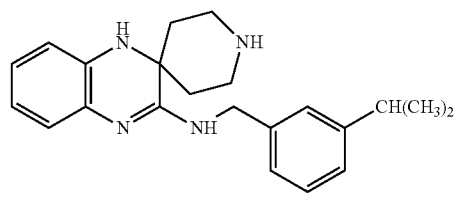 [SMILES: CC(C)c1cccc(CNC2=Nc3ccccc3NC23CCNCC3)c1] N-20
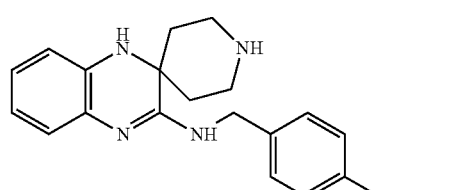 N-21
TABLE 1-N-continued
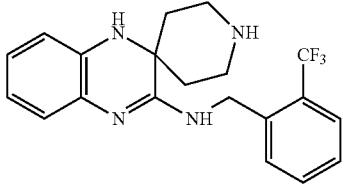 N-22
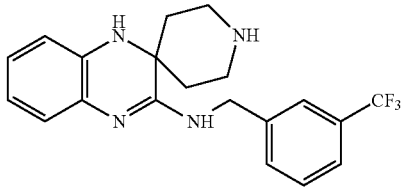 [SMILES: FC(F)(F)c1cccc(CNC2=Nc3ccccc3NC23CCNCC3)c1] N-23
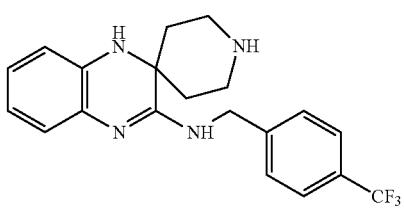 N-24
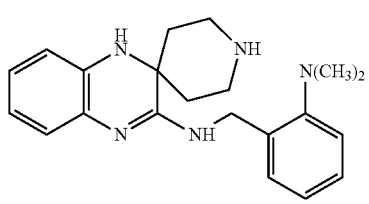 [SMILES: CN(C)c1ccccc1CNC1=Nc2ccccc2NC12CCNCC2] N-25
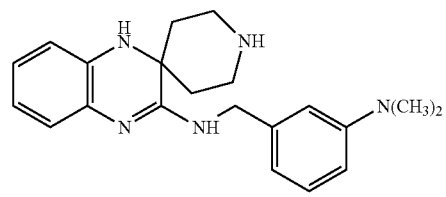 N-26
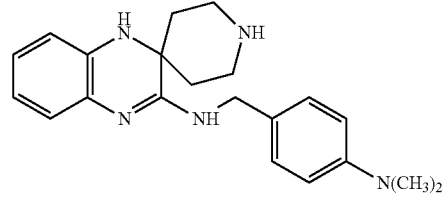 N-27
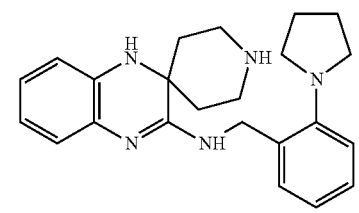 N-28

TABLE 1-N-continued
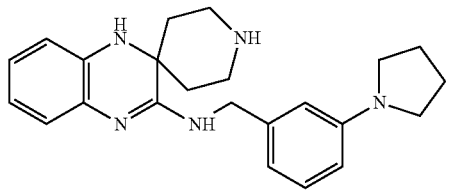 N-29
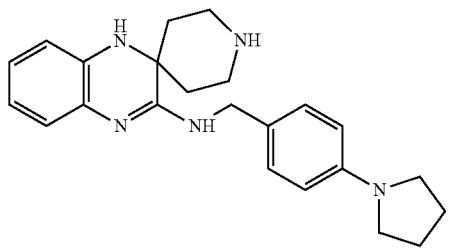 N-30
 N-31
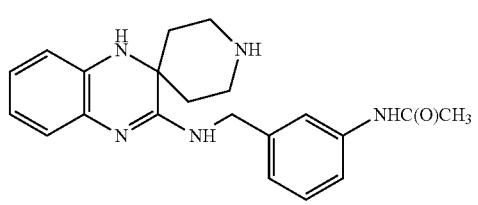 N-32
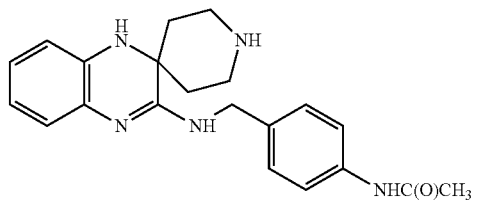 N-33
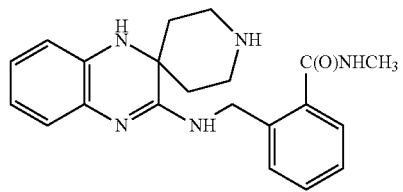 N-34
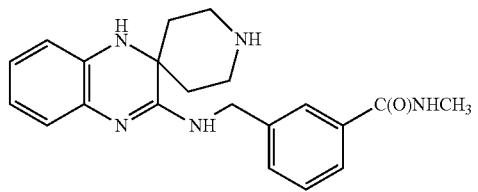 N-35
TABLE 1-N-continued
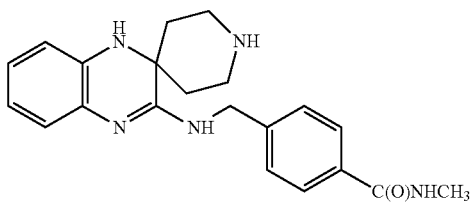 N-36
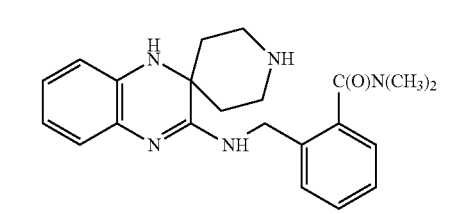 N-37
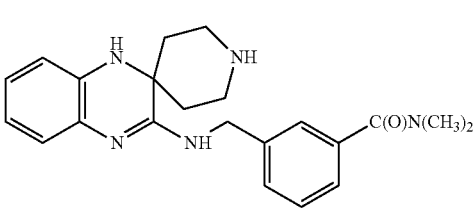 N-38
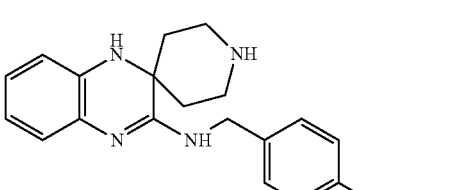 N-39
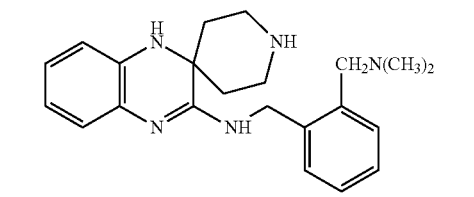 N-40
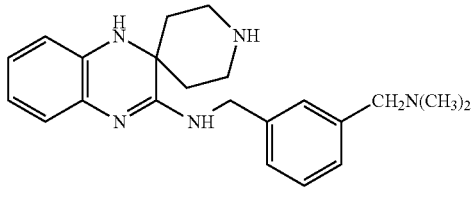 N-41
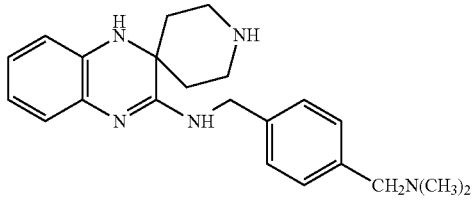 N-42

TABLE 1-N-continued
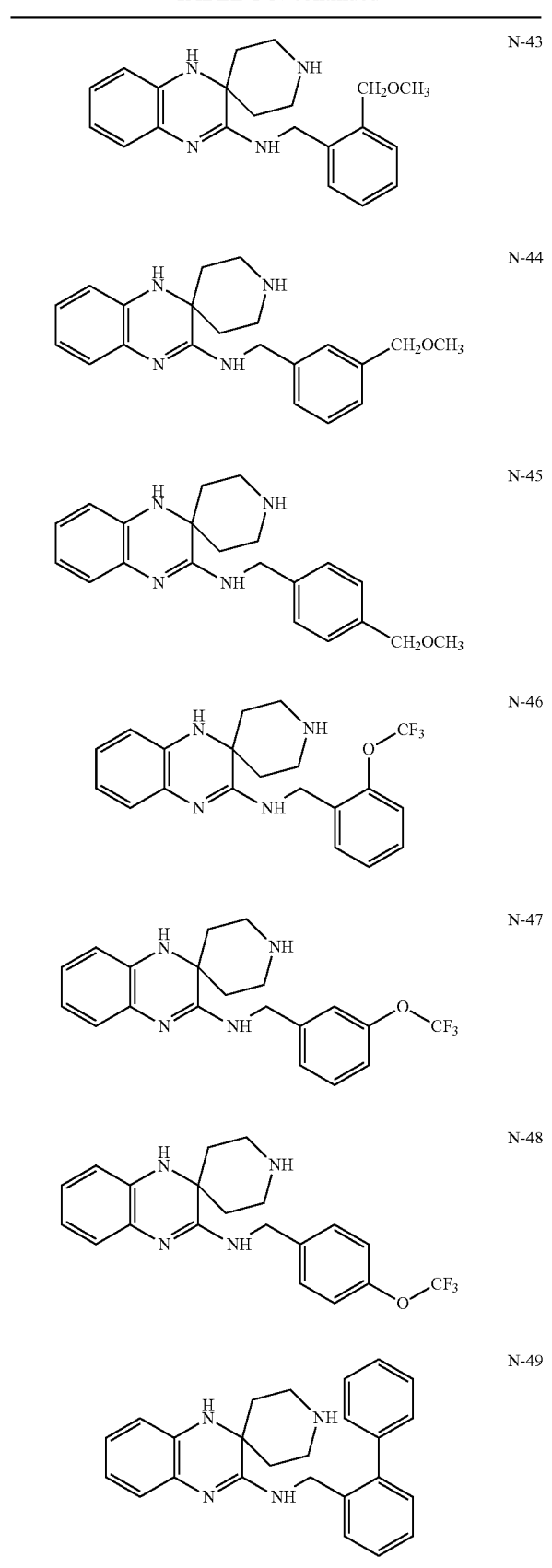
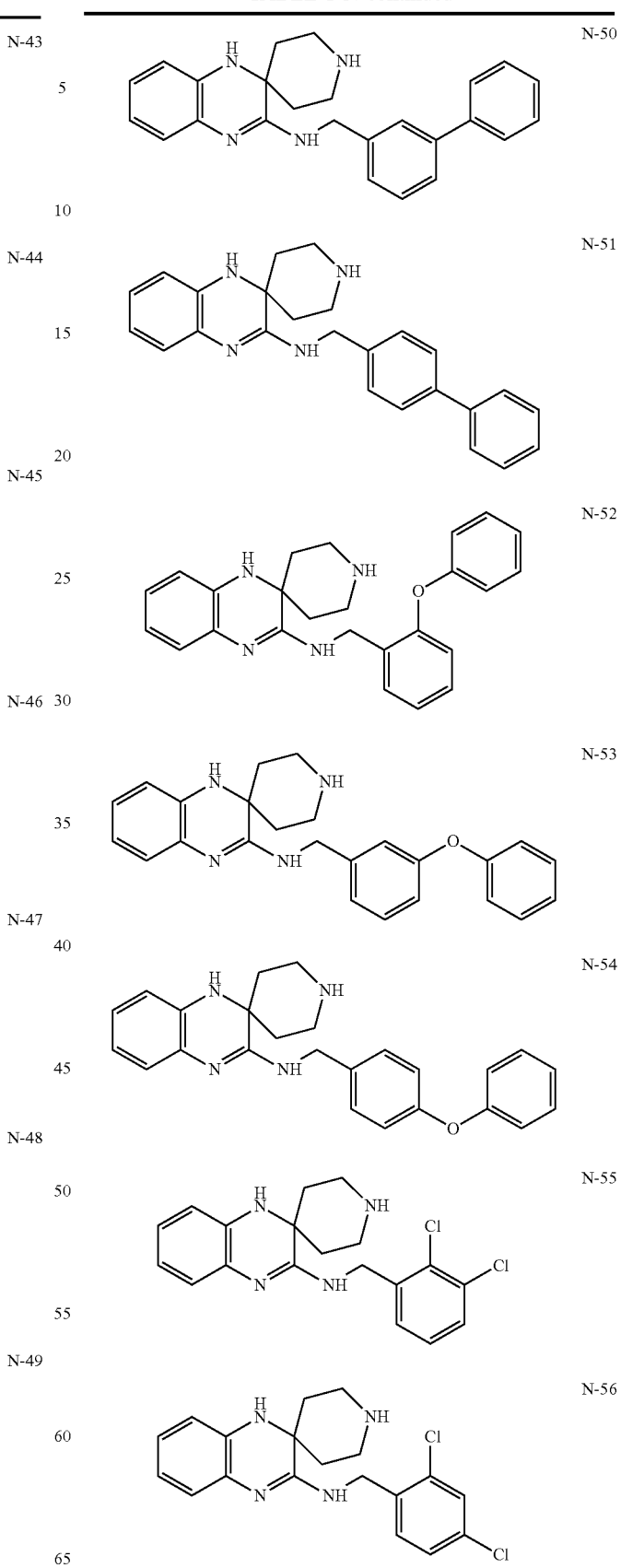

TABLE 1-N-continued
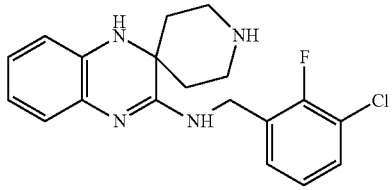 [SMILES: Fc1c(Cl)cccc1CNC1=Nc2ccccc2NC12CCNCC2]
N-57
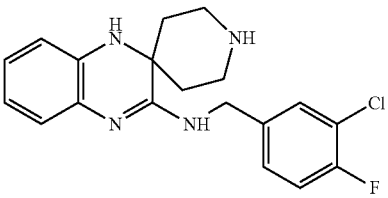 [SMILES: Fc1ccc(CNC2=Nc3ccccc3NC23CCNCC3)cc1Cl]
N-64
N-58
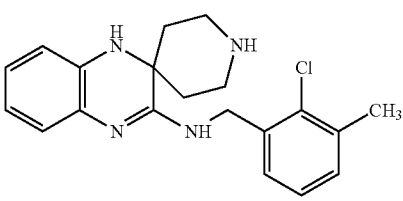
N-65
N-59
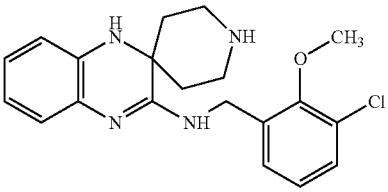 [SMILES: COc1c(Cl)cccc1CNC1=Nc2ccccc2NC12CCNCC2]
N-66
N-60
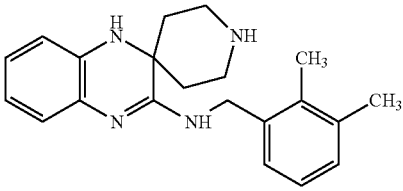
N-67
N-61
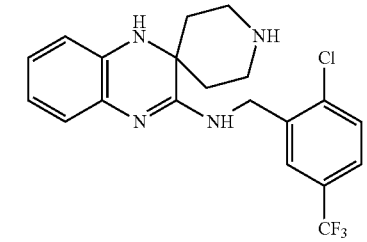
N-68
N-62
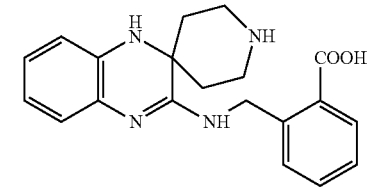 [SMILES: O=C(O)c1ccccc1CNC1=Nc2ccccc2NC12CCNCC2]
N-69
N-63
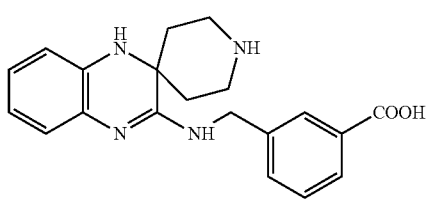 [SMILES: O=C(O)c1cccc(CNC2=Nc3ccccc3NC23CCNCC3)c1]
N-70

TABLE 1-N-continued
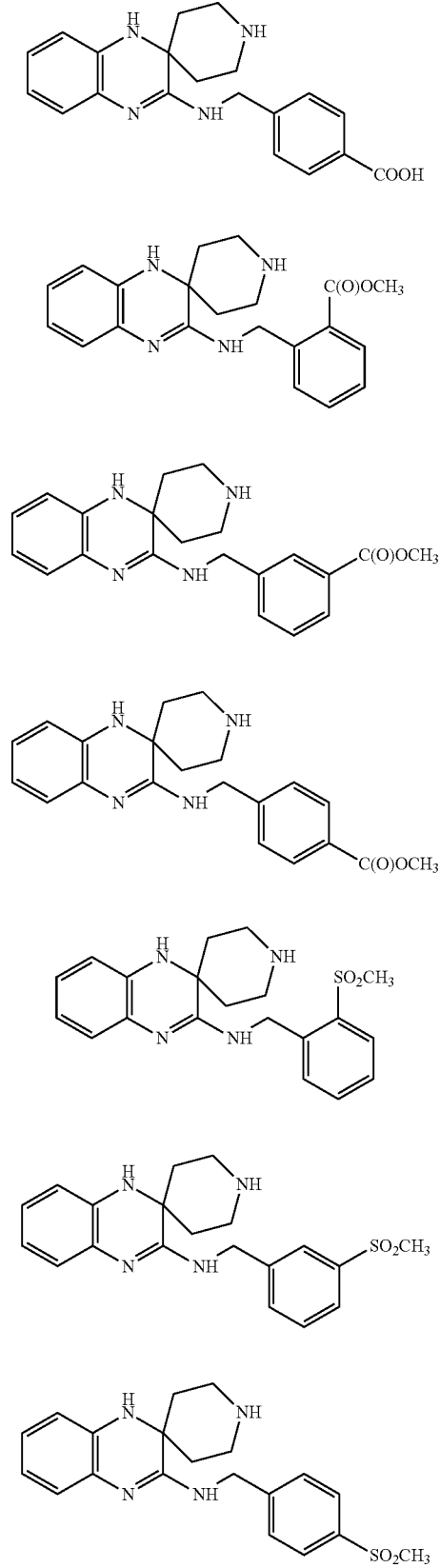
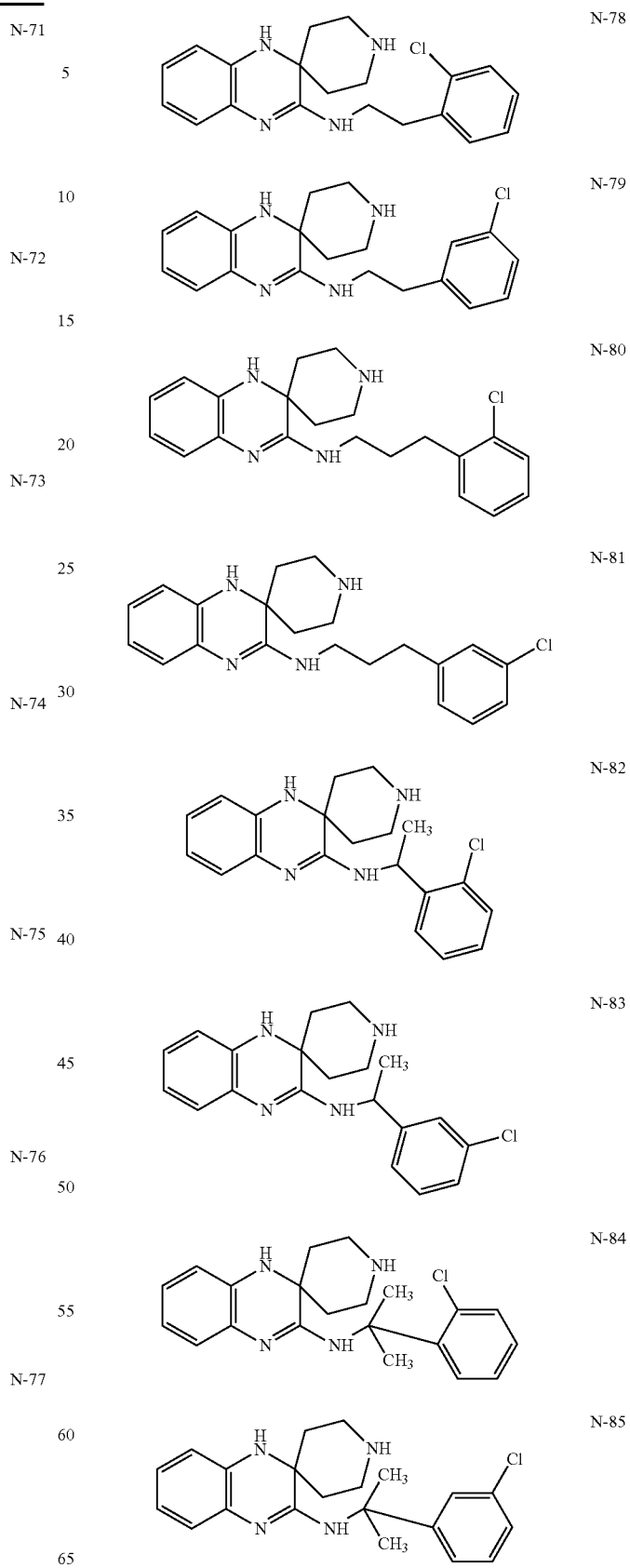

TABLE 1-N-continued
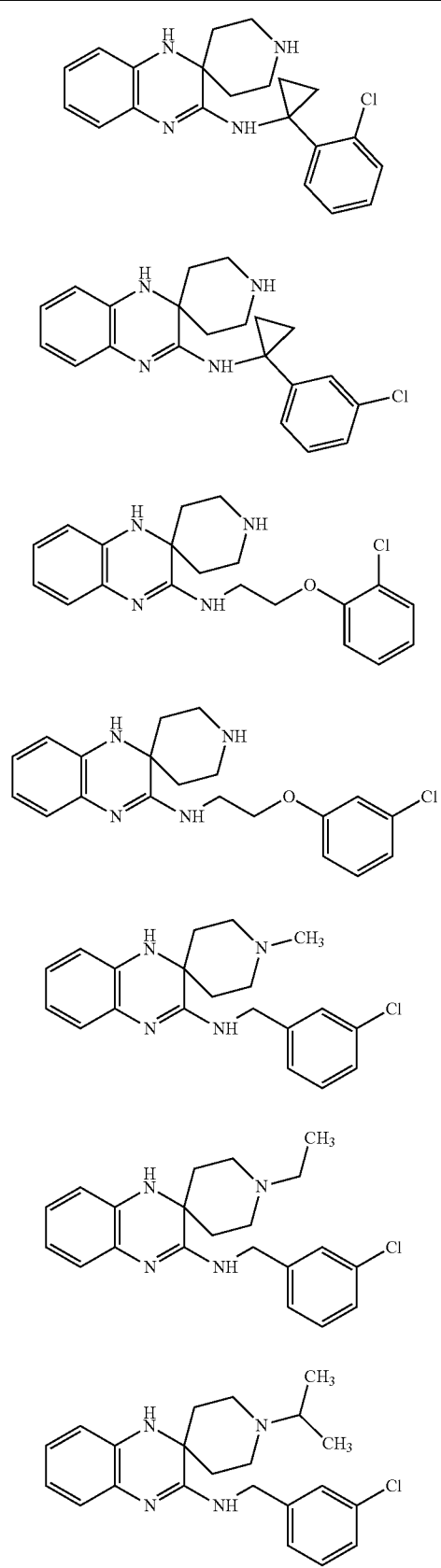
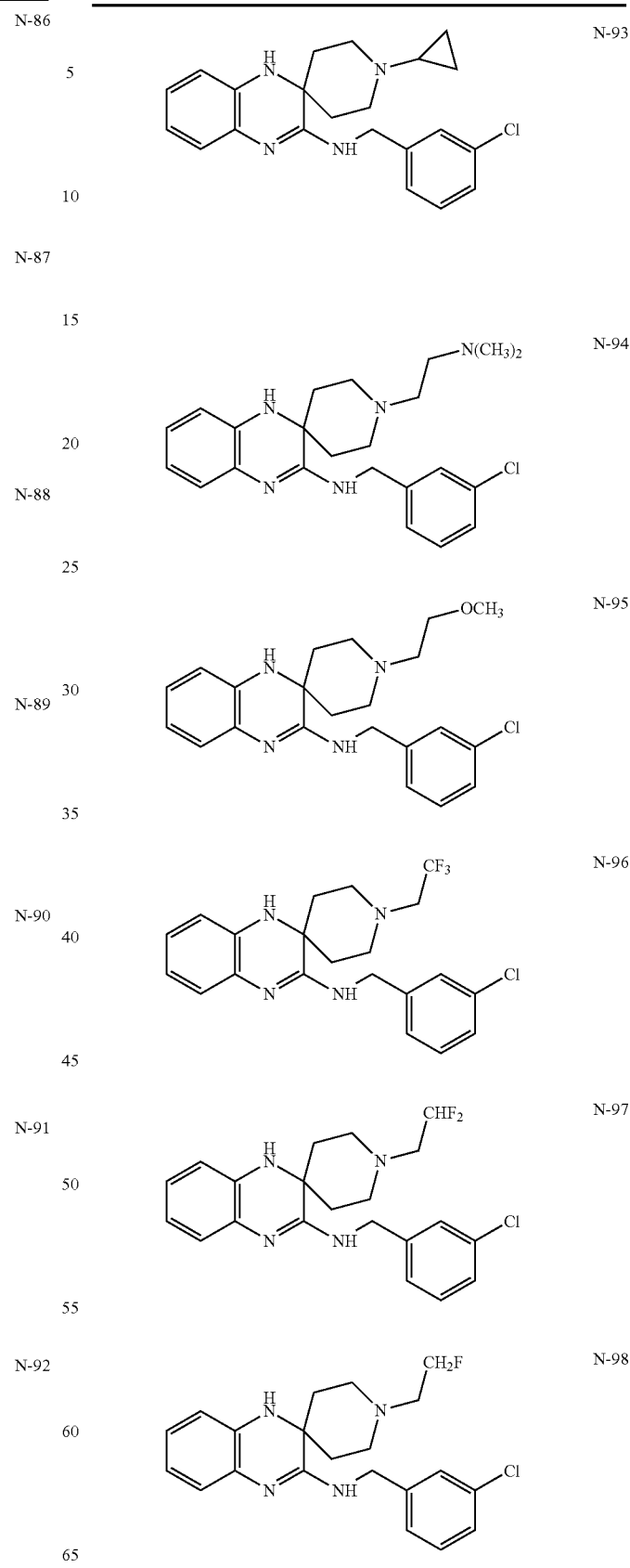

TABLE 1-N-continued
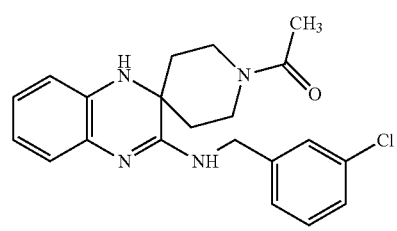 [SMILES: CC(=O)N1CCC2(CC1)Nc1ccccc1N=C2NCc1cccc(Cl)c1]
N-99
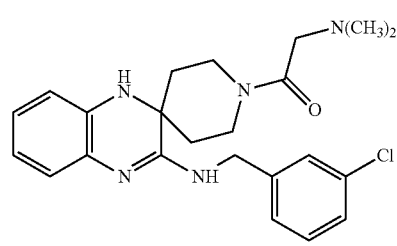 [SMILES: CN(C)CC(=O)N1CCC2(CC1)Nc1ccccc1N=C2NCc1cccc(Cl)c1]
N-100
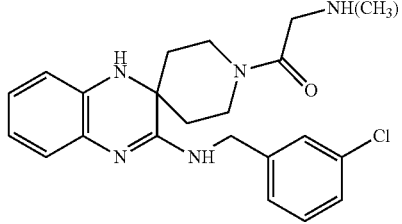
N-101
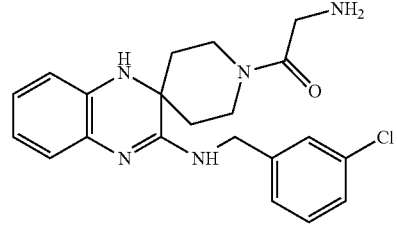 [SMILES: NCC(=O)N1CCC2(CC1)Nc1ccccc1N=C2NCc1cccc(Cl)c1]
N-102
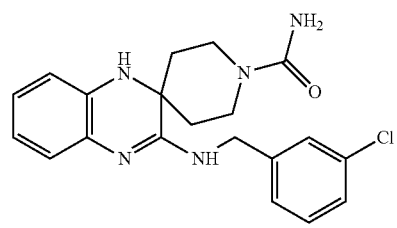 [SMILES: NC(=O)N1CCC2(CC1)Nc1ccccc1N=C2NCc1cccc(Cl)c1]
N-103
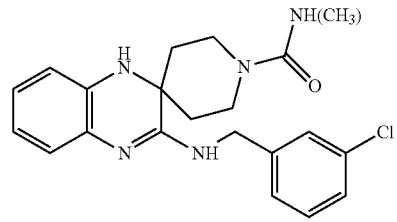
N-104
TABLE 1-N-continued
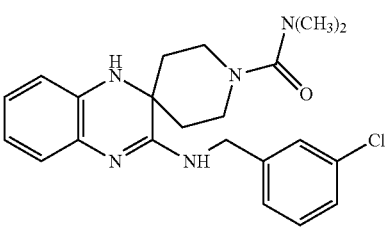 [SMILES: CN(C)C(=O)N1CCC2(CC1)Nc1ccccc1N=C2NCc1cccc(Cl)c1]
N-105
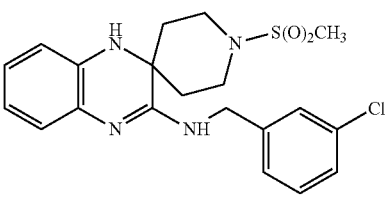
N-106
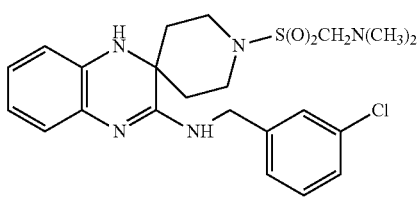
N-107
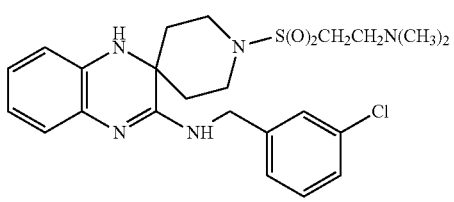
N-108
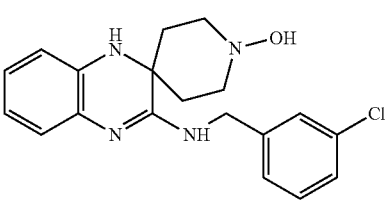
N-109
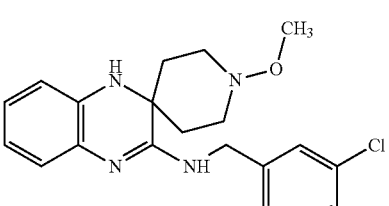
N-110
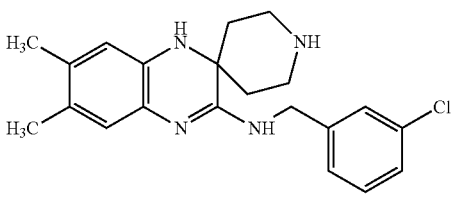 [SMILES: Cc1cc2c(cc1C)NC1(CCNCC1)C(NCc1cccc(Cl)c1)=N2]
N-111

TABLE 1-N-continued
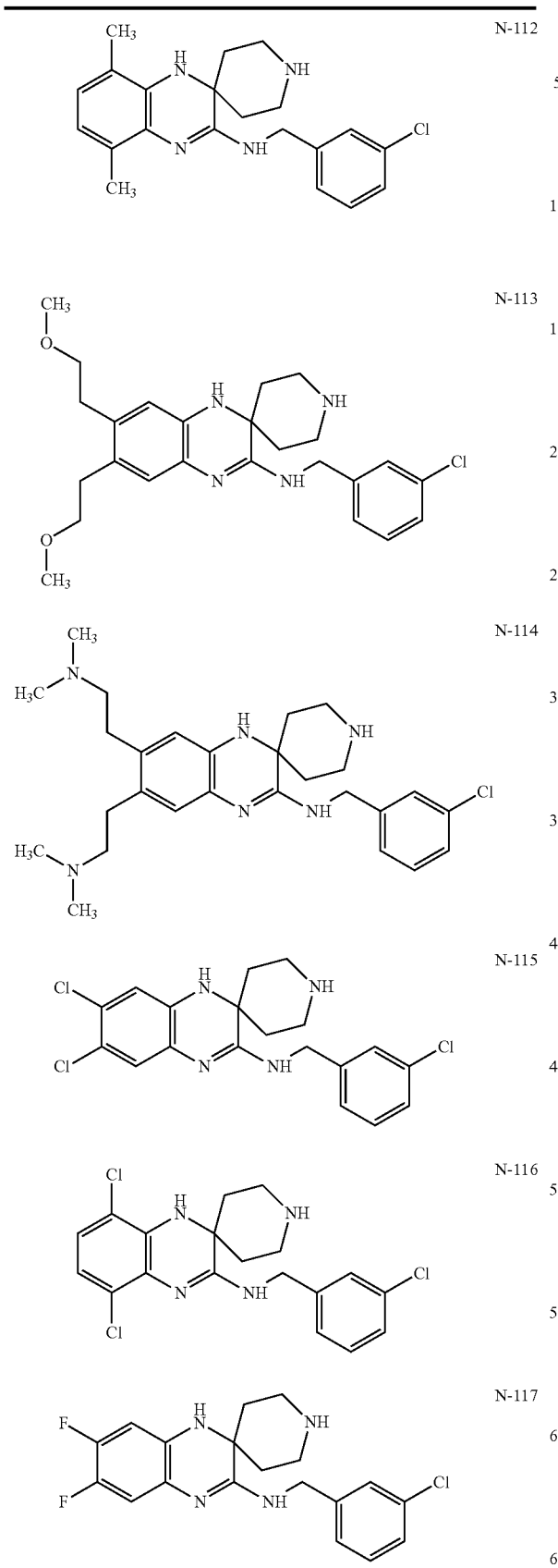
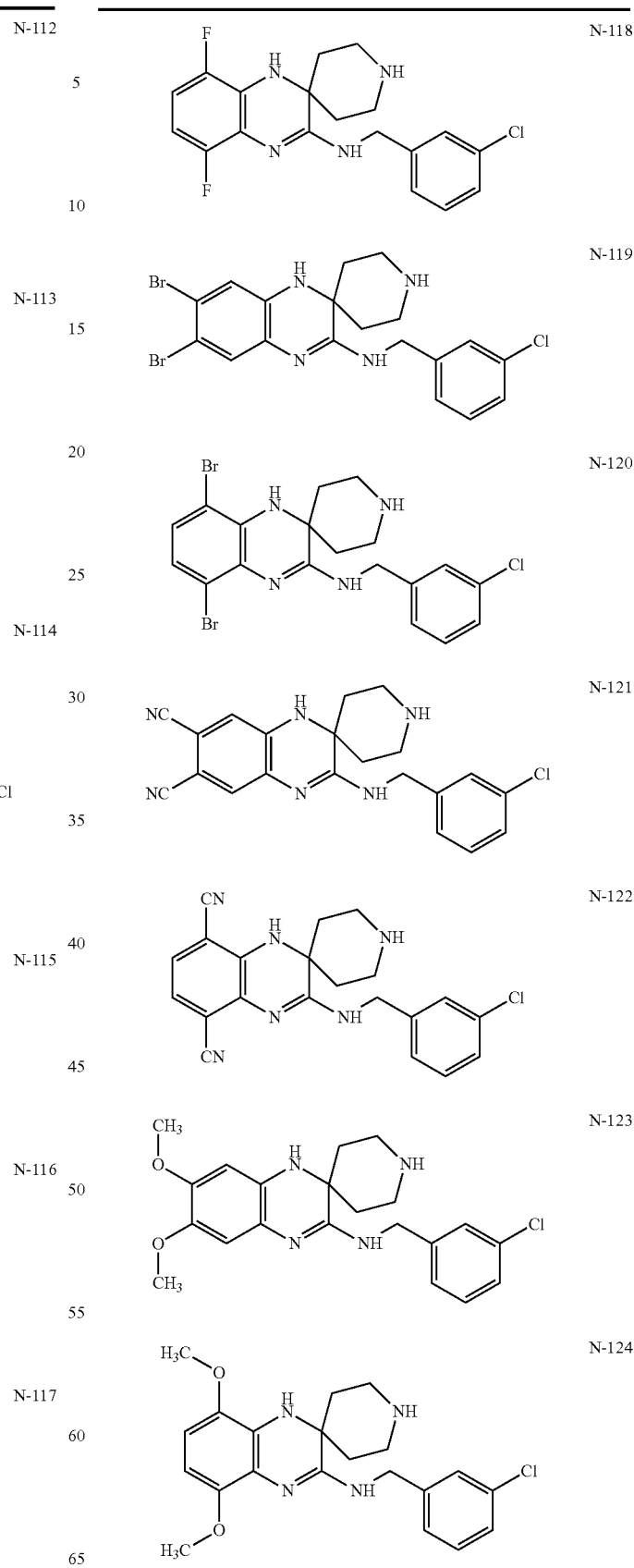

TABLE 1-N-continued
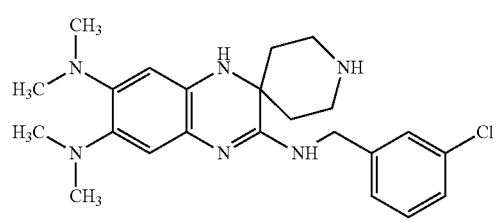
N-125
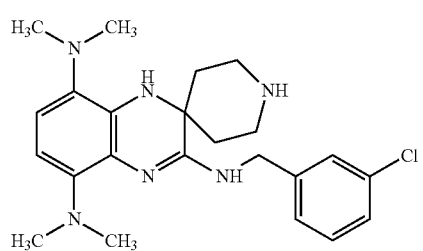
N-126
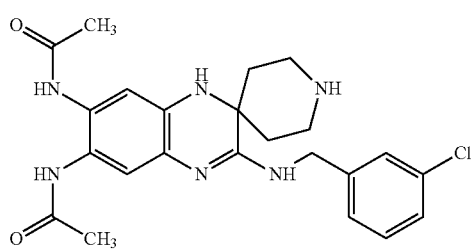
N-127
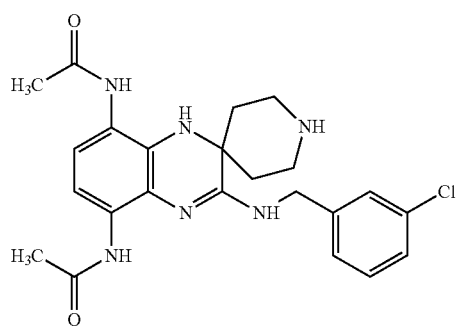 [SMILES: CC(=O)Nc1ccc(NC(C)=O)c2c1N=C(NCc1cccc(Cl)c1)C1(CCNCC1)N2]
N-128
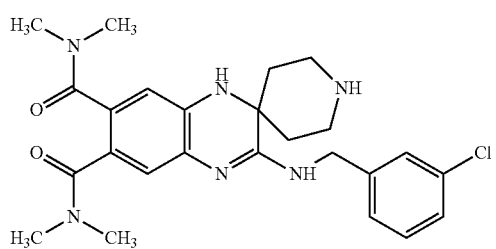
N-129
TABLE 1-N-continued
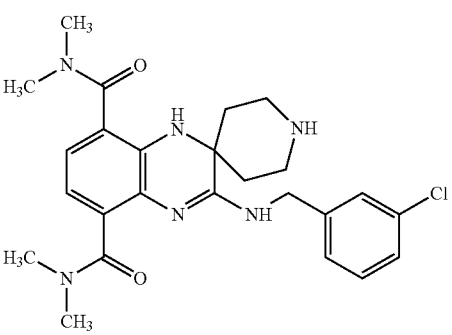
N-130
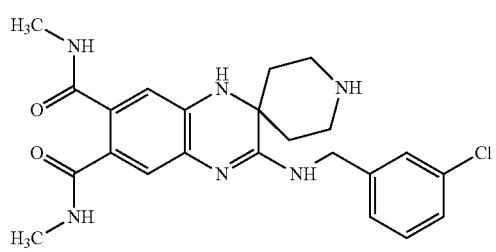
N-131
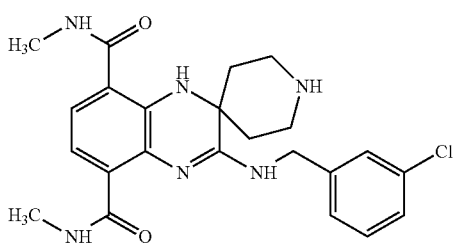 [SMILES: CNC(=O)c1ccc(C(=O)NC)c2c1N=C(NCc1cccc(Cl)c1)C1(CCNCC1)N2]
N-132
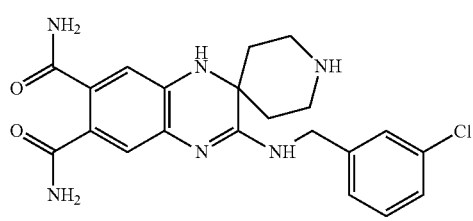 [SMILES: NC(=O)c1cc2c(cc1C(N)=O)NC1(CCNCC1)C(NCc1cccc(Cl)c1)=N2]
N-133
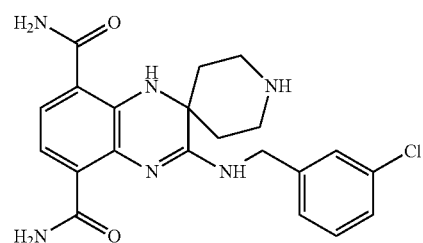
N-134
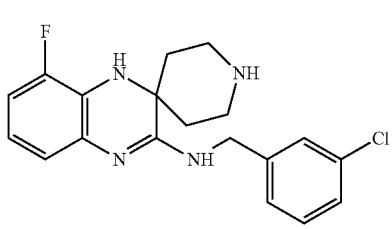 [SMILES: Fc1cccc2c1NC1(CCNCC1)C(NCc1cccc(Cl)c1)=N2]
N-135

TABLE 1-N-continued
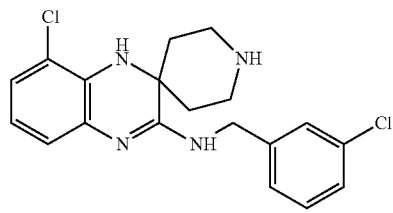
N-136
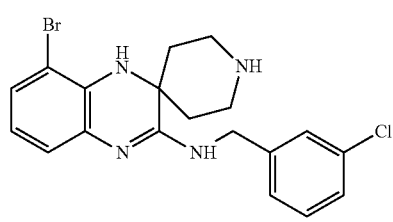 [SMILES: Clc1cccc(CNC2=Nc3cccc(Cl)c3NC23CCNCC3)c1]
N-137
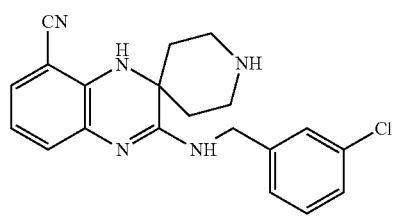 [SMILES: N#Cc1cccc2c1NC1(CCNCC1)C(NCc1cccc(Cl)c1)=N2]
N-138
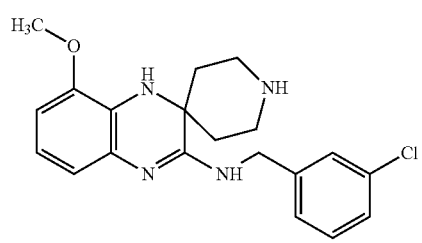 [SMILES: COc1cccc2c1NC1(CCNCC1)C(NCc1cccc(Cl)c1)=N2]
N-139
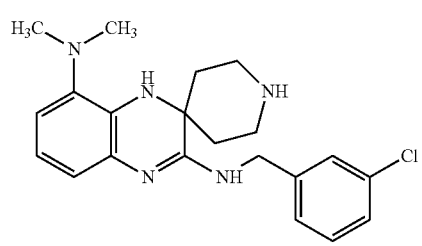 [SMILES: CN(C)c1cccc2c1NC1(CCNCC1)C(NCc1cccc(Cl)c1)=N2]
N-140
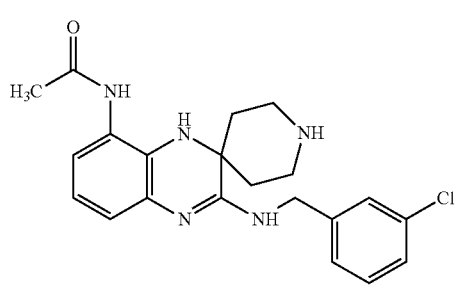 [SMILES: CC(=O)Nc1cccc2c1NC1(CCNCC1)C(NCc1cccc(Cl)c1)=N2]
N-141
TABLE 1-N-continued
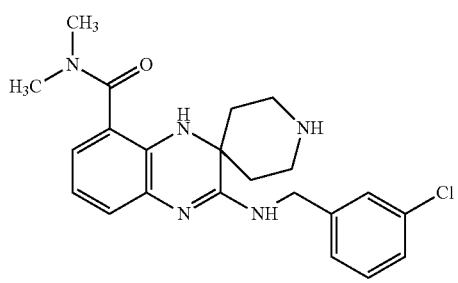 [SMILES: CN(C)C(=O)c1cccc2c1NC1(CCNCC1)C(NCc1cccc(Cl)c1)=N2]
N-142
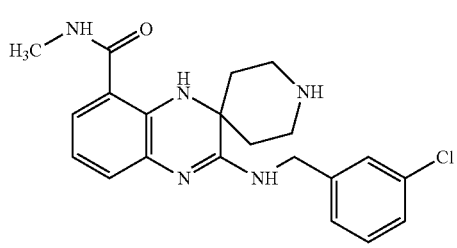 [SMILES: CNC(=O)c1cccc2c1NC1(CCNCC1)C(NCc1cccc(Cl)c1)=N2]
N-143
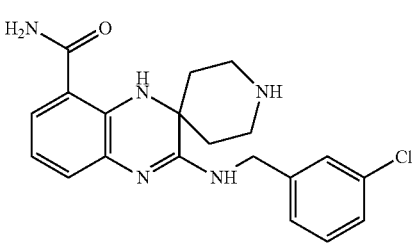 [SMILES: NC(=O)c1cccc2c1NC1(CCNCC1)C(NCc1cccc(Cl)c1)=N2]
N-144
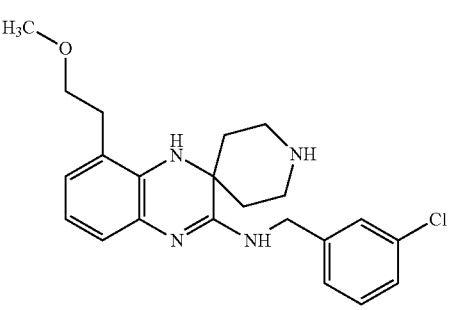 [SMILES: COCCc1cccc2c1NC1(CCNCC1)C(NCc1cccc(Cl)c1)=N2]
N-145
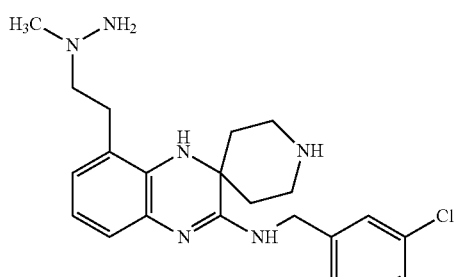
N-146
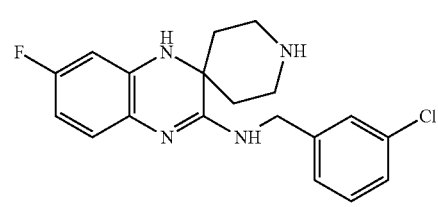
N-147

TABLE 1-N-continued
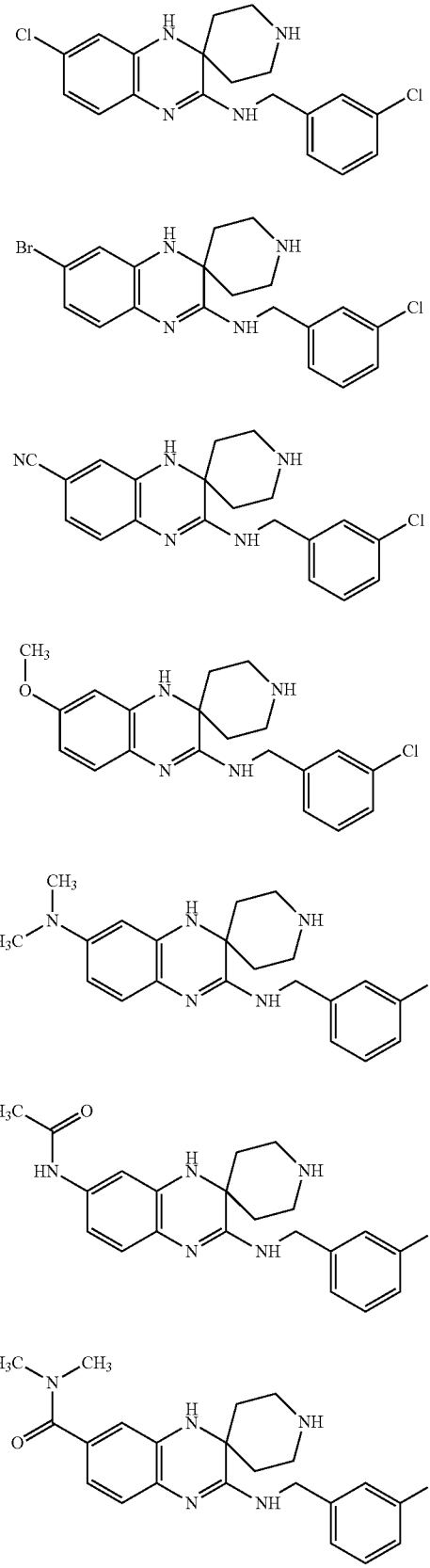
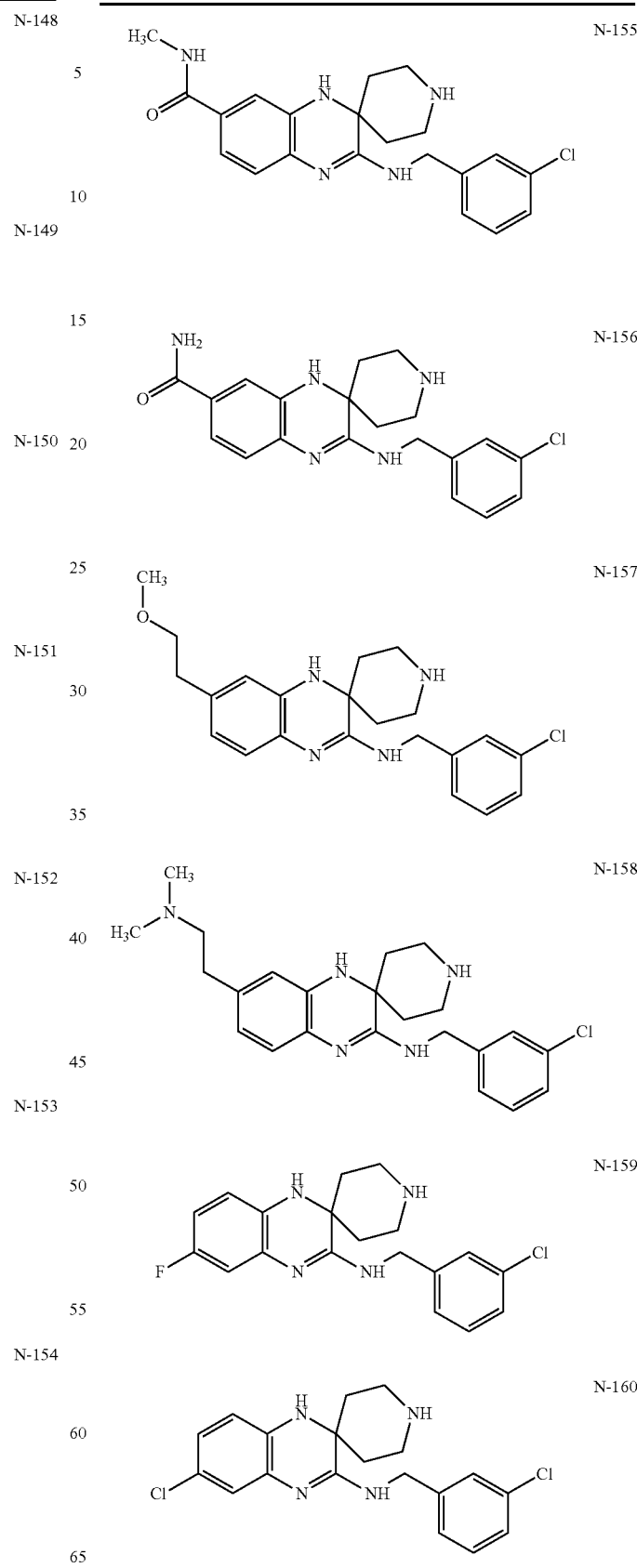

TABLE 1-N-continued
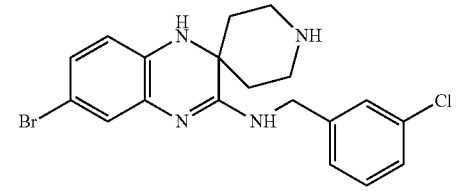 N-161
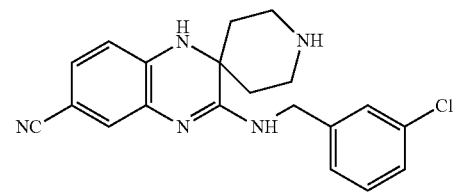 [SMILES: N#Cc1ccc2c(c1)N=C(NCc1cccc(Cl)c1)C1(CCNCC1)N2] N-162
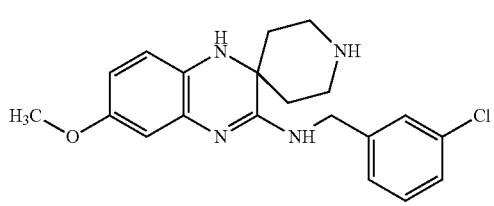 N-163
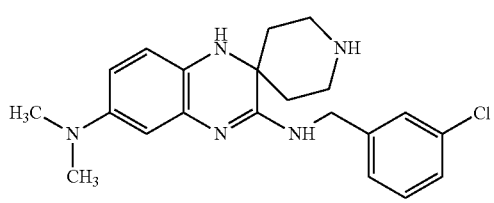 N-164
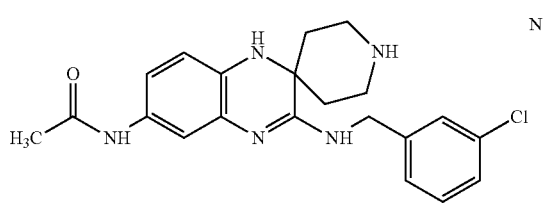 N-165
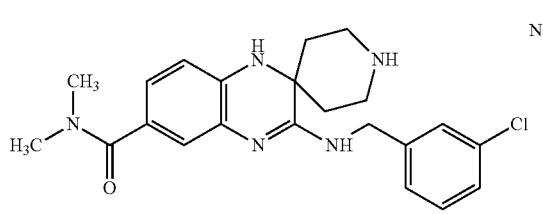 N-166
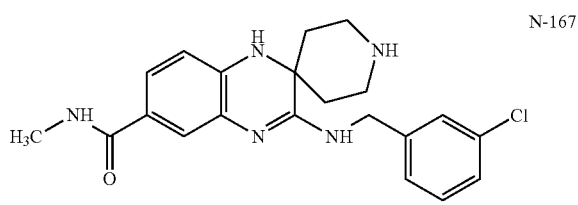 N-167
TABLE 1-N-continued
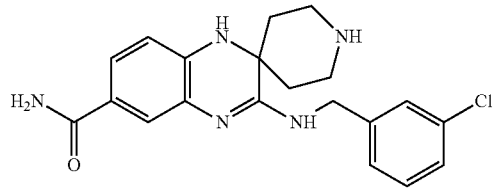 [SMILES: NC(=O)c1ccc2c(c1)N=C(NCc1cccc(Cl)c1)C1(CCNCC1)N2] N-168
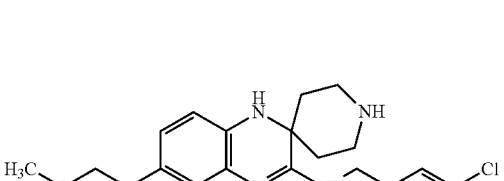 N-169
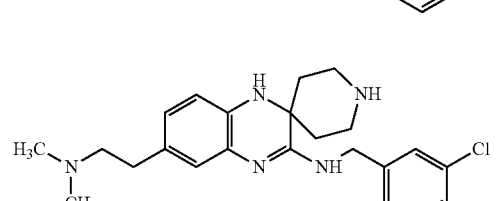 N-170
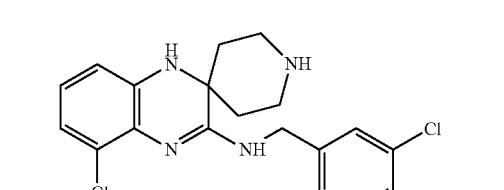 N-171
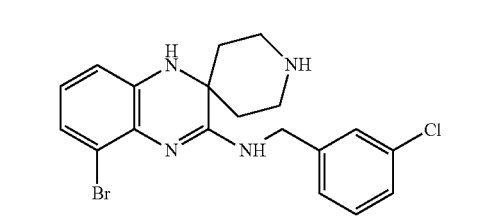 [SMILES: Clc1cccc(CNC2=Nc3c(Br)cccc3NC23CCNCC3)c1] N-172
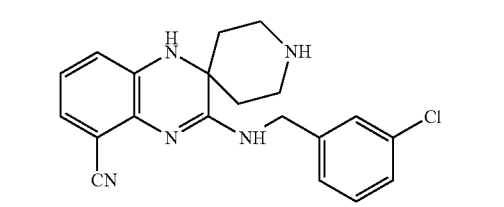 [SMILES: N#Cc1cccc2c1N=C(NCc1cccc(Cl)c1)C1(CCNCC1)N2] N-173
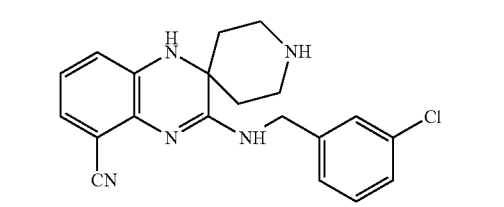 [SMILES: N#Cc1cccc2c1N=C(NCc1cccc(Cl)c1)C1(CCNCC1)N2] N-174

TABLE 1-N-continued
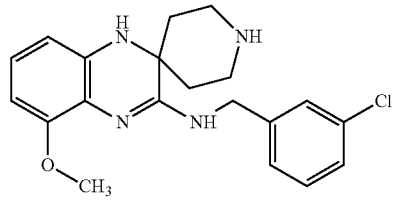
N-175
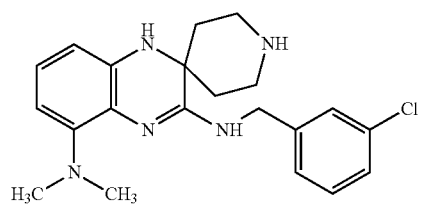
N-176
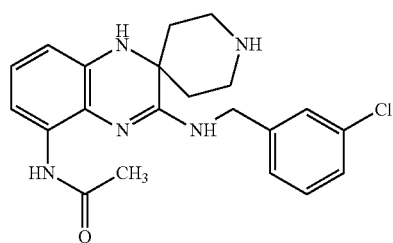 [SMILES: CC(=O)Nc1cccc2c1N=C(NCc1cccc(Cl)c1)C1(CCNCC1)N2]
N-177
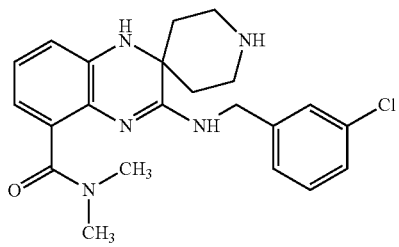
N-178
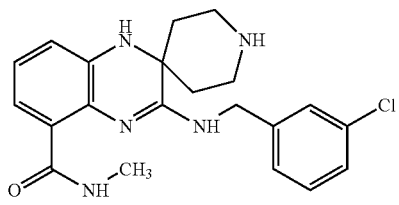 [SMILES: CNC(=O)c1cccc2c1N=C(NCc1cccc(Cl)c1)C1(CCNCC1)N2]
N-179
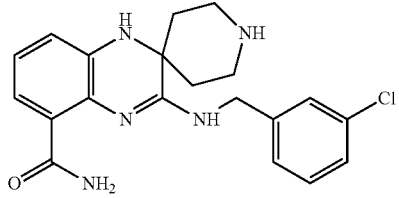
N-180
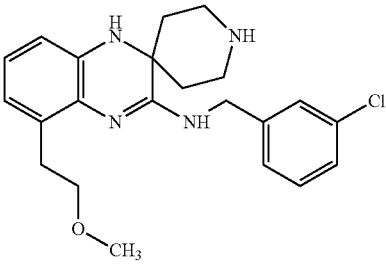 [SMILES: COCCc1cccc2c1N=C(NCc1cccc(Cl)c1)C1(CCNCC1)N2]
N-181
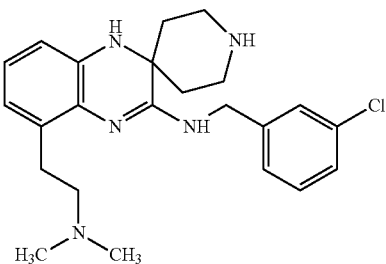 [SMILES: CN(C)CCc1cccc2c1N=C(NCc1cccc(Cl)c1)C1(CCNCC1)N2]
N-182
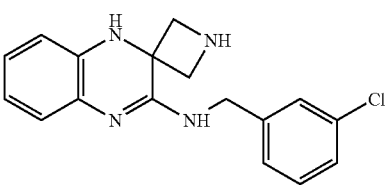 [SMILES: Clc1cccc(CNC2=Nc3ccccc3NC23CNC3)c1]
N-183
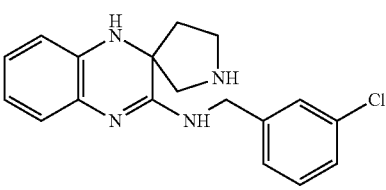 [SMILES: Clc1cccc(CNC2=Nc3ccccc3NC23CCNC3)c1]
N-184
N-185
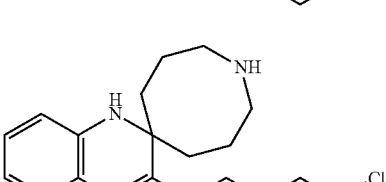
N-186
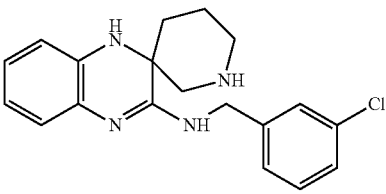 [SMILES: Clc1cccc(CNC2=Nc3ccccc3NC23CCCNC3)c1]
N-187

TABLE 1-N-continued

N-188
N-189
N-190
N-191
N-192
N-193
N-194
N-195
N-196
N-197
N-198
N-199
N-200

TABLE 1-N-continued
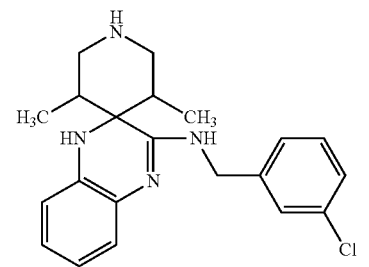 [SMILES: CC1CNCC(C)C12Nc1ccccc1N=C2NCc1cccc(Cl)c1] N-201
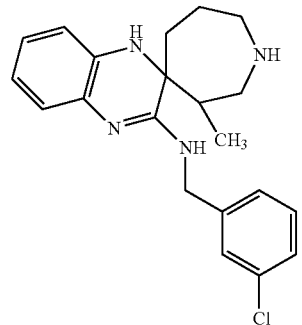 [SMILES: CC1CNCCCC12Nc1ccccc1N=C2NCc1cccc(Cl)c1] N-202
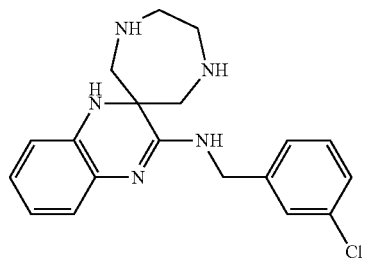 [SMILES: Clc1cccc(CNC2=Nc3ccccc3NC23CNCCNC3)c1] N-203
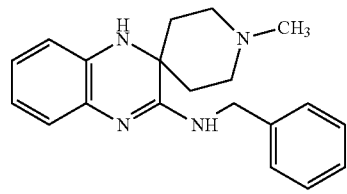 N-204
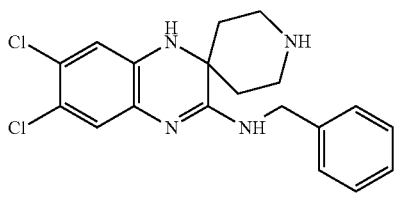 [SMILES: Clc1cc2c(cc1Cl)NC1(CCNCC1)C(NCc1ccccc1)=N2] N-205
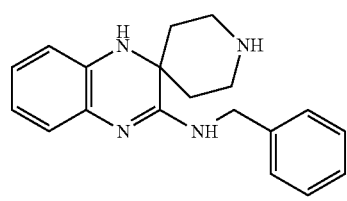 [SMILES: c1ccc(CNC2=Nc3ccccc3NC23CCNCC3)cc1] N-206
TABLE 1-N-continued
 N-207
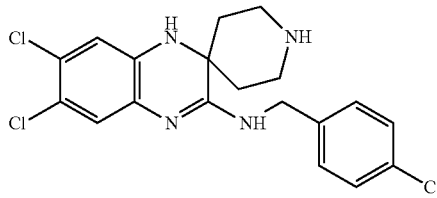 N-208
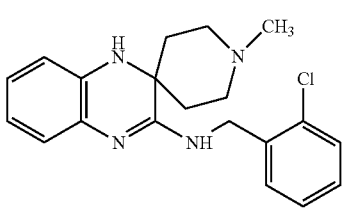 [SMILES: CN1CCC2(CC1)Nc1ccccc1N=C2NCc1ccccc1Cl] N-209
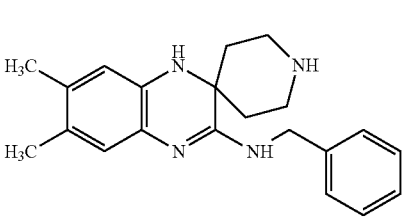 N-210
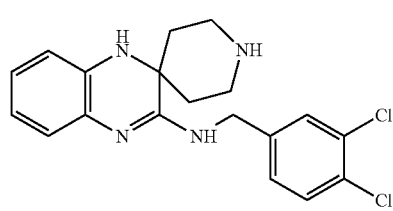 [SMILES: Clc1ccc(CNC2=Nc3ccccc3NC23CCNCC3)cc1Cl] N-211
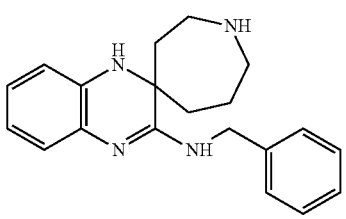 [SMILES: c1ccc(CNC2=Nc3ccccc3NC23CCCNCC3)cc1] N-212
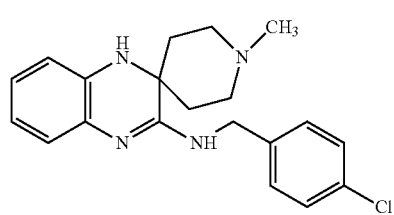 [SMILES: CN1CCC2(CC1)Nc1ccccc1N=C2NCc1ccc(Cl)cc1] N-213

TABLE 1-N-continued
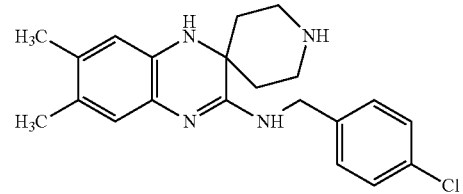 [SMILES: Cc1cc2c(cc1C)NC1(CCNCC1)C(NCc1ccc(Cl)cc1)=N2]
N-214
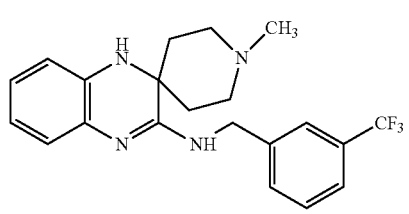 [SMILES: CN1CCC2(CC1)Nc1ccccc1N=C2NCc1cccc(C(F)(F)F)c1]
N-215
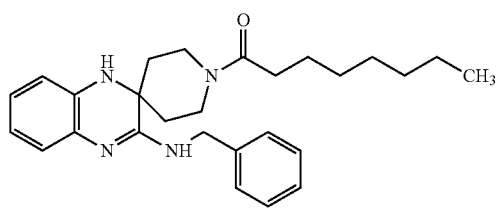 [SMILES: CCCCCCCC(=O)N1CCC2(CC1)Nc1ccccc1N=C2NCc1ccccc1]
N-216
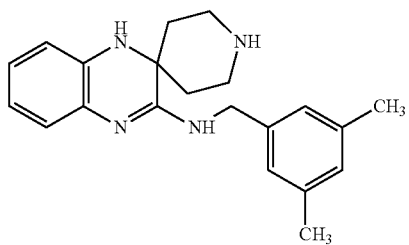 [SMILES: Cc1cc(C)cc(CNC2=Nc3ccccc3NC23CCNCC3)c1]
N-217
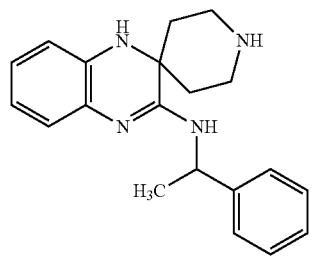 [SMILES: CC(NC1=Nc2ccccc2NC12CCNCC2)c1ccccc1]
N-218
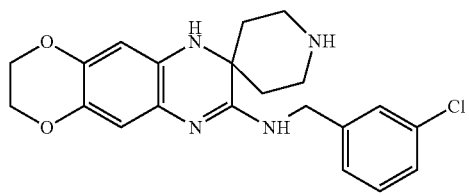 [SMILES: Clc1cccc(CNC2=Nc3cc4c(cc3NC23CCNCC3)OCCO4)c1]
N-219
TABLE 1-N-continued
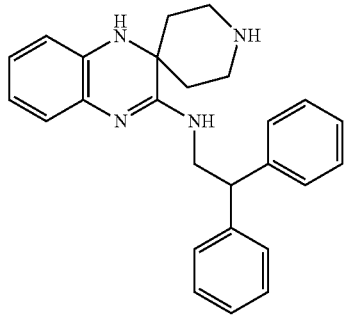 [SMILES: c1ccc(C(CNC2=Nc3ccccc3NC23CCNCC3)c2ccccc2)cc1]
N-220
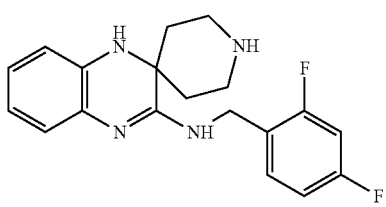
N-221
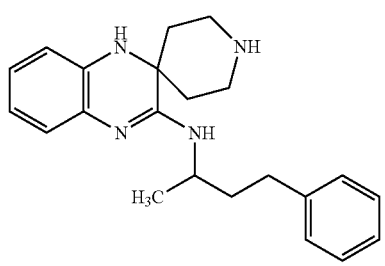
N-222
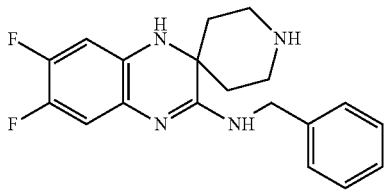 [SMILES: Fc1cc2c(cc1F)NC1(CCNCC1)C(NCc1ccccc1)=N2]
N-223
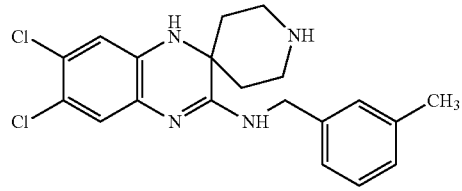 [SMILES: Cc1cccc(CNC2=Nc3cc(Cl)c(Cl)cc3NC23CCNCC3)c1]
N-224
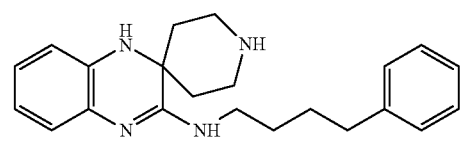
N-225
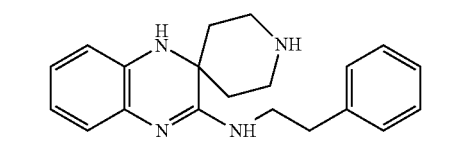 [SMILES: c1ccc(CCNC2=Nc3ccccc3NC23CCNCC3)cc1]
N-226

TABLE 1-N-continued
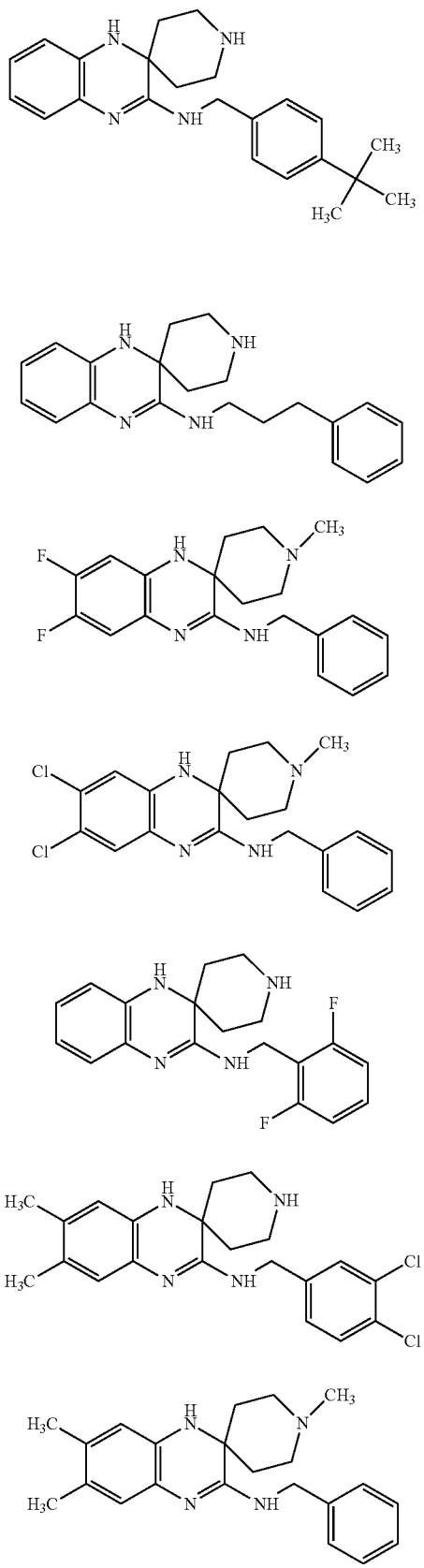
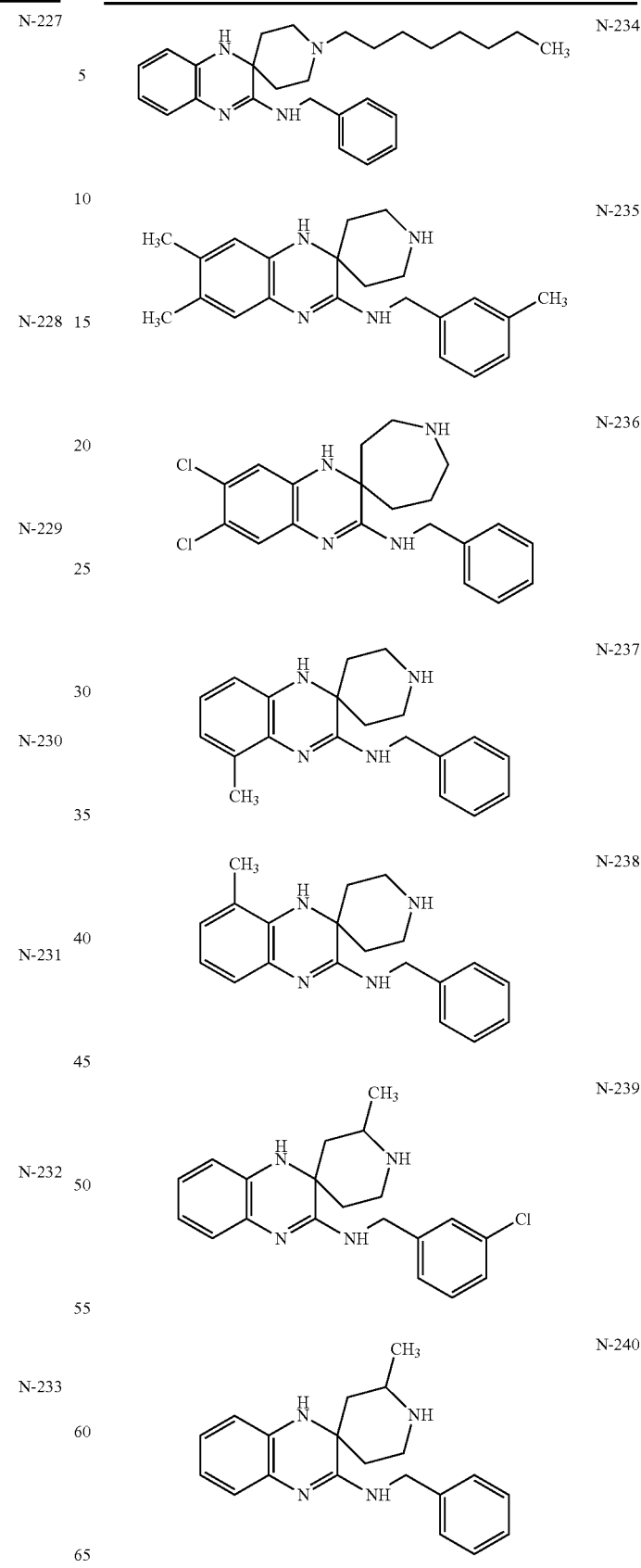

TABLE 1-N-continued
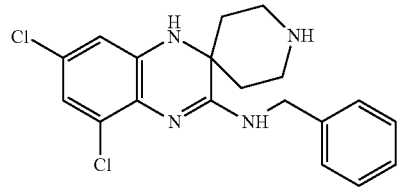 [SMILES: Clc1cc(Cl)c2c(c1)NC1(CCNCC1)C(NCc1ccccc1)=N2] N-241
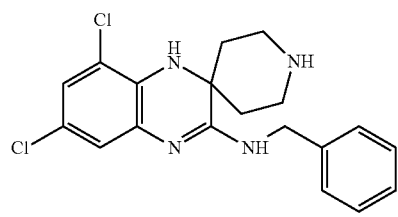 [SMILES: Clc1cc(Cl)c2c(c1)N=C(NCc1ccccc1)C1(CCNCC1)N2] N-242
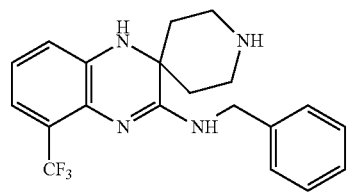 N-243
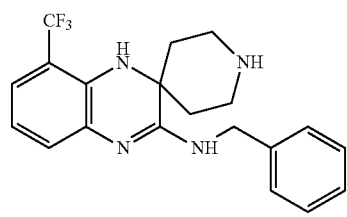 N-244
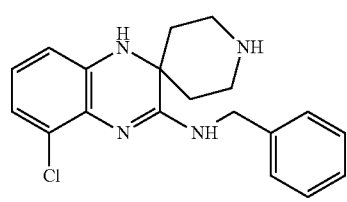 [SMILES: Clc1cccc2c1N=C(NCc1ccccc1)C1(CCNCC1)N2] N-245
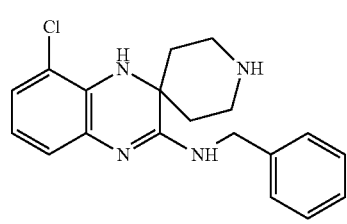 [SMILES: Clc1cccc2c1NC1(CCNCC1)C(NCc1ccccc1)=N2] N-246
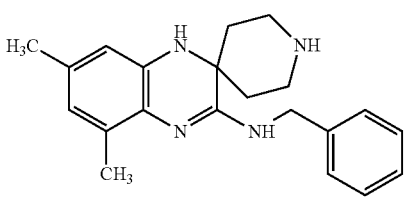 [SMILES: Cc1cc(C)c2c(c1)NC1(CCNCC1)C(NCc1ccccc1)=N2] N-247
TABLE 1-N-continued
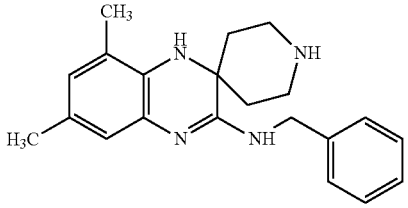 N-248
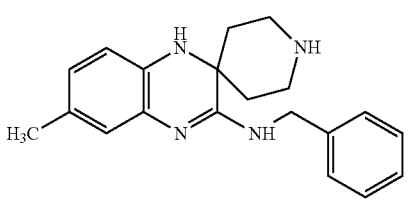 [SMILES: Cc1ccc2c(c1)N=C(NCc1ccccc1)C1(CCNCC1)N2] N-249
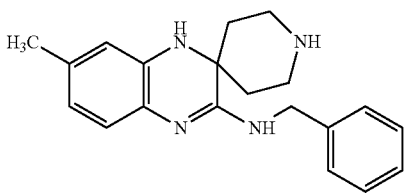 [SMILES: Cc1ccc2c(c1)NC1(CCNCC1)C(NCc1ccccc1)=N2] N-250
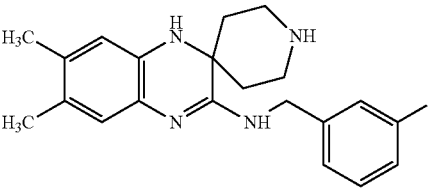 N-251
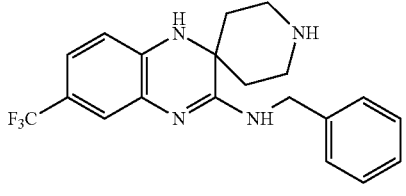 [SMILES: FC(F)(F)c1ccc2c(c1)N=C(NCc1ccccc1)C1(CCNCC1)N2] N-252
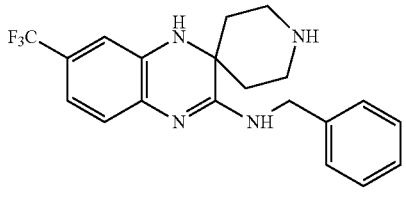 [SMILES: FC(F)(F)c1ccc2c(c1)NC1(CCNCC1)C(NCc1ccccc1)=N2] N-253
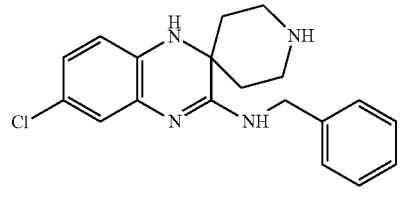 [SMILES: Clc1ccc2c(c1)N=C(NCc1ccccc1)C1(CCNCC1)N2] N-254

TABLE 1-N-continued
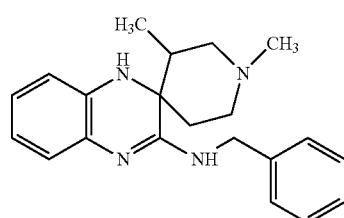
N-255
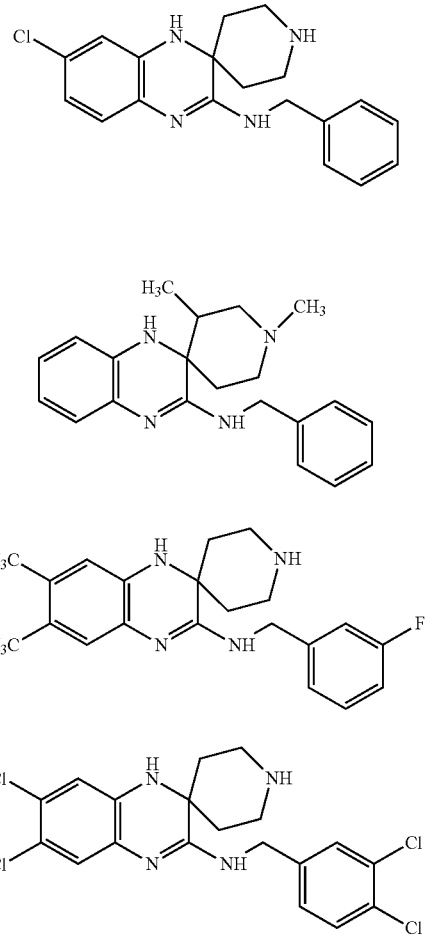
N-256
N-257
N-258
TABLE 1-N-continued
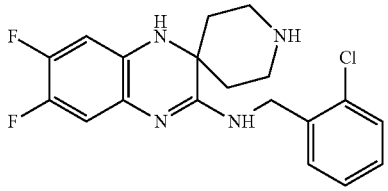 [SMILES: Fc1cc2c(cc1F)NC1(CCNCC1)C(NCc1ccccc1Cl)=N2]
N-259
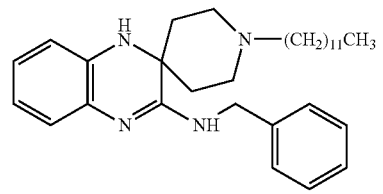
N-260
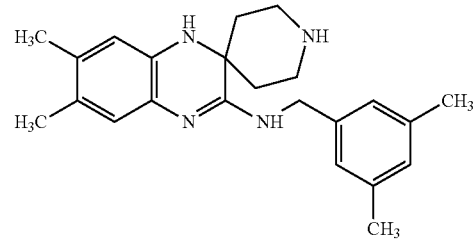
N-261
N-262
TABLE 1-O/S
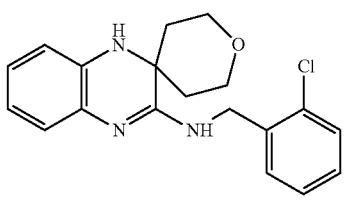
O/S-1
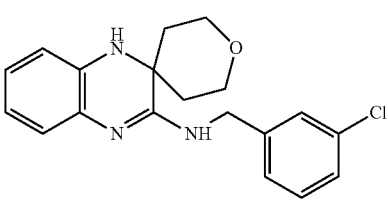
O/S-2
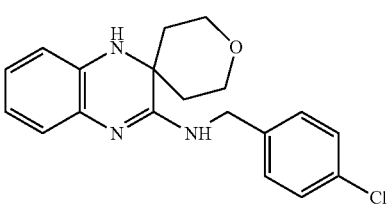
O/S-3

TABLE 1-O/S-continued
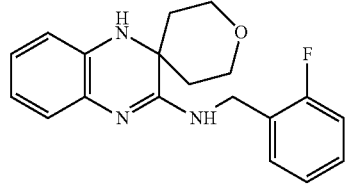 [SMILES: Fc1ccccc1CNC1=Nc2ccccc2NC12CCOCC2] O/S-4
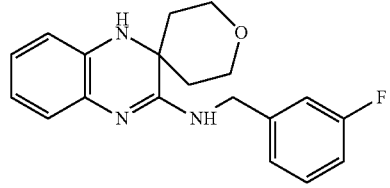 O/S-5
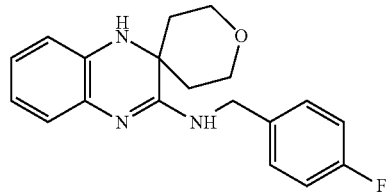 O/S-6
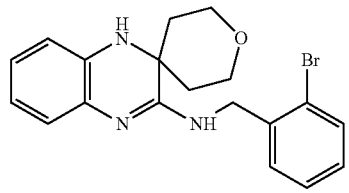 O/S-7
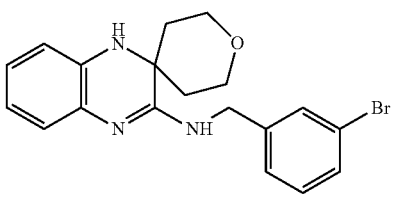 O/S-8
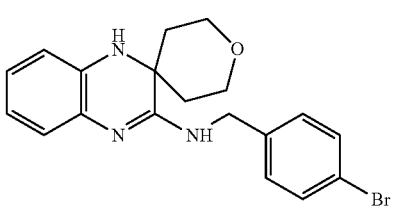 O/S-9
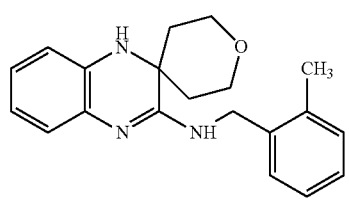 O/S-10

TABLE 1-O/S-continued
 O/S-11
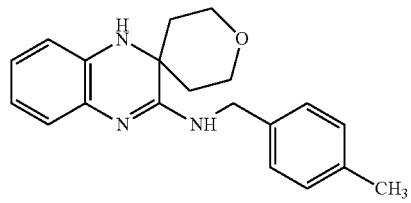 O/S-12
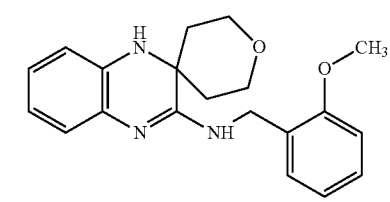 [SMILES: COc1ccccc1CNC1=Nc2ccccc2NC12CCOCC2] O/S-13
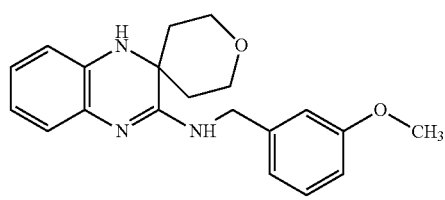 O/S-14
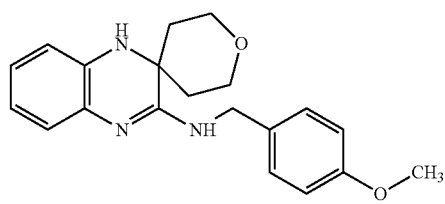 O/S-15
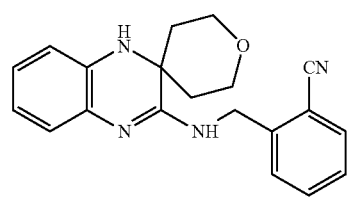 [SMILES: N#Cc1ccccc1CNC1=Nc2ccccc2NC12CCOCC2] O/S-16
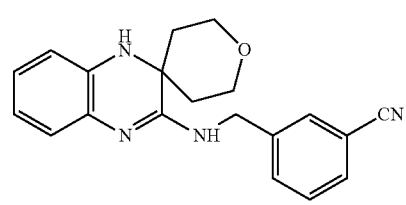 O/S-17

TABLE 1-O/S-continued
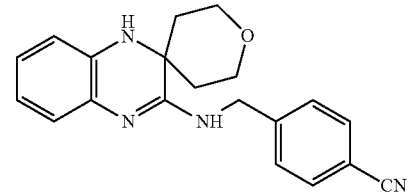
O/S-18
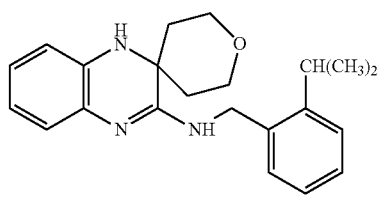 [SMILES: CC(C)c1ccccc1CNC1=Nc2ccccc2NC12CCOCC2]
O/S-19
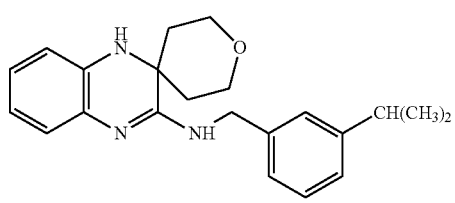
O/S-20
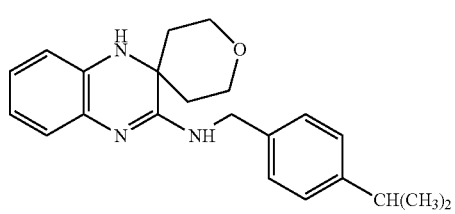
O/S-21
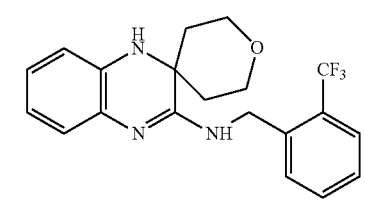
O/S-22
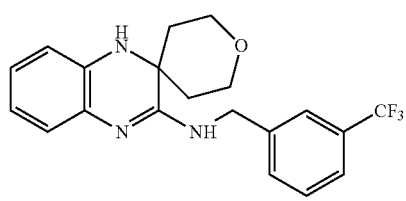 [SMILES: FC(F)(F)c1cccc(CNC2=Nc3ccccc3NC23CCOCC3)c1]
O/S-23
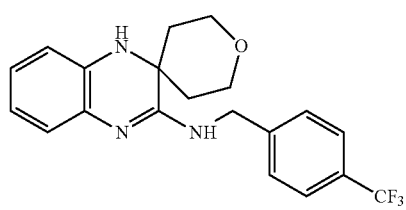
O/S-24

TABLE 1-O/S-continued
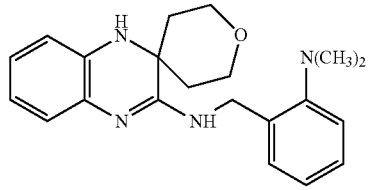 O/S-25
 O/S-26
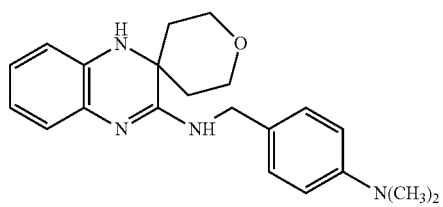 O/S-27
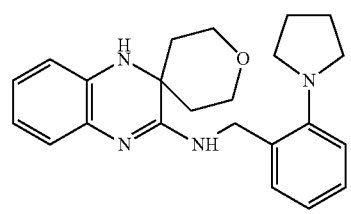 [SMILES: c1ccc(N2CCCC2)c(CNC2=Nc3ccccc3NC23CCOCC3)c1] O/S-28
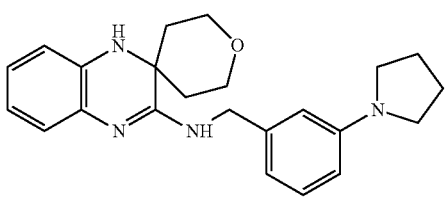 O/S-29
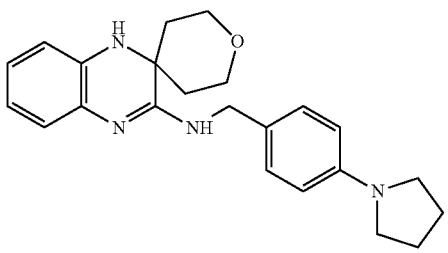 [SMILES: c1ccc2c(c1)N=C(NCc1ccc(N3CCCC3)cc1)C1(CCOCC1)N2] O/S-30
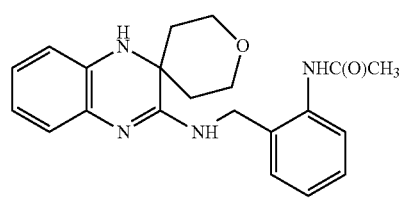 O/S-31

TABLE 1-O/S-continued
 O/S-32
 O/S-33
 O/S-34
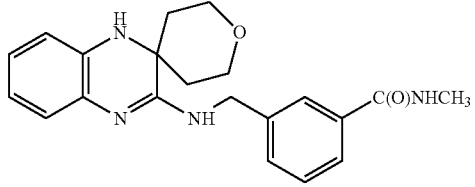 O/S-35
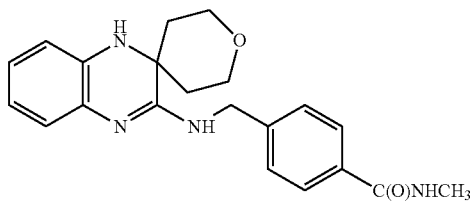 O/S-36
 O/S-37
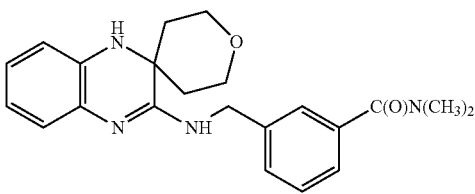 O/S-38

TABLE 1-O/S-continued
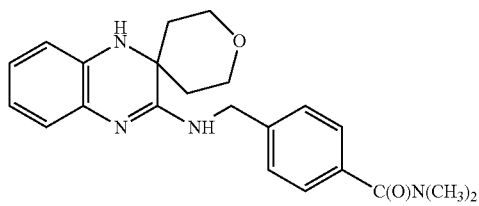
O/S-39
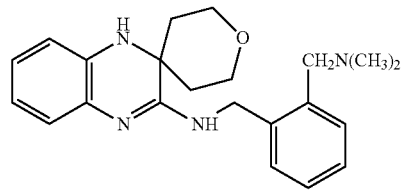
O/S-40
O/S-41
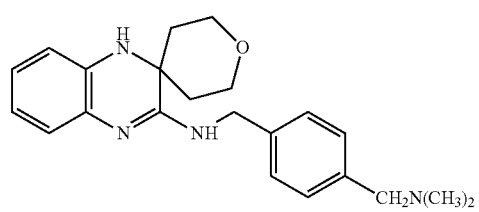
O/S-42
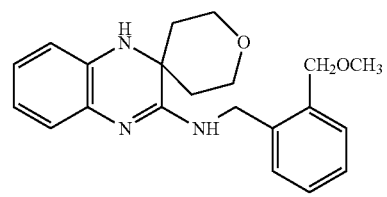
O/S-43
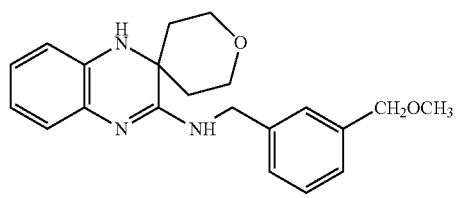
O/S-44
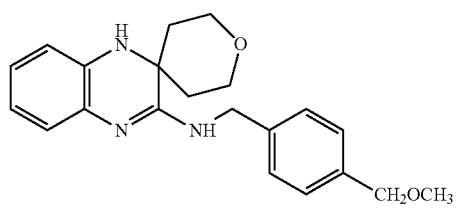
O/S-45

TABLE 1-O/S-continued
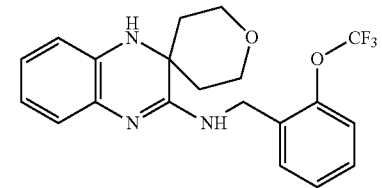 O/S-46
 O/S-47
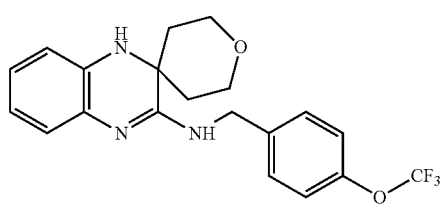 O/S-48
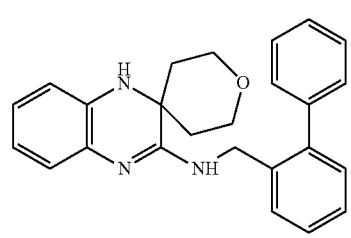 O/S-49
 O/S-50
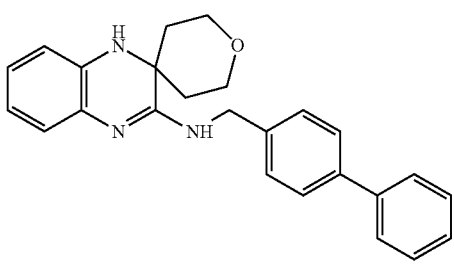 [SMILES: c1ccc(-c2ccc(CNC3=Nc4ccccc4NC34CCOCC4)cc2)cc1] O/S-51
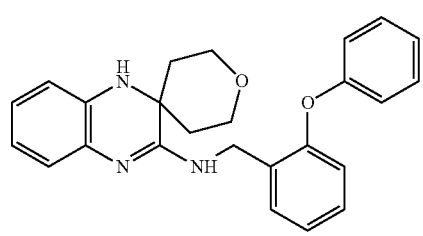 O/S-52

TABLE 1-O/S-continued
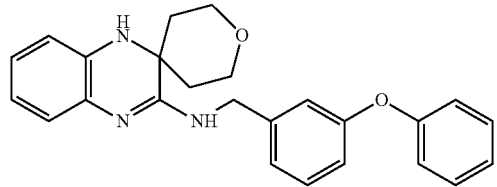 O/S-53
 O/S-54
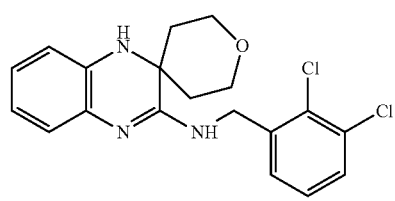 O/S-55
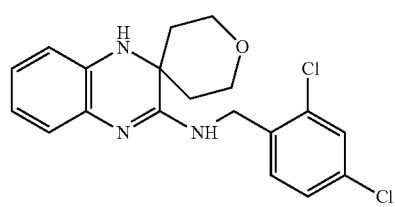 O/S-56
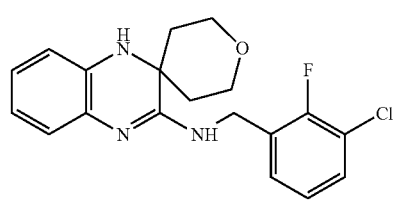 O/S-57
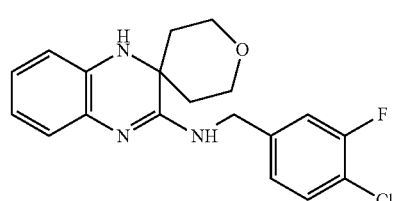 O/S-58
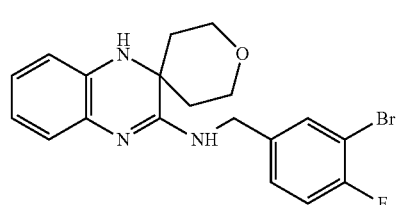 O/S-59

TABLE 1-O/S-continued
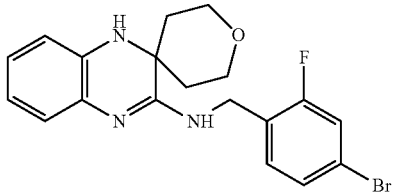 O/S-60
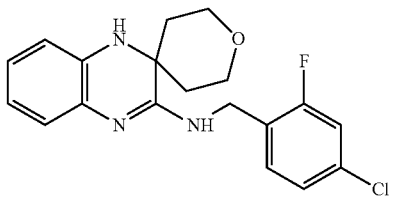 O/S-61
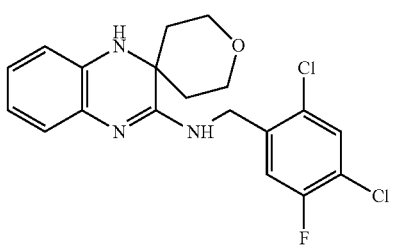 O/S-62
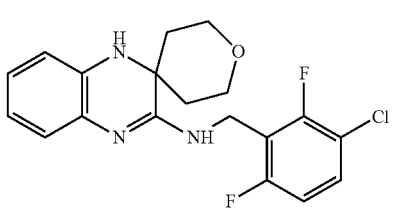 O/S-63
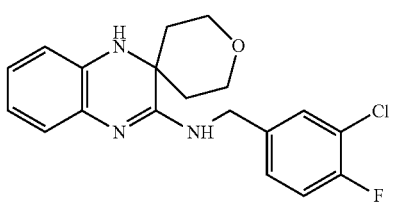 O/S-64
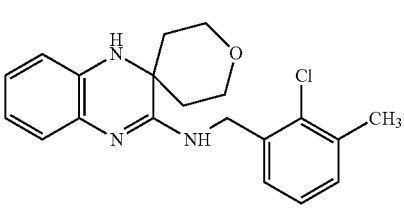 [SMILES: Cc1cccc(CNC2=Nc3ccccc3NC23CCOCC3)c1Cl] O/S-65
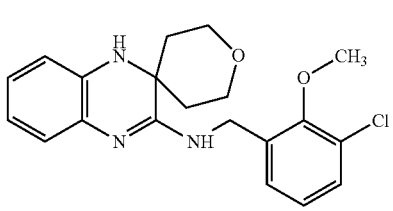 [SMILES: COc1c(Cl)cccc1CNC1=Nc2ccccc2NC12CCOCC2] O/S-66

TABLE 1-O/S-continued
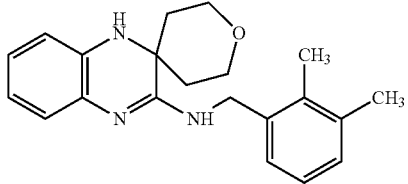 [SMILES: Cc1cccc(CNC2=Nc3ccccc3NC23CCOCC3)c1C]
O/S-67
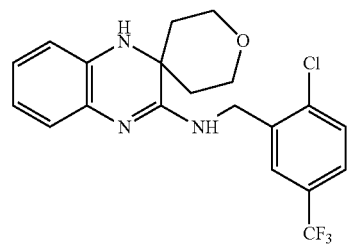
O/S-68
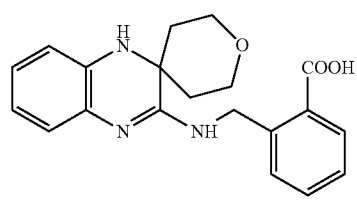
O/S-69
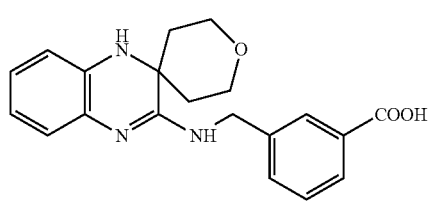 [SMILES: O=C(O)c1cccc(CNC2=Nc3ccccc3NC23CCOCC3)c1]
O/S-70
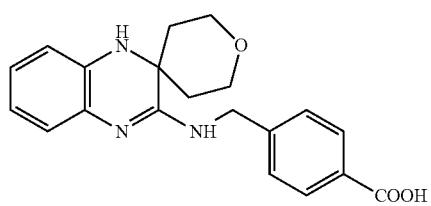
O/S-71
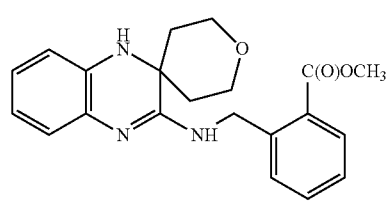
O/S-72
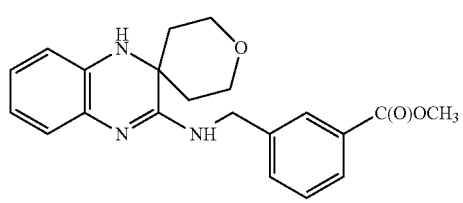
O/S-73

TABLE 1-O/S-continued
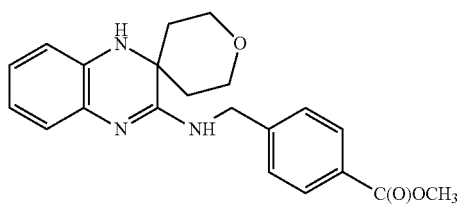 O/S-74
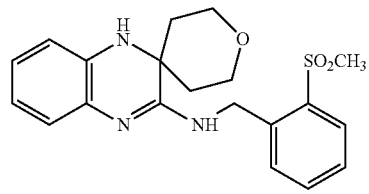 O/S-75
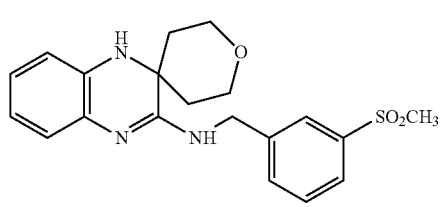 O/S-76
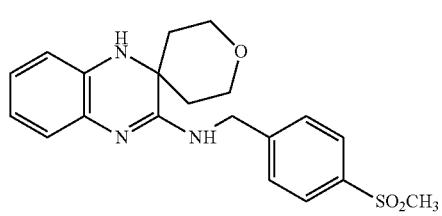 O/S-77
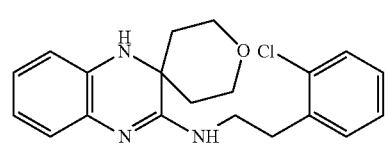 [SMILES: Clc1ccccc1CCNC1=Nc2ccccc2NC12CCOCC2] O/S-78
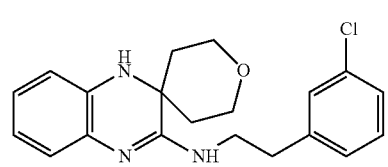 [SMILES: Clc1cccc(CCNC2=Nc3ccccc3NC23CCOCC3)c1] O/S-79
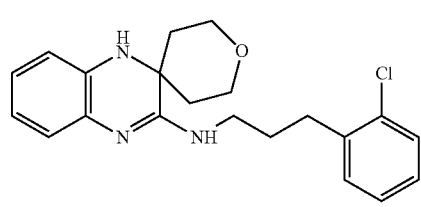 O/S-80
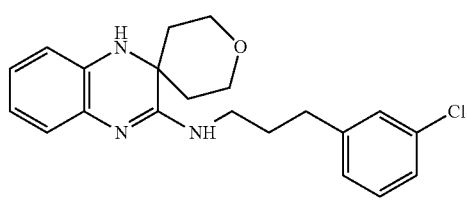 [SMILES: Clc1cccc(CCCNC2=Nc3ccccc3NC23CCOCC3)c1] O/S-81

TABLE 1-O/S-continued
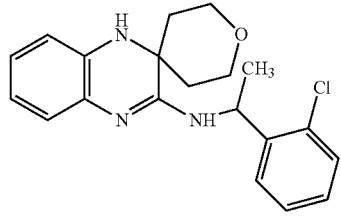 [SMILES: CC(NC1=Nc2ccccc2NC12CCOCC2)c1ccccc1Cl] O/S-82
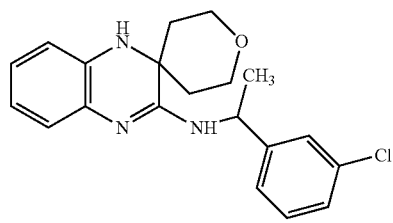 [SMILES: CC(NC1=Nc2ccccc2NC12CCOCC2)c1cccc(Cl)c1] O/S-83
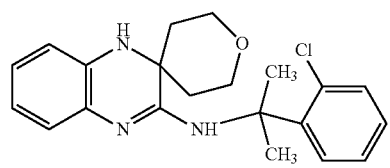 [SMILES: CC(C)(NC1=Nc2ccccc2NC12CCOCC2)c1ccccc1Cl] O/S-84
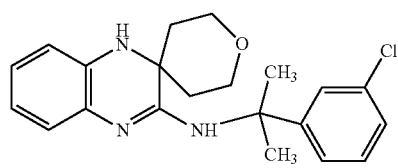 [SMILES: CC(C)(NC1=Nc2ccccc2NC12CCOCC2)c1cccc(Cl)c1] O/S-85
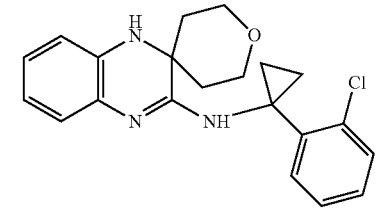 [SMILES: Clc1ccccc1C1(NC2=Nc3ccccc3NC23CCOCC3)CC1] O/S-86
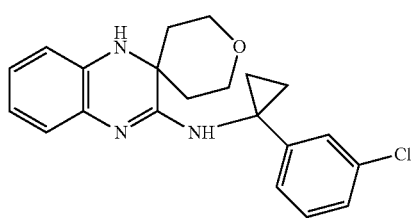 [SMILES: Clc1cccc(C2(NC3=Nc4ccccc4NC34CCOCC4)CC2)c1] O/S-87
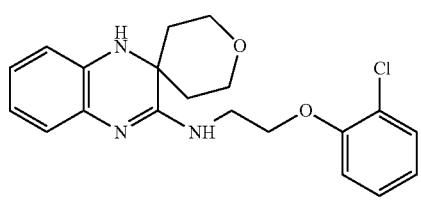 O/S-88

TABLE 1-O/S-continued
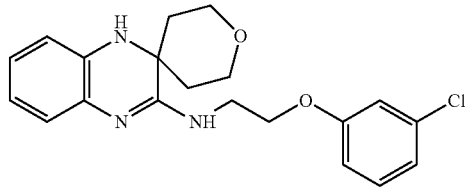 [SMILES: Clc1cccc(OCCNC2=Nc3ccccc3NC23CCOCC3)c1]
O/S-89
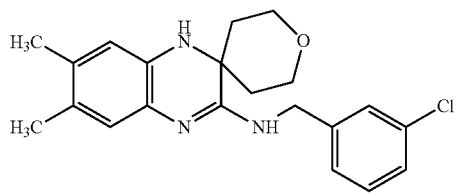
O/S-90
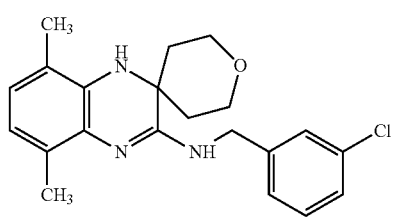
O/S-91
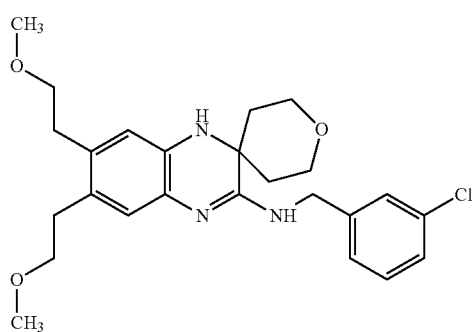 [SMILES: COCCc1cc2c(cc1CCOC)NC1(CCOCC1)C(NCc1cccc(Cl)c1)=N2]
O/S-92
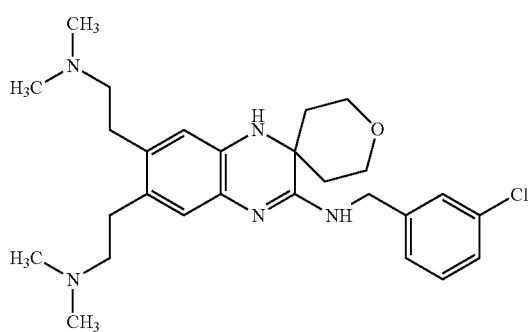
O/S-93
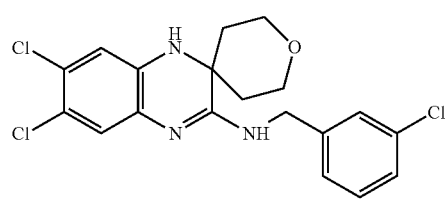 [SMILES: Clc1cccc(CNC2=Nc3cc(Cl)c(Cl)cc3NC23CCOCC3)c1]
O/S-94

TABLE 1-O/S-continued
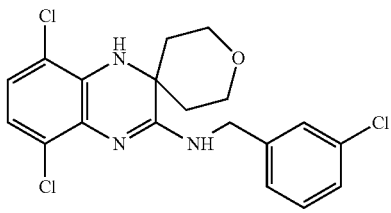 O/S-95
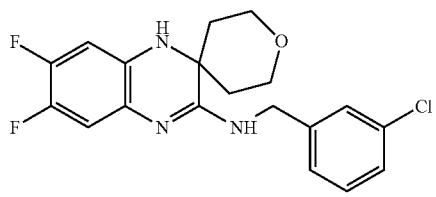 [SMILES: Fc1cc2c(cc1F)NC1(CCOCC1)C(NCc1cccc(Cl)c1)=N2] O/S-96
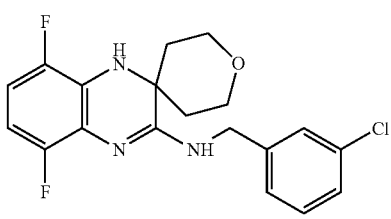 [SMILES: Fc1ccc(F)c2c1N=C(NCc1cccc(Cl)c1)C1(CCOCC1)N2] O/S-97
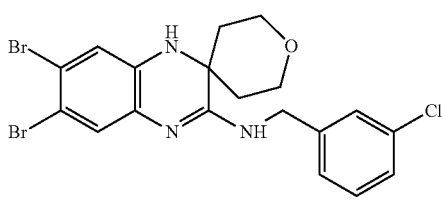 O/S-98
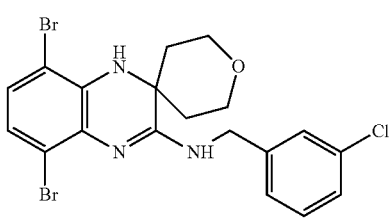 O/S-99
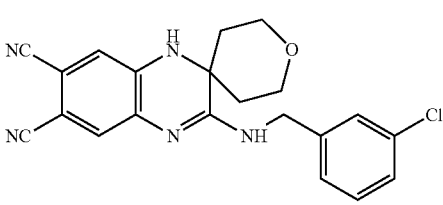 O/S-100
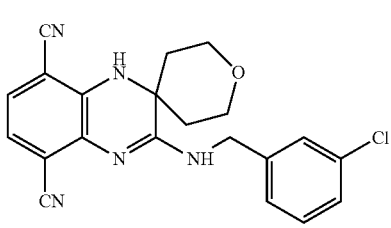 O/S-101

TABLE 1-O/S-continued
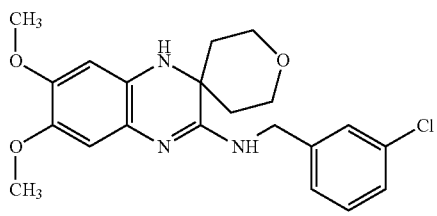 [SMILES: COc1cc2c(cc1OC)NC1(CCOCC1)C(NCc1cccc(Cl)c1)=N2] O/S-102
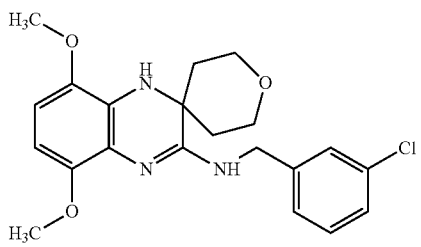 O/S-103
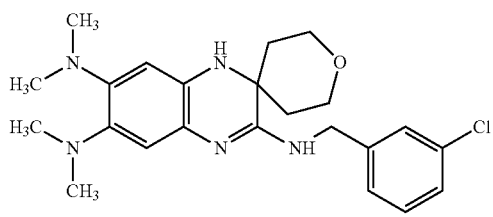 [SMILES: CN(C)c1cc2c(cc1N(C)C)NC1(CCOCC1)C(NCc1cccc(Cl)c1)=N2] O/S-104
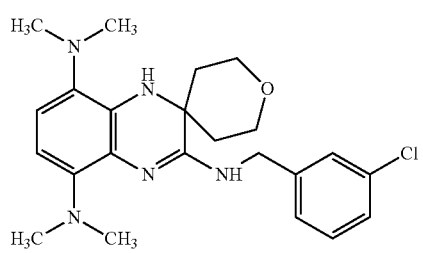 O/S-105
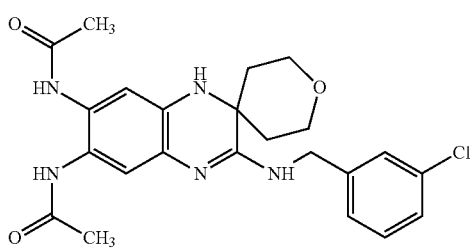 O/S-106
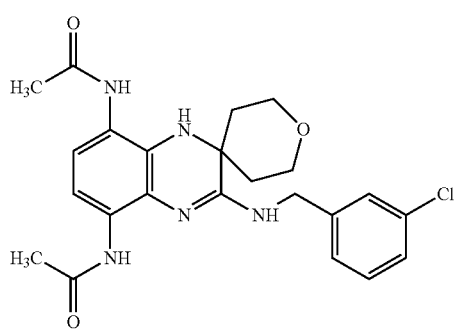 O/S-107

TABLE 1-O/S-continued
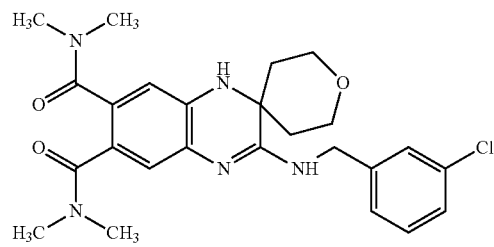 O/S-108
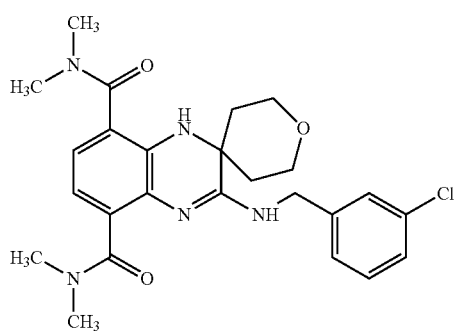 O/S-109
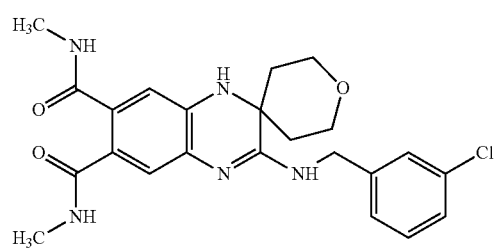 O/S-110
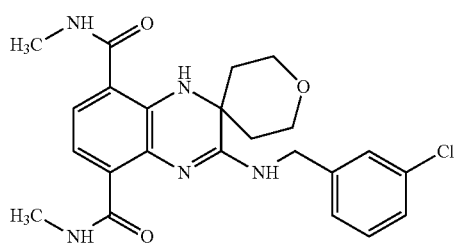 O/S-111
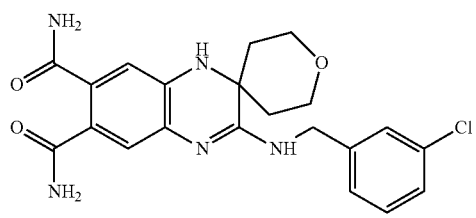 [SMILES: NC(=O)c1cc2c(cc1C(N)=O)NC1(CCOCC1)C(NCc1cccc(Cl)c1)=N2] O/S-112
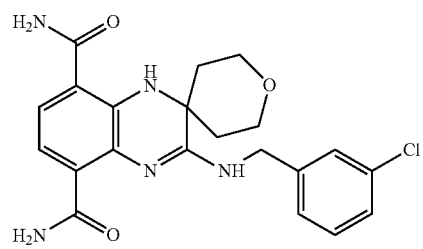 O/S-113

TABLE 1-O/S-continued
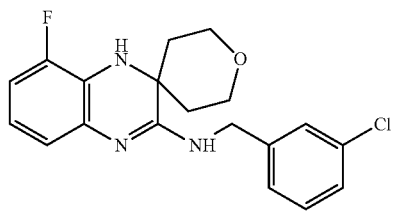
O/S-114
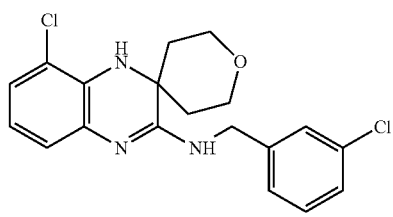
O/S-115
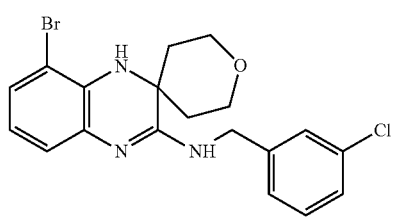
O/S-116
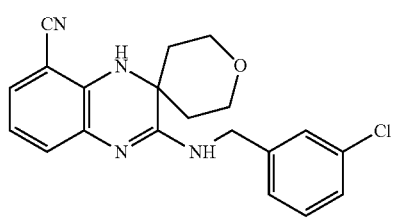
O/S-117
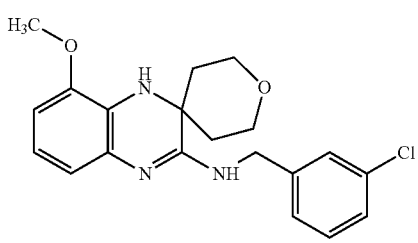
O/S-118
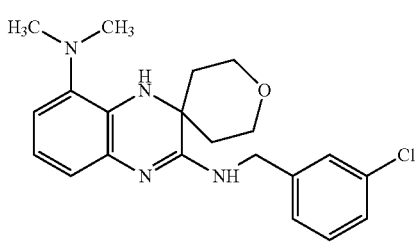 [SMILES: CN(C)c1cccc2c1NC1(CCOCC1)C(NCc1cccc(Cl)c1)=N2]
O/S-119

TABLE 1-O/S-continued
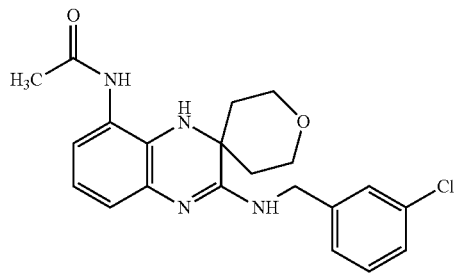
O/S-120
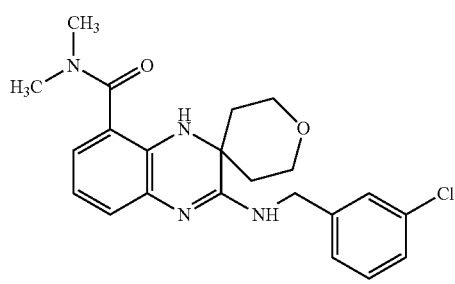
O/S-121
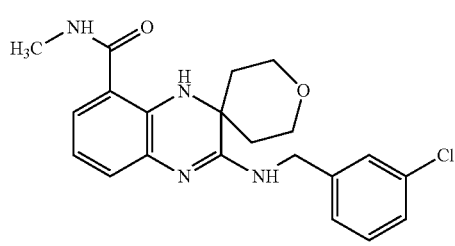
O/S-122
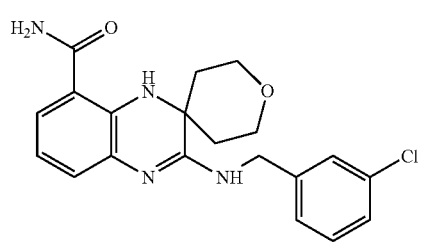 [SMILES: NC(=O)c1cccc2c1NC1(CCOCC1)C(NCc1cccc(Cl)c1)=N2]
O/S-123
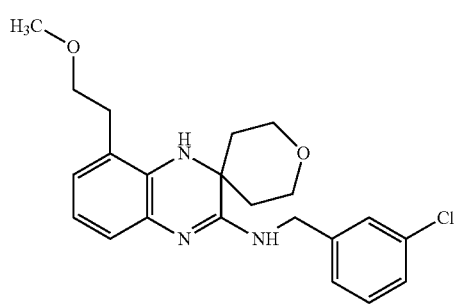
O/S-124

TABLE 1-O/S-continued
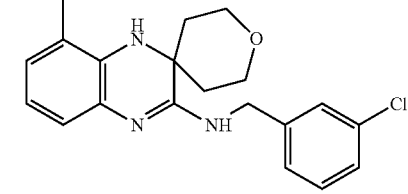 O/S-125
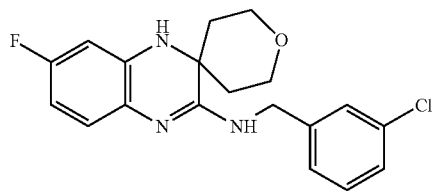 [SMILES: Fc1ccc2c(c1)NC1(CCOCC1)C(NCc1cccc(Cl)c1)=N2] O/S-126
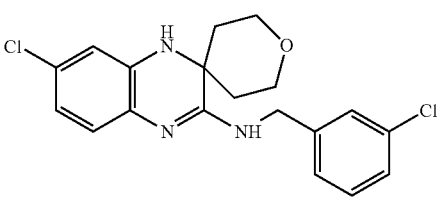 [SMILES: Clc1cccc(CNC2=Nc3ccc(Cl)cc3NC23CCOCC3)c1] O/S-127
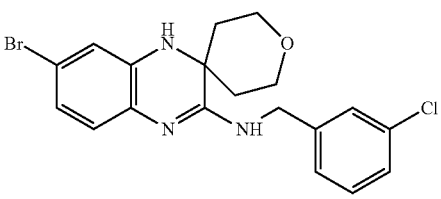 O/S-128
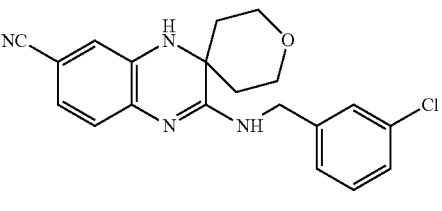 [SMILES: N#Cc1ccc2c(c1)NC1(CCOCC1)C(NCc1cccc(Cl)c1)=N2] O/S-129
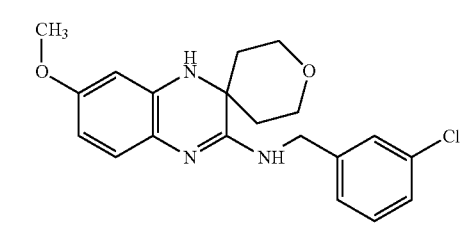 [SMILES: COc1ccc2c(c1)NC1(CCOCC1)C(NCc1cccc(Cl)c1)=N2] O/S-130
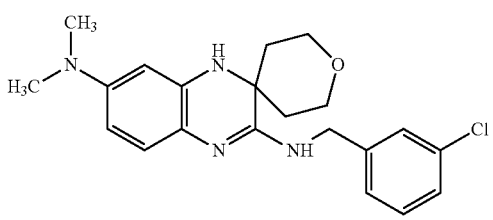 [SMILES: CN(C)c1ccc2c(c1)NC1(CCOCC1)C(NCc1cccc(Cl)c1)=N2] O/S-131

TABLE 1-O/S-continued
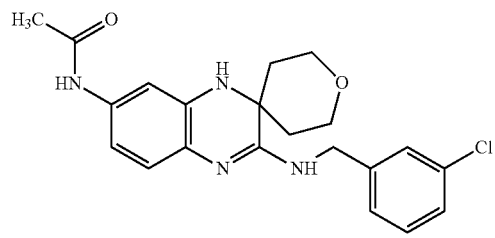
O/S-132
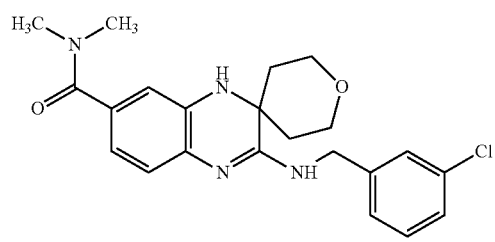 [SMILES: CN(C)C(=O)c1ccc2c(c1)NC1(CCOCC1)C(NCc1cccc(Cl)c1)=N2]
O/S-133
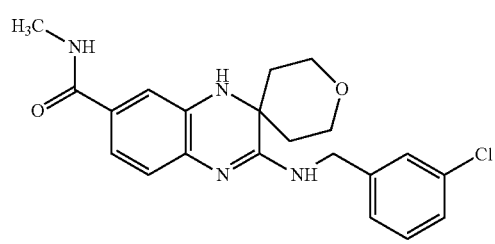
O/S-134
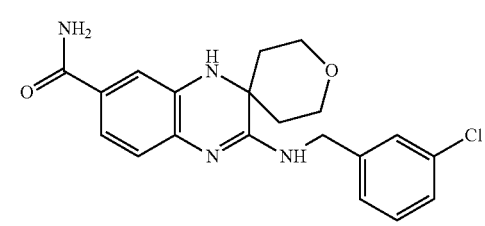 [SMILES: NC(=O)c1ccc2c(c1)NC1(CCOCC1)C(NCc1cccc(Cl)c1)=N2]
O/S-135
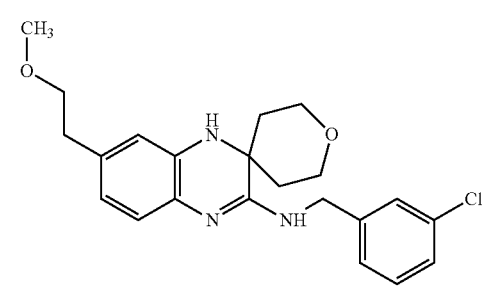
O/S-136
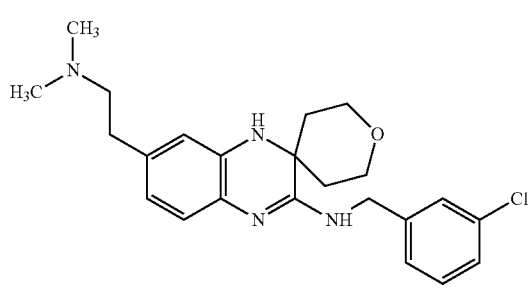
O/S-137

TABLE 1-O/S-continued
 O/S-138
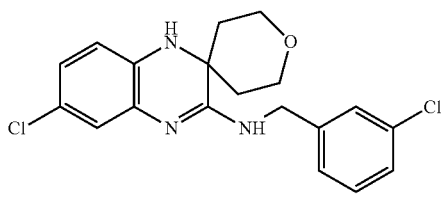 [SMILES: Clc1cccc(CNC2=Nc3cc(Cl)ccc3NC23CCOCC3)c1] O/S-139
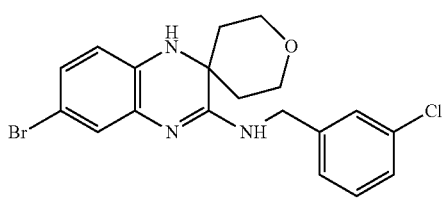 O/S-140
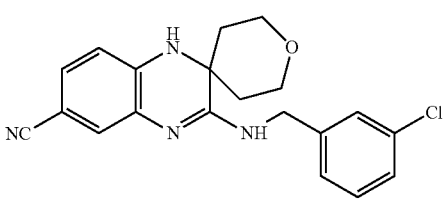 O/S-141
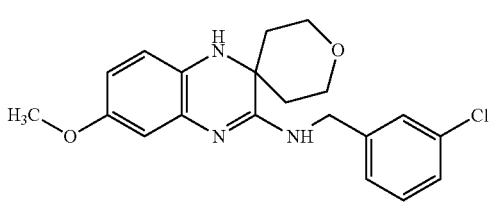 [SMILES: COc1ccc2c(c1)N=C(NCc1cccc(Cl)c1)C1(CCOCC1)N2] O/S-142
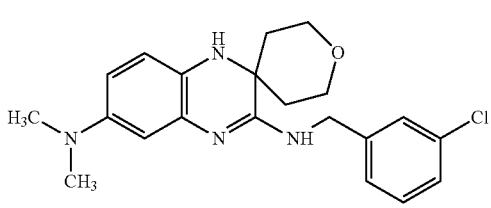 [SMILES: CN(C)c1ccc2c(c1)N=C(NCc1cccc(Cl)c1)C1(CCOCC1)N2] O/S-143
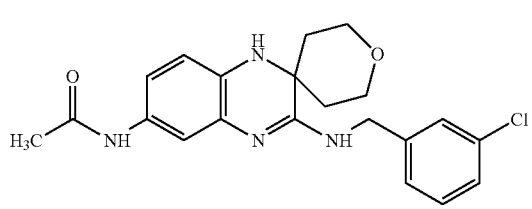 O/S-144

TABLE 1-O/S-continued
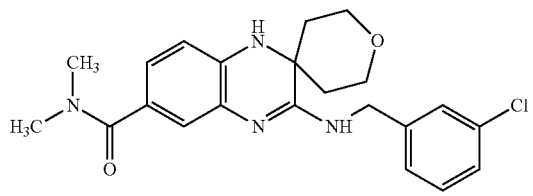 [SMILES: CN(C)C(=O)c1ccc2c(c1)N=C(NCc1cccc(Cl)c1)C1(CCOCC1)N2] O/S-145
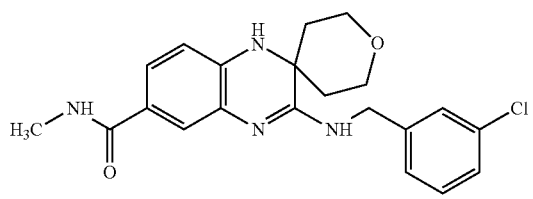 [SMILES: CNC(=O)c1ccc2c(c1)N=C(NCc1cccc(Cl)c1)C1(CCOCC1)N2] O/S-146
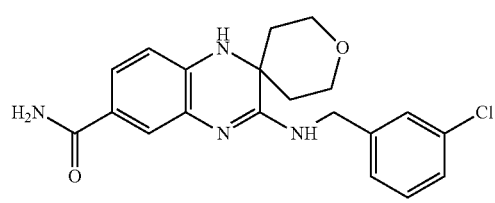 [SMILES: NC(=O)c1ccc2c(c1)N=C(NCc1cccc(Cl)c1)C1(CCOCC1)N2] O/S-147
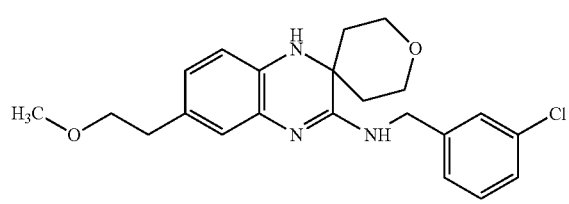 O/S-148
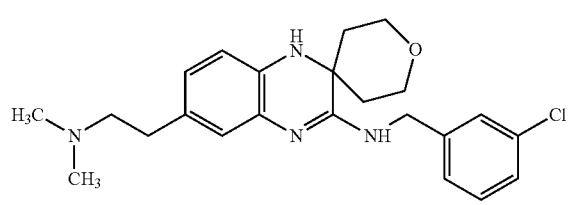 [SMILES: CN(C)CCc1ccc2c(c1)N=C(NCc1cccc(Cl)c1)C1(CCOCC1)N2] O/S-149
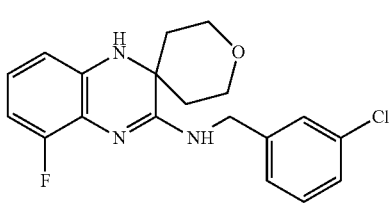 O/S-150
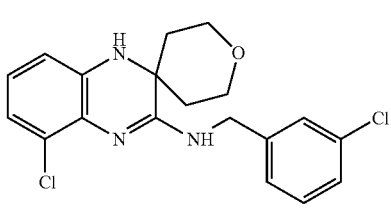 O/S-151

TABLE 1-O/S-continued
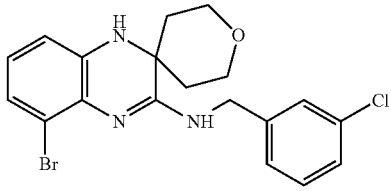 O/S-152
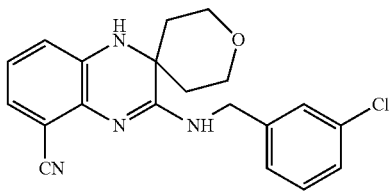 O/S-153
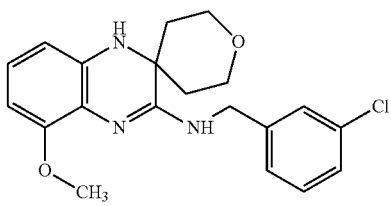 [SMILES: COc1cccc2c1N=C(NCc1cccc(Cl)c1)C1(CCOCC1)N2] O/S-154
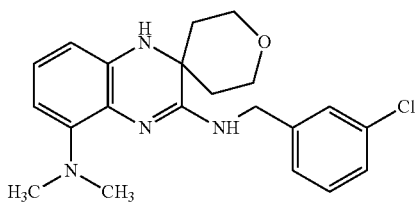 [SMILES: CN(C)c1cccc2c1N=C(NCc1cccc(Cl)c1)C1(CCOCC1)N2] O/S-155
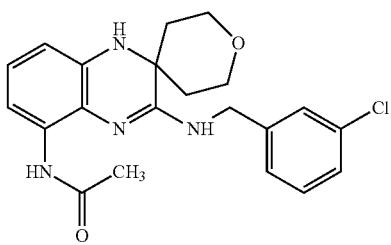 O/S-156
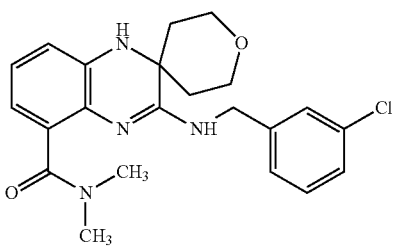 O/S-157
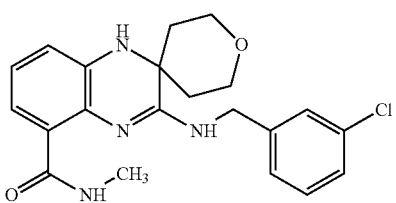 O/S-158

TABLE 1-O/S-continued
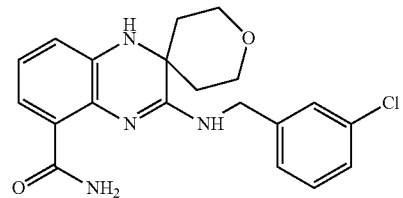 [SMILES: NC(=O)c1cccc2c1N=C(NCc1cccc(Cl)c1)C1(CCOCC1)N2] O/S-159
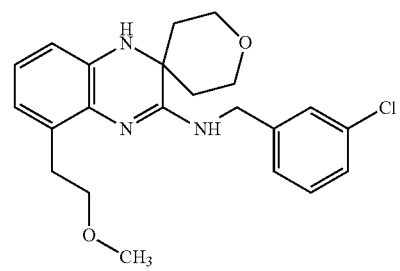 O/S-160
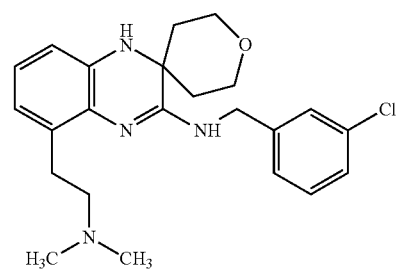 O/S-161
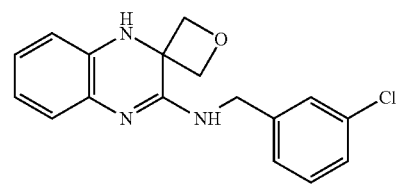 [SMILES: Clc1cccc(CNC2=Nc3ccccc3NC23COC3)c1] O/S-162
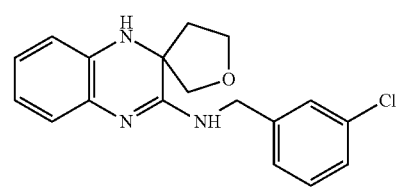 [SMILES: Clc1cccc(CNC2=Nc3ccccc3NC23CCOC3)c1] O/S-163
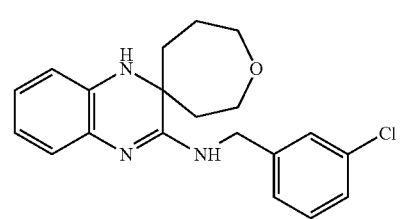 [SMILES: Clc1cccc(CNC2=Nc3ccccc3NC23CCCOCC3)c1] O/S-164
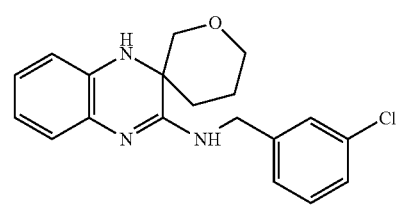 O/S-165

TABLE 1-O/S-continued
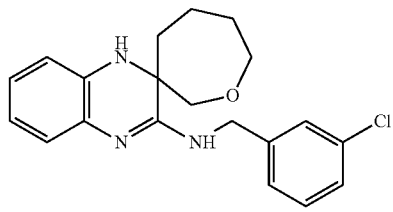 [SMILES: Clc1cccc(CNC2=Nc3ccccc3NC23CCCCOC3)c1] O/S-166
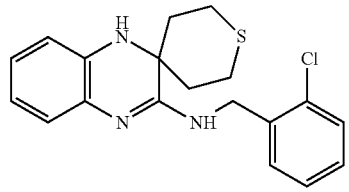 [SMILES: Clc1ccccc1CNC1=Nc2ccccc2NC12CCCCC2] O/S-167
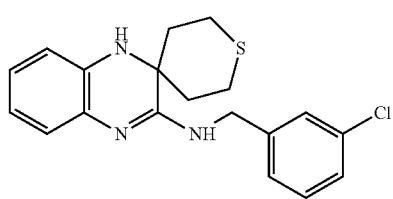 [SMILES: Clc1cccc(CNC2=Nc3ccccc3NC23CCCCC3)c1] O/S-168
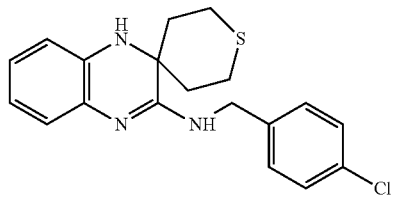 [SMILES: Clc1ccc(CNC2=Nc3ccccc3NC23CCCCC3)cc1] O/S-169
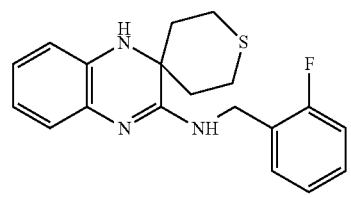 O/S-170
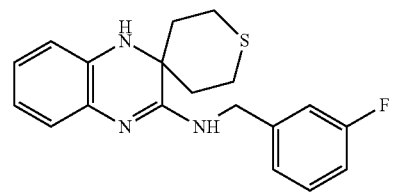 [SMILES: Fc1cccc(CNC2=Nc3ccccc3NC23CCCCC3)c1] O/S-171
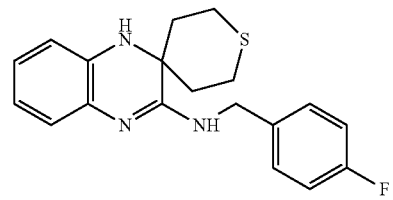 [SMILES: Fc1ccc(CNC2=Nc3ccccc3NC23CCCCC3)cc1] O/S-172

TABLE 1-O/S-continued
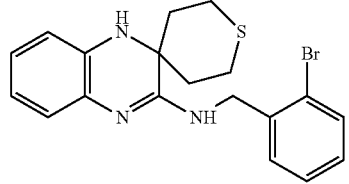 O/S-173
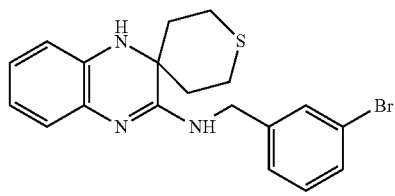 [SMILES: Brc1cccc(CNC2=Nc3ccccc3NC23CCCCC3)c1] O/S-174
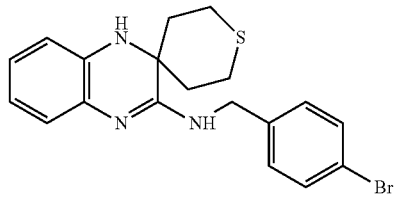 [SMILES: Brc1ccc(CNC2=Nc3ccccc3NC23CCCCC3)cc1] O/S-175
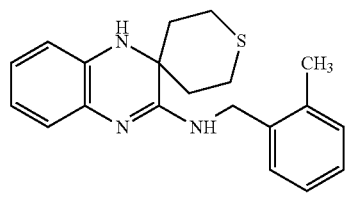 O/S-176
 O/S-177
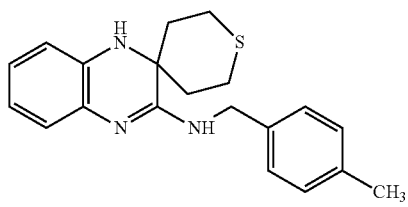 [SMILES: Cc1ccc(CNC2=Nc3ccccc3NC23CCCCC3)cc1] O/S-178
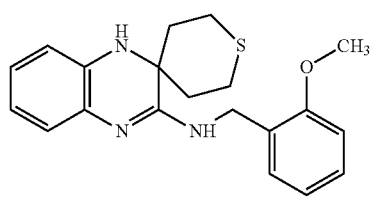 O/S-179

TABLE 1-O/S-continued
 O/S-180
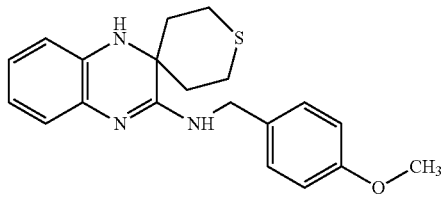 [SMILES: COc1ccc(CNC2=Nc3ccccc3NC23CCCCC3)cc1] O/S-181
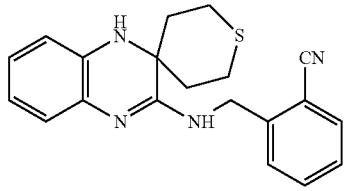 O/S-182
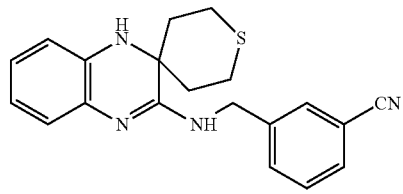 [SMILES: N#Cc1cccc(CNC2=Nc3ccccc3NC23CCCCC3)c1] O/S-183
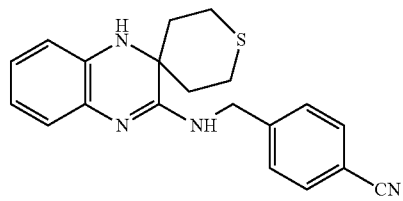 [SMILES: N#Cc1ccc(CNC2=Nc3ccccc3NC23CCCCC3)cc1] O/S-184
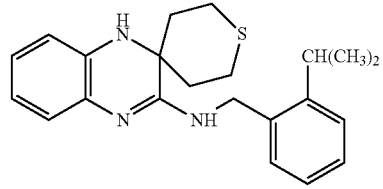 O/S-185
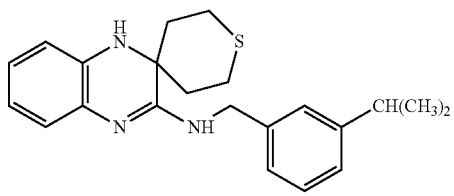 [SMILES: CC(C)c1cccc(CNC2=Nc3ccccc3NC23CCCCC3)c1] O/S-186

TABLE 1-O/S-continued
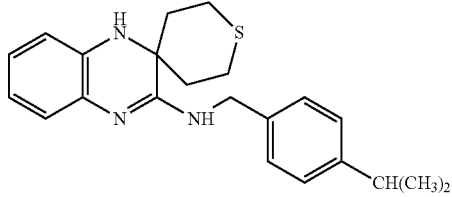 [SMILES: CC(C)c1ccc(CNC2=Nc3ccccc3NC23CCCCC3)cc1] O/S-187
 O/S-188
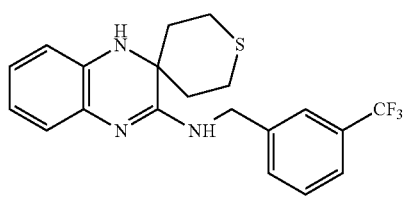 [SMILES: FC(F)(F)c1cccc(CNC2=Nc3ccccc3NC23CCCCC3)c1] O/S-189
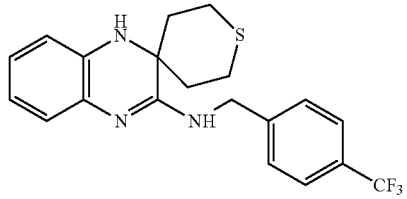 [SMILES: FC(F)(F)c1ccc(CNC2=Nc3ccccc3NC23CCCCC3)cc1] O/S-190
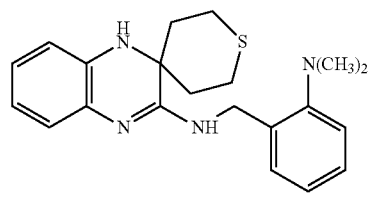 [SMILES: CN(C)c1ccccc1CNC1=Nc2ccccc2NC12CCCCC2] O/S-191
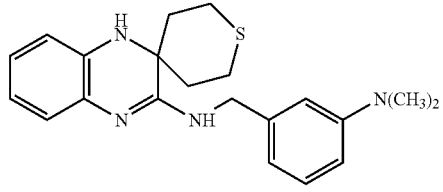 O/S-192
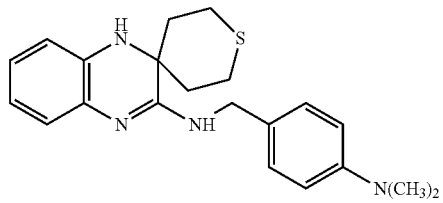 O/S-193

TABLE 1-O/S-continued
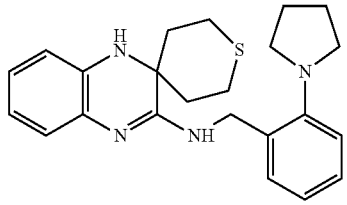 O/S-194
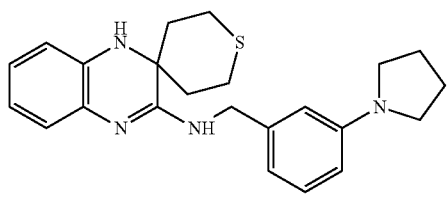 [SMILES: c1cc(CNC2=Nc3ccccc3NC23CCCCC3)cc(N2CCCC2)c1] O/S-195
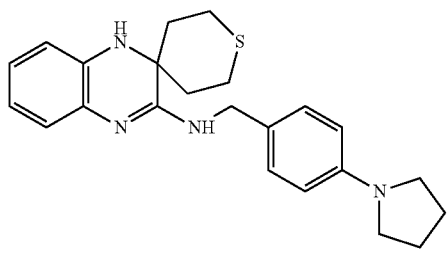 O/S-196
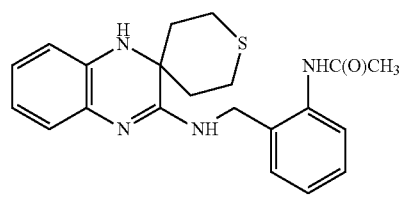 O/S-197
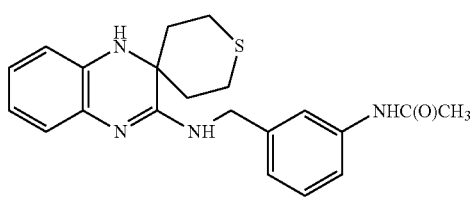 O/S-198
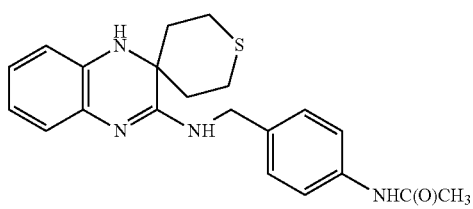 O/S-199
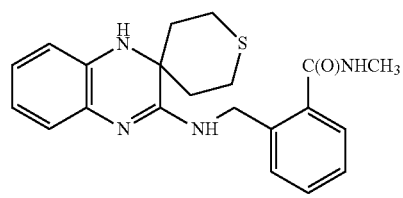 O/S-200

TABLE 1-O/S-continued
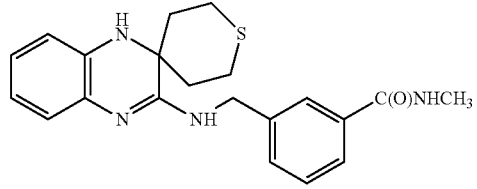 O/S-201
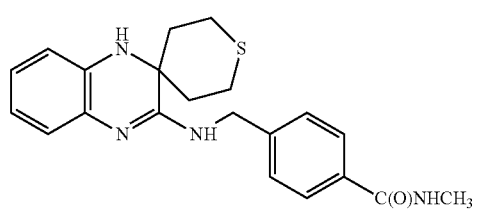 O/S-202
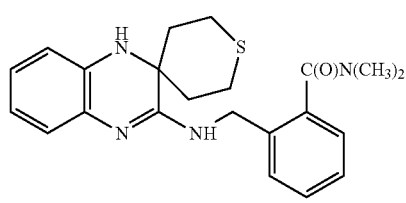 O/S-203
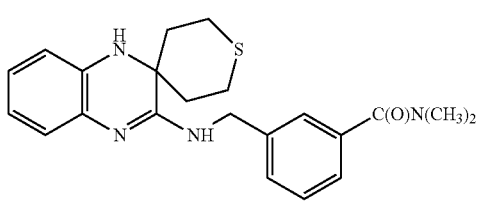 O/S-204
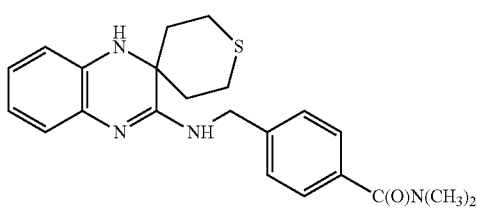 O/S-205
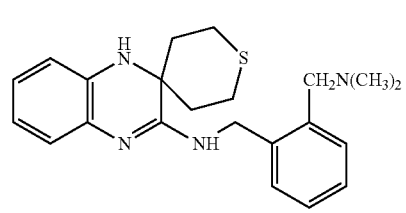 O/S-206
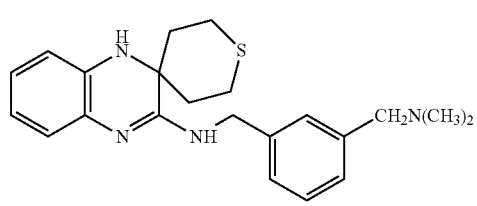 O/S-207

TABLE 1-O/S-continued
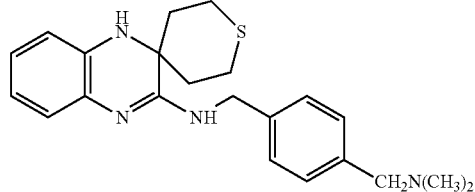 O/S-208
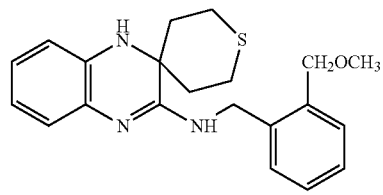 O/S-209
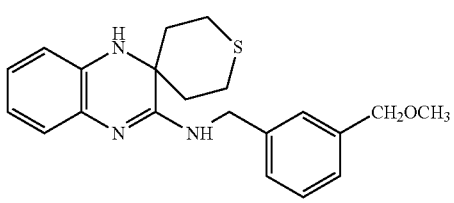 O/S-210
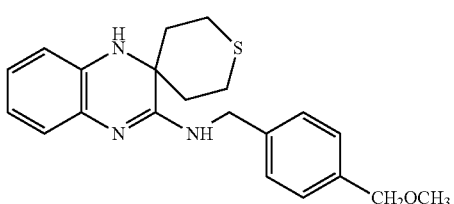 O/S-211
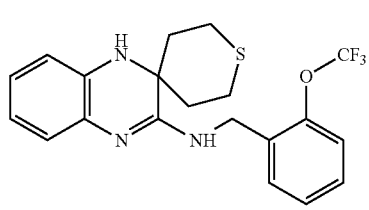 [SMILES: FC(F)(F)Oc1ccccc1CNC1=Nc2ccccc2NC12CCCCC2] O/S-212
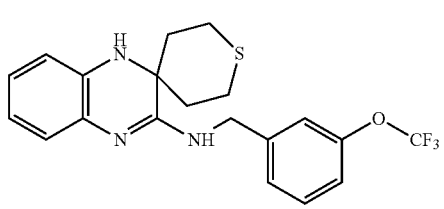 O/S-213
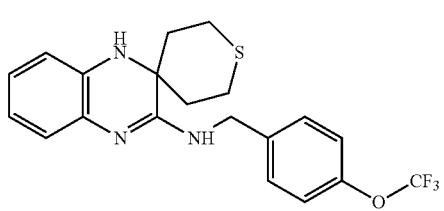 [SMILES: FC(F)(F)Oc1ccc(CNC2=Nc3ccccc3NC23CCCCC3)cc1] O/S-214

TABLE 1-O/S-continued
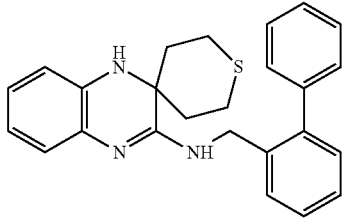 [SMILES: c1ccc(-c2ccccc2CNC2=Nc3ccccc3NC23CCCCC3)cc1] O/S-215
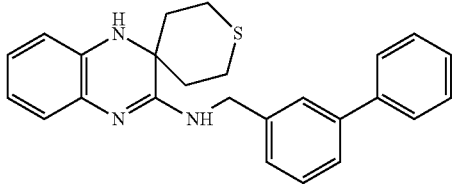 O/S-216
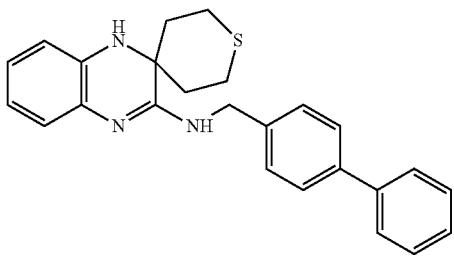 O/S-217
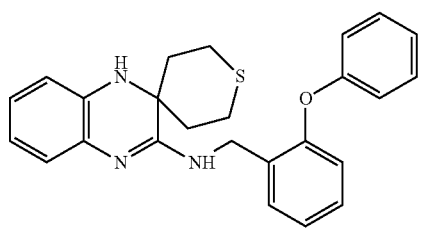 [SMILES: c1ccc(Oc2ccccc2CNC2=Nc3ccccc3NC23CCCCC3)cc1] O/S-218
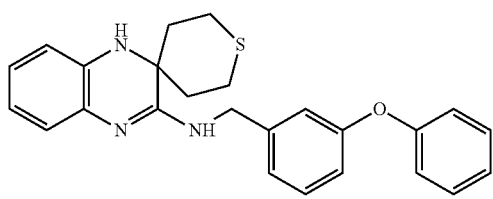 O/S-219
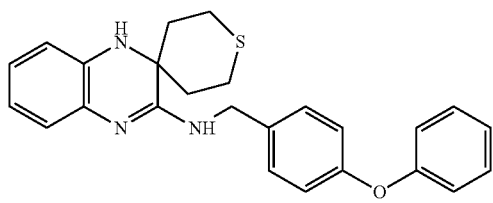 O/S-220
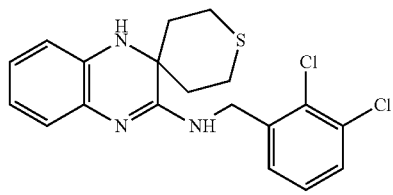 [SMILES: Clc1cccc(CNC2=Nc3ccccc3NC23CCCCC3)c1Cl] O/S-221

TABLE 1-O/S-continued
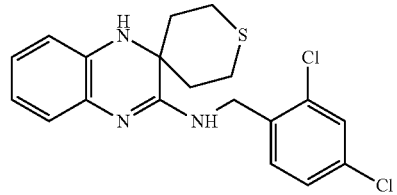 [SMILES: Clc1ccc(CNC2=Nc3ccccc3NC23CCCCC3)c(Cl)c1] O/S-222
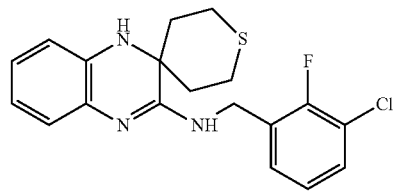 [SMILES: Fc1c(Cl)cccc1CNC1=Nc2ccccc2NC12CCCCC2] O/S-223
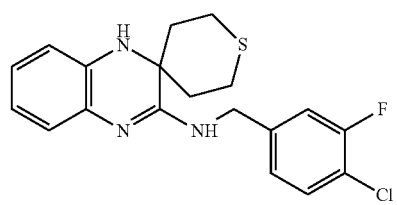 O/S-224
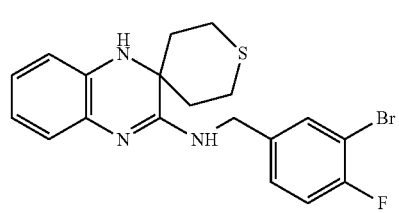 O/S-225
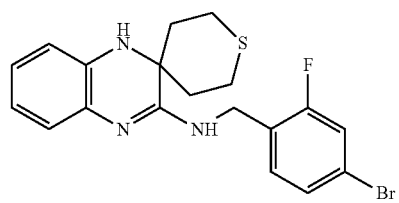 [SMILES: Fc1cc(Br)ccc1CNC1=Nc2ccccc2NC12CCCCC2] O/S-226
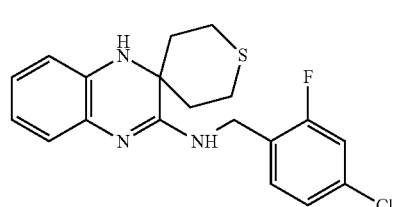 O/S-227
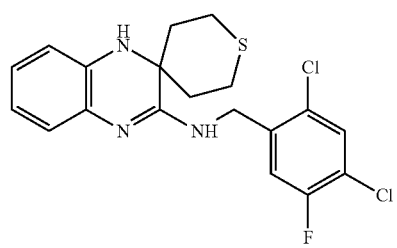 [SMILES: Fc1cc(CNC2=Nc3ccccc3NC23CCCCC3)c(Cl)cc1Cl] O/S-228

TABLE 1-O/S-continued
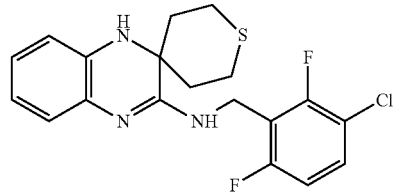 [SMILES: Fc1ccc(Cl)c(F)c1CNC1=Nc2ccccc2NC12CCCCC2] O/S-229
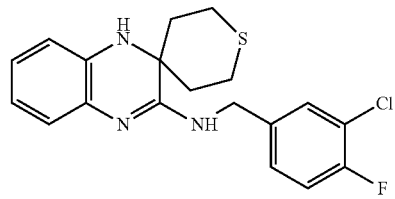 O/S-230
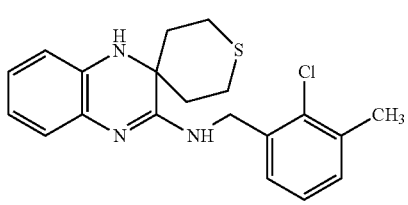 O/S-231
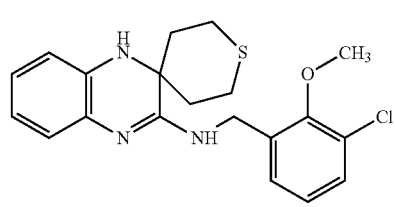 [SMILES: COc1c(Cl)cccc1CNC1=Nc2ccccc2NC12CCCCC2] O/S-232
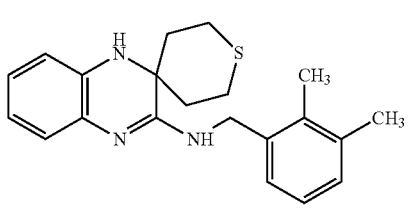 O/S-233
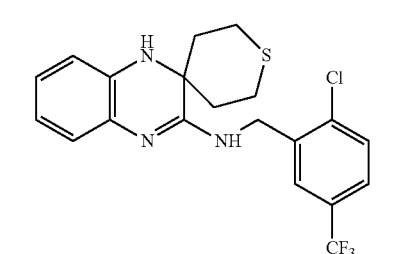 O/S-234
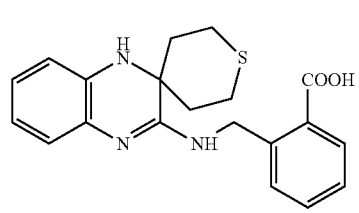 O/S-235

TABLE 1-O/S-continued
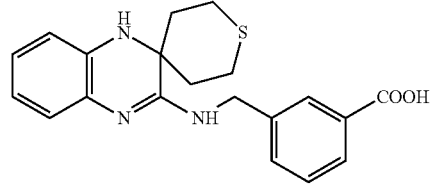 O/S-236
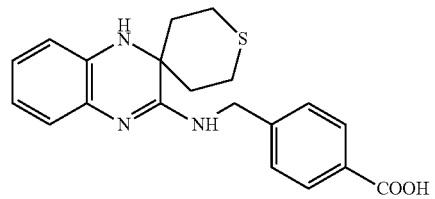 O/S-237
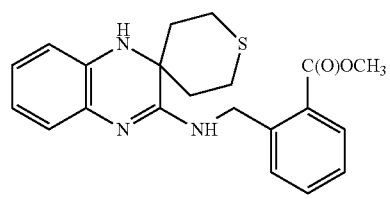 O/S-238
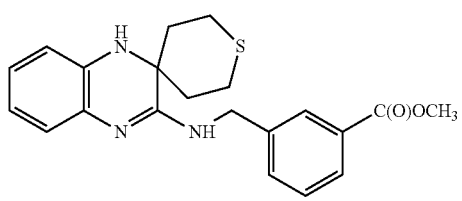 O/S-239
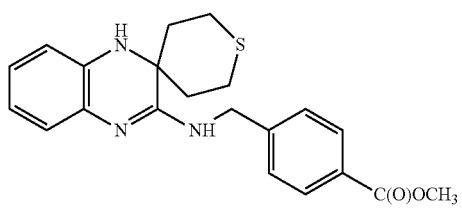 O/S-240
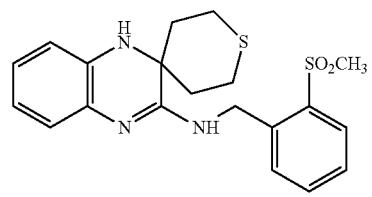 [SMILES: CS(=O)(=O)c1ccccc1CNC1=Nc2ccccc2NC12CCCCC2] O/S-241
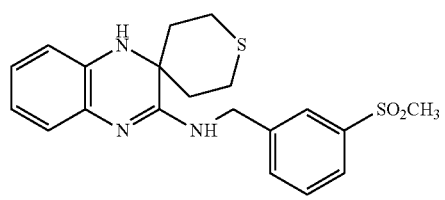 [SMILES: CS(=O)(=O)c1cccc(CNC2=Nc3ccccc3NC23CCCCC3)c1] O/S-242

TABLE 1-O/S-continued
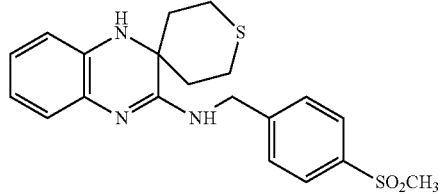 [SMILES: CS(=O)(=O)c1ccc(CNC2=Nc3ccccc3NC23CCCCC3)cc1] O/S-243
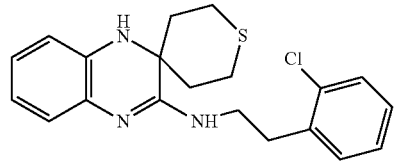 [SMILES: Clc1ccccc1CCNC1=Nc2ccccc2NC12CCCCC2] O/S-244
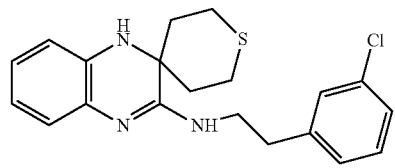 [SMILES: Clc1cccc(CCNC2=Nc3ccccc3NC23CCCCC3)c1] O/S-245
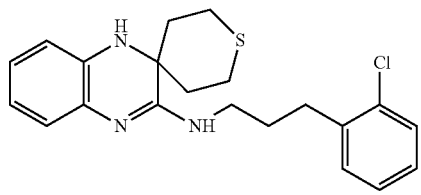 [SMILES: Clc1ccccc1CCCNC1=Nc2ccccc2NC12CCCCC2] O/S-246
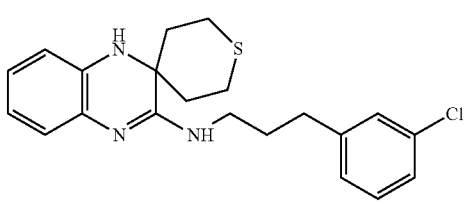 O/S-247
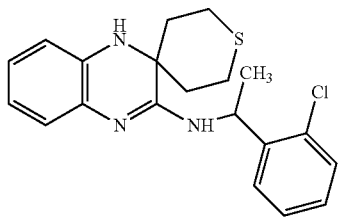 O/S-248
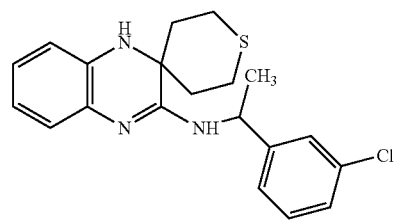 O/S-249

TABLE 1-O/S-continued
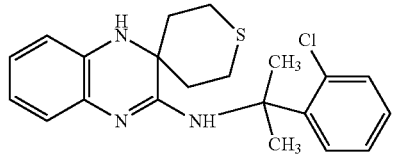  O/S-250
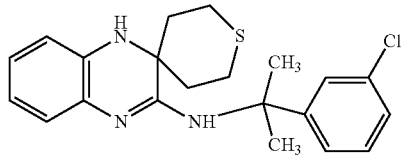  O/S-251
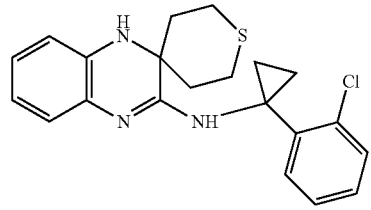  O/S-252
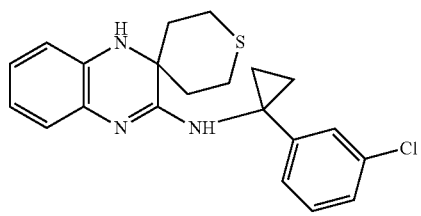  O/S-253
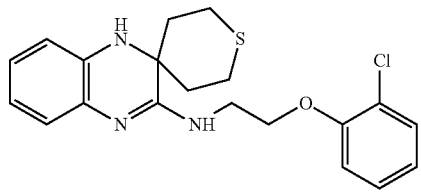 [SMILES: Clc1ccccc1OCCNC1=Nc2ccccc2NC12CCCCC2]  O/S-254
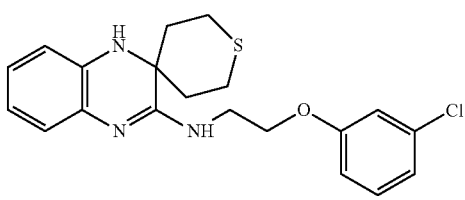  O/S-255
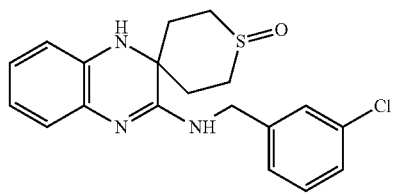  O/S-256

TABLE 1-O/S-continued
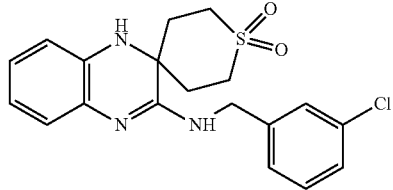 O/S-257
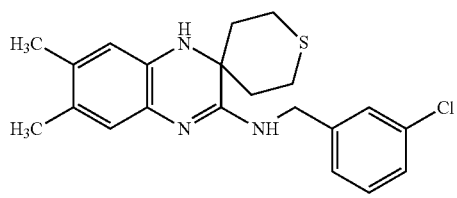 O/S-258
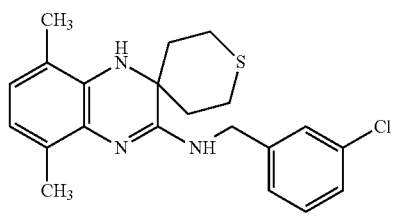 O/S-259
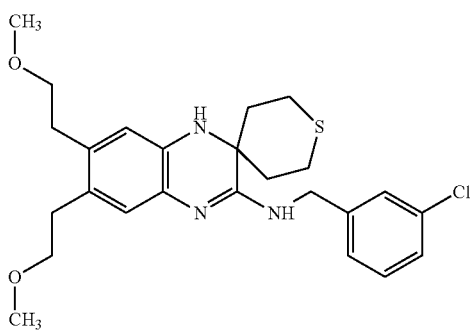 O/S-260
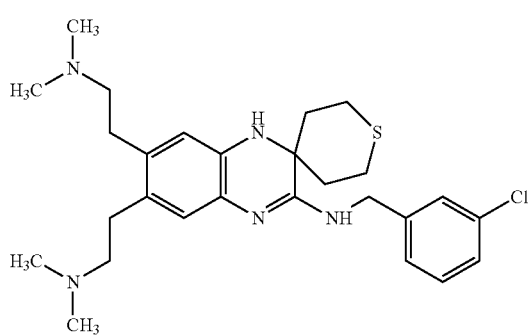 O/S-261
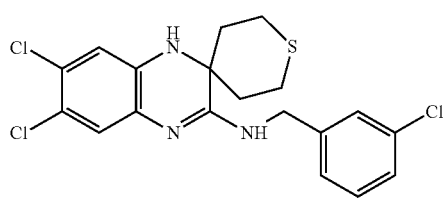 O/S-262

TABLE 1-O/S-continued
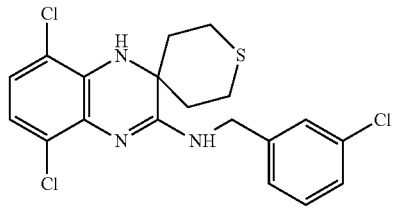 [SMILES: Fc1ccc(F)c2c1N=C(NCc1cccc(Cl)c1)C1(CCCCC1)N2]
O/S-263
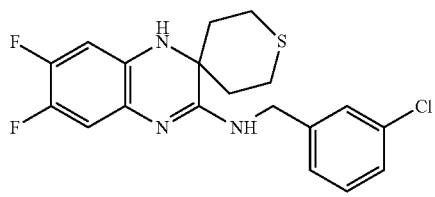
O/S-264
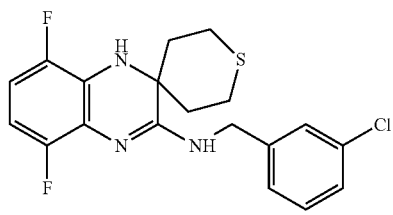
O/S-265
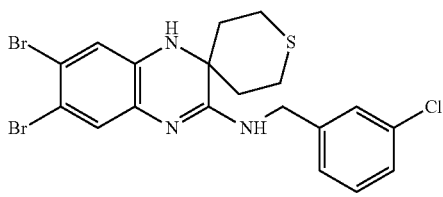
O/S-266
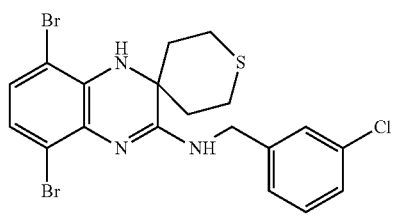 [SMILES: Clc1cccc(CNC2=Nc3c(Br)ccc(Br)c3NC23CCCCC3)c1]
O/S-267
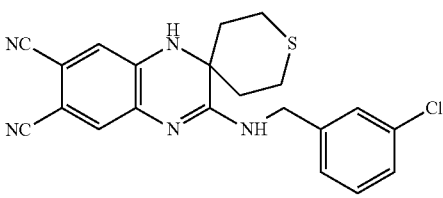
O/S-268
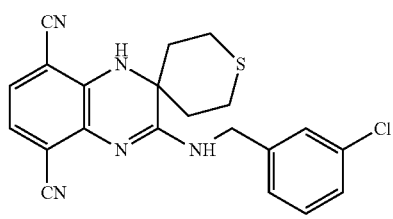 [SMILES: N#Cc1ccc(C#N)c2c1N=C(NCc1cccc(Cl)c1)C1(CCCCC1)N2]
O/S-269

TABLE 1-O/S-continued
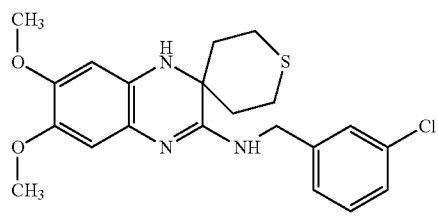
O/S-270
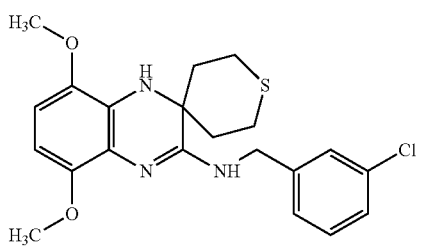 [SMILES: COc1ccc(OC)c2c1N=C(NCc1cccc(Cl)c1)C1(CCCCC1)N2]
O/S-271
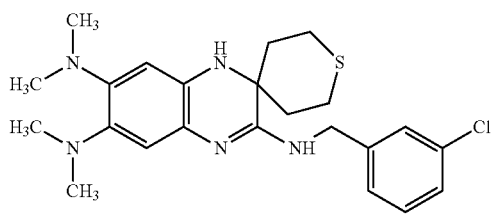
O/S-272
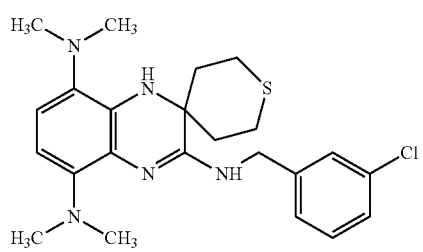
O/S-273
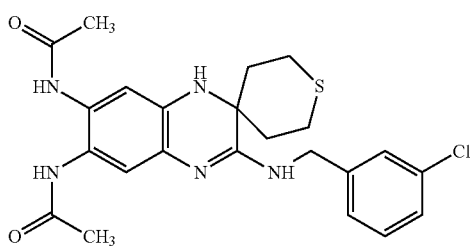 [SMILES: CC(=O)Nc1cc2c(cc1NC(C)=O)NC1(CCCCC1)C(NCc1cccc(Cl)c1)=N2]
O/S-274
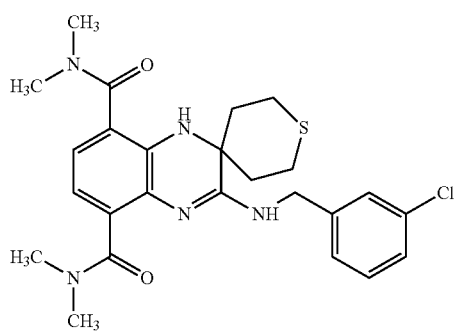
O/S-275

TABLE 1-O/S-continued
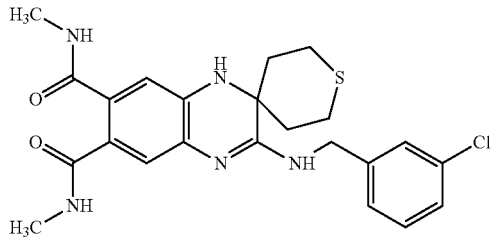 [SMILES: CNC(=O)c1cc2c(cc1C(=O)NC)NC1(CCCCC1)C(NCc1cccc(Cl)c1)=N2]
O/S-276
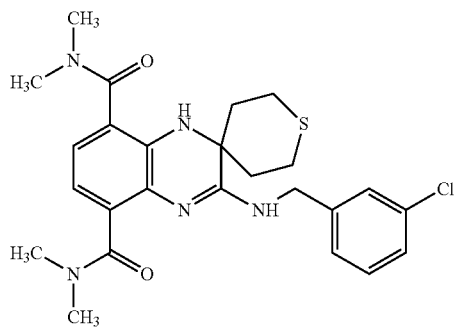
O/S-277
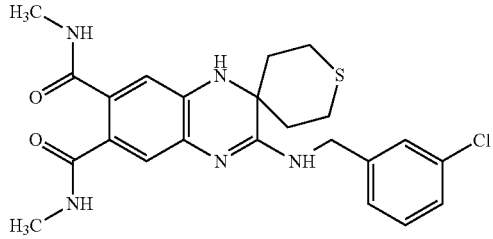
O/S-278
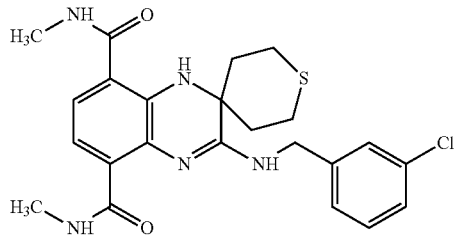 [SMILES: CNC(=O)c1ccc(C(=O)NC)c2c1N=C(NCc1cccc(Cl)c1)C1(CCCCC1)N2]
O/S-279
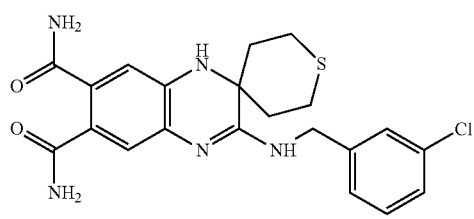
O/S-280
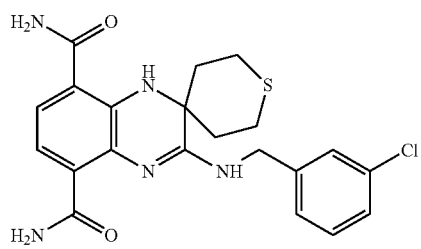
O/S-281

TABLE 1-O/S-continued
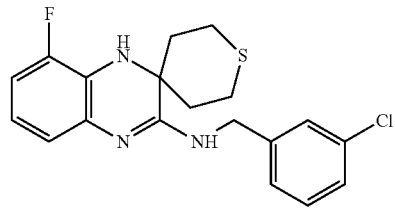 [SMILES: Fc1cccc2c1NC1(CCCCC1)C(NCc1cccc(Cl)c1)=N2] O/S-282
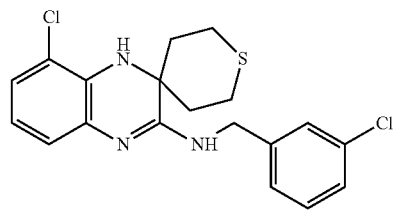 [SMILES: Clc1cccc(CNC2=Nc3cccc(Cl)c3NC23CCCCC3)c1] O/S-283
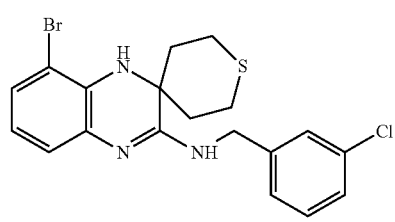 [SMILES: Clc1cccc(CNC2=Nc3cccc(Br)c3NC23CCCCC3)c1] O/S-284
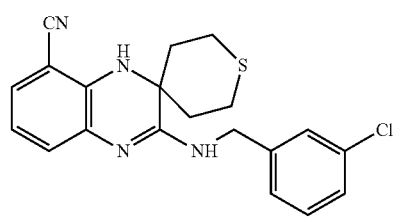 [SMILES: N#Cc1cccc2c1NC1(CCCCC1)C(NCc1cccc(Cl)c1)=N2] O/S-285
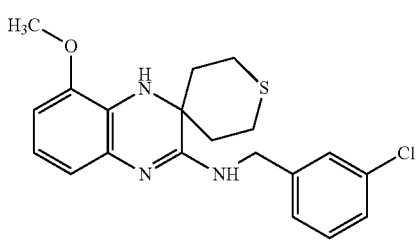 O/S-286
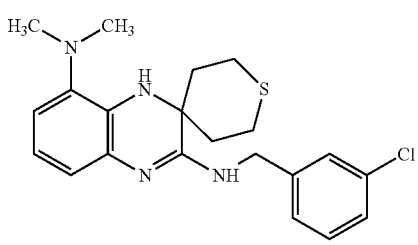 O/S-287

TABLE 1-O/S-continued
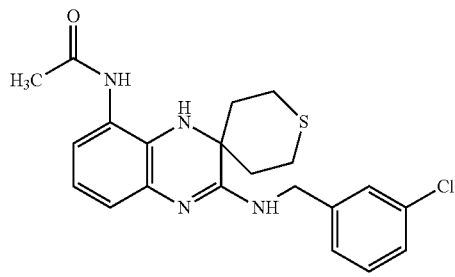 [SMILES: CC(=O)Nc1cccc2c1NC1(CCCCC1)C(NCc1cccc(Cl)c1)=N2]
O/S-288
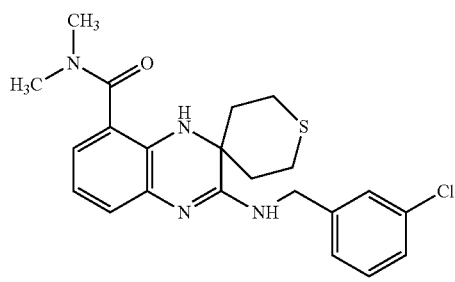 [SMILES: CN(C)C(=O)c1cccc2c1NC1(CCCCC1)C(NCc1cccc(Cl)c1)=N2]
O/S-289
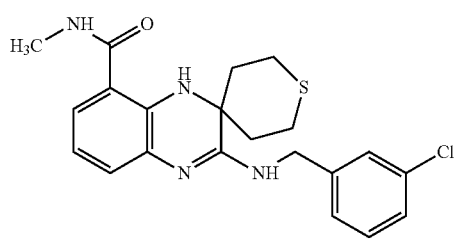 [SMILES: CNC(=O)c1cccc2c1NC1(CCCCC1)C(NCc1cccc(Cl)c1)=N2]
O/S-290
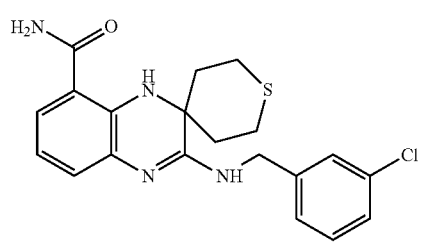
O/S-291
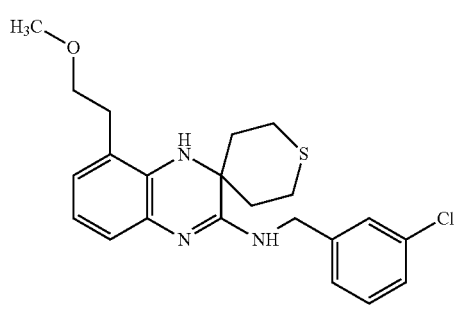 [SMILES: COCCc1cccc2c1NC1(CCCCC1)C(NCc1cccc(Cl)c1)=N2]
O/S-292

TABLE 1-O/S-continued
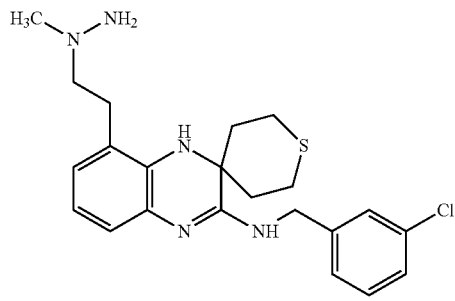 [SMILES: CN(N)CCc1cccc2c1NC1(CCCCC1)C(NCc1cccc(Cl)c1)=N2] O/S-293
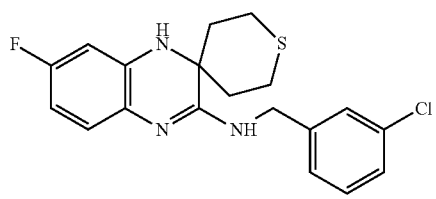 O/S-294
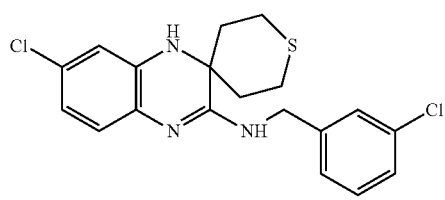 O/S-295
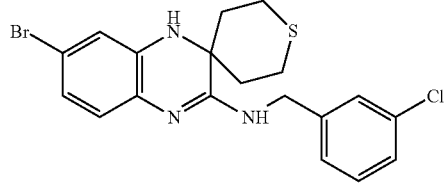 O/S-296
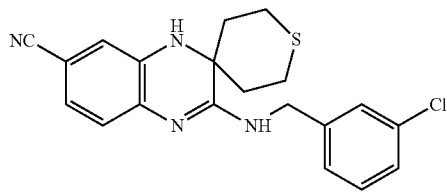 O/S-297
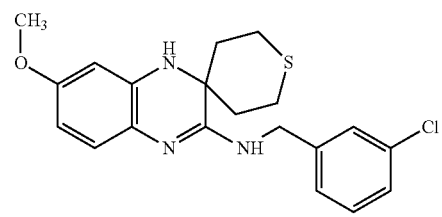 [SMILES: COc1ccc2c(c1)NC1(CCCCC1)C(NCc1cccc(Cl)c1)=N2] O/S-298
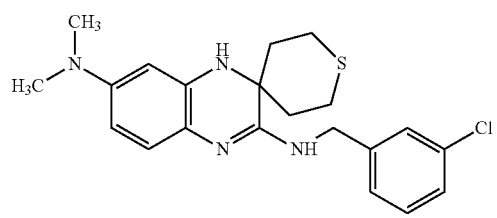 O/S-299

TABLE 1-O/S-continued
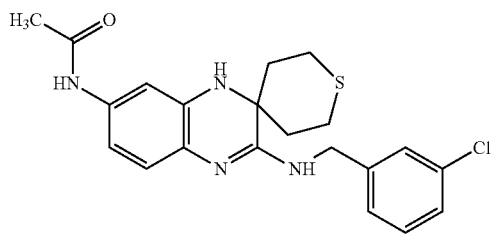 [SMILES: CC(=O)Nc1ccc2c(c1)NC1(CCCCC1)C(NCc1cccc(Cl)c1)=N2]
O/S-300
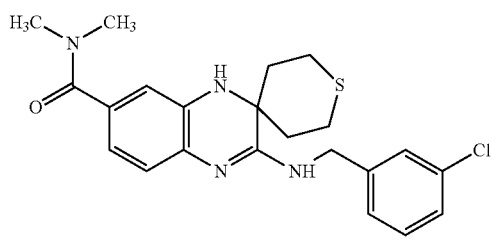 [SMILES: CN(C)C(=O)c1ccc2c(c1)NC1(CCCCC1)C(NCc1cccc(Cl)c1)=N2]
O/S-301
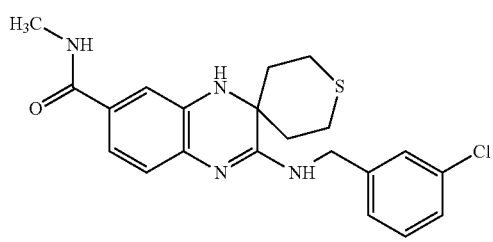 [SMILES: CNC(=O)c1ccc2c(c1)NC1(CCCCC1)C(NCc1cccc(Cl)c1)=N2]
O/S-302
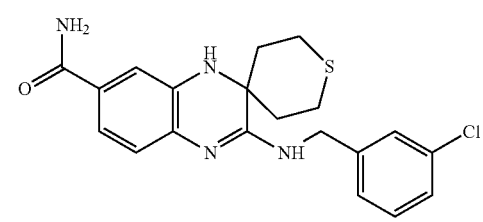
O/S-303
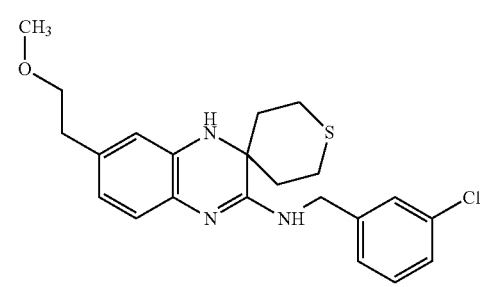 [SMILES: COCCc1ccc2c(c1)NC1(CCCCC1)C(NCc1cccc(Cl)c1)=N2]
O/S-304
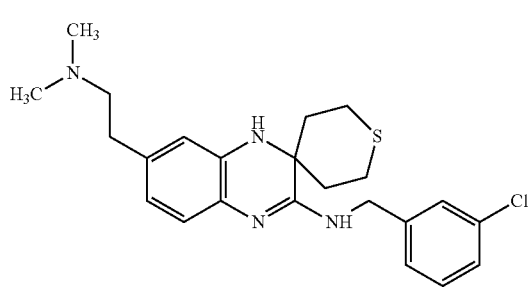 [SMILES: CN(C)CCc1ccc2c(c1)NC1(CCCCC1)C(NCc1cccc(Cl)c1)=N2]
O/S-305

TABLE 1-O/S-continued
 O/S-306
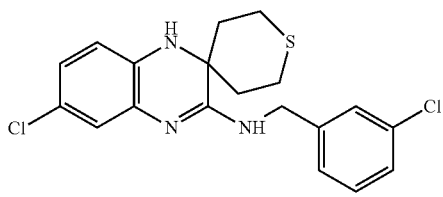 O/S-307
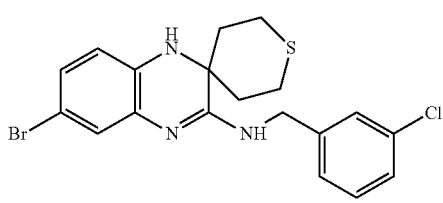 O/S-308
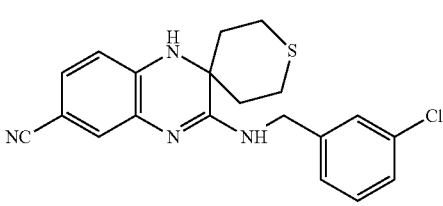 O/S-309
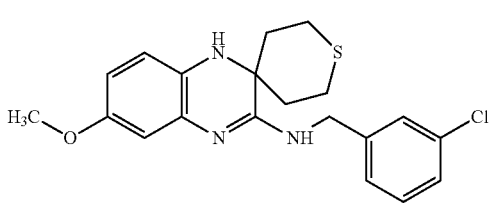 [SMILES: COc1ccc2c(c1)N=C(NCc1cccc(Cl)c1)C1(CCCCC1)N2] O/S-310
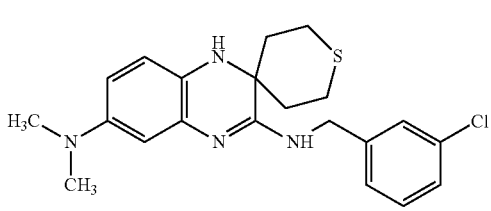 [SMILES: CN(C)c1ccc2c(c1)N=C(NCc1cccc(Cl)c1)C1(CCCCC1)N2] O/S-311
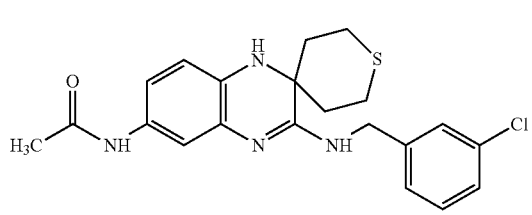 O/S-312

TABLE 1-O/S-continued
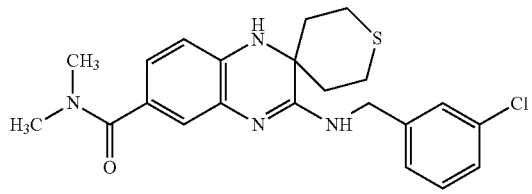
O/S-313
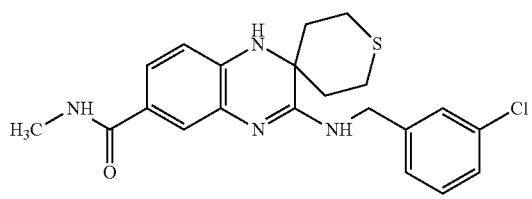
O/S-314
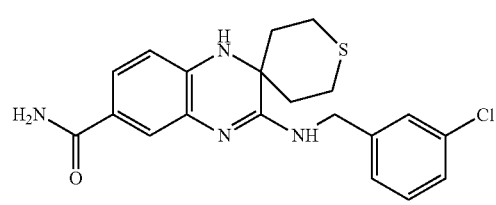
O/S-315
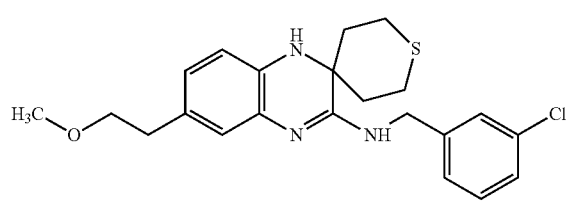
O/S-316
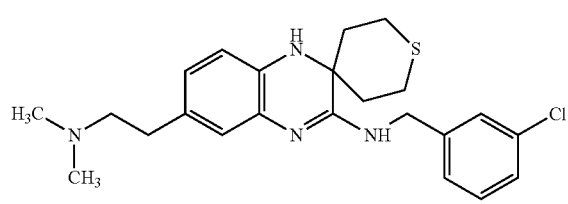
O/S-317
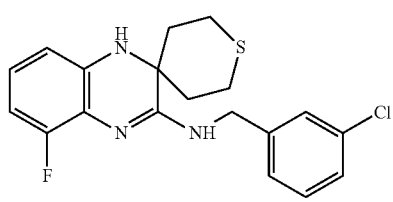 [SMILES: Fc1cccc2c1N=C(NCc1cccc(Cl)c1)C1(CCCCC1)N2]
O/S-318
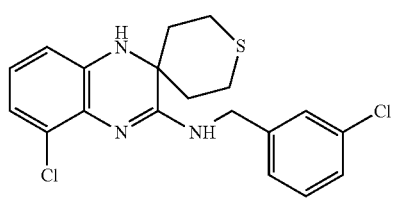 [SMILES: Clc1cccc(CNC2=Nc3c(Cl)cccc3NC23CCCCC3)c1]
O/S-319

TABLE 1-O/S-continued
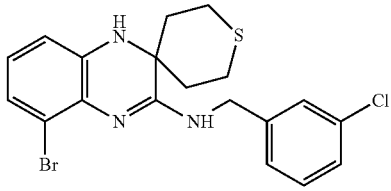 [SMILES: Clc1cccc(CNC2=Nc3c(Br)cccc3NC23CCCCC3)c1]
O/S-320
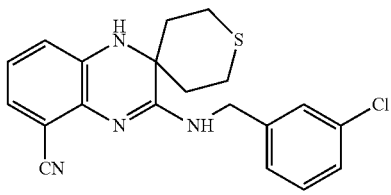 [SMILES: N#Cc1cccc2c1N=C(NCc1cccc(Cl)c1)C1(CCCCC1)N2]
O/S-321
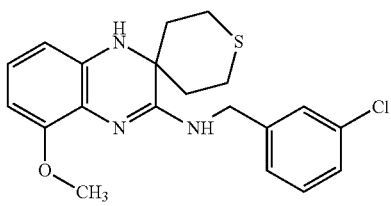 [SMILES: COc1cccc2c1N=C(NCc1cccc(Cl)c1)C1(CCCCC1)N2]
O/S-322
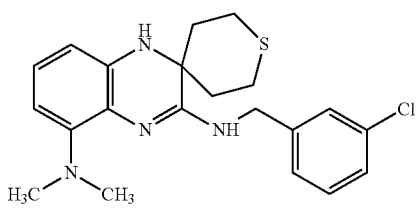
O/S-323
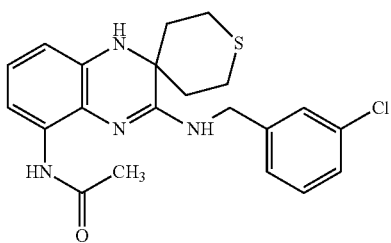 [SMILES: CC(=O)Nc1cccc2c1N=C(NCc1cccc(Cl)c1)C1(CCCCC1)N2]
O/S-324
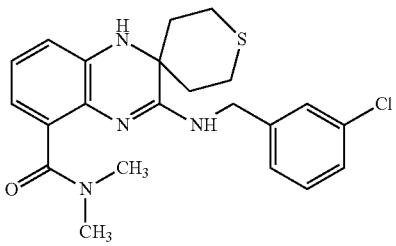
O/S-325
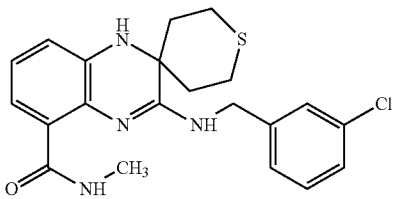
O/S-326

TABLE 1-O/S-continued
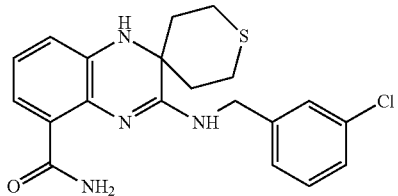 O/S-327
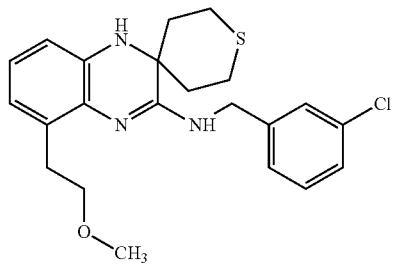 [SMILES: COCCc1cccc2c1N=C(NCc1cccc(Cl)c1)C1(CCCCC1)N2] O/S-328
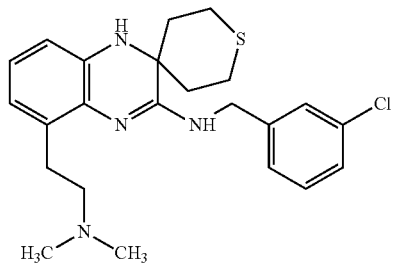 O/S-329
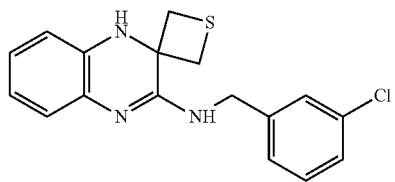 [SMILES: Clc1cccc(CNC2=Nc3ccccc3NC23CCC3)c1] O/S-330
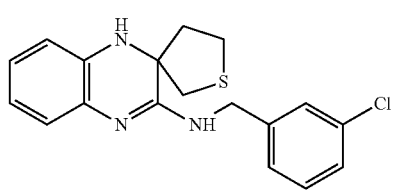 O/S-331
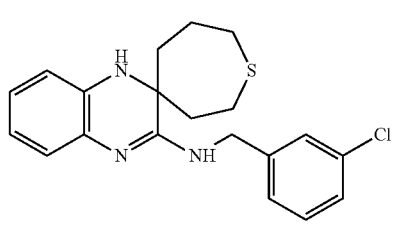 O/S-332
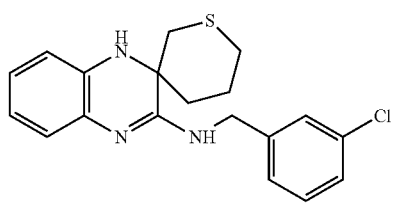 O/S-333

TABLE 1-O/S-continued
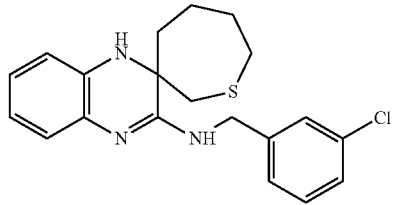
O/S-334
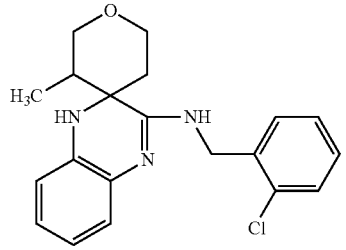
O/S-335
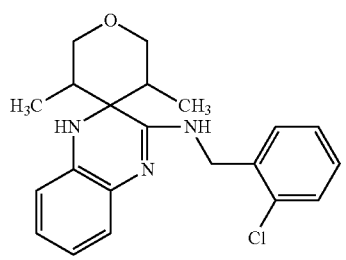
O/S-336
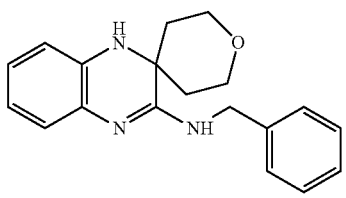
O/S-337
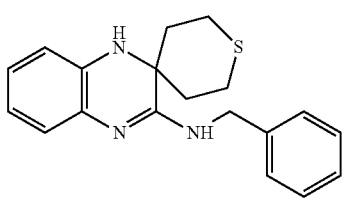 [SMILES: c1ccc(CNC2=Nc3ccccc3NC23CCCCC3)cc1]
O/S-338
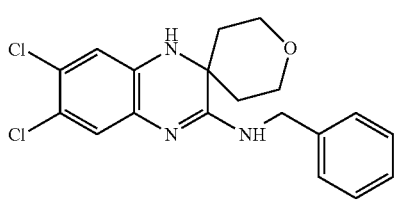
O/S-339
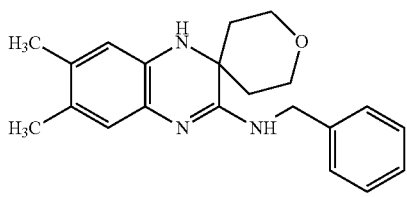
O/S-340

TABLE 1-O/S-continued
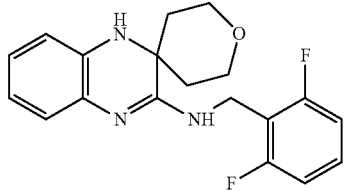 O/S-341
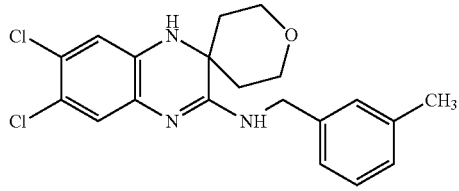 O/S-342
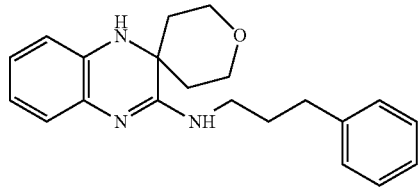 O/S-343
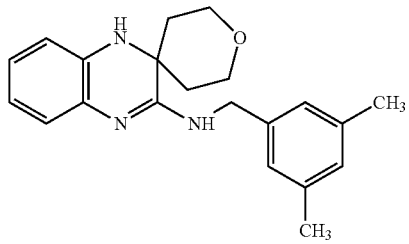 O/S-344
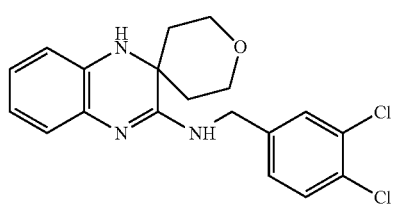 O/S-345
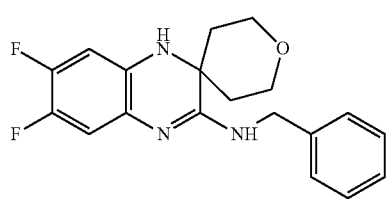 O/S-346
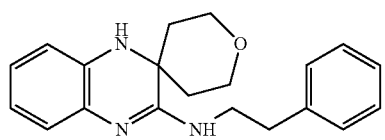 O/S-347

TABLE 1-O/S-continued
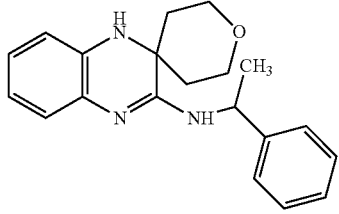
O/S-348
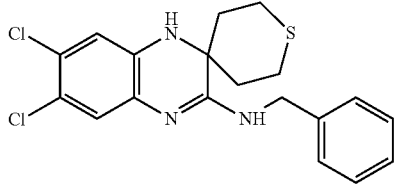 [SMILES: Clc1cc2c(cc1Cl)NC1(CCCCC1)C(NCc1ccccc1)=N2]
O/S-349
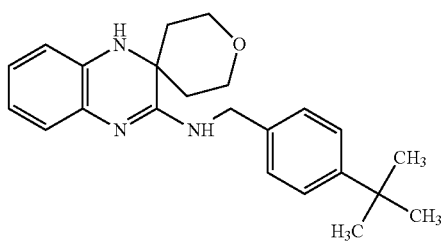
O/S-350
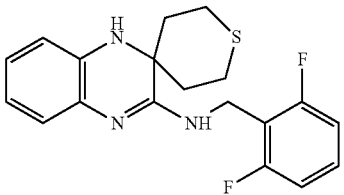
O/S-351
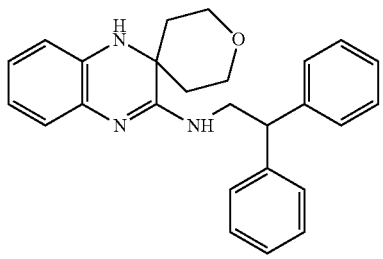
O/S-352
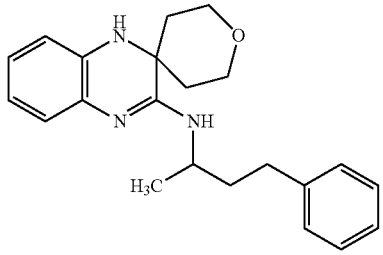
O/S-353

TABLE 1-O/S-continued
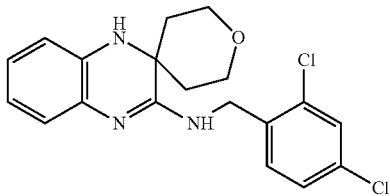 O/S-354
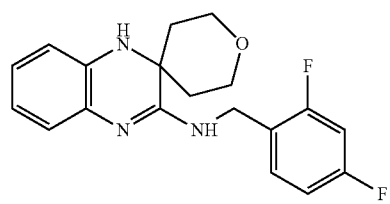 O/S-355
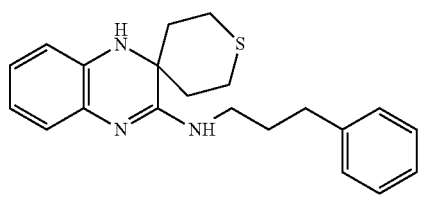 O/S-356
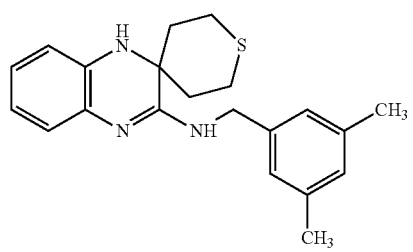 O/S-357
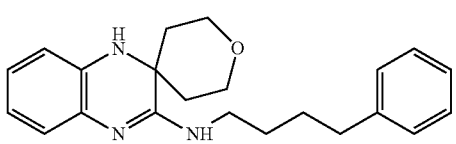 O/S-358
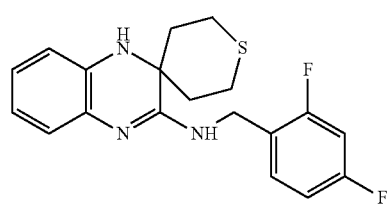 O/S-359
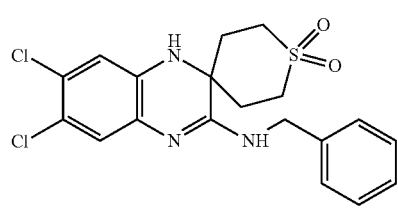 O/S-360

TABLE 1-O/S-continued
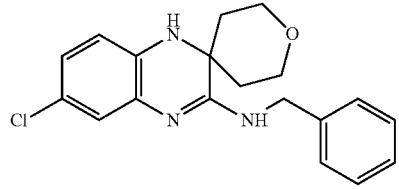 O/S-361
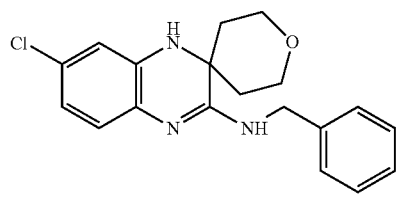 O/S-362
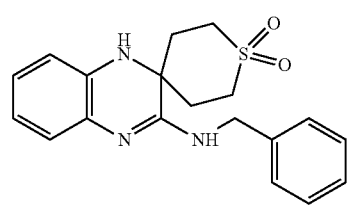 O/S-363
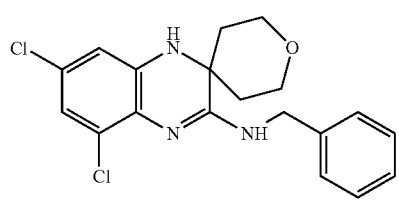 O/S-364
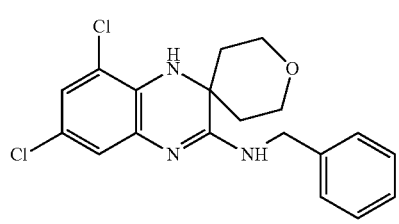 O/S-365
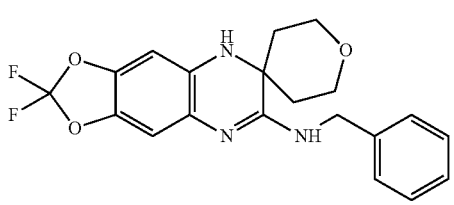 O/S-366
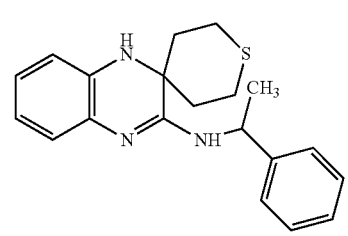 O/S-367

TABLE 1-O/S-continued
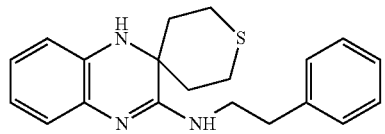
O/S-368
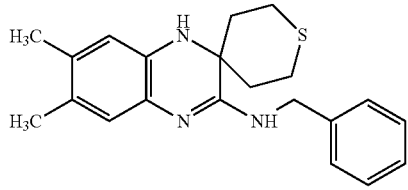
O/S-369
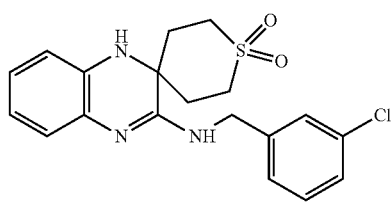
O/S-370
| TABLE 1-C | TABLE 1-C-continued |
|---|---|
| 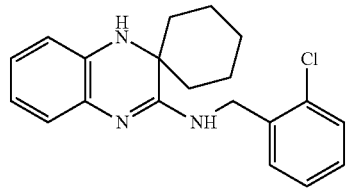 C-1 | 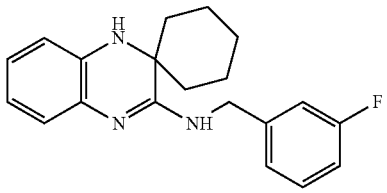 C-5 |
| 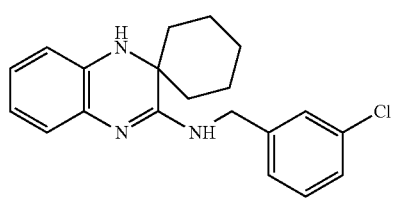 C-2 | 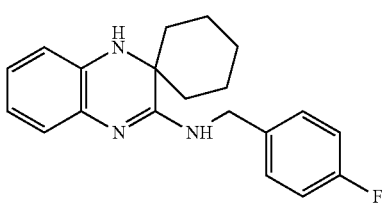 C-6 |
| 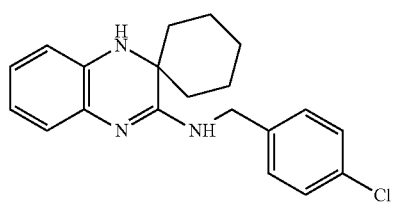 C-3 | 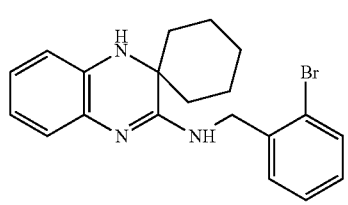 C-7 |
| 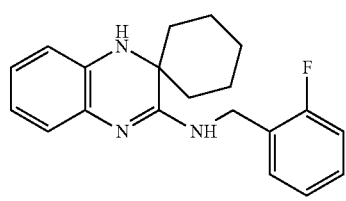 C-4 | 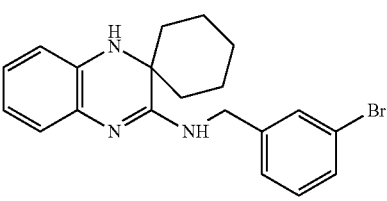 C-8 |

TABLE 1-C-continued
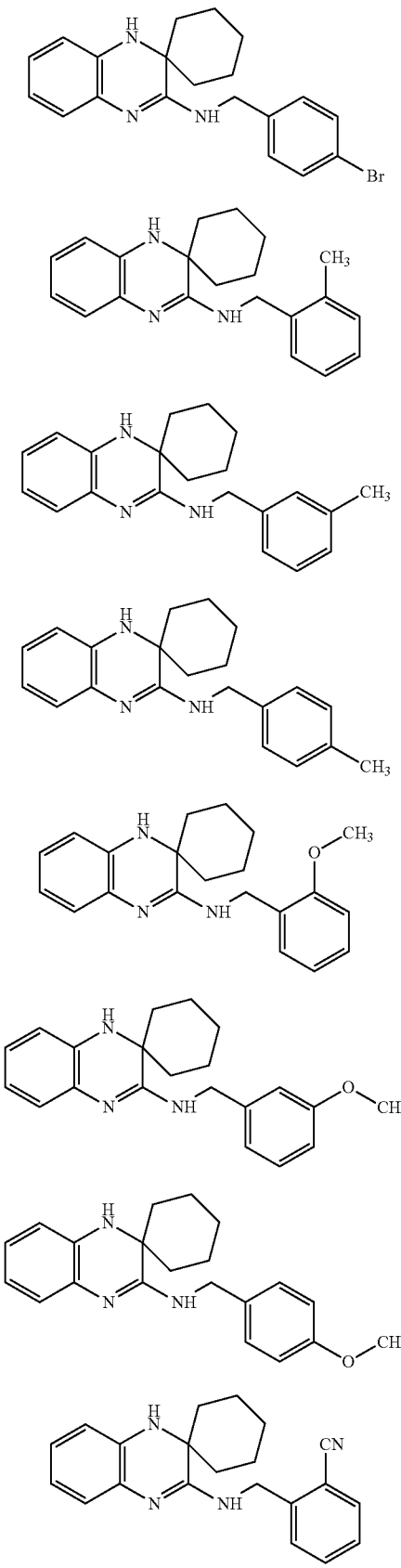
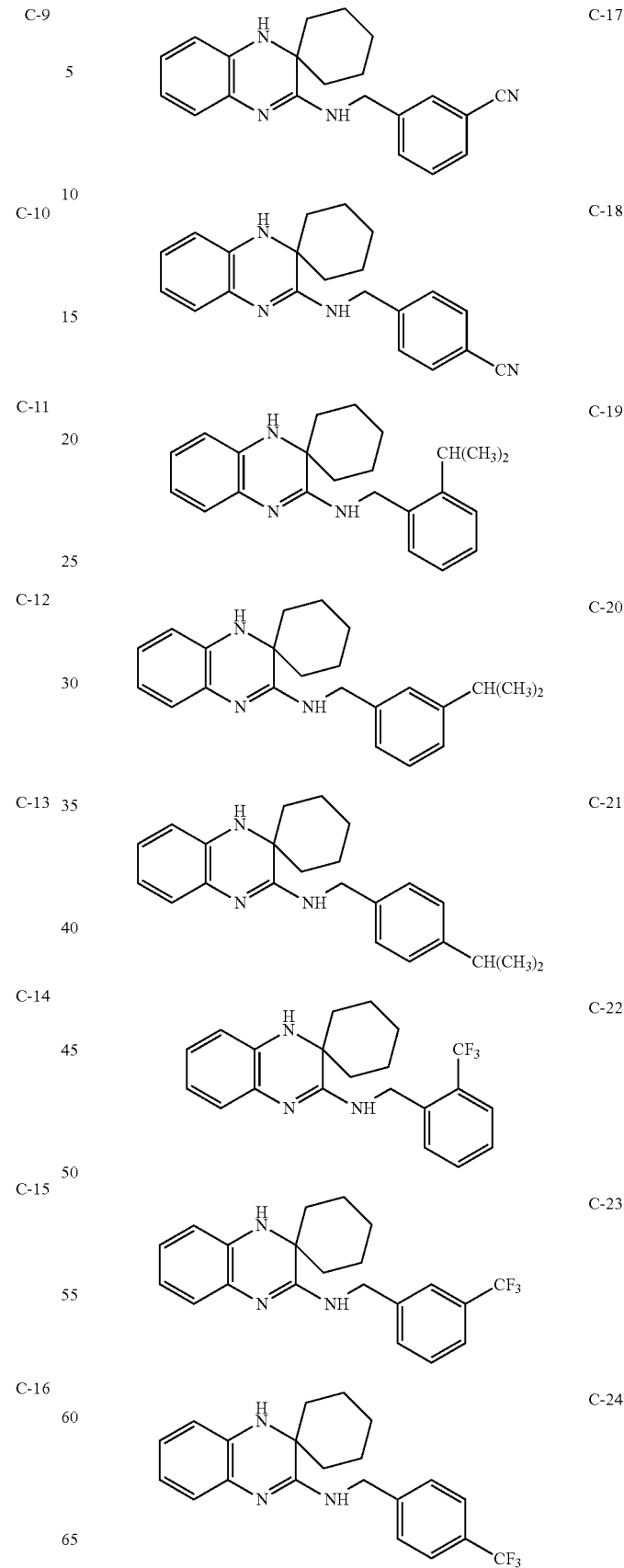

TABLE 1-C-continued
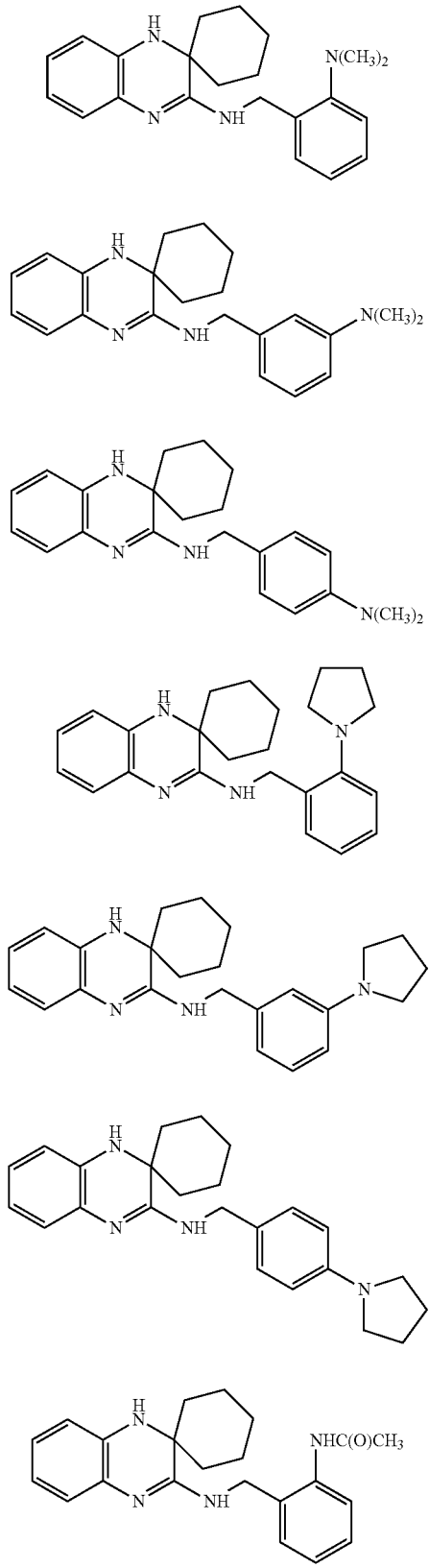
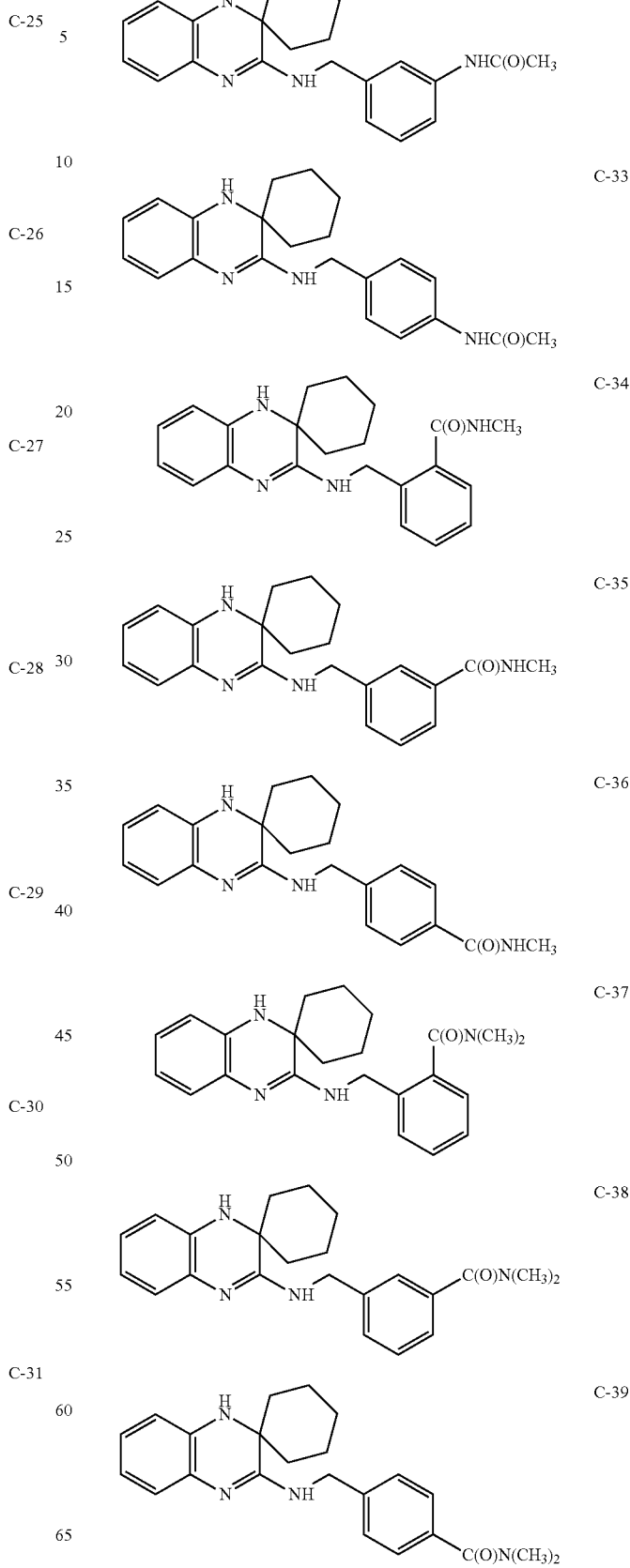

TABLE 1-C-continued
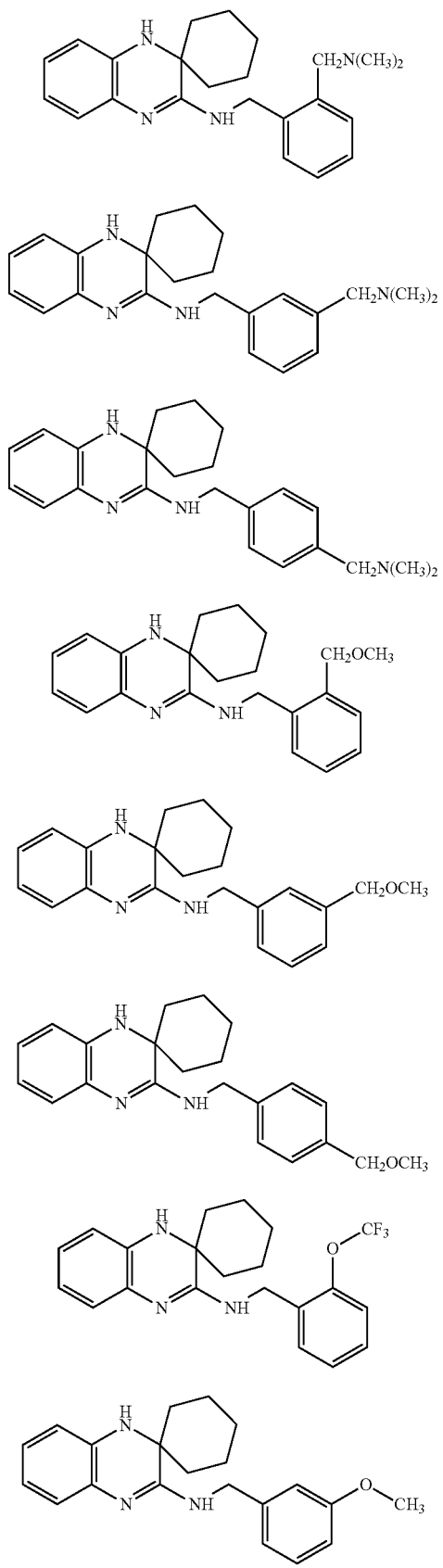
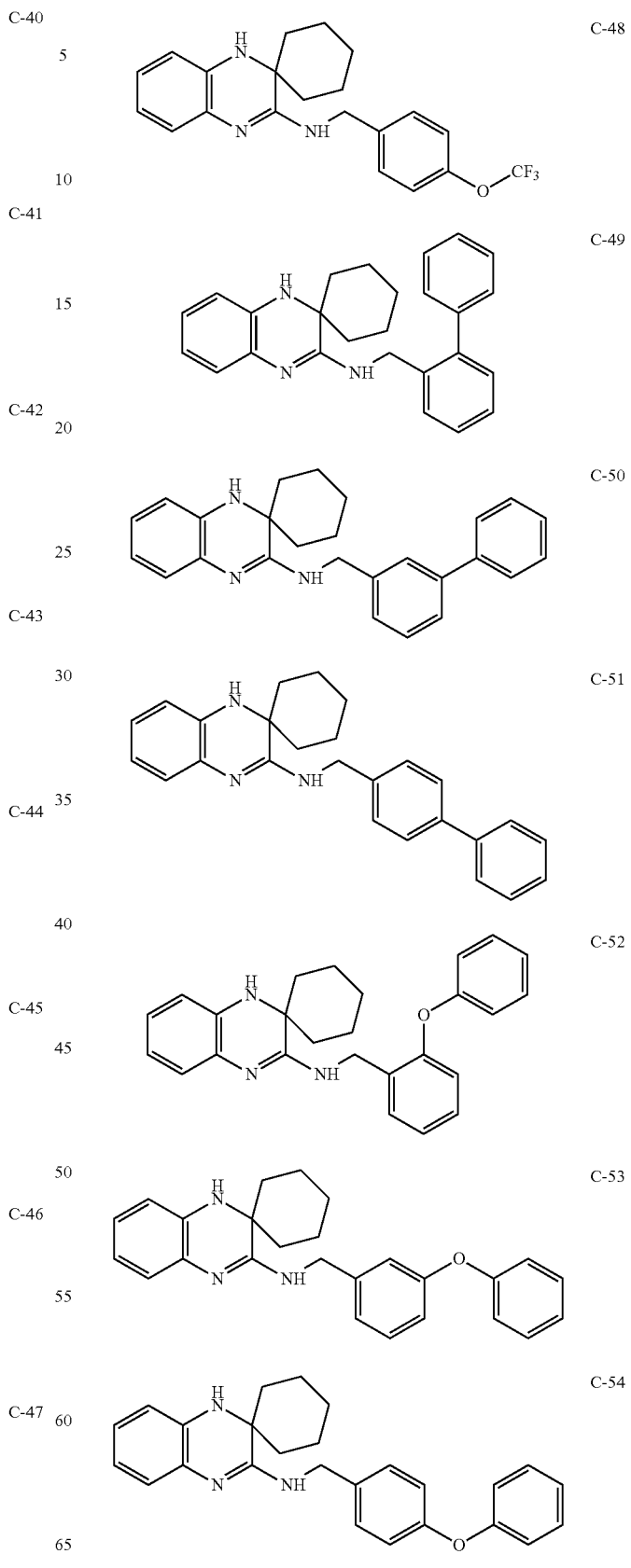

TABLE 1-C-continued
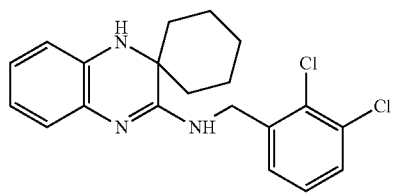 C-55
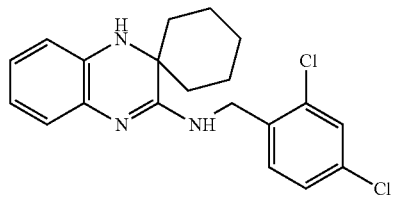 C-56
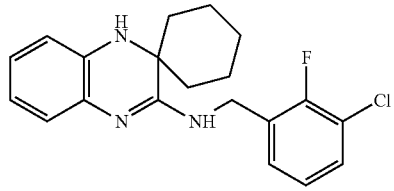 C-57
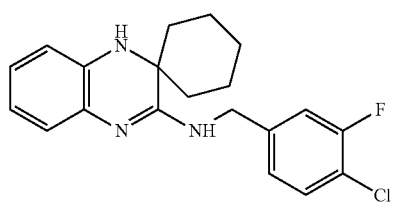 C-58
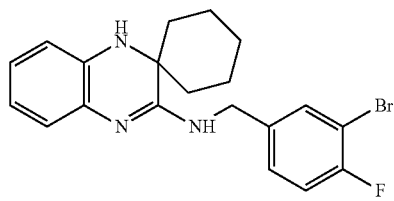 C-59
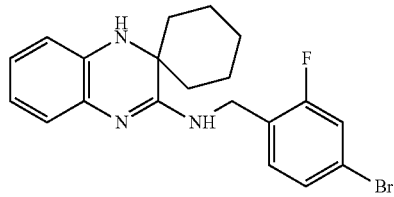 C-60
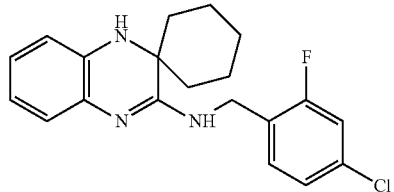 C-61
TABLE 1-C-continued
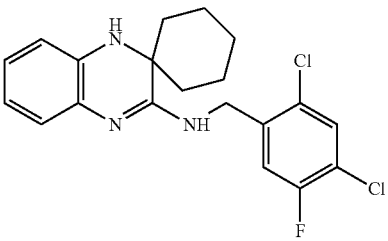 C-62
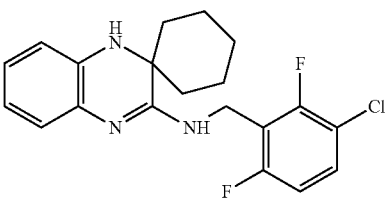 C-63
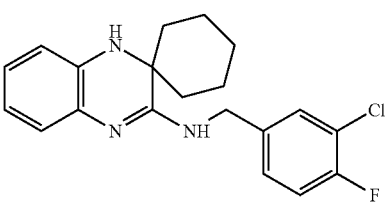 C-64
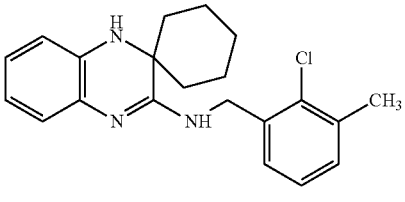 C-65
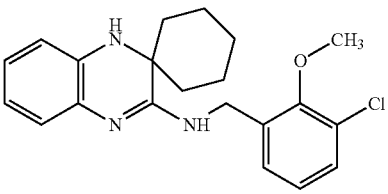 C-66
 C-67
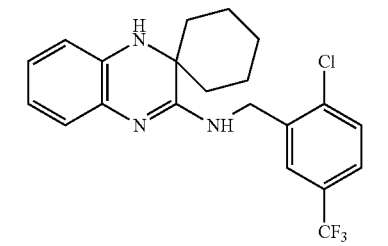 C-68

TABLE 1-C-continued
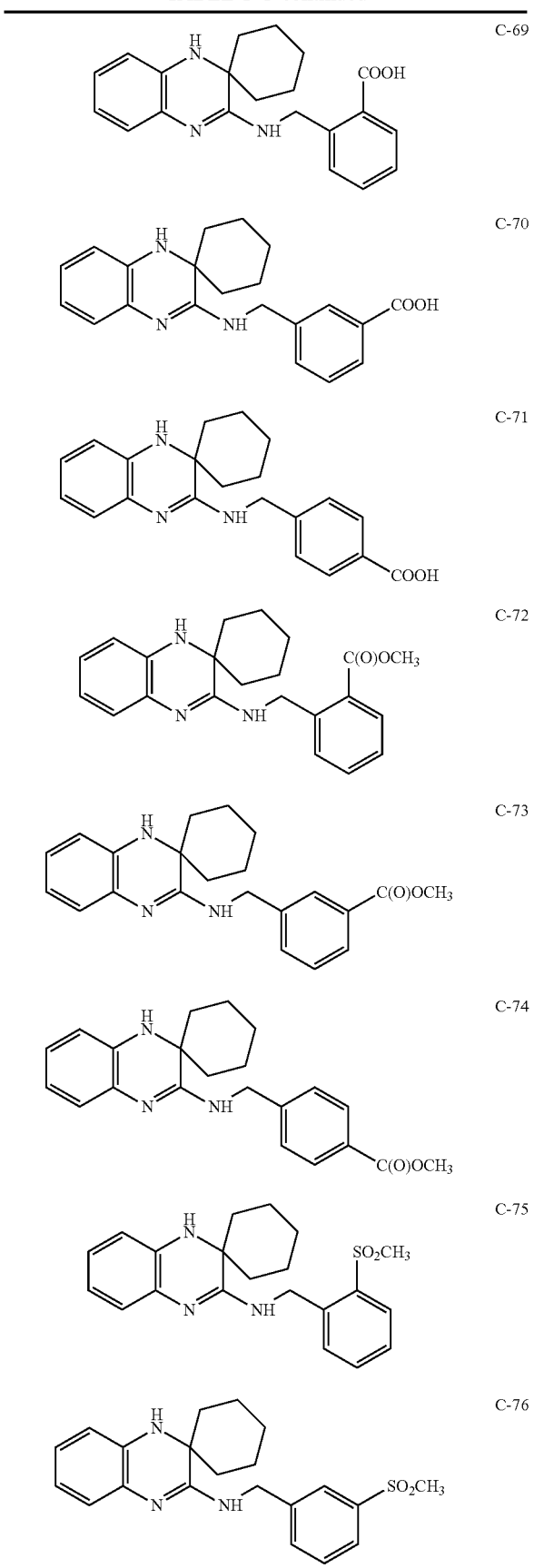
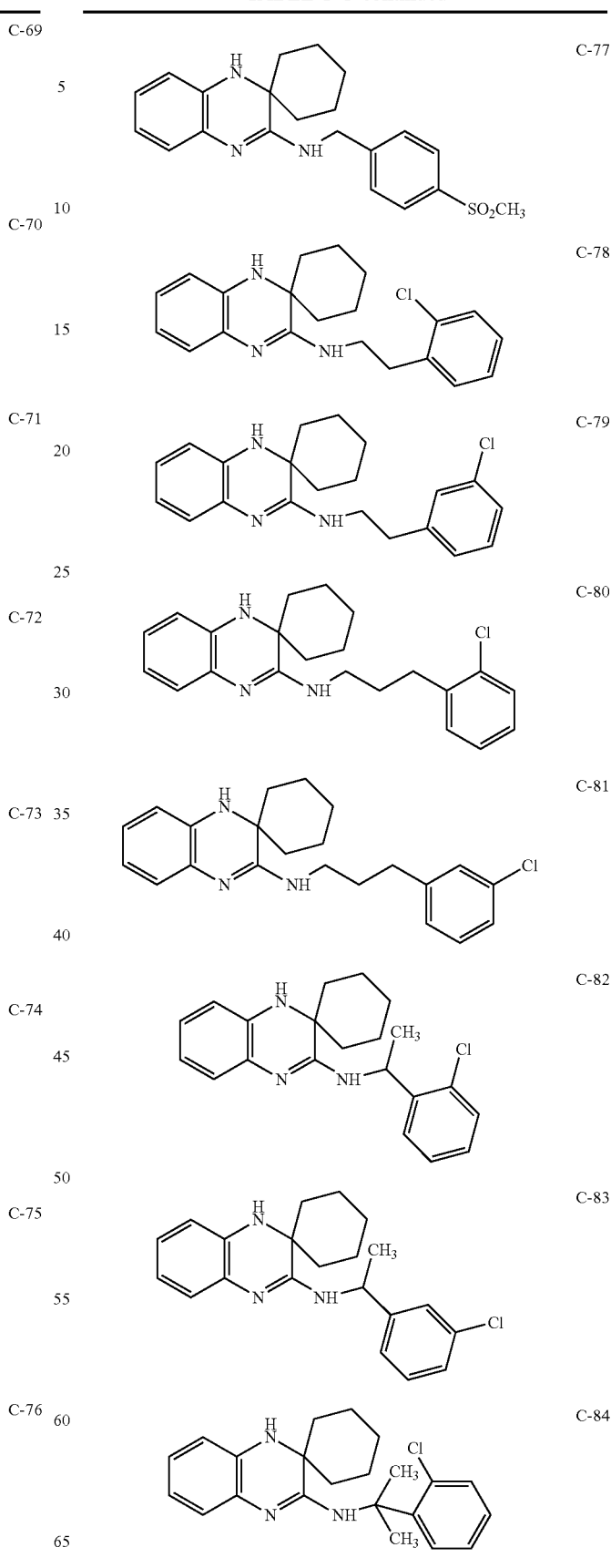

TABLE 1-C-continued
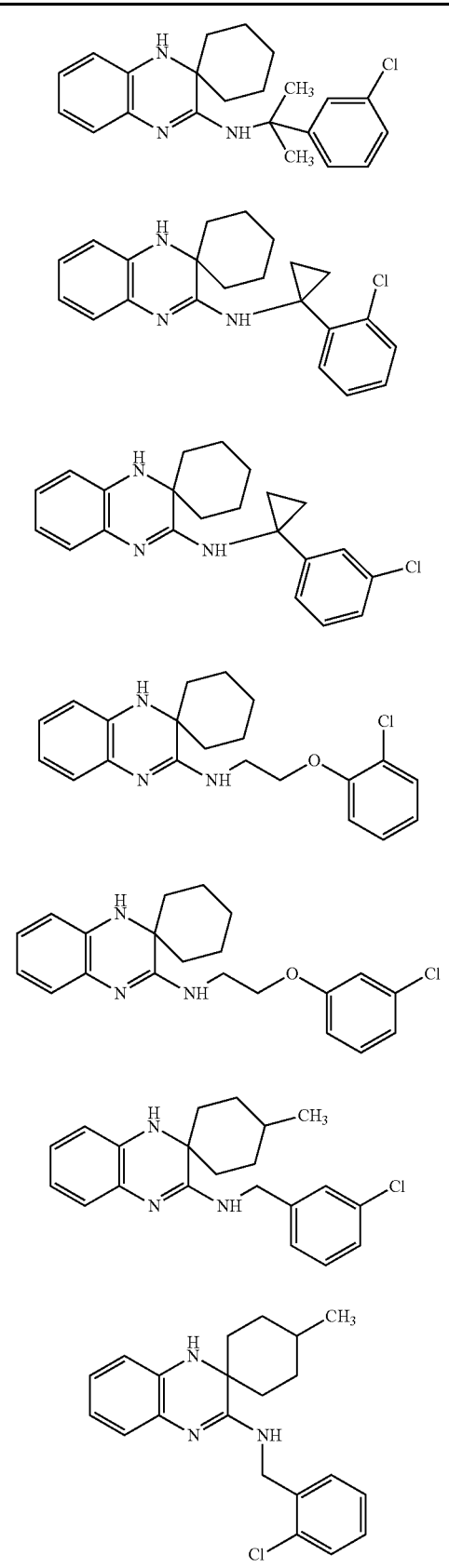
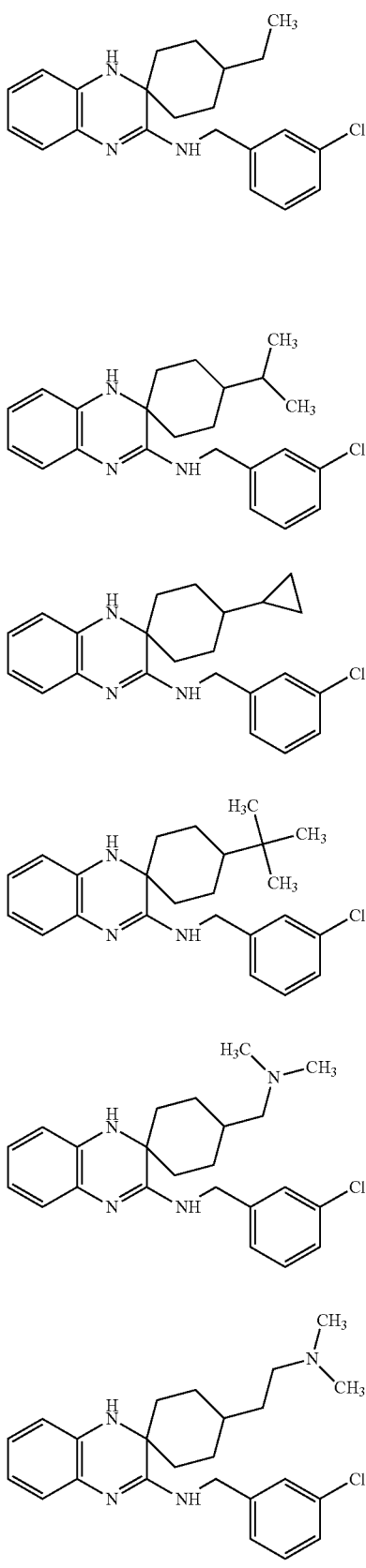

TABLE 1-C-continued
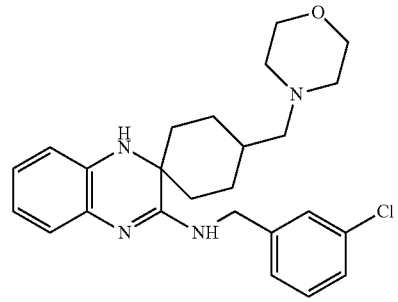
C-98
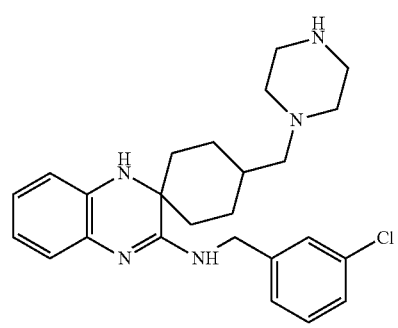
C-99
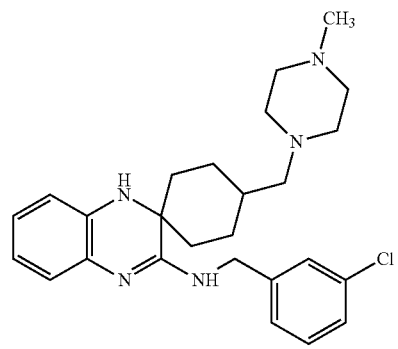
C-100
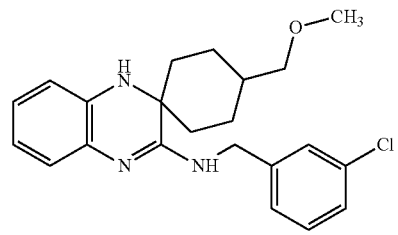
C-101
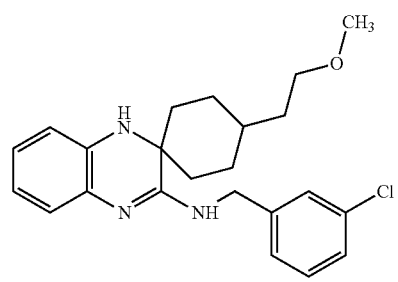
C-102
TABLE 1-C-continued
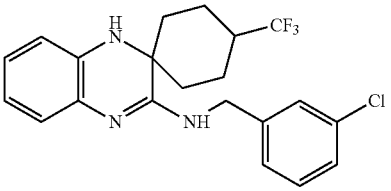
C-103
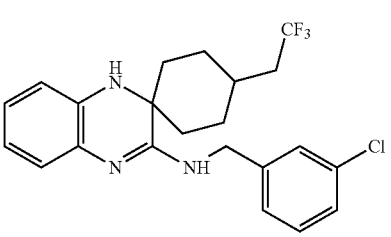
C-104
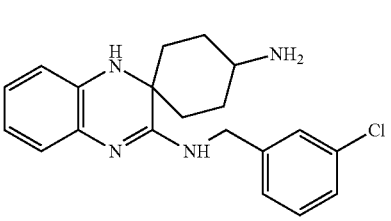
C-105
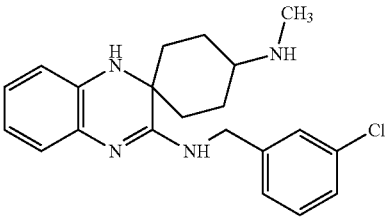
C-106
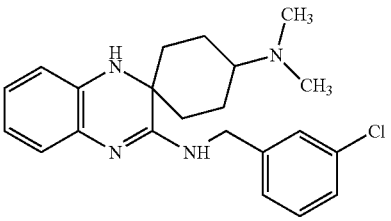
C-107
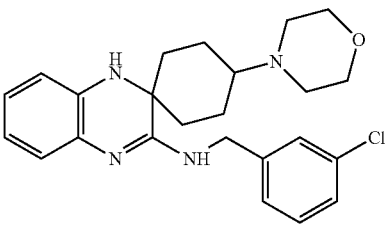
C-108
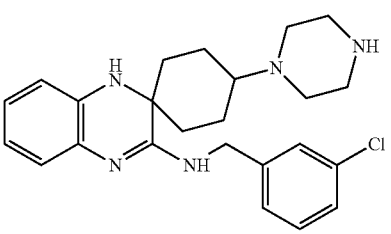
C-109

TABLE 1-C-continued
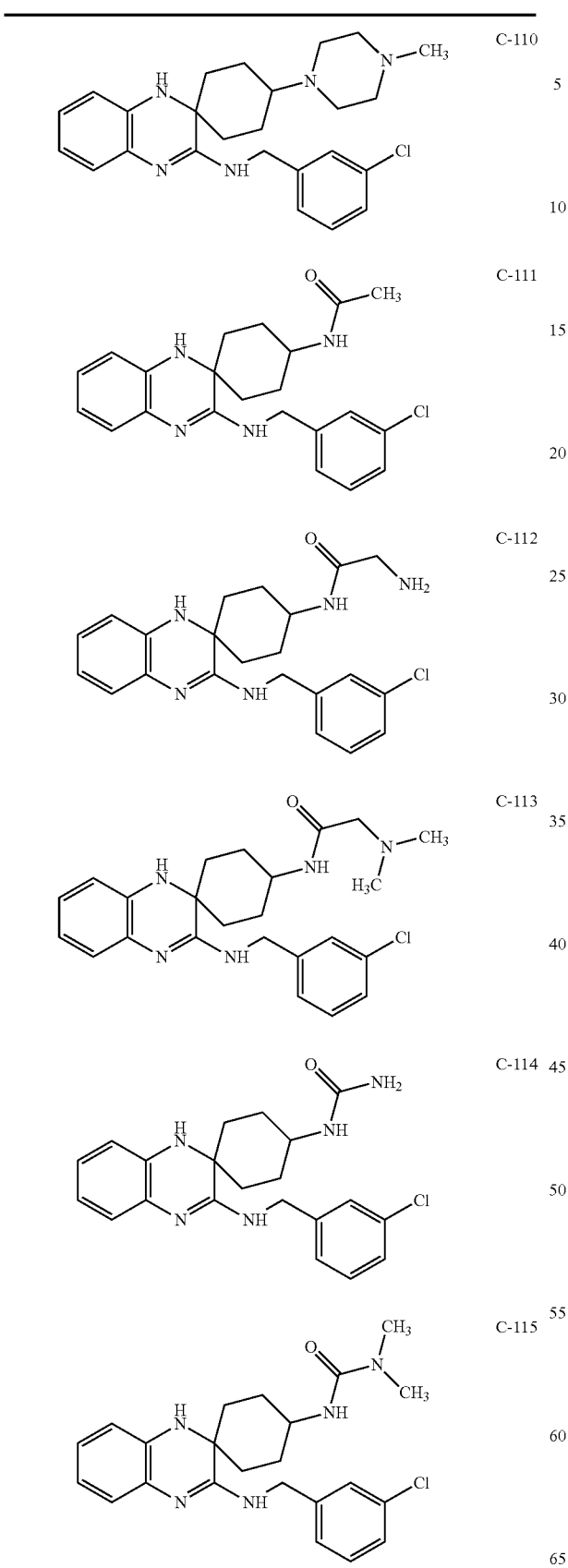
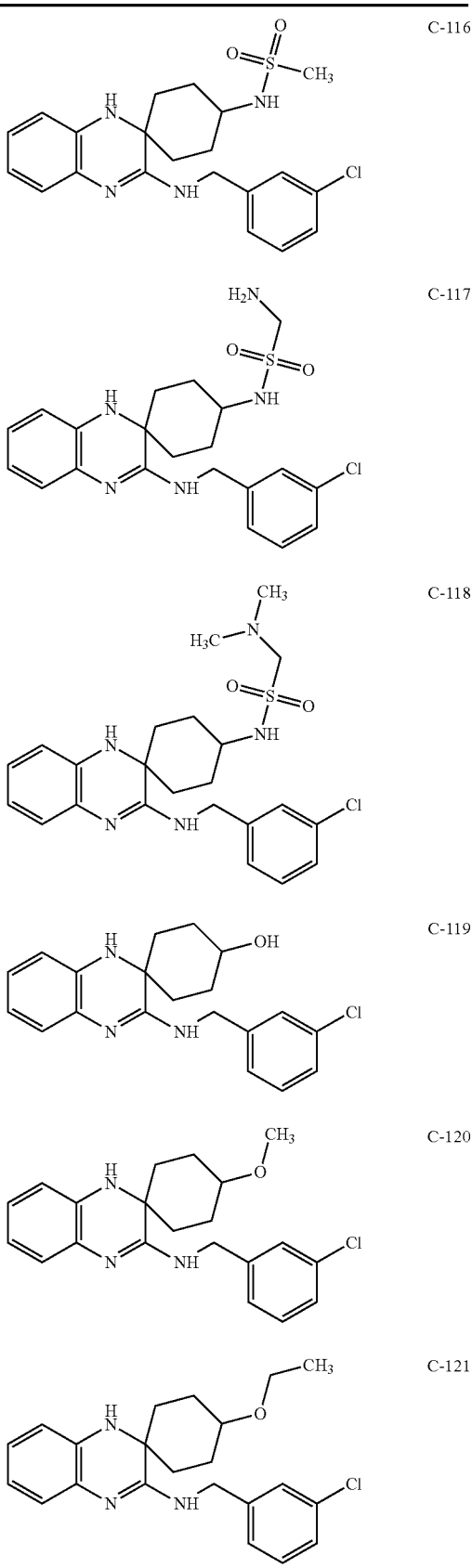

TABLE 1-C-continued
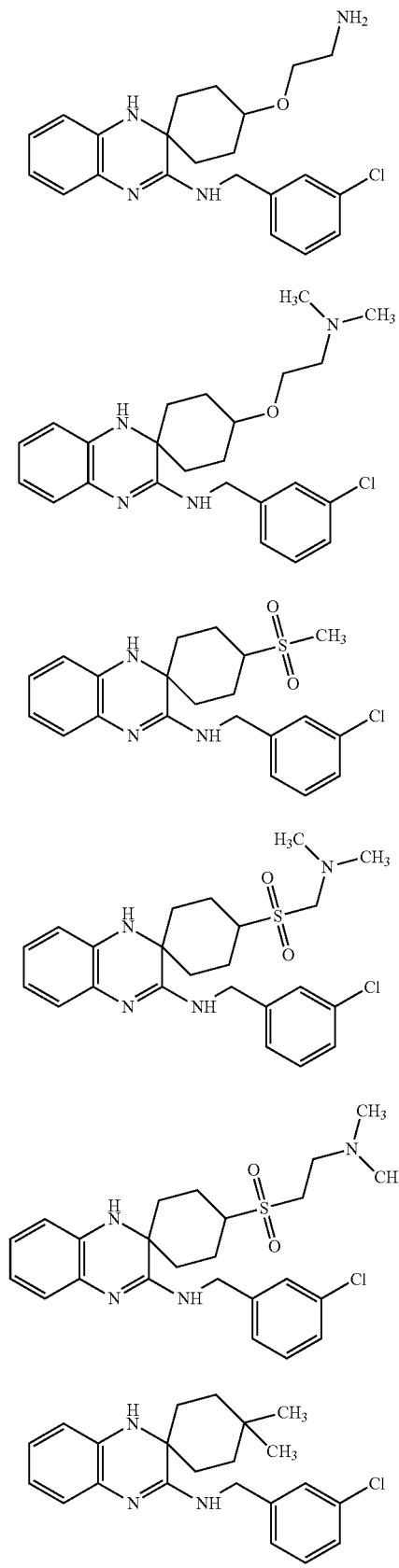
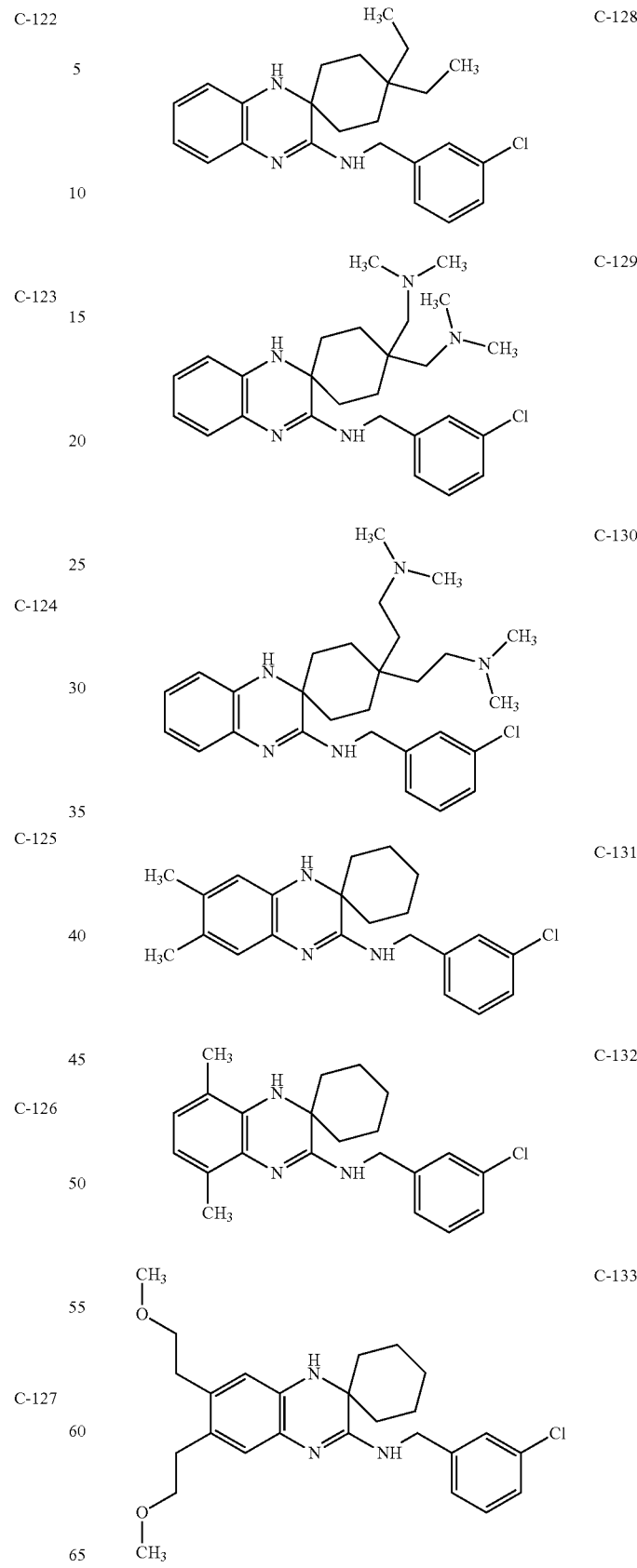

TABLE 1-C-continued
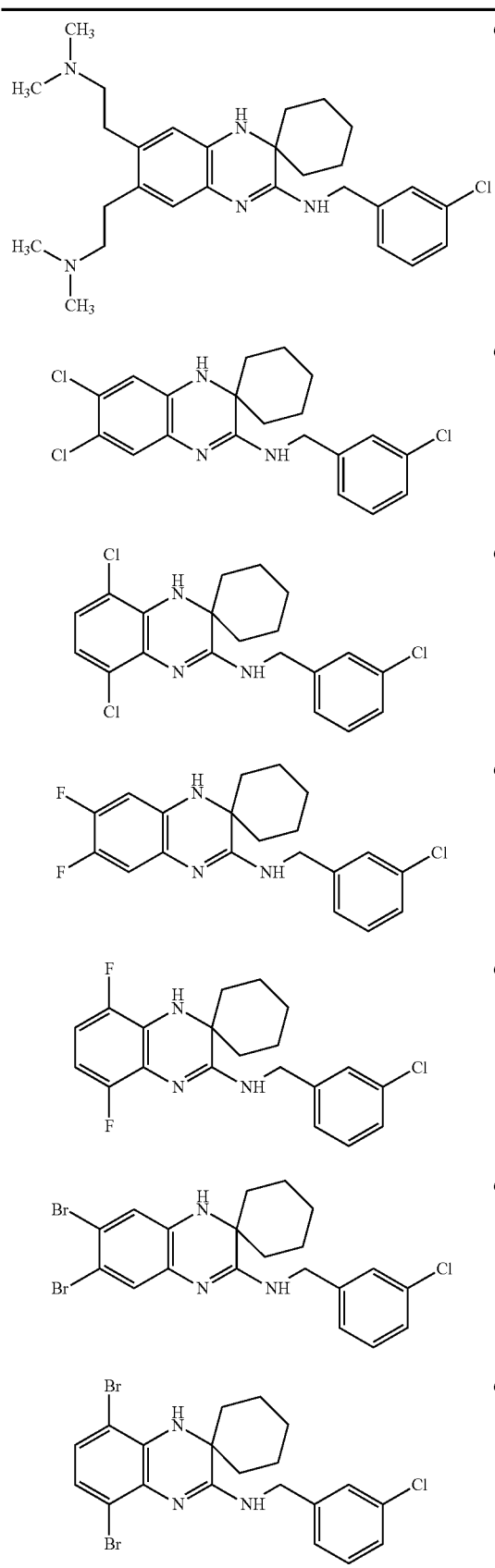
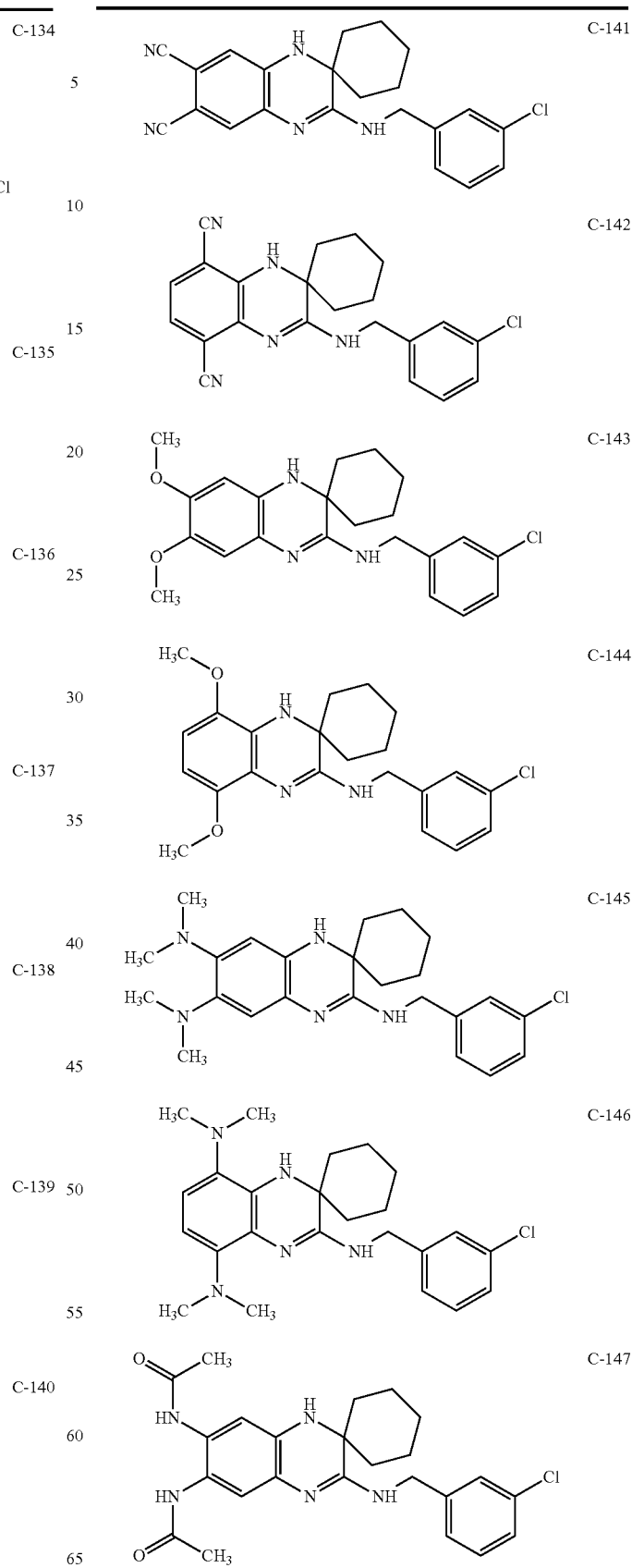

TABLE 1-C-continued
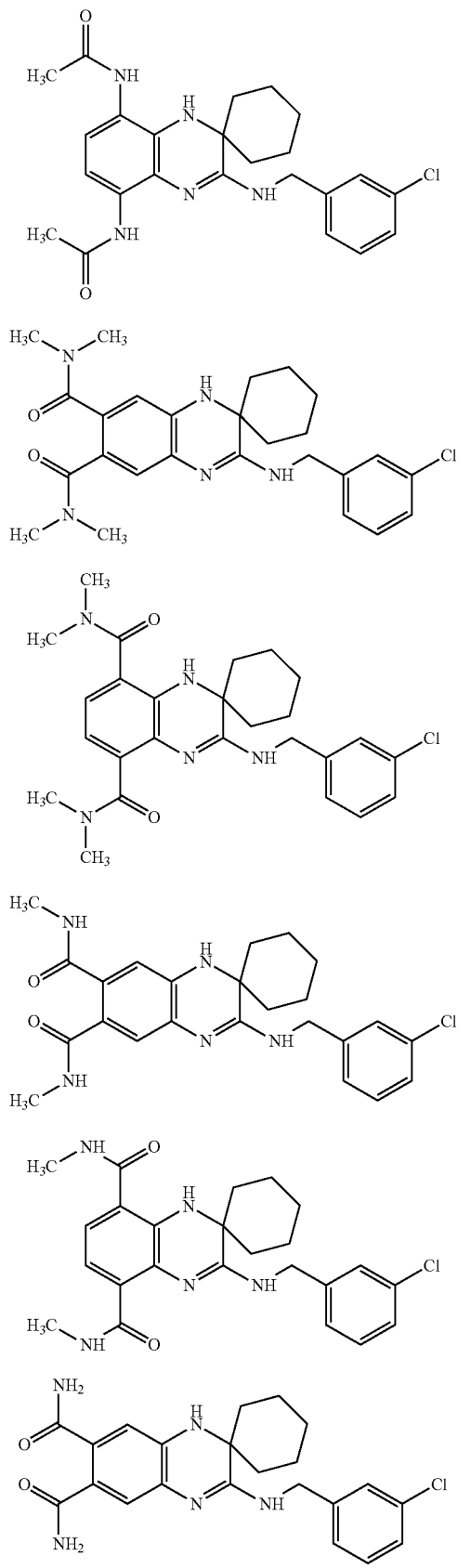
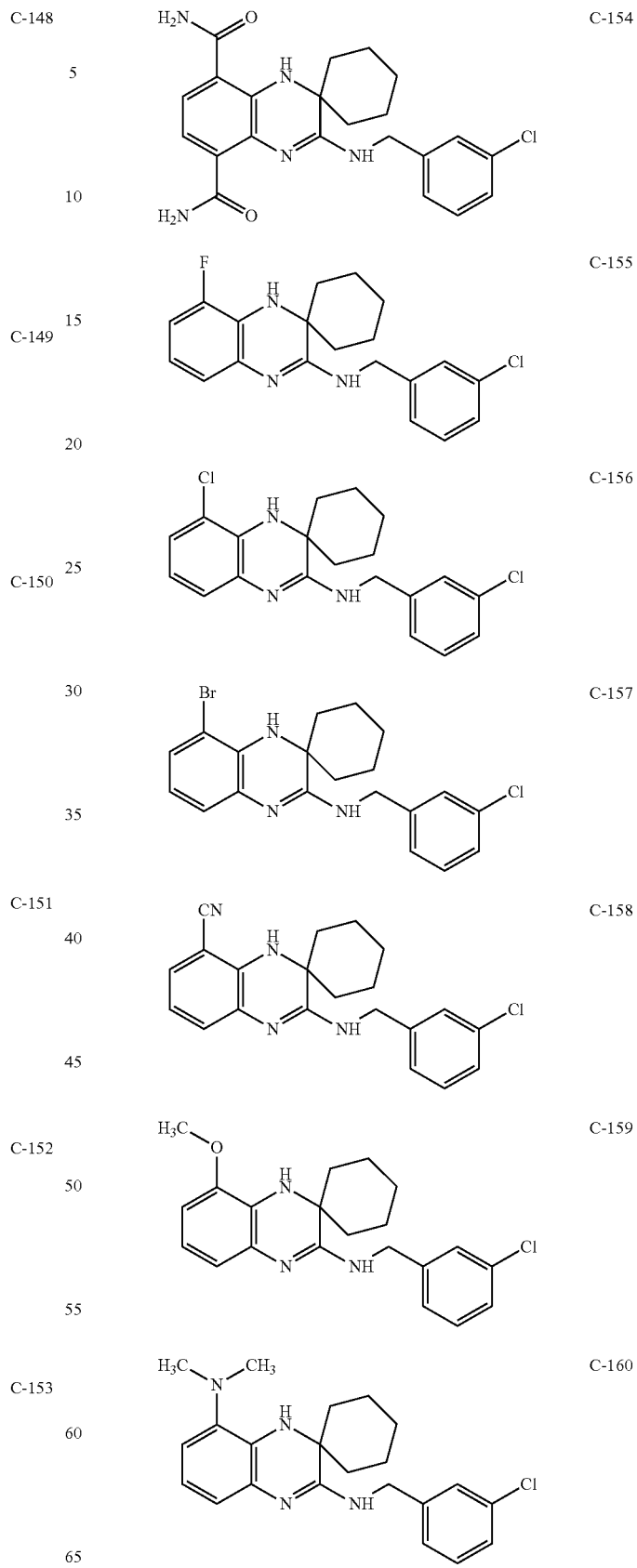

TABLE 1-C-continued
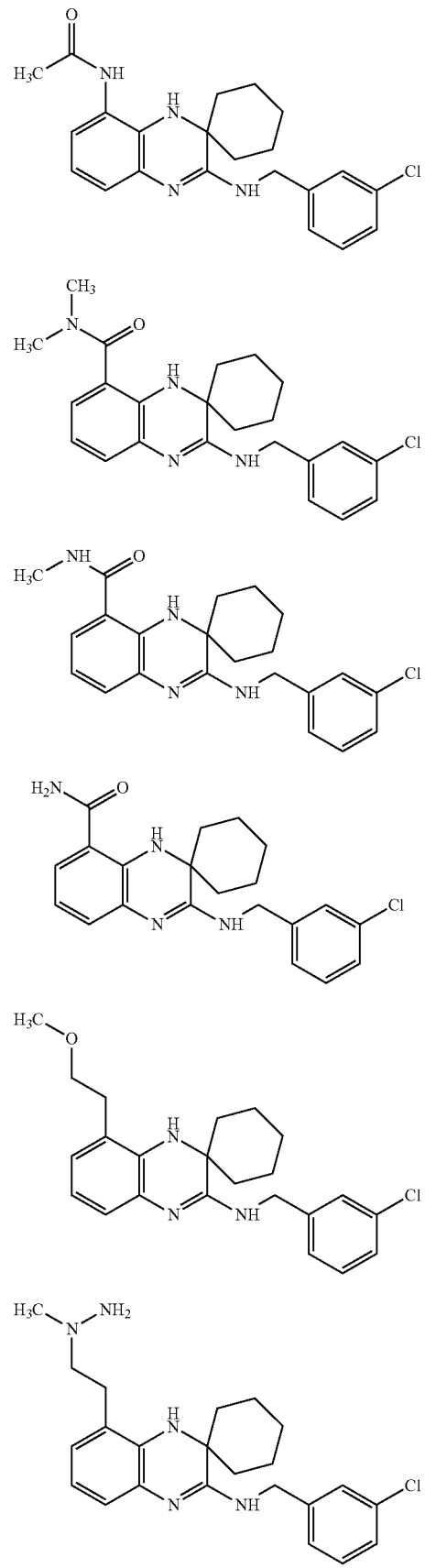
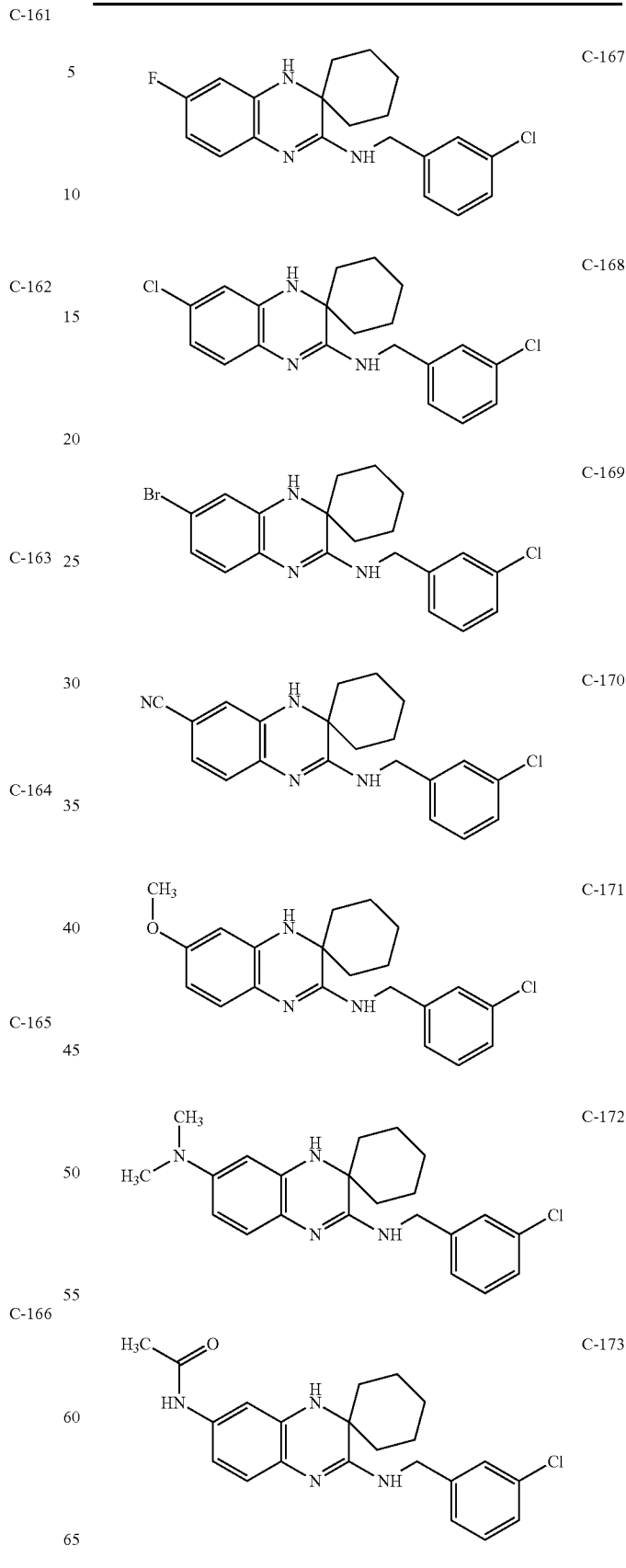

TABLE 1-C-continued
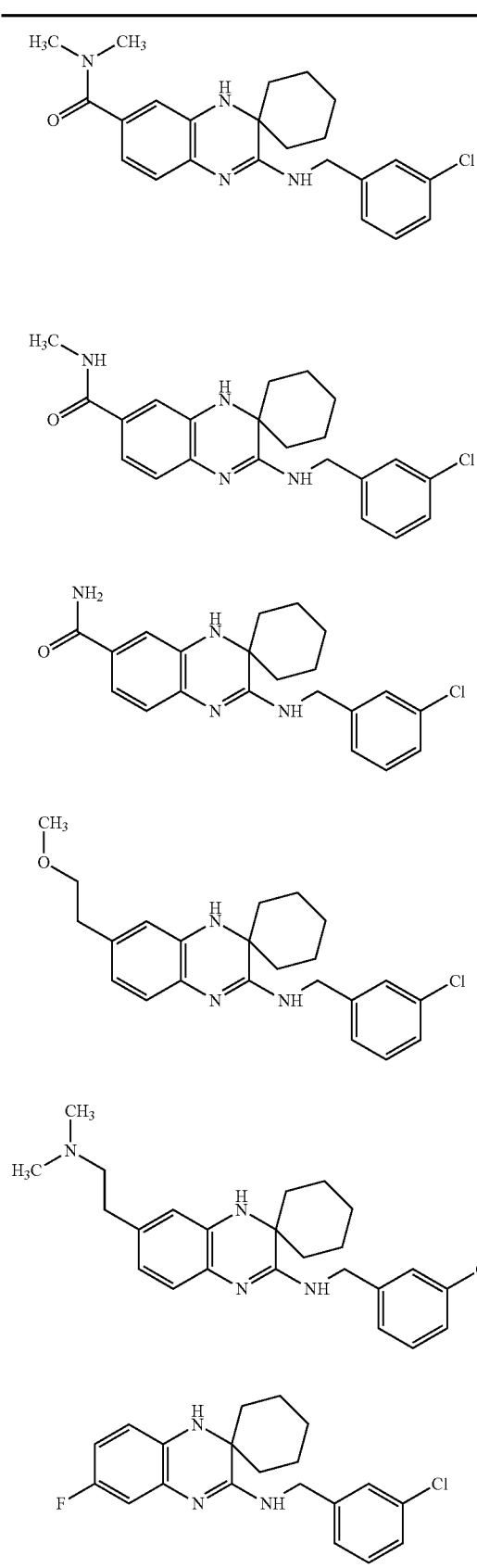
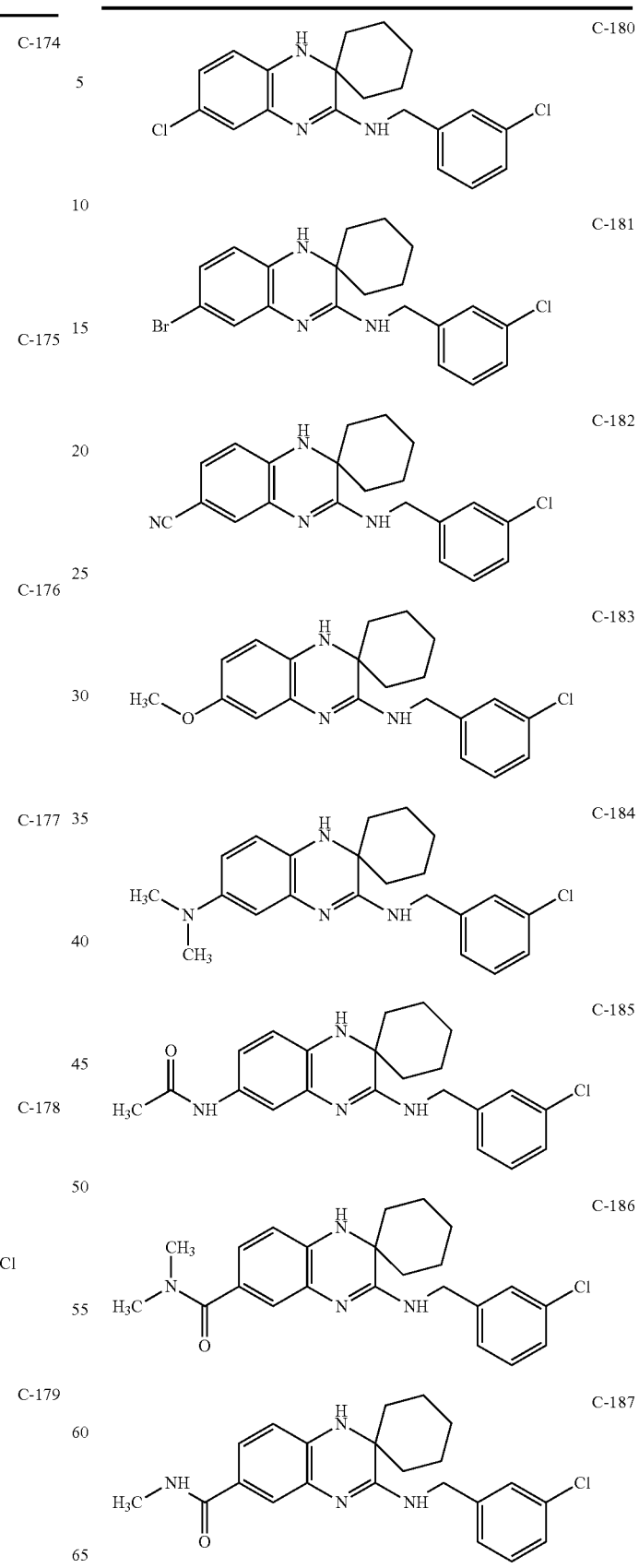

TABLE 1-C-continued
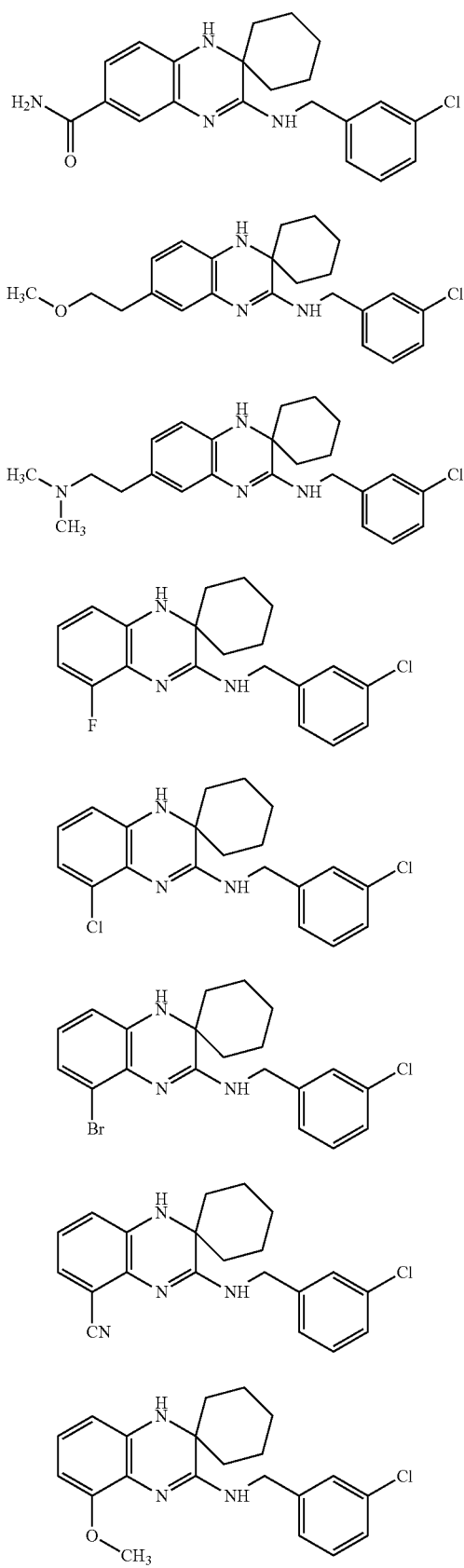
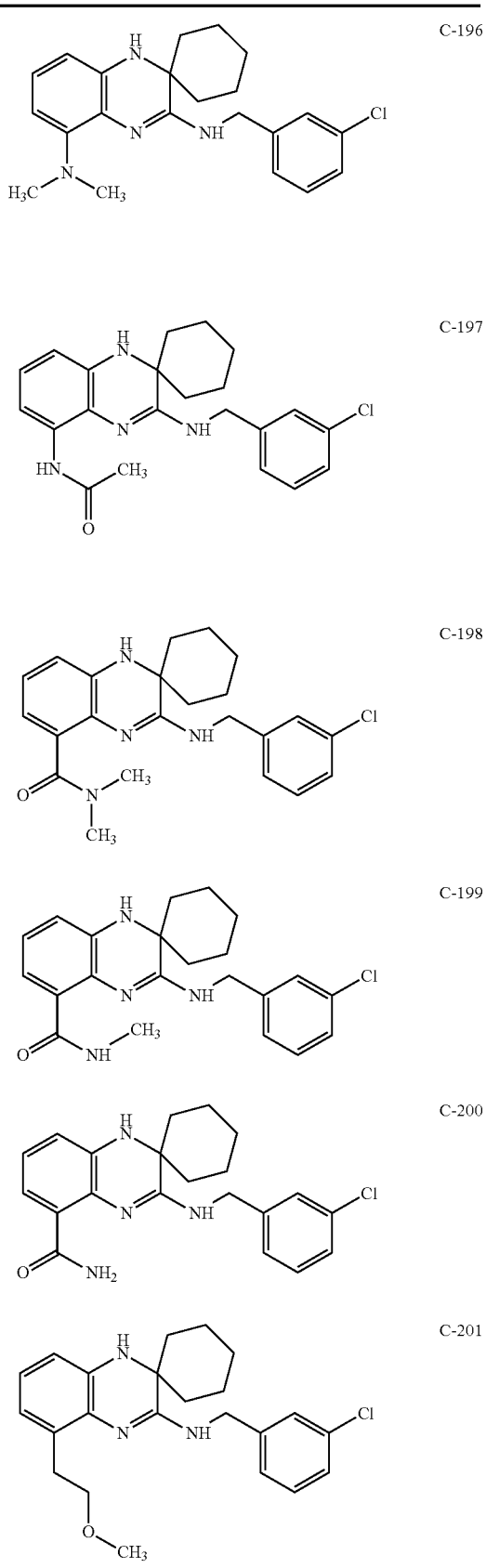

TABLE 1-C-continued
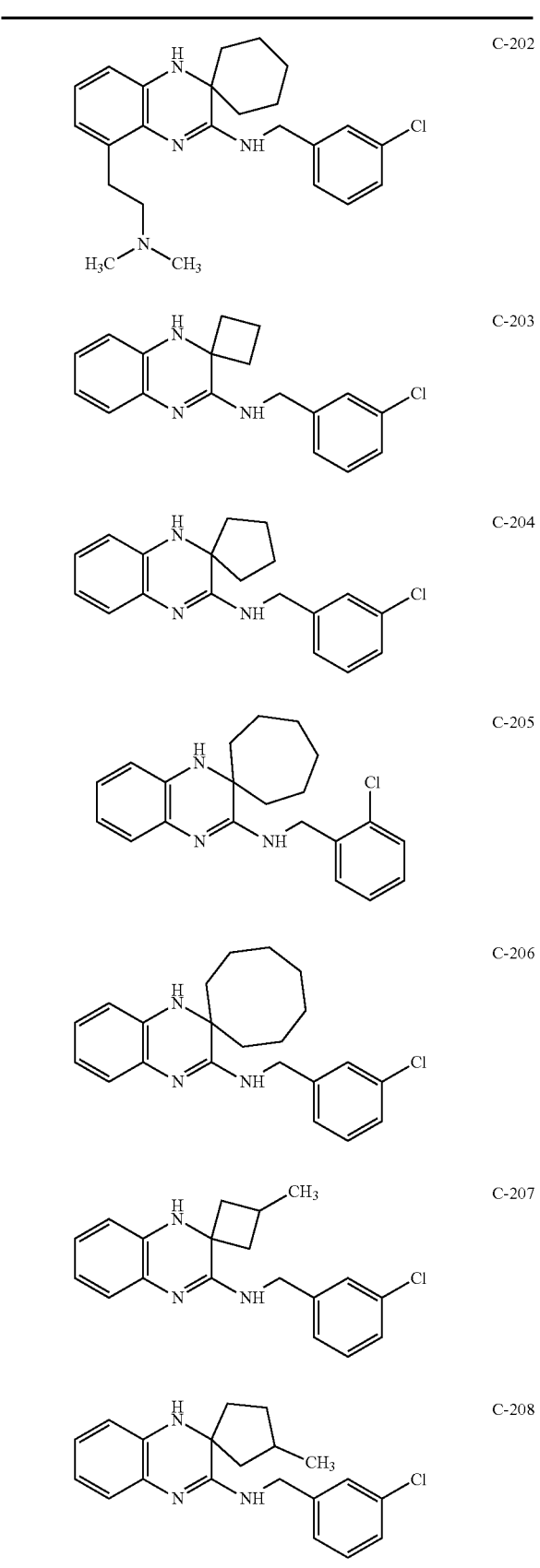
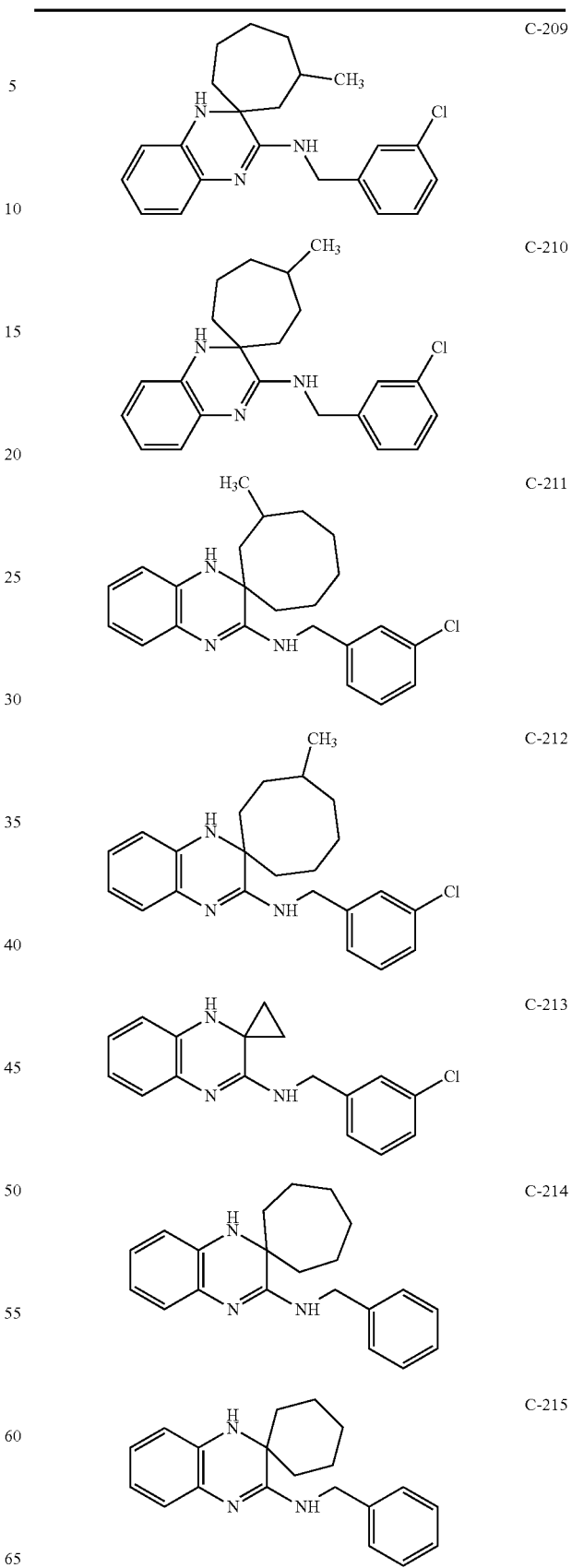

TABLE 1-C-continued
C-216
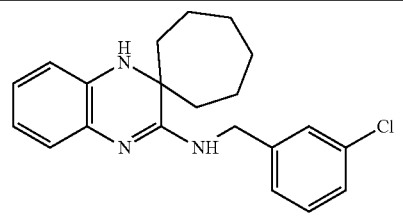
C-217
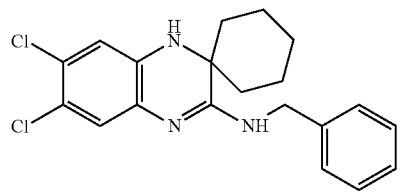
C-218
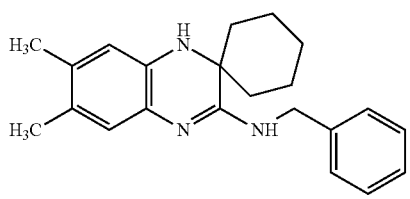 [SMILES: Cc1cc2c(cc1C)NC1(CCCCC1)C(NCc1ccccc1)=N2]
C-219
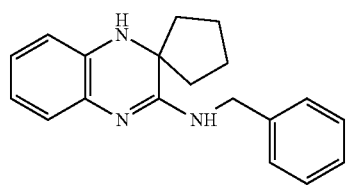 [SMILES: c1ccc(CNC2=Nc3ccccc3NC23CCCC3)cc1]
C-220
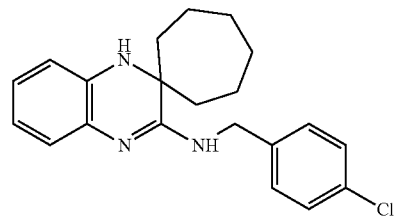 [SMILES: Clc1ccc(CNC2=Nc3ccccc3NC23CCCCCC3)cc1]
C-221
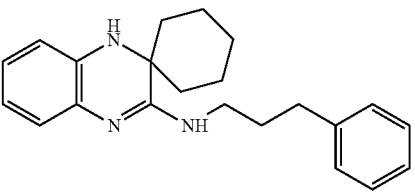 [SMILES: c1ccc(CCCNC2=Nc3ccccc3NC23CCCCC3)cc1]
C-222
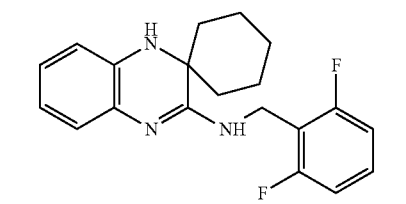
C-223
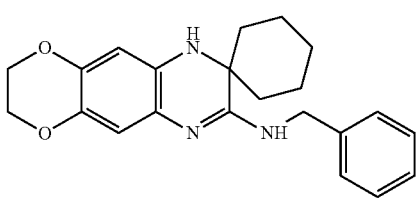 [SMILES: c1ccc(CNC2=Nc3cc4c(cc3NC23CCCCC3)OCCO4)cc1]
TABLE 1-C-continued
C-224
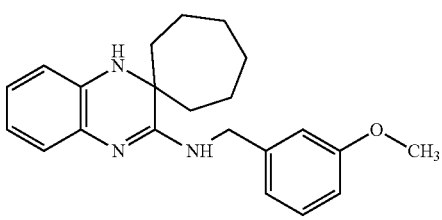 [SMILES: COc1cccc(CNC2=Nc3ccccc3NC23CCCCCC3)c1]
C-225
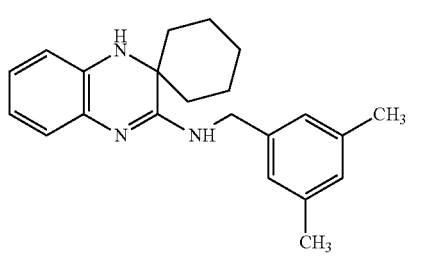 [SMILES: Cc1cc(C)cc(CNC2=Nc3ccccc3NC23CCCCC3)c1]
C-226
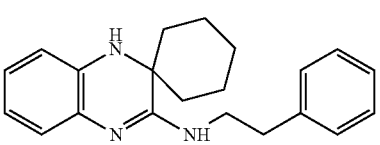
C-227
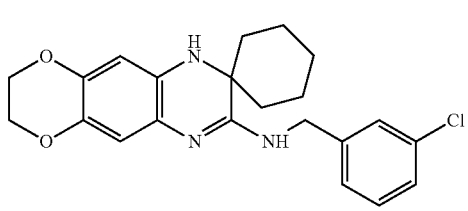 [SMILES: Clc1cccc(CNC2=Nc3cc4c(cc3NC23CCCCC3)OCCO4)c1]
C-228
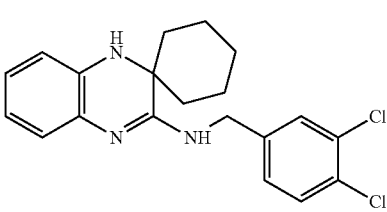 [SMILES: Clc1ccc(CNC2=Nc3ccccc3NC23CCCCC3)cc1Cl]
C-229
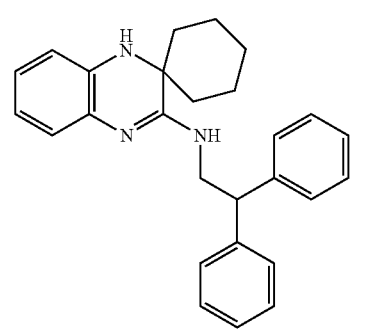 [SMILES: c1ccc(C(CNC2=Nc3ccccc3NC23CCCCC3)c2ccccc2)cc1]
C-230
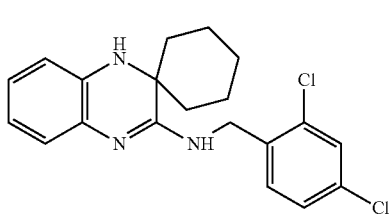 [SMILES: Clc1ccc(CNC2=Nc3ccccc3NC23CCCCC3)c(Cl)c1]

TABLE 1-C-continued
| | |
|---|---|
| 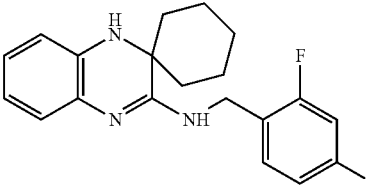 C-231 | 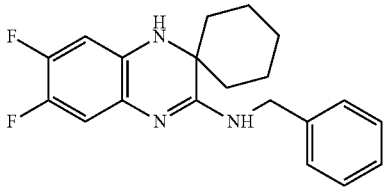 C-238 |
| 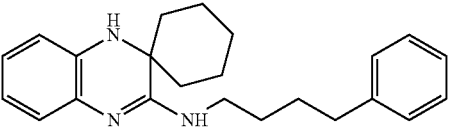 [SMILES: c1ccc(CCCCNC2=Nc3ccccc3NC23CCCCC3)cc1] C-232 | 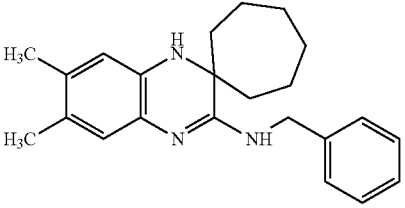 C-239 |
| 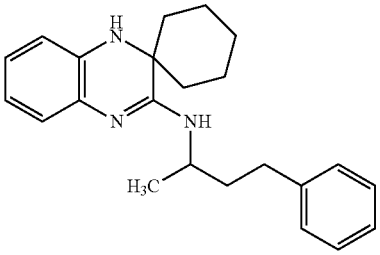 [SMILES: CC(CCc1ccccc1)NC1=Nc2ccccc2NC12CCCCC2] C-233 | 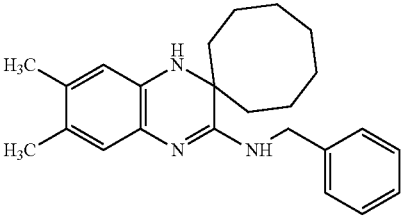 C-240 |
| 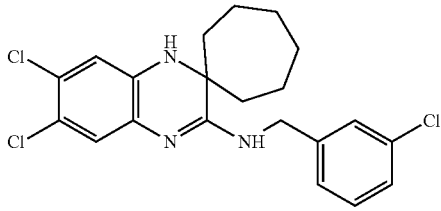 [SMILES: Clc1cccc(CNC2=Nc3cc(Cl)c(Cl)cc3NC23CCCCCC3)c1] C-234 | 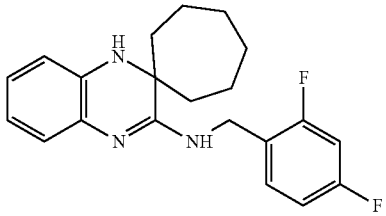 C-241 |
| 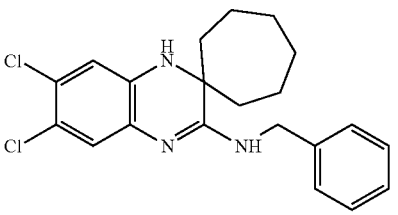 [SMILES: Clc1cc2c(cc1Cl)NC1(CCCCCC1)C(NCc1ccccc1)=N2] C-235 | 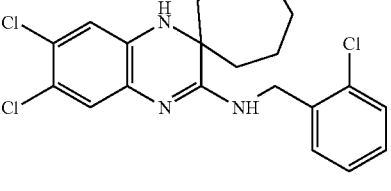 C-242 |
| 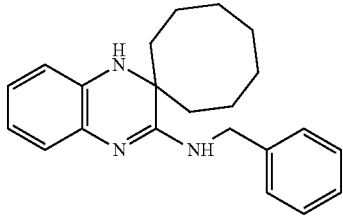 [SMILES: c1ccc(CNC2=Nc3ccccc3NC23CCCCCCC3)cc1] C-236 | 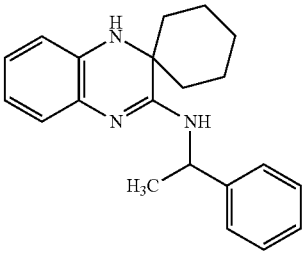 C-243 |
| 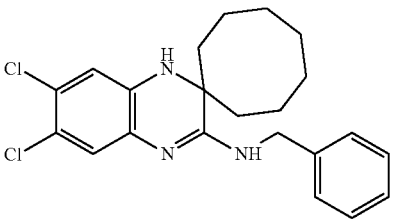 [SMILES: Clc1cc2c(cc1Cl)NC1(CCCCCCC1)C(NCc1ccccc1)=N2] C-237 | C-244 |

TABLE 1-C-continued

TABLE 1-C-continued

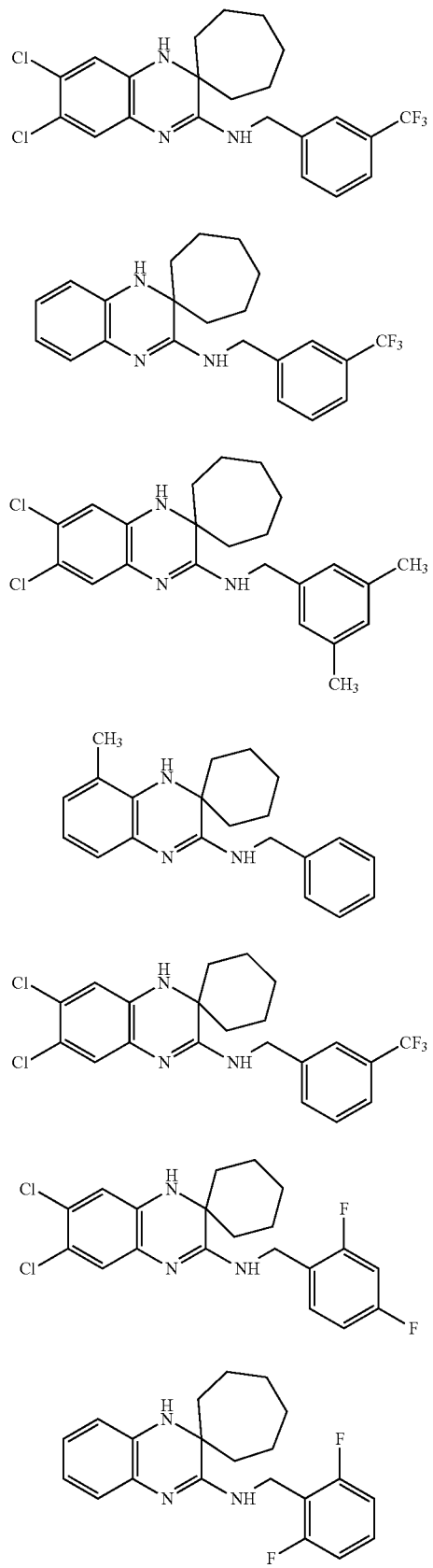

C-260
C-261
C-262
C-263
C-264
C-265
C-266

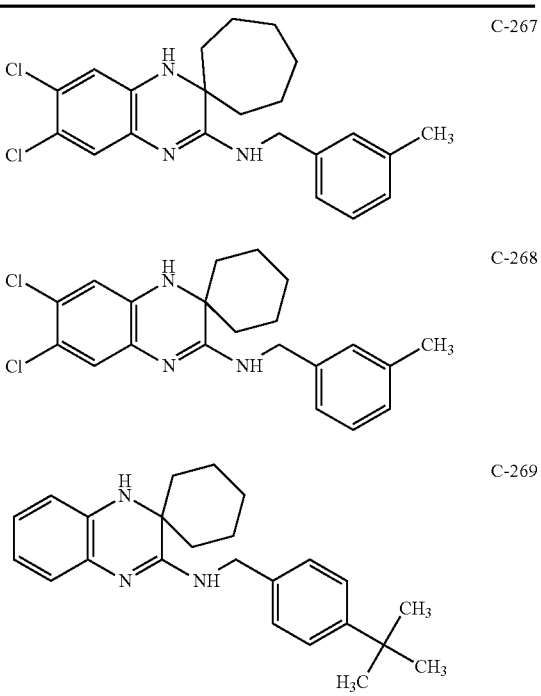

C-267
C-268
C-269

In one embodiment, the compounds of the invention do not encompass compounds of formula (I) wherein (1) $R^2$ to $R^5$ are each H, L is —CH$_2$—, (i) G is unsubstituted phenyl, and ring A is

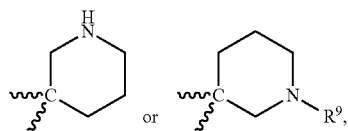

wherein $R^9$ is —S(O)$_2$N(CH$_3$)$_2$, (cyclopropyl)sulfonyl, or (3-pyridinyl)sulfonyl, or $R^9$ is —C(O)Z, wherein Z is methyl, tert-butyl, methoxymethyl, 2-methoxyethyl, —CH$_2$NHC(O)CH$_3$, 2-methoxyethylamino, morpholin-4-ylmethyl, 2-furanylmethylamino, (2-methyl-1H-imidazol-1-yl)methyl, 2-franyl, 3-franyl, pyridin-2-yl, pyridin-3-yl, pyridin-4-yl, pyrazin-2-yl, 1-ethyl-1H-pyrazol-3-yl, or 1-ethyl-1H-pyrazol-5-yl;

(ii) G is unsubstituted phenyl, and ring A is

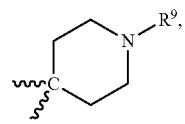

wherein $R^9$ is (1,3,5-trimethyl-1H-pyrazol-4-yl)sulfonyl or —C(O)Z, wherein Z is 2-methoxyethylamino, methoxycarbonylmethylamino, (2-trifluoromethylphenyl)amino, 5-chloro-1H-indol-2-yl, 4,5,6,7-tetrahydro-1H-indazol-3-yl, or 3-(2-thienyl)-1H-pyrazol-5-yl;

(iii) G is 2-chlorophenyl, 3-chlorophenyl, 4-chlorophenyl, 3-fluorophenyl, 4-fluorophenyl, 2-methylphenyl, 3-methylphenyl, 4-methylphenyl, 3-methoxyphenyl, or 4-methoxyphenyl, and ring A is

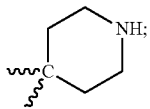

(iv) G is 3-methoxyphenyl, and ring A is

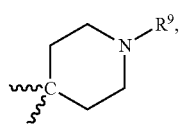

wherein $R^9$ is (3,5-dimethyl-1H-pyrazol-4-yl)sulfonyl;
(v) G is 4-fluorophenyl, and ring A is

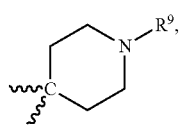

wherein $R^9$ is —C(O)Z, wherein Z is 6-methoxy-1H-indol-2-yl or 3,4-dimethoxyphenyl; or
(vi) G is 4-chlorophenyl, and ring A is

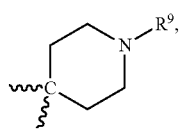

wherein $R^9$ is —C(O)Z, wherein Z is 1-methyl-2-(2-methyl-1H-imidazol-1-yl)ethyl;
(2) ring A is

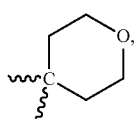

$R^2$ and $R^5$ are both H, L is —CH$_2$—, and
(i) $R^3$ and $R^4$ are both H, and G is 3-methylphenyl, 3-methoxyphenyl, 4-chlorophenyl, or 4-fluorophenyl; or
(ii) $R^3$ and $R^4$ are both methyl, and G is 4-fluorophenyl; and/or
(3) $R^2$ and $R^5$ are both H, L is —CH$_2$—, and
(i) $R^3$ and $R^4$ are both H, ring A is

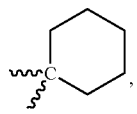

and G is unsubstituted phenyl, 4-methylphenyl, 3-methoxyphenyl, or 4-methoxyphenyl;
(ii) $R^3$ and $R^4$ are both H, ring A is

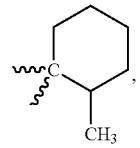

and G is 4-methylphenyl, 4-fluorophenyl, 3,5-difluorophenyl, or 3-methoxyphenyl;
(iii) $R^3$ and $R^1$ are both H, ring A is

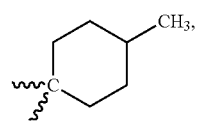

and G is unsubstituted phenyl, 3-methylphenyl, 4-fluorophenyl, 2-chlorophenyl, 4-chlorophenyl, 3-chloro-4-fluorophenyl, 3,5-difluorophenyl, or 4-trifluoromethylphenyl;
(iv) $R^3$ and $R^4$ are both H, ring A is

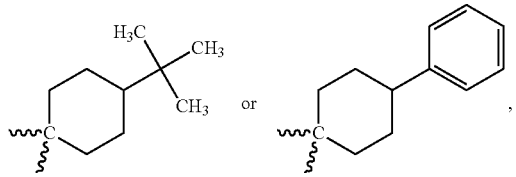

and G is 3-methoxyphenyl;
(v) $R^3$ and $R^4$ are both H, ring A is

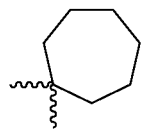

and G is unsubstituted phenyl, 2-methylphenyl, 3-methylphenyl, 4-methylphenyl, 3-fluorophenyl, 4-fluorophenyl, 2-chlorophenyl, 3,5-difluorophenyl, 3-methoxyphenyl, 4-methoxyphenyl, or 4-trifluoromethylphenyl;
(vi) $R^3$ and $R^4$ are both methyl, ring A is

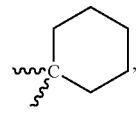

and G is 3-fluorophenyl or 3,5-difluorophenyl;

(vii) $R^3$ and $R^4$ are both methyl, ring A is

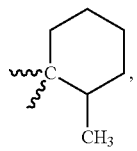

and G is 3-fluorophenyl or 3-methoxyphenyl; or (viii) $R^3$ and $R^4$ are both methyl, ring A is

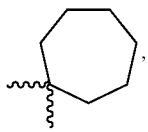

and G is substituted phenyl, 2-methylphenyl, 2-fluorophenyl, 3-fluorophenyl, 4-fluorophenyl, or 3-methoxyphenyl.

In one embodiment, the compounds of the invention have the general formula (N-I)(such as (N-II), (N-III), (N-IV), or (N-V)) but do not encompass compounds of formula (N-I) wherein $R^2$ to $R^5$ are each H, L is —$CH_2$—, (i) G is unsubstituted phenyl, and ring A is

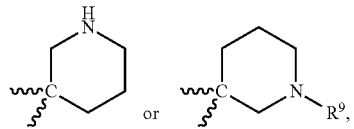

wherein $R^9$ is —$S(O)_2N(CH_3)_2$, (cyclopropyl)sulfonyl, or (3-pyridinyl)sulfonyl, or $R^9$ is —C(O)Z, wherein Z is methyl, tert-butyl, methoxymethyl, 2-methoxyethyl, —$CH_2NHC(O)CH_3$, 2-methoxyethylamino, morpholin-4-ylmethyl, 2-furanylmethylamino, (2-methyl-1H-imidazol-1-yl)methyl, 2-furanyl, 3-furanyl, pyridin-2-yl, pyridin-3-yl, pyridin-4-yl, pyrazin-2-yl, 1-ethyl-1H-pyrazol-3-yl, or 1-ethyl-1H-pyrazol-5-yl;

(ii) G is unsubstituted phenyl, and ring A is

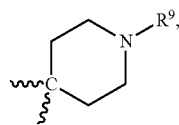

wherein $R^9$ is (1,3,5-trimethyl-1H-pyrazol-4-yl)sulfonyl or —C(O)Z, wherein Z is 2-methoxyethylamino, methoxycarbonylmethylamino, (2-trifluoromethylphenyl)amino, 5-chloro-1H-indol-2-yl, 4,5,6,7-tetrahydro-1H-indazol-3-yl, or 3-(2-thienyl)-1H pyrazol-5-yl;

(iii) G is 2-chlorophenyl, 3-chlorophenyl, 4-chlorophenyl, 3-fluorophenyl, 4-fluorophenyl, 2-methylphenyl, 3-methylphenyl, 4-methylphenyl, 3-methoxyphenyl, or 4-methoxyphenyl, and ring A is

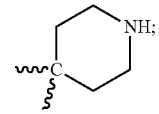

(iv) G is 3-methoxyphenyl, and ring A is

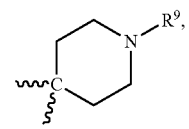

wherein $R^9$ is (3,5-dimethyl-1H-pyrazol-4-yl)sulfonyl;

(v) G is 4-fluorophenyl, and ring A is

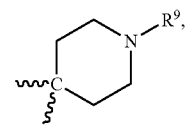

wherein $R^9$ is —C(O)Z, wherein Z is 6-methoxy-1H-indol-2-yl or 3,4-diethoxyphenyl; or (vi) G is 4-chlorophenyl, and ring A is

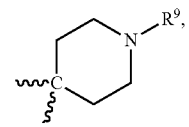

wherein $R^9$ is —C(O)Z, wherein Z is 1-methyl-2-(2-methyl-H-imidazol-1-yl)ethyl.

In one embodiment, the compounds of the invention have the general formula (O/S-I)(such as (O/S-II), (O/S-III), (O/S-IV), or (O/S-V)) but do not encompass compounds of formula (O/S-I) wherein ring A is

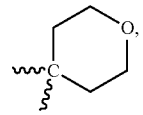

$R^2$ and $R^5$ are both H, L is —$CH_2$—, and (i) $R^3$ and $R^4$ are both H, and G is 3-methylphenyl, 3-methoxyphenyl, 4-chlorophenyl, or 4-fluorophenyl or (ii) $R^3$ and $R^4$ are both methyl, and G is 4-fluorophenyl.

In one embodiment, the compounds of the invention have the general formula (C-I)(such as (C-II), (C-III), (C-IV), or (C-V)) but do not encompass compounds of formula (C-I) wherein $R^2$ and $R^5$ are both H, L is —$CH_2$—, and (i) R³ and R⁴ are both H, ring A is

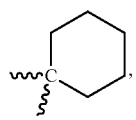

and G is unsubstituted phenyl, 4-methylphenyl, 3-methoxyphenyl, or 4-methoxyphenyl;

(ii) R³ and R⁴ are both H, ring A is

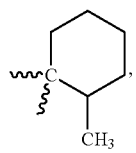

and G is 4-methylphenyl, 4-fluorophenyl, 3,5-difluorophenyl, or 3-methoxyphenyl;

(iii) R³ and R⁴ are both H, ring A is

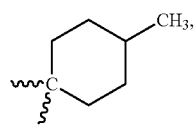

and G is unsubstituted phenyl, 3-methylphenyl, 4-fluorophenyl, 2-chlorophenyl, 4-chlorophenyl, 3-chloro-4-fluorophenyl, 3,5-difluorophenyl, or 4-trifluoromethylphenyl;

(iv) R¹ and R⁴ are both H, ring A is

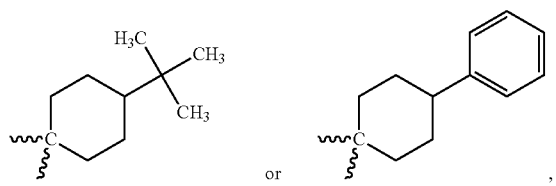

and G is 3-methoxyphenyl;

(v) R³ and R⁴ are both H, ring A is

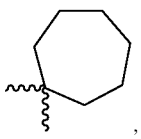

and G is unsubstituted phenyl, 2-methylphenyl, 3-methylphenyl, 4-methylphenyl, 3-fluorophenyl, 4-fluorophenyl, 2-chlorophenyl, 3,5-difluorophenyl, 3-methoxyphenyl, 4-ethoxyphenyl, or 4-trifluoromethylphenyl;

(vi) R³ and R⁴ are both methyl, ring A is

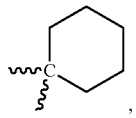

and G is 3-fluorophenyl or 3,5-difluorophenyl;

(vii) R³ and R⁴ are both methyl, ring A is

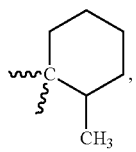

and G is 3-fluorophenyl or 3-methoxyphenyl; or (viii) R³ and R⁴ are both methyl, ring A is

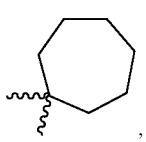

and G is unsubstituted phenyl, 2-methylphenyl, 2-fluorophenyl, 3-fluorophenyl, 4-fluorophenyl, or 3-methoxyphenyl.

The compounds of the invention which contain a basic functionality may form salts b a variety of inorganic or organic acids. Exemplary inorganic and organic acids/bases as well as exemplary acid/base addition salts of the compounds of the present invention are given in the definition of "pharmaceutically acceptable salt" in the section "Pharmaceutical composition", below. The compounds of the invention which contain an acidic functionality may form salts with a variety of inorganic or organic bases. The compounds of the invention which contain both basic and acidic functionalities may be converted into either base or acid addition salt. The neutral forms of the compounds of the invention may be regenerated by contacting the salt with a base or acid and isolating the parent compound in the conventional manner.

The compounds of the invention may be in a prodrug form. Prodrugs of the compounds of the invention are those compounds that upon administration to an individual undergo chemical conversion under physiological conditions to provide the compounds of the invention. Additionally, prodrugs can be converted to the compounds of the invention by chemical or biochemical methods in an ex vivo environment. For example, prodrugs can be slowly converted to the compounds of the invention when, for example, placed in a transdermal patch reservoir with a suitable enzyme or chemical reagent. Exemplary prodrugs are esters or amides which are hydrolyzable in vivo.

In a further aspect, the present invention provides a compound of the invention (in particular those specified above with respect to any of formulas (I), (N-I), (O/S-I), (C-I), (II), (N-II), (O/S-II), (C-II), (II), (N-III), (O/S-III), (C-III), (IV), (N-IV), (O/S-IV), (C-IV), (V), (N-V), (O/S-V), and (C-V)) for use as medicament.

As it is evident from the examples, the inventors have found that the compounds of the invention inhibit non-apoptotic regulated cell death and/or reduce oxidative stress but do not inhibit apoptotic cell death. In one embodiment, the compounds of the invention are selective inhibitors of non-apoptotic regulated cell death and/or oxidative stress, i.e., they inhibit non-apoptotic regulated cell death and/or oxidative stress, but do not inhibit apoptotic cell death. In one embodiment, the compounds of the invention exhibit pharmacological properties (bioavailability, toxicity, side effects, dosing, patient compliance, compatibility, stability, half-life, etc.), which are in at least one aspect superior to the pharmacological properties exhibited by Necrostatin-1 and/or Ferrostatin.

Pharmaceutical Compositions

In a further aspect, the present invention provides a pharmaceutical composition comprising a compound as specified above under the heading "Compounds" and one or more pharmaceutically acceptable excipients.

The pharmaceutical composition may be administered to an individual by any route, such as enterally or parenterally.

The compositions according to the present invention are generally applied in "pharmaceutically acceptable amounts" and in "pharmaceutically acceptable preparations". Such compositions may contain salts, buffers, preserving agents, carriers and optionally other therapeutic agents. "Pharmaceutically acceptable salts" comprise, for example, acid addition salts which may, for example, be formed by mixing a solution of compounds with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compound carries an acidic moiety, suitable pharmaceutically acceptable salts thereof may include alkali metal salts (e.g., sodium or potassium salts); alkaline earth metal salts (e.g., calcium or magnesium salts); and salts formed with suitable organic ligands (e.g., ammonium, quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

The term "excipient" when used herein is intended to indicate all substances in a pharmaceutical composition which are not active ingredients (e.g., which are therapeutically inactive ingredients that do not exhibit any therapeutic effect in the amount/concentration used), such as, e.g., carriers, binders, lubricants, thickeners, surface active agents, preservatives, emulsifiers, buffers, flavoring agents, colorants, or antioxidants.

The compositions according to the present invention may comprise a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The "pharmaceutically acceptable carrier" may be in the form of a solid, semisolid, liquid, or combinations thereof. Preferably, the carrier is suitable for enteral (such as oral) or parenteral administration (such as intravenous, intramuscular, subcutaneous, spinal or epidermal administration (e.g., by injection or infusion)). Depending on the route of administration, the active compound, i.e., the compound of the invention, may be coated in a material to protect the compound from the action of acids and other natural conditions that may inactivate the compound.

A composition of the present invention can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to an individual in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7: 27 (1984)).

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof.

The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the individuals to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

For the therapeutic/pharmaceutical formulations, compositions of the present invention include those suitable for enteral administration (such as oral or rectal) or parenteral administration (such as nasal, topical (including vaginal, buccal and sublingual)). The compositions may conveniently be presented in unit dosage form and may be prepared by any methods known in the art of pharmacy. The amount of active ingredient (in particular, the amount of a compound of the present invention) which can be combined with a carrier material to produce a pharmaceutical composition (such as a single dosage form) will vary depending upon the individual being treated, and the particular mode of administration. The amount of active ingredient which can be combined with a carrier material to produce a single dosage form will generally be that amount of the composition which produces a therapeutic effect.

Generally, out of 100% (for the pharmaceutical formulations/compositions), the amount of active ingredient (in particular, the amount of the compound of the present invention, optionally together with other therapeutically active agents, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active ingredient, e.g., a compound of the invention, in a unit dosage form and/or when administered to an individual or used in therapy, may range from about 0.1 mg to about 1000 mg (for example, from about 1 mg to about 500 mg, such as from about 10 mg to about 200 mg) per unit, administration or therapy. In certain embodiments, a suitable amount of such active ingredient may be calculated using the mass or body surface area of the individual, including amounts of between about 1 mg/Kg and 10 mg/Kg (such as between about 2 mg/Kg and 5 mg/Kg), or between about 1 mg/m$^2$ and about 400 mg/m$^2$ (such as between about 3 mg/m$^2$ and about 350 mg/m$^2$ or between about 10 mg/m$^2$ and about 200 mg/m$^2$).

Compositions of the present invention which are suitable for vaginal administration also include pessaries, tampons, creams, gels, pastes, foams or spray formulations containing such carriers as are known in the art to be appropriate. Dosage forms for the topical or transdermal administration of compositions of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The expressions "enteral administration" and "administered enterally" as used herein mean that the drug administered is taken up by the stomach and/or the intestine. Examples of enteral administration include oral and rectal administration. The expressions "parenteral administration" and "administered parenterally" as used herein mean modes of administration other than enteral administration, usually by injection or topical application, and include, without limitation, intravenous, intramuscular, intraarterial, intrathecal, intracapsular, intraosseous, intraorbital, intracardiac, intradermal, intraperitoneal, transtracheal, subcutaneous, subcuticular, intraarticular, subcapsular, intracerebral, intracerebroventricular, subarachnoid, intraspinal, epidural and intrasternal administration (such as by injection and/or infusion) as well as topical administration (e.g., epicutaneous, inhalational, or through mucous membranes (such as buccal, sublingual or vaginal)).

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, pH buffering agents, and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the lie into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art (cf., e.g., Remington, "The Science and Practice of Pharmacy" edited by Allen, Loyd V., Jr., $22^{nd}$ edition, Pharmaceutical Sciences, September 2012; Ansel et al, "Pharmaceutical Dosage Forms and Drug Delivery Systems", $7^{th}$ edition, Lippincott Williams & Wilkins Publishers, 1999).

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. It is preferred that administration be oral, intravenous, intramuscular, intraperitoneal, or subcutaneous, preferably administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation/composition.

In one embodiment, the compounds or compositions of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

In yet another embodiment, the compounds or compositions of the invention are administered by maintenance therapy, such as, e.g., once a week for a period of 6 months or more.

For oral administration, the pharmaceutical composition of the invention can take the form of, for example, tablets or capsules prepared by conventional means with pharmaceutical acceptable excipients such as binding agents (e.g., pregelatinised maize starch, polyvinylpyrrolidone, hydroxypropyl methylcellulose), fillers (e.g., lactose, microcrystalline cellulose, calcium hydrogen phosphate), lubricants (e.g., magnesium stearate, talc, silica), disintegrants (e.g., potato starch, sodium starch glycolate), or wetting agents (e.g., sodium lauryl sulphate). Liquid preparations for oral administration can be in the form of, for example, solutions, syrups, or suspensions, or can be presented as a dry product for constitution with water or other suitable vehicle before use. Such liquid preparation can be prepared by conventional means with pharmaceutically acceptable additives such as suspending agents (e.g., sorbitol, syrup, cellulose derivatives, hydrogenated edible fats), emulsifying agents (e.g., lecithin, acacia), non-aqueous vehicles (e.g., almond oil, oily esters, ethyl alcohol, fractionated vegetable oils), preservatives (e.g., methyl or propyl-hydroxycarbonates, sorbic acids). The preparations can also contain buffer salts, flavouring, coloring and sweetening agents as deemed appropriate. Preparations for oral administration can be suitably formulated to give controlled release of the pharmaceutical composition of the invention.

The pharmaceutical composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

For administration by inhalation, the pharmaceutical composition of the invention is conveniently delivered in the form of an aerosol spray presentation from a pressurised pack or a nebulizer, with the use of a suitable propellant (e.g., dichlorodifluoromethane, trichlorofluoromethane, dichlorotetrafluoroethane, carbon dioxide, nitrogen, or other suitable gas). In the case of a pressurised aerosol, the dosage unit can be determined by providing a valve to deliver a metered amount. Capsules and cartridges of, for example, gelatine, for use in an inhaler or insufflator can be formulated containing a powder mix of the pharmaceutical composition of the invention and a suitable powder base such as lactose or starch.

The pharmaceutical composition of the invention can be formulated for parenteral administration by injection, for example, by bolus injection or continuous infusion. Formulations for injection can be presented in units dosage form (e.g., in phial, in multi-dose container), and with an added preservative. The pharmaceutical composition of the invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, compositions for intravenous administration are solutions in sterile isotonic aqueous buffer. Where necessary, the composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Therapeutic/pharmaceutical compositions can be administered with medical devices known in the art. For example, in a preferred embodiment, a therapeutic/pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the compounds of the invention can be formulated to ensure proper distribution in vivo. For example, the blood-brain barrier (BBB) excludes many highly hydrophilic compounds. To ensure that the compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposones may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochen. Biophys. Res. Commun. 153: 1038); antibodies (P. G. Bloeman et al (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment of the invention, the compounds of the invention are formulated in liposomes. In a more preferred embodiment, the liposomes include a targeting moiety. In a most preferred embodiment, the compounds in the liposomes are delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective dosage" for therapy/treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective response.

A "therapeutically effective dosage" for therapy/treatment can also be measured by its ability to stabilize the progression of a condition, disorder or disease. The ability of a compound to inhibit, reduce or ameliorate non-apoptotic regulated cell-death and/or to reduce oxidative stress can be evaluated in appropriate animal model systems as such as one or more of those set fourth below. Alternatively, these properties of a compound of the present invention can be evaluated by examining the ability of the compound using in vitro assays known to the skilled practitioner such as one or more of those set fourth below. A therapeutically effective amount of a compound of the present invention can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the individual's size, the severity of the individual's symptoms, and the particular composition or route of administration selected.

An injectable composition should be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof.

The pharmaceutical composition of the invention can also, if desired, be presented in a pack, or dispenser device which can contain one or more unit dosage forms containing the said agent. The pack can for example comprise metal or plastic foil, such as blister pack. The pack or dispenser device can be accompanied with instruction for administration.

The pharmaceutical composition of the invention can be administered as sole active agent or can be administered in combination with other therapeutically and/or cosmetically active agents.

Therapeutic and other Applications

In further aspects, the present application provides a compound as specified above under the heading "Compounds" or a pharmaceutical composition as specified above under the heading "Pharmaceutical compositions" for use in therapy.

It is contemplated that the compound as specified above under the heading "Compounds" may be used for the inhibition, reduction or amelioration of non-apoptotic regulated cell death and/or the reduction of oxidative stress in vitro, such as in an isolated cell, an isolated cell culture, or a sample, tissue or organ isolated from an individual. In certain embodiments, such cell, cell culture, sample, tissue or organ is used in research; while in other embodiments it is exposed to the compound ex-vivo prior to reintroduction to the same (or a different) individual, such as in tissue or organ transplant, and the inhibition, reduction or amelioration of regulated necrosis of such cell, cell culture, sample, tissue or organ takes place when ex-vivo.

The compounds and/or pharmaceutical compositions of the invention may be used in the treatment (including prophylactic treatment) of a condition, disorder or disease:
  that is characterised by non-apoptotic regulated cell-death (including regulated necrosis, necroptosis or ferroptosis), or where non-apoptotic regulated cell-death is likely to play or plays a substantial role;
  that is characterised by oxidative stress (including increased level of reactive oxygen species (ROS)), or where oxidative stress is likely to play or plays a substantial role; and/or that is characterised by activation of:
one or more components of the necrosome such as RIP1 and/or RIP3;
Death domain receptors such as TNFR1, TNFR2, Fas/CD95 and/or TRAIL-R; and/or
Toll-like receptors such as TLR3 and/or TLR4,
or where activation of any of the foregoing component and/ort receptor is likely to play or plays a substantial role.

The compounds and/or pharmaceutical compositions of the invention may be used in the treatment (including prophylactic treatment) of a condition, disorder or disease that is selected from the group consisting of:
a neurodegenerative disease of the central or peripheral nervous system, a condition or disorder caused by and forms of neurodegeneration;
muscle wasting or muscular dystrophy; organ ischemia (e.g., stroke, myocardial infarction and heart, mesenteric, retinal, hepatic or brain ischemic injury), ischemic-reperfusion injury (such as associated with surgery, especially solid organ transplantation), ischemic injury during organ storage, limb or organ ischemic injury (such as associated with surgery, tourniquet use or trauma);
compartment syndrome, gangrene, pressure sores, sepsis (e.g., aseptic necrosis), degenerative arthritis;
retinal necrosis (e.g., acute retinal necrosis (ARN) cased by or associated with optic nerve detachment);
cardiovascular (heart) disease, including stroke, coronary heart disease, cardiomyopathy;
liver, gastrointestinal or pancreatic disease (e.g., acute necrotizing pancreatitis);
avascular necrosis (e.g., bone avascular necrosis), diabetes, sickle cell disease, alteration of blood vessels (e.g., vascular dystrophy or cerebrovascular disease);
cancer-chemo/radiation therapy-induced cell-death (e.g., mucositis or chemotherapy induced alopecia (CIA)); and
cell, tissue, organ or organism intoxication (e.g., nephrotoxicity), such as that the result of, arising from or associated with drug treatment (e.g., complications from steroid treatment, kidney toxicity from cisplatin, cardiotoxicity from doxorubicin or ototoxicity from gentamicin), drug overdose (e.g., liver toxicity from paracetamol) or acute poisoning (e.g., from alcohol, paraquat or environmental toxins), or contrast-agent-induced toxicity; and
priapism;
or is the result of, arises from or is associated with any of the foregoing.

The compounds and/or pharmaceutical compositions of the invention may be used in the treatment (including prophylactic treatment) of a condition, disorder or disease that is the result of, arises from or is associated with a circumstance selected from the group consisting of:
forms of infection of viruses, bacteria, fungi or other microorganisms (e.g., septic shock, tuberculosis);
a reduction in cell-proliferation, or an alteration in cell-differentiation or intracellular signalling;
an undesirable inflammation, such as an immune disorder;
retinal neuronal cell death, cell death of cardiac muscle, cell death of cells of the immune system, cell death associated with renal failure;
neonatal respiratory distress, asphyxia, incarcerated hernia, placental infarct, iron-load complications, endometriosis, congenital disease, including congenital mitochondrial disease (e.g., tyrosinemia, phenylketonuria, Anderson disease);
head trauma/traumatic brain injury, liver injury;
injuries from environmental radiation (e.g., UV exposure and sunburn);
burns;
cold injuries (e.g., hyperthermia), mechanical injuries (e.g., brain and spinal cord injuries); and
decompression sickness;
snake, scorpion or spider bites; and
side effects of medications.

In certain of such embodiments, the condition, disorder or disease is not cancer, and/or is not one the result of, arising from or associated with cancer.

Without being bound by theory, apoptosis (e.g., as assays in Example B.3) is believed to occur under or as a result of normal physiological conditions or events in a highly programmed manner as part of normal tissue homeostasis and cell turnover; while, conversely, non-apoptotic regulated cell death is thought to be triggered by abnormal physiological conditions or events such as external damaging stimuli and/or oxidative stress. Compounds that inhibit non-apoptotic regulated cell-death but do not appear to inhibit apoptotic cell-death may have preferred utility in the methods and applications of the present invention, as they may not interfere with the individual's (such) innate cell-death mechanism and regulation, but preferentially only that caused by abnormal physiological conditions or events such as external damaging stimuli and/or oxidative stress and/or triggering events of the immune system.

In particular embodiments, the condition, disorder or disease is a neurodegenerative disease, including of either or both of the central or peripheral nervous systems, or is a condition or disorder caused by and forms of neurodegeneration, or is a condition or symptom the result of, arising from or associated with such condition, disorder or disease.

Exemplary neurodegenerative such conditions or diseases include, but are not limited to, Alzheimer's disease, Huntington's disease, Parkinson's disease, amyotrophic lateral sclerosis (ALS), HIV-associated dementia, cerebral ischemia, multiple sclerosis, Lewy body disease, Menke's disease, Wilson's disease, Creutzfeldt-Jakob disease, Fahr disease, and frontotemporal dementia, amyloidosis, Tay-Sachs disease and periventricular leukomalacia.

In some of such embodiments, the condition, disorder or disease is muscle wasting (e.g., that associated with cancer, AIDS, congestive heart failure, chronic obstructive disease, and necrotizing myopathy of intensive care). In particular embodiments the condition, disorder or disease is muscular dystrophies or related diseases (e.g., Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease), or is a condition or symptom the result of, arising from or associated with such condition, disorder or disease.

In other embodiments, the condition, disorder or disease is cell, tissue, organ or organism intoxication, such as that the result of, arising from or associated with drug treatment, drug overdose or acute poisoning. Exemplary circumstances of such intoxication include alcoholism and administration and/or self-administration with, and/or exposure to, illicit drugs (e.g., cocaine, heroin, crack), medical drugs (e.g., anti-cancer agents, paracetamol, antibiotics, adriamycin, NSAID, cyclosporine), chemical toxins (e.g., carbon tetrachloride, cyanide, methanol, ethylene glycol and mustard gas, agrochemicals such as organophosphates and paraquat, and warfare organophosphates), or heavy metals (e.g., lead, mercury).

In other particular embodiments, the condition, disorder or disease is the result of, arising from or associated with one or more forms of infection of viruses (e.g., acute, latent and/or persistent), bacteria, fungi, or other microorganisms, or is one in which a reduction in cell-proliferation, or an alteration in cell-differentiation or intracellular signalling, is a causative factor, and include infection e.g., by viruses (e.g., acute, latent and/or persistent), bacteria, fungi, or other microorganisms, and mycoplasma disease.

Exemplary viruses include, but are not limited to, are human immunodeficiency virus (HIV), Epstein-Barr virus (EBV), cytomegalovirus (CMV)(e.g., CMV5), human herpesviruses (HHV)(e.g., HHV6, 7 or 8), herpes simplex viruses (HSV), bovine herpes virus (BHV)(e.g., BHV4), equine herpes virus (EHV)(e.g., EHV2), human T-Cell leukemia viruses (HTLV)5, Varicella-Zoster virus (VZV), measles virus, papovaviruses (JC and BK), hepatitis viruses (E.g., HBV or HCV), myxoma virus, adenovirus, parvoviruses, polyoma virus, influenza viruses, papillomaviruses and poxviruses such as vaccinia virus, and molluscum contagiosum virus (MCV), and lyssaviruses. Such virus may or may not express an apoptosis inhibitor. Exemplary diseases caused by viral infection include, but are not limited to, chicken pox, Cytomegalovirus infections, genital herpes, Hepatitis B and C, influenza, and shingles, and rabies.

Exemplary bacteria include, but are not limited to, *Campylobacter jejuni, Enterobacter* species, *Enterococcus faecium, Enterococcus faecalis, Escherichia coli* (e.g., *F. coli* O157:H7), Group A streptococci, *Haemophilus influenzae, Helicobacter pylori*, listeria, *Mycobacterium tuberculosis, Pseudomonas aeruginosa, S. pneumoniae, Salmonella, Shigella, Staphylococcus aureus*, and *Staphylococcus epidermidis*, and *Borrelia* and *Rickettsia*. Exemplary diseases caused by bacterial infection include, but are not limited to, anthrax, cholera, diphtheria, foodborne illnesses, leprosy, meningitis, peptic ulcer disease, pneumonia, sepsis, septic shock, syphilis, tetanus, tuberculosis, typhoid fever, and urinary tract infection, and Lyme disease and Rocky Mountain spotted fever.

In further particular embodiments, the condition, disorder or disease is the result of, arising from or associated with undesirable inflammation, such as an immune disorder.

Exemplary immune disorders include, but are not limited to, autoimmune diseases (for example, diabetes mellitus, arthritis—including rheumatoid arthritis, juvenile rheumatoid arthritis, osteoarthritis and psoriatic arthritis-, multiple sclerosis, encephalomyelitis, myasthenia gravis, systemic lupus erythematosis, autoimmune thyroiditis, dermaitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, sepsis and septic shock, inflammatory bowel disorder, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorimeural hearing loss, aplastic anemia, pure red cell anemia, idiopathic thrombocytopenia, polychondritis, Wegener's granulomatosis, chronic active hepatitis, Stevens-Johnson syndrome, glomerulonephritis, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Compounds and methods of the invention can additionally be used to boost the immune system, whether or not the patient being treated has an immunocompromising condition. For example, the compounds described herein can be used in a method to strengthen the immune system during immunisation, e.g., by functioning as an adjuvant, or by being combined with an adjuvant.

Ischemia-reperfusion injury (IRI) remains a primary complication of transplant surgery, accounting for the majority of liver transplant failures, with non-apoptotic regulated cell death believed to be a main contributor to IRI. In contrast to apoptosis where cell death is limited to the affected cell, non-apoptotic regulated cell death, such as regulated necrosis, may cause inflammatory conditions damaging surrounding tissue. Compounds of the inventions that reduce IRI damage in the liver can be proposed as drug-candidates and have utility as medicines for limiting organ trauma upon transplantation and other diseases or conditions caused by ischemia-reperfusion and such utility can be tested in an in vivo model, for example, as described by Abe et al. (Free Radic. Biol. Med. 46: 1-7 (2009)).

Ischemia-reperfusion injury remains a primary complication of transplant surgery, accounting for the majority of kidney transplant failures, acute kidney tubular necrosis and delayed graft function. Compounds of the invention that reduce IRI damage in the kidney can be proposed as drug-candidates and have utility as medicines for limiting organ trauma upon transplantation and other diseases or conditions caused by ischemia-reperfusion, and such utility can be tested in an in vivo model, for example, as described by Wu et al. (J. Clin. Invest. 117:2847-59 (2007)) and Linkermann et al. (Kidney Int. 81: 751-761 (2012)).

Overdose of APAP is the most common cause of drug-induced liver damage, morbidity and mortality in humans in the United States, Great Britain, and other parts of the world. Metabolic bioactivation of APAP to the reactive electrophile N-acetyl-p-benzoquinone imine (NAPQI) causes extensive and rapid glutathione (GSH) depletion, and ultimately, hepatotoxicity. At present, N-acetylcysteine (NAC) is the antidote of choice for acetaminophen overdoses, although it is only protective for the injured liver when administered shortly after intoxication of an APAP overdose. Compounds of the invention that inhibit non-apoptotic regulated cell-death can be proposed as drug-candidates and have utility as medicines for limiting the effects of APA intoxication, and such utility can be tested in an in vivo model, for example, as described by Patterson et al (Chem. Res. Toxicol. 26:1088-96 (2013)).

Cisplatin is a widely used and potent chemotherapeutic agent to treat a wide spectrum of mainly solid malignancies. Upon entering cells, the chloride atoms in cisplatin are replaced by $H_2O$. The hydrolysis product is a reactive molecule that reacts with DNA, but also with GSH. These cisplatin-DNA intra-strand crosslinks result in cytotoxicity towards tumour cells, however, side-reactions with GSH mediate toxic effects such as nephrotoxicity, which in fact is the dose-limiting side effect, GSH depletion and concomitant cell death injury primarily the S3 segment of the proximal tubule in kidney and lead to renal failure (renal tubular dysfunction). Compounds of the invention that inhibit non-apoptotiec regulated cell-death can be proposed as drug-candidates and have utility as medicines for limiting the effects of cisplatin intoxication, and such utility can be tested in an in vivo model, for example, as described by Tristao et al. (Ren. Fail. 34:373-7 (2012)).

Non-apoptotic regulated cell death plays a major role in the pathogenesis of traumatic brain injury (TBI), and the utility of compounds of the invention as a medicine for such condition/disorder/disease can be investigated using an in-vivo murine model for example as described by You et al. (J. Cereb. Blood Flow Metab. 28:1564-73 (2008)), or Rauen et al (J. Neurotrauma 30:1442-8 (2013)).

TNF-alpha overproduction and increased ROS levels are major contributors to RA. The collagen-induced arthritis (CIA) mouse model is the most commonly studied autoimmune model of rheumatoid arthritis, for example as described by Brand et al. (Nat. Protoc. 2:1269-75 (2007)), and can be used to study the utility of compounds of the invention to treat RA.

Oxidative stress plays a major role in the pathogenesis of multiple sclerosis (MS). Reactive oxygen species (ROS) have been implicated as mediators of demyelination and axonal damage in both MS and its animal model, experimental autoimmune encephalomyelitis (EAE). Experimental autoimmune encephalomyelitis (EAE) is the most commonly used experimental model for the human inflammatory demyelinating disease, multiple sclerosis (MS), for example as described by Racke (Curr. Protoc. Neurosci. 9:unit 9.7 (2001)), and can be used to study the utility of compounds of the invention to treat MS.

Septic shock is linked to GSH depletion and multi-organ failure. Children, immune-compromised individuals and elderly people are most affected. Septic shock patients are cared for in intensive care units and the mortality rate is a shocking 25-50%. The disease is caused by gram-negative bacteria that produce endotoxins, also known as bacterial wall lipopolysaccharides. LPS is well known for its ability to trigger oxidative stress and activate the innate immune response by inducing the CD14/TLR4/MD2 receptor complex. This in turn leads to the secretion of pro-inflammatory cytokines in many cell types, particularly in B cells and macrophages. Compounds of the invention that inhibit non-apoptotic regulated cell-death can be proposed as drug-candidates and have utility as medicines for limiting the effects of LPS-induced endotoxic shock, and this utility can be investigated using an in-vivo murine model for example as described by Duprez et al. (Immunity 35:908-18 (2011)).

The compounds of the invention may be used for treatment alone or in conjunction with one or more other therapeutically active agents, for example in combination with apoptosis inhibitors.

Treatment including the compounds of the invention may be provided at home, the doctor's office, a clinic, a hospital's outpatient department, or a hospital. Treatment generally begins under medical supervision so that medical personnel can observe the treatment's effects closely and make any adjustments that are needed. The duration of the treatment depends on the age and condition of the patient, as well as how the patient responds to the treatment.

A person having a greater risk of developing a condition, disorder or disease may receive prophylactic treatment to inhibit or delay symptoms of the condition, disorder or disease.

The term "treatment" is known to the person of ordinary skill, and includes the application or administration of an agent (e.g., a pharmaceutical composition containing said agent) or procedure to a patient or application or administration of an agent (e.g., a pharmaceutical composition containing said agent) or procedure to a cell, cell culture, cell line, sample, tissue or organ isolated from a patient, who has a condition, disorder or disease, a symptom of the condition, disorder or disease or a predisposition toward a condition, disorder or disease, with the purpose to cure, heal, alleviate, relieve, alter, remedy, ameliorate, improve, affect or prevent the condition, disorder or disease, the symptoms of the condition, disorder or disease or the predisposition toward the condition, disorder or disease. Hence, the term "treatment" can include prophylactic treatment of a condition, disorder or disease, or the symptom of a condition, disorder or disease. An agent, when used in treatment, includes the compounds described herein and includes, but is not limited to, other therapeutically active agents that may be small molecules, peptides, peptidomimetics, polypeptides/proteins, antibodies, nucleotides such as DNA or RNA, cells, viruses, ribozymes, siRNA, and antisense oligonucleotides In an alternative aspect, the compounds of the present invention may be evaluated for their pharmacological properties in animal models of disease. The compounds identified to decrease non-apoptotic regulated cell-death may be structurally modified and subsequently used to decrease non-apoptotic regulated cell-death, or in treatment (including prophylactic treatment) of a condition, disorder or disease as described herein. The methods used to generate structural derivatives of the small molecules that decrease non-apoptotic regulated cell-death are readily known to those skilled in the fields of organic and medicinal chemistry.

Also in alternative aspect, the compounds of the invention may be used in the cosmetic treatment (including prophylactic and cosmetic treatment) of an aesthetic feature associated with UV-damage in skin, ageing in skin, and/or hair loss.

Also, in an additional alternative aspect, the invention relates to a storage solution for organ transport and/or transplant comprising a compound of the invention.

The inventors have identified the compounds of the present invention as a class of small molecules that effectively and selectively inhibit non-apoptotic regulated cell death and/or reduce oxidative stress but do not inhibit apoptotic cell death.

Thus, the present invention provides (i) a compound of the invention (or a pharmaceutical composition comprising such compound optionally together with a pharmaceutically acceptable excipient) for use in a method of treating (a) a condition, disorder or disease that is characterised by non-apoptotic regulated cell-death or where non-apoptotic regulated cell-death is likely to play or plays a substantial role; (b) a condition, disorder or disease that is characterised by oxidative stress or where oxidative stress is likely to play or plays a substantial role; and/or (c) a condition, disorder or disease that is characterised by activation of (1) one or more components of the necrosome; (2) death domain receptors; and/or (3) Toll-like receptors; and/or (4) players in ferroptotic/ferroptosis signalling, or where activation of any one of (1) to (3) and/or (4) is likely to play or plays a substantial role; and (ii) a method of treating an individual with a need thereof, comprising administering a pharmaceutically effective amount of a compound of the invention, in particular those specified above with respect to any of formulas (I), (N-I), (O/S-I), (C-I), (II), (N-II), (O/S-II), (C-II), (III), (N-II), (O/S-III), (C-I), (IV), (N-IV), (O/S-IV), (C-IV), (V), (N-V), (O/S-V), and (C-V)(or a pharmaceutical composition comprising such compound optionally together with a pharmaceutically acceptable excipient), to the individual. In one embodiment, the individual is suffering from, or is susceptible to or at risk of, one or more of the conditions, disorders or diseases disclosed herein. The condition, disorder or disease may be selected from the group consisting of a neurodegenerative disease of the central or peripheral nervous system, muscle wasting, muscular dystrophy, ischemia, compartment syndrome, gangrene, pressure sores, sepsis, degenerative arthritis, retinal necrosis, heart disease, liver, gastrointestinal or pancreatic disease, avascular necrosis, diabetes, sickle cell disease, alteration of blood vessels, cancer-chemo/radiation therapy-induced cell-death, intoxication, or is the result of, arises from or is associated with any of the foregoing. In a further embodiment, the condition, disorder or disease is the result of, arises from or is associated with a circumstance selected from the group consisting of forms of infection of viruses, bacteria, fungi, or other microorganisms; a reduction in cell-proliferation, an alteration in cell-differentiation or intracellular signalling; an undesirable inflammation; cell death of retinal neuronal cells, cardiac muscle cells, or cells of the immune system, cell death associated with renal failure; neonatal respiratory distress, asphyxia, incarcerated hernia, placental infarct, iron-load complications, endometriosis, congenital disease; head trauma/traumatic brain injury, liver injury; injuries from environmental radiation; burns; cold injuries; mechanical injuries, and decompression sickness. Moreover, the individual is preferably a mammal and more preferably a human.

The compounds of the invention may be used in such therapeutic or other applications as described above for the following particular embodiments:

the treatment (including prophylactic treatment) of a condition, disorder or disease that is characterised by sequelae and associated pathophysiological responses, including but not limited to immunological, damage-associated molecular pattern molecules (DAMPs);

to improve cell and tissue regeneration, including in a therapeutic or ex-vivo application;

the treatment (including prophylactic treatment) of a condition, disorder or disease that is characterised by the involvement of players in ferroptotic/ferroptosis signalling, such as GPx4, or of xCT (SLC7A11) of the xc-amino acid transport system, or where the contribution of the foregoing is likely to play or plays a substantial role;

the treatment (including prophylactic treatment) of a condition, disorder or disease: selected from the group consisting of: cardiovascular (heart) disease, contrast-agent-induced toxicity, and priapism, Lyme disease, Rocky Mountain spotted fever and rabies;

the treatment (including prophylactic treatment) of a condition, disorder or disease that is the result of, arises from or is associated with: the side effects of medications, or of snake, scorpion or spider bites;

to decrease and/or delay non-apoptotic cell death, including in a therapeutic or ex-vivo application; and/or to increase cellular resistance against cell-death stimuli, including in a therapeutic or ex-vivo application.

The compounds of the invention (or the pharmaceutical composition comprising such compound) may be administered to the individual by any route, preferably by any route described above in section "Pharmaceutical compositions" for the administration of the pharmaceutical composition of the invention.

Synthesis and Intermediates

The compounds of the present invention can be prepared as described below or prepared by methods analogous thereto, which are readily known and available to one of ordinary skill in the art of organic synthesis.

Compounds disclosed herein may be prepared by the general synthetic sequence shown in Scheme 1, below.

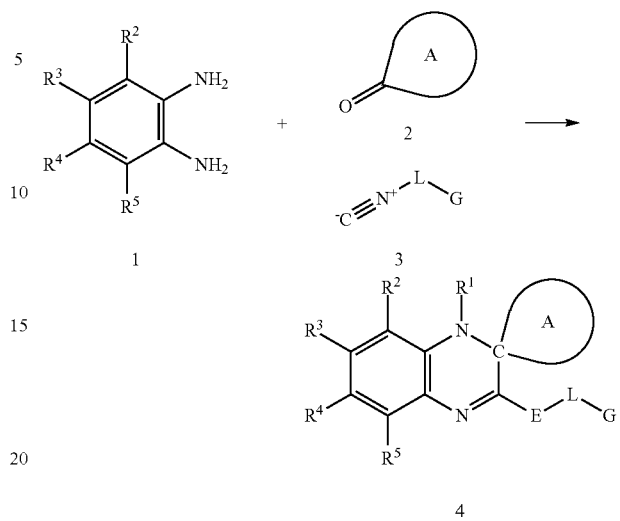

Scheme 1

For example, compounds 4 (i.e., compounds of the present invention) may be synthesized in a one-step reaction from applicable derivatives of diamine 1, ketone 2 and isocyanide 3. The synthesis can be conducted as follows. A mixture of 0.5 mmol of diamine 1 and 0.5 mmol of ketone 2 in 0.5 mL methanol is stirred under nitrogen atmosphere at 40-45° C. for 3 h. To this mixture, solutions of 0.5 mmol TMSCl in 0.5 mL acetonitrile and 0.5 mmol of isocyanide 3 in 0.5 mL methanol are added and the resulting mixture stirred at 50-60° C. for 4 h and then for 1 day at 40-50° C., resulting in full conversion of starting materials (monitoring can be done by using LC-MS). The reaction mixture is evaporated under reduced pressure, treated with dry ethylacetate and kept in an ultrasonic bath until completion of precipitate formation. The reaction mixture is then centrifuged and the precipitate washed twice with ethylacetate, acetonitrile and ether with centrifugation each time and finally dried under reduced pressure. Compounds 4 are obtained as monohydrochloride salts, typically in pure form, and at yields of 50-90%.

Compounds 4 which bear a functional group that may interfere with the reaction set forth in Scheme 1 can be prepared according to Scheme 1 using a corresponding starting material (e.g., diamine 1, ketone 2 and/or isocyanide 3 or a suitable synthon of any of the foregoing) which is suitably protected at the functional group so that the corresponding protected starting material no longer interferes with the reaction set forth in Scheme 1, followed by a subsequent deprotection step of the protected precursor version of 4. For example, compounds 4 which are unsubstituted on a ring nitrogen atom of ring A (i.e., N—R$^9$ being N—H; cf., e.g., compounds N-1 to N-89, N-111 to N-190 and N-199 to N-203 of Table 1-N) can be prepared according to Scheme 1, generally in accordance with the method described above using a ketone 2 which is suitably protected at the ring nitrogen atom(s) of ring A, followed by a subsequent deprotection step of the protected precursor version of 4. The skilled person knows suitable protecting groups (for example, N-protecting groups, such as the BOC protecting group), reagents and reaction conditions in order to covert a "free" functional group (e.g., an amino group having at least one hydrogen bound to the nitrogen atom, such as —NH—) into a corresponding protected functional group (such as —N(PG)-, wherein PG is a protecting group), as well as reagents and reaction conditions in order to remove the protecting group (cf., e.g., Protective Groups in Organic Synthesis (Theosora W. Greene & Peter G. M. Wuts; John Wiley & Sons Inc., 1999). In case of the BOC protecting group, the deprotection step may be performed as follows. A mixture of 0.5 mmol of compound 4 (with —N($R^9$)—being —N(C(O)O-tBu)— prepared by using the applicable —CO—O-tBu containing ketone 2) in 2 mL methylenechloride and 1 mL TFA is stirred overnight at room temperature and the reaction mixture evaporated to dryness under reduced pressure. The residue is dissolved in THF and treated with an excess of HCl in dioxane (8M) and then with acetonitrile. The precipitate is collected by centrifugation, washed with acetonitrile and then ethyl acetate, followed each time by centrifugation; and thereafter is dried under reduced pressure to yield deprotected compound 4, typically in pure forms and in yields of 85-90%. Alternatively, if, for example, a starting material (e.g., a specific diamine 1, ketone 2 and/or isocyanide 3) as such cannot be handled under the reaction conditions utilized to prepare compounds 4 according to Scheme 1, a suitable synthon of the specific diamine 1, ketone 2 and/or isocyanide 3 may be used instead. E.g., the skilled person knows that a synthon of a cyclic keton is its corresponding hemiacetal; for example, a synthon of cyclopropanone is cyclopropanone ethyl hemiacetal (such as 1-ethoxy-1-(trimethylsilyloxy) cyclopropane) which is much easier and safer to handle than cyclopropanone and which easily reacts with amines (cf., e.g., Organic Syntheses, Coll. Vol. 7, p. 131 (1990); Vol. 63, p. 147 (1985)).

Precursors 1, 2 and 3 (wherein $R^2$, $R^3$, $R^4$, $R^5$, ring A, L, and G are as defined above for the compounds of the invention) are obtained from commercial sources, or are synthesised by standard procedures. In particular, derivatives of isocyanide 3 may be obtained using the procedures described by Hoefle and Lange (Organic Syntheses (1983) 61:14).

Thus, in further aspects, the present invention relates to intermediates 1, 2, and/or 3 which are useful in the preparation of a compound of the present invention as well as to a method of preparing a compound of the present invention comprising the step of reacting a diamine of formula 1, a ketone of formula 2 and an isocyanide of formula 3. Preferably, such preparation or method is represented by scheme 1.

Regioisomers of compounds 4 (e.g., compounds N-135 to N-182 of Table 1-N, compounds O/S-114 to O/S-161 and O/S-282 to O/S-329 of Table 1-O/S, and compounds C-155 to C-202 of Table 1-C) may be isolated by chromatography separation, for example HPLC separation, as will be recognised and practicable by the person of ordinary skill. Enantiomers of racemic mixtures of compounds 4 (e.g., compounds N-82 and N-83 of Table 1-N, compounds O/S-82, O/S-83, O/S-248, and O/S-249 of Table 1-O/S, and compounds C-82 and C-83 of Table 1-C) may be isolated by separation using commercial services and/or products, e.g., those from Chiral Technologies Europe SAS (www.chiral.fr).

A person of ordinary skill will appreciate that other routes of synthesis or separation may be employed as well. In particular, other routes of synthesis may in fact be applied to certain embodiments of the compounds disclosed herein. The person of ordinary skill is referred to general textbooks, such as March's Advanced Organic Chemistry (Michael B. Smith & Jerry March, Wiley-iterscience, 2000), The Practice of Medicinal Chemistry (Camile G. Wermuth, Academia Press, 2003) and Protective Groups in Organic Synthesis (Theosora W. Greene & Peter G. M. Wuts; John Wiley & Sons Inc, 1999).

EXAMPLES

A selection of compounds within the scope of, or for use within the methods of, the present invention is listed in Tables 1-N, 1-O/S, and 1-C. The compounds in Tables 1-N, 1-O/S, and 1-C are synthesised according to Example A, and the surprising cell-death inhibitory activities in cellular assays of non-apoptotic regulated cell-death of such compounds are shown in Table 2, Table 3 and FIGS. 1(*a*), (*b*), and (*c*), FIG. 2(*a*), (*b*), and (*C*), and FIGS. 3 and 4, respectively, as determined according to Examples B.1 to B.3, B.4, and B.5. The use of such compounds in animal models of certain medical conditions, disorders and diseases is described in Examples C.1 to C.8, and procedures to further select and/or develop one or more of such compounds as drugs are described in Example D.

Example A

Synthesis of Spiroquinoxaline Derivatives

Analytical Devices Used

Analytical LC/ESI-MS: Waters 2700 Autosampler. Waters 1525 Multisolvent Delivery System. 5 µL sample loop. Column, Phenomenex Onyx Monolythic C18 50×2 mm, with stainless steel 2 µm prefilter. Eluent A, $H_2O$+0.1% HCOOH; eluent B, acetonitrile. Gradient, 5% B to 100% B within 3.80 min, then isocratic for 0.20 min, then back to 5% B within 0.07 min, then isocratic for 0.23 min; flow, 0.6 ml/min and 1.2 ml/min.

Waters Micromass ZQ 4000 single quadrupol mass spectrometer with electrospray source. MS method, MS4_15 minPM-80-800-35V; positive/negative ion mode scanning, m/z 80-800 in 0.5 s; capillary voltage, 3.50 kV; cone voltage, 50 V; multiplier voltage, 650 V; source block and desolvation gas temperature, 120° C. and 300° C., respectively. Waters 2487 Dual λAbsorbance Detector, set to 254 nm. Software, Waters Masslynx V 4.0.

Waters Micromass LCZ Platform 4000 single quadrupol mass spectrometer with electrospray source. MS method, MS4_15 minPM-80-800-35V; positive/negative ion mode scanning, m/z 80-800 in 1 s; capillary voltage, 4.0 kV; cone voltage, 30 V; multiplier voltage, 900 V; source block and desolvation gas temperature, 120° C. and 300° C., respectively. Waters 996 Photodiode Array Detector, set 200 to 400 nm. Software, Waters Masslynx V4.0.

Values for [M+H]$^+$ given in Table 3 are those found within the corresponding LC/MS chromatogram for the respective compound. These values were all found within tolerable margins of +/−0.3 units compared to calculated exact mass upon protonation of the compound.

Preparative thinlayer chromatography (preparative TLC): Merck PLC plates, silica gel 60 $F_{254}$, 0.5 mm, 1.0 mm or 2.0 mm. Eluents for preparative TLC or column chromatography (CC) on silica gel were: (1) EluentN1: $CH_2Cl_2$/methanol; EluentN2: $CH_2Cl_2$/methanol/$NEt_3$ for spiroquinoxaline derivatives having an N-heterocycloalkylene as ring A; (2) EluentO1: $CH_2Cl_2$/ethyl acetate/methanol; EluentO2: $CH_2Cl_2$/methanol; EluentO3: petroleum ether/ethyl acetate for spiroquinoxaline derivatives having an O/S-heterocycloalkylene as ring A; or (3) EluentC1: $CH_2C_2$/ethyl acetate/ methanol; EluentC2: $CH_2Cl_2$/methanol; EluentC3: petroleum ether/ethyl acetate; EluentC4: $CH_2Cl_2$/methanol/$NEt_3$ for spiroquinoxaline derivatives having a cycloalkylene as ring A. For each eluent, the aforementioned solvents were used in different ratios, depending on the respective compound.

Preparative HPLC-MS: Waters 2767 Autosampler, Waters 600 Multisolvent Delivery System with analytical pump heads (100 µL); Waters 600 Controller; Waters 2525 Binary Gradient Modul with preparative pump heads (500 µL). At-Column-Dilution: solvent1, acetonitrile:$H_2O$ 70:30 (v/v), solvent2, acetonitrile:methanol:dimethylformamide 80:15:5 (v/v/v); flow rate, 5 mL/min Autosampler 2767 with 10 mL syringe and 10 mL Sample loop. Column 6-position valve Flom 401 with Waters X-Terra RP18, 5 µm, 19×150 mm with X-Terra RP18 guard cartridge 5 µm, 19×10 mm, used at flow rate 20 mL/min; Waters SunFire Prep OBD 5 µm, 30×50 mm with SunFire RP18 guard cartridge 5 µm, 19×10 mm, used at flow rate 25 mL/min; Waters Atlantis Prep T3 OBD 5 µm, 30×50 mm with Atlantis guard cartridge, used at flow rate 50 mL/min. Waters X-Bridge Prep OBD 5 µm, 19×150 mm with X-Bridge RP18 guard cartridge 5 µm, 19×10 mm used at flow rate 20 mL/min; Waters Atlantis Prep T3 OBD 5 µm, 19×50 mm with Atlantis guard cartridge, used at flow rate 25 mL/min and YMC-Actus Hydrosphere C18 5 µm, 20×50 mm with Actus guard cartridge, used at flow rate 20 mL/min. Eluent A, $H_2O$ containing 0.1% (v/v) $HCO_2H$ or $H_2O$ containing 0.1% (v/v) $NEt_3$ eluent B, acetonitrile. Different linear gradients, individually adapted to sample. Injection volume, 9 mL, depending on sample. Make-up solvent, methanol-acetonitrile-$H_2O$—$HCO_2H$ 80:15:4.95:0.05 (v/v/v/v). Make-up pump, Waters Reagent Manager, flow rate 0.5 mL/min. Waters ZQ single quadrupole mass spectrometer with electrospray source. Positive or negative ion mode scanning m/z 105-950 in 1 s; capillary, 3.6 kV; cone voltage, 45 V; multiplier voltage, 700 V; probe and desolvation gas temperature, 120° C. and 250° C., respectively Waters Fraction Collector 2767 with mass or UV-triggered fraction collection. Waters 2487 Dual λ Absorbance Detector, set to 254 m/z. Software, Waters Masslynx V 4.0 SP4.

$^1H$ NMR spectra were recorded at room temperature on a Bruker Supraleitendes Fourier NMR Spektrometer, Avance™ 300 MHz. Chemical shifts δ were recorded in ppm. Multiplicity of a certain signal (singlet, doublet, triplet, quartet, multiplet) was recorded by the respective abbreviation (s, d, t, q, m respectively), with "$_{Sbr}$" indicating a broad singlet, and "mC" a centered multiplet. The solvent residual signals were used as internal standards: $\delta(CDCl_3)$=7.26, $\delta(d6\text{-}DMSO)$=2.50, $\delta(CD_3OD)$=3.31, $\delta(d6\text{-}acetone)$=2.05.

General Methods for Synthesis and Workup

Compounds disclosed herein may be prepared by the synthetic sequence according to Scheme 1 as set fourth above (cf. chapter "Synthesis and intermediates", above).

(I) For example, compounds 4 may be formed in a one-step reaction from applicable derivatives of diamine 1, ketone 2 and isocyanide 3 as follows. A mixture of 0.5 mmol of diamine 1 and 0.5 mmol of ketone 2 in 0.5 mL methanol is stirred under nitrogen atmosphere at 40-45° C. for 3 h. To this mixture, solutions of 0.5 mmol TMSCl in 0.5 mL acetonitrile and 0.5 mol of isocyanide 3 in 0.5 mL methanol are added and the resulting mixture stirred at 50-60° C. for 4 h and then for 1 day at 40-50° C., resulting in full conversion of starting materials (monitoring can be done by using LC-MS). The reaction mixture is evaporated under reduced pressure, treated with dry ethylacetate and kept in an ultrasonic bath until completion of precipitate formation. The reaction mixture is then centrifuged and the precipitate washed twice with ethylacetate, acetonitrile and ether with centrifugation each time and finally dried under reduced pressure. Compounds 4 are obtained as monohydrochloride salts, typically in pure form, and at yields of 50-90%.

(I.1) A general method for the synthesis of compound 4, wherein ring A is an N-heterocycloalkylene and $R^9$ bound to a ring nitrogen atom is not H, is as follows. A mixture of 0.46 mmol of diamine 1 and 0.46 mmol of ketone 2 in 2.0 mL methanol was stirred at 50° C. for 4 hours. To this mixture, solutions of 0.46 mmol TMSCl in 0.50 mL acetonitrile and 0.46 mmol of isocyanide 3 in 0.50 mL methanol were added and the resulting mixture was stirred at 50-60° C. for 4 hours and then at r.t. (room temperature, i.e., usually about 25° C.) overnight which resulted in full consumption of starting materials (LC-MS). Workup and purification was performed by one of the following procedures PN1a and PN1b. Procedure PN1a: The reaction mixture was diluted with 1N HCl and water and then extracted twice with ethyl acetate. The combined organic layers (F1) contained no or only minor product (LC-MS) and were thus discarded. The aqueous layer was then basified with 1N NaOH and extracted several times with $CH_2Cl_2$. The combined organic layers (F2) were dried over $Na_2SO_4$ and concentrated in vacuo. The residue was purified by preparative HPLC and/or preparative TLC. Procedure PN1b: The reaction mixture was diluted with water, neutralized with saturated aqueous $NaHCO_3$ and then extracted several times with $CH_2Cl_2$. The combined organic layers were dried over $Na_2SO_4$ and concentrated in vacuo. The residue was purified by preparative HPLC and/or preparative TLC and/or was transferred into to the corresponding HCl salt by dissolving in diethyl ether and/or $CH_2Cl_2$, adding 4N HCl in dioxane and filtering off the resulting precipitate.

(I.2) A general method for the synthesis of compound 4, wherein ring A is an N-heterocycloalkylene and $R^9$ bound to a ring nitrogen atom is H, is as follows. A mixture of 0.46 mmol of diamine 1 and 0.46 mmol of Boc-protected ketone 2 in 2.0 mL methanol was stirred at 50° C. for 4 hours. To this mixture, solutions of 0.46 mmol TMSCl in 0.50 mL acetonitrile and 0.46 mmol of isocyanide 3 in 0.50 mL methanol were added and the resulting mixture was stirred at 50-60° C. for 4 hours and then at r.t. overnight which resulted in full consumption of starting materials (LC-MS). Workup and purification was performed by one of the procedures PN2a to PN2c described below, followed by the general Workup PW below. Procedure PN2a: The reaction mixture was diluted with 2.0 mL ethyl acetate and/or 2.0 mL $CH_2Cl_2$, then 1.0 mL HCl 4M in dioxane was added and the mixture was stirred at r.t. for 1-3 days. Procedure PN2b: The reaction mixture was diluted with water, neutralized with saturated aqueous $NaHCO_3$ and extracted several times with $CH_2Cl_2$. The combined organic layers were dried over $Na_2SO_4$ and concentrated in vacuo. The residue was purified by preparative TLC and then dissolved in 2.0 mL ethyl acetate. 1.0 mL HCl 4.0 M in dioxane was added and the mixture was stirred at r.t. for 1-3 days. Procedure PN2c: The reaction mixture was diluted with water, neutralized with saturated aqueous $NaHCO_3$ and extracted several times with $CH_2Cl_2$. The combined organic layers were dried over $Na_2SO_4$ and concentrated in vacuo. The residue was dissolved in 2.0 mL ethyl acetate and/or 2.0 mL $CH_2Cl_2$ and/or 2.0 mL methanol. 1.0 mL HCl 4.0 M in dioxane was added and the mixture was stirred at r.t. for 1-3 days. Workup PW: The reaction mixture was diluted with water and then extracted twice with ethyl acetate. The combined organic layers (F1) contained no or only minor product (LC-MS) and were thus discarded. The aqueous layer was then basified with 1N NaOH and extracted several times with CH$_2$Cl$_2$. The combined organic layers (F2) were dried over Na$_2$SO$_4$ and concentrated in vacuo. The residue was purified by preparative HPLC and/or preparative TLC.

(I.3) A general method for the synthesis of compound 4, wherein ring A is an O/S-heterocycloalkylene, is as follows. A mixture of 0.46 mmol of diamine 1 and 0.46 mmol of ketone 2 in 2.0 mL methanol was stirred at 50° C. for 4 hours. To this mixture, solutions of 0.46 mol TMSCl in 0.50 mL acetonitrile and 0.46 mmol of isocyanide 3 in 0.50 mL methanol were added and the resulting mixture was stirred at 50-60° C. for 4 hours and then at r.t. overnight which resulted in full consumption of starting materials (LC-MS). Workup and purification was performed by one of the following procedures POa to POd. Procedure POa: The reaction mixture was diluted with 1N HCl and water. The resulting precipitate was filtered off and washed with water. The filtrate contained no product (LC-MS) and was thus discarded. The crude product was taken up in CH$_2$Cl$_2$, dried over Na$_2$SO$_4$, filtered and concentrated in vacuo. The residue was purified by preparative TLC. Procedure POb: The reaction mixture was diluted with 1N HCl and water and then extracted twice with ethyl acetate. The combined organic layers (F1) contained no or only minor product (LC-MS) and were thus discarded. The aqueous layer was then basified with 1N NaOH and extracted several times with CH$_2$Cl$_2$. The combined organic layers (F2) were dried over Na$_2$SO$_4$ and concentrated in vacuo. The residue was purified by preparative HPLC and/or preparative TLC and/or recrystallization from ethanol and/or was transferred into to the corresponding HCl salt by dissolving in diethyl ether and/or CH$_2$Cl$_2$, adding 4N HCl in dioxane and filtering off the resulting precipitate. Procedure POc: The reaction mixture was diluted with water (40 mL) and extracted several times with CH$_2$Cl$_2$. The combined organic layers were washed with brine, dried over Na$_2$SO$_4$ and concentrated in vacuo. The residue was purified by preparative HPLC and/or preparative TLC and/or recrystallization from ethanol and/or was transferred into to the corresponding HCl salt by dissolving in diethyl ether and/or CH$_2$Cl$_2$, adding 4N HCl in dioxane and filtering off the resulting precipitate. Procedure POd: The reaction mixture was diluted with water (40 mL), neutralized with sat. NaHCO$_3$ and extracted several times with CH$_2$Cl$_2$. The combined organic layers were washed with brine, dried over Na$_2$SO$_4$ and concentrated in vacuo. The residue was purified by preparative HPLC and/or preparative TLC and/or recrystallization from ethanol and/or was transferred into to the corresponding HCl salt by dissolving in diethyl ether and/or CH$_2$Cl$_2$, adding 4N HCl in dioxane and filtering off the resulting precipitate.

(I.4) A general method for the synthesis of compound 4, wherein ring A is a C-heterocycloalkylene, is as follows. A mixture of 0.46 mmol of diamine 1 and 0.46 mmol of ketone 2 in 2.0 mL methanol was stirred at 50° C. for 4 hours. To this mixture, solutions of 0.46 mmol TMSCl in 0.50 mL acetonitrile and 0.46 mmol of isocyanide 3 in 0.50 mL methanol were added and the resulting mixture was stirred at 50-60° C. for 4 hours and then at r.t. overnight which resulted in full consumption of starting materials (LC-MS). Workup and purification was performed by one of the procedures PCa to PCc. Procedure PCa: The reaction mixture was evaporated. The residue was treated with ethyl acetate under sonication, the formed precipitate was filtered off. The solid was washed with acetone and then partitioned between saturated, aqueous NaHCO$_3$ and CH$_2$Cl$_2$, the organic phase was washed several times with water and the combined aqueous phases were extracted several times with CH$_2$Cl$_2$. The combined organic phases were dried over Na$_2$SO$_4$ and evaporated. The residue was purified by preparative TLC and/or recrystallization from ethanol. Procedure PCb: The reaction mixture was diluted with 1N HCl and water and then extracted twice with ethyl acetate. The combined organic layers (F1) contained no or only minor product (LC-MS) and were thus discarded. The aqueous layer was then basified with 1N NaOH and extracted several times with CH$_2$Cl$_2$. The combined organic layers (F2) were dried over Na$_2$SO$_4$ and concentrated in vacuo. The residue was purified by preparative HPLC and/or preparative TLC and/or recrystallization from ethanol and/or was transferred into to the corresponding HCl salt by dissolving in diethyl ether and/or CH$_2$Cl$_2$, adding 4N HCl in dioxane and filtering off the resulting precipitate. Procedure PCc: The reaction mixture was diluted with water (40 mL) and extracted several times with CH$_2$Cl$_2$. The combined organic layers were washed with brine and dried over Na$_2$SO$_4$ and concentrated in vacuo. The residue was purified by preparative HPLC and/or preparative TLC and/or recrystallization from ethanol and/or was transferred into to the corresponding HCl salt by dissolving in diethyl ether and/or CH$_2$Cl$_2$, adding 4N HCl in dioxane and filtering off the resulting precipitate.

(I.5) A general method for the synthesis of compound 4 with a free NH$_2$-group by deprotection of a BOC-protected compound 4 is as follows. A mixture of 0.46 mmol of diamine 1 and 0.46 mmol of Boc-protected ketone 2 in 2.0 mL methanol was stirred at 50° C. for 4 hours. To this mixture, solutions of 0.46 mmol TMSCl in 0.50 mL acetonitrile and 0.46 mmol of isocyanide 3 in 0.50 mL methanol were added and the resulting mixture was stirred at 50-60° C. for 4 hours and then at r.t. overnight which resulted in full consumption of starting materials (LC-MS). The reaction mixture was diluted with 1N HCl (5.0 mL) and water and extracted several times with CH$_2$Cl$_2$. The combined organic layers were dried over Na$_2$SO$_4$ and concentrated in vacuo. The residue was purified by preparative TLC and dissolved in 2.0 mL ethyl acetate. 1.0 mL HCl 4.0 M in dioxane was added and the mixture was stirred at room temperature for 1 day. The reaction mixture was diluted with water and extracted twice with ethyl acetate. The combined organic layers (F1) contained no product and were thus discarded. The aqueous layer was basified with 1N NaOH and extracted several times with CH$_2$Cl$_2$. The combined organic layers (F2) were dried over Na$_2$SO$_4$ and concentrated in vacuo. The residue was purified by preparative TLC.

Examples B

Cellular Activity Assays

The in-vitro cellular activity of compounds disclosed herein was demonstrated by one or more assays including those described in more detail below.

Example B.1

Inhibition of BSO-induced Non-apoptotic Cell Death by Compounds Disclosed Herein As shown in Table 2, the present inventors observed the surprising finding that compounds disclosed herein are (presumed) able to penetrate cell membranes and showed activity as inhibitors of non-apoptotic cell death induced in cells of the human neuroblastoma cell line SH-SY5Y grown in-vitro.

L-Buthionine sulfoximine (BSO) is a well-known glutathione (GSH) depletory, which inhibits gamma-glutamyl-cysteine-synthetase, the enzyme catalyzing the rate-limiting step in GSH biosynthesis. The human neuroblastoma cell line SH-SY5Y is sensitive to BSO-induced intracellular glutathione depletion, which causes high levels of reactive oxygen species (ROS) and cellular stress mimicking cellular conditions following ischemia (cf, e.g., Yamada et al., Neurochem. Int. 59:1003-9 (2011)).

Compounds disclosed herein were evaluated for their ability to promote cell survival upon administration of a lethal dose of BSO to cell-culture medium. Briefly, SH-SY5Y cells (ATCC® CRL-2266™) were propagated in DMEM supplemented with 10% FBS/1% Penicillin-Streptomycin, and then seeded onto 96-well plates at a concentration of 750 cells/well in 100 μL of media, to which BSO (Sigma Aldrich) was added (to a final concentration of 50 μM) together with increasing concentrations of the compound to be tested, and the plates incubated at 37° C./5% $CO_2$ for 72 hours. Compound dilutions (0.5 μM to 100 μM) were prepared from 10 mM stocks dissolved in DMSO and diluted in media. Cells treated with BSO alone were used as negative control and alpha-Tocopherol (Sigma Aldrich) was used as positive control. Compound concentrations were tested in triplicate. After incubation, cell survival was detected using the live/dead cell assay AquaBluer™ (MultiTarget Pharmaceuticals) and quantified using a fluorescence plate reader (excitation filter: 530-560 nm/emission filter: 590 nm)(SpectraMax M4; Molecular Devices). Fluorescence data so obtained was normalised to the percentage of surviving cells and $IC_{50}$ values calculated using the GraphPad Prism (GraphPad Software, Ic) software package. Such $IC_{50}$ values obtained for certain compounds disclosed herein are shown in Table 2 and Table 3.

TABLE 2

| Compound No. | SH-SY5Y/BSO (Example B.1) $IC_{50}$ (nM) | Ht22/GLU (Example B.2) $IC_{50}$ (nM) |
|---|---|---|
| N-1 | 6.51 | 10.3 |
| N-2 | 2.81 | ~10 |
| N-10 | ~5 | 10-50 |
| O/S-3 | ~100 | ~100 |
| O/S-6 | 68.28 | 218.4 |
| C-12 | 468 | 297.6 |
| C-91 | 9.33 | ~50 |
| C-205 | 46.67 | ~100 |

TABLE 3

| Cmpd. No. | MW (theor./meas.) $[M + H]^+$ | SH-SY5Y/BSO $IC_{50}$ [μM] | Ht22/GLU [μM] | Pfa1/TAM $IC_{50}$ [μM] | $TC_{50}$ [μM] | Therapeutic Window (approx.. fold) |
|---|---|---|---|---|---|---|
| N-1 | 340.86/340.88 | <0.02 | <0.2 | <0.05 | 10-20 | >500 |
| N-2 | 340.86/340.88 | <0.02 | <0.2 | <0.02 | 5-10 | >500 |
| N-10 | 320.43/NT | <0.02 | <0.05 | <0.1 | 5-10 | >100 |
| C-12 | 319.44/NT | <0.5 | <0.5 | <0.5 | 50-100 | >100 |
| C-91 | 353.89/NT | <0.02 | <0.2 | <0.2 | 10-20 | >100 |
| O/S-6 | 325.38/NT | <0.5 | <0.5 | <1 | 50-100 | >200 |
| O/S-3 | 341.84/341.90 | <0.5 | <0.1 | <0.5 | 20-50 | >50 |
| C-205 | 353.89/353.99 | <0.1 | <0.5 | <0.2 | 20-50 | >200 |
| O/S-337 | 307.17/307.99 | <0.5 | <5 | <5 | 50-100 | >20 |
| C-214 | 319.21/320.04 | <0.5 | <1 | <0.5 | 10-20 | >20 |
| O/S-338 | 323.15/323.96 | <0.5 | <5 | <1 | 50-100 | >100 |
| C-215 | 305.19/306.05 | <0.2 | <1 | <1 | 20-50 | >50 |
| N-204 | 320.20/320.97 | <0.05 | <0.5 | <0.5 | 20-50 | >50 |
| O/S-339 | 375.09/375.86 | <0.02 | <0.2 | <0.05 | 20-50 | >1000 |
| O/S-1 | 341.13/341.91 | <0.5 | <1 | <1 | 50-100 | >100 |
| C-1 | 339.86/339.94 | <0.5 | <1 | <0.5 | 20-50 | >100 |
| O/S-2 | 341.13/341.89 | <0.2 | <1 | <0.5 | 20-50 | >50 |
| N-205 | 375.30/374.84 | <0.02 | <0.05 | <0.01 | 1-2 | >100 |
| O/S-340 | 335.20/336.02 | <0.2 | <0.5 | <0.5 | 20-50 | >100 |
| O/S-168 | 357.11/357.88 | <0.1 | <0.5 | <0.2 | 20-50 | >200 |
| N-99 | 382.16/382.95 | <0.2 | <1 | <1 | 50-100 | >100 |
| C-216 | 353.89/353.99 | <0.05 | <0.5 | <0.1 | 10-20 | >100 |
| C-217 | 373.11/373.91 | <0.05 | <0.2 | <0.05 | 20-50 | >500 |
| O/S-167 | 357.11/357.89 | | <1 | <0.5 | 20-50 | >100 |
| C-218 | 333.22/334.01 | | <0.1 | <0.1 | 20-50 | >200 |
| N-206 | 306.18/306.97 | | <0.5 | <0.2 | 20-50 | >100 |
| C-219 | 291.17/291.97 | | <5 | <2 | 20-50 | >20 |
| C-5 | 323.18/324.02 | | <5 | <0.5 | 20-50 | >50 |
| O/S-5 | 325.16/326.02 | | <5 | <2 | 50-100 | >50 |
| N-5 | 324.18/324.96 | | <0.05 | <0.1 | 5-10 | >200 |
| O/S-11 | 321.18/322.02 | | <5 | <2 | 50-100 | >50 |
| C-2 | 339.15/339.93 | <0.1 | <0.5 | <0.1 | 10-20 | >100 |
| N-207 | 408.07/408.77 | | <0.05 | <0.01 | 0.5-1 | >500 |
| N-115 | 408.07/408.77 | | <0.05 | <0.01 | 0.2-0.5 | >200 |
| C-23 | 373.18/373.98 | | <0.5 | <0.05 | 10-20 | >100 |
| C-3 | 339.15/339.95 | | <0.5 | <0.2 | 20-50 | >200 |
| N-208 | 408.07/408.77 | | <0.05 | <0.01 | 0.5-1 | >500 |
| N-3 | 340.15/340.89 | <0.05 | <0.05 | <0.01 | 5-10 | >5000 |
| N-209 | 354.16/354.92 | | <0.5 | <0.1 | 5-10 | >100 |
| N-90 | 354.16/354.92 | | <0.2 | <0.02 | 10-20 | >500 |
| N-210 | 334.22/334.99 | <0.05 | <0.05 | <0.01 | 2-5 | >1000 |
| C-11 | 319.20/320.06 | | <1 | <0.5 | 10-20 | >20 |
| N-111 | 368.18/368.92 | | <0.01 | <0.01 | 1-2 | >1000 |
| O/S-23 | 375.16/375.97 | | <1 | <0.5 | 20-50 | >100 |
| O/S-169 | 357.11/357.88 | | <1 | <1 | 20-50 | >50 |
| C-220 | 353.89/354.01 | | <0.5 | <0.2 | 10-20 | >50 |

TABLE 3-continued

| Cmpd. No. | MW (theor./meas. [M + H]⁺) | SH-SY5Y/BSO IC$_{50}$ [μM] | Ht22/GLU [μM] | Pfa1/TAM IC$_{50}$ [μM] | TC$_{50}$ [μM] | Therapeutic Window (approx.. fold) |
|---|---|---|---|---|---|---|
| C-268 | 387.13/387.93 | | <0.5 | <0.1 | 10-20 | >100 |
| C-47 | 335.20/336.04 | | <1 | <0.5 | 20-50 | >50 |
| C-221 | 333.22/334.07 | | <1 | <1 | 5-10 | >10 |
| O/S-341 | 343.15/343.95 | | <2 | <2 | 50-100 | >50 |
| C-222 | 341.17/342.01 | | <1 | <0.2 | 20-50 | >200 |
| C-223 | 363.45/364.03 | <0.5 | <1 | <0.2 | 20-50 | >200 |
| O/S-94 | 409.05/409.83 | <0.05 | <0.5 | <0.05 | 10-20 | >200 |
| C-224 | 363.45/350.07 | | <1 | <0.5 | 20-50 | >50 |
| C-79 | 353.89/354.00 | | <0.5 | <0.5 | 2-5 | >10 |
| O/S-342 | 389.11/389.89 | <0.1 | <0.5 | <0.05 | 20-50 | >500 |
| N-211 | 374.11/374.85 | | <0.05 | <0.01 | 1-2 | >1000 |
| N-212 | 320.20/320.97 | | <1 | <1 | 10-20 | >10 |
| C-225 | 333.22/334.03 | | <0.5 | <0.5 | 10-20 | >20 |
| N-213 | 354.16/354.92 | | <0.2 | <0.1 | 5-10 | >100 |
| N-214 | 368.18/368.90 | | <0.05 | <0.01 | 1-2 | >1000 |
| O/S-14 | 337.18/338.02 | | <5 | <5 | 50-100 | >20 |
| O/S-343 | 335.20/336.03 | | <5 | <2 | 20-50 | >20 |
| C-226 | 319.20/320.04 | | <2 | <1 | 10-20 | >10 |
| O/S-344 | 335.20/336.04 | | <2 | <1 | 20-50 | >50 |
| C-227 | 397.16/397.94 | <0.5 | <1 | <0.05 | 20-50 | >1000 |
| O/S-345 | 375.09/375.84 | <0.1 | <0.5 | <0.1 | 20-50 | >500 |
| C-228 | 373.11/373.92 | <0.05 | <0.5 | <0.05 | 20-50 | >500 |
| N-215 | 388.19/388.93 | | <0.05 | <0.05 | 5-10 | >500 |
| C-229 | 395.24/396.01 | | <1 | <0.2 | 2-5 | >10 |
| O/S-346 | 343.15/343.94 | | <1 | <0.5 | 50-100 | >200 |
| N-56 | 374.11/374.85 | | <0.05 | <0.01 | 1-2 | >1000 |
| C-269 | 361.25/362.04 | | <0.5 | <0.2 | 5-10 | >20 |
| O/S-347 | 321.18/321.98 | | <5 | <5 | 50-100 | >20 |
| C-230 | 373.11/373.88 | | <0.5 | <0.1 | 20-50 | >200 |
| N-216 | 432.29/433.03 | | <0.5 | <0.5 | 10-20 | >20 |
| N-217 | 334.22/334.98 | <0.05 | <0.05 | <0.1 | 20-50 | >200 |
| N-79 | 354.16/354.92 | | <0.05 | <0.1 | 2-5 | >50 |
| N-218 | 320.20/320.99 | | <0.5 | <0.5 | 20-50 | >100 |
| N-219 | 398.15/398.86 | <0.5 | <1 | <1 | 20-50 | >50 |
| O/S-348 | 321.18/321.99 | | <5 | <5 | 50-100 | >20 |
| O/S-79 | 355.15/355.97 | | <1 | <1 | 20-50 | >50 |
| N-220 | 396.23/396.99 | <0.05 | <0.02 | <0.05 | 2-5 | >200 |
| C-231 | 341.17/342.00 | | <1 | <0.5 | 20-50 | >50 |
| O/S-349 | 391.07/391.87 | | <0.5 | <0.2 | 20-50 | >200 |
| N-221 | 342.17/342.95 | | <0.2 | <0.2 | 20-50 | >200 |
| C-232 | 347.24/348.06 | | <1 | <2 | 20-50 | >20 |
| N-222 | 348.23/349.00 | | <0.05 | <0.2 | 20-50 | >200 |
| C-233 | 347.24/348.04 | | <1 | <1 | 20-50 | >20 |
| O/S-350 | 363.23/363.98 | | <0.5 | <0.5 | 20-50 | >100 |
| O/S-351 | 359.13/359.94 | | <1 | <1 | 50-100 | >100 |
| O/S-352 | 397.22/398.00 | | <1 | <1 | 20-50 | >50 |
| N-14 | 336.20/336.98 | | <0.2 | <0.5 | 20-50 | >100 |
| N-23 | 374.17/374.92 | <0.02 | <0.05 | <0.05 | 20-50 | >1000 |
| C-61 | 357.14/357.95 | | <0.5 | <0.2 | 20-50 | >100 |
| N-61 | 358.14/358.92 | <0.05 | <0.05 | <0.05 | 20-50 | >1000 |
| N-223 | 342.17/342.95 | <0.05 | <0.05 | <0.05 | 20-50 | >1000 |
| N-224 | 388.12/388.83 | | <0.05 | <0.01 | 1-2 | >1000 |
| C-137 | 375.13/375.91 | <0.2 | <0.2 | <0.2 | 10-20 | >100 |
| C-234 | 421.09/421.89 | | <0.5 | <0.5 | 20-50 | >100 |
| C-235 | 387.13/387.06 | | <0.5 | <0.2 | 10-20 | >50 |
| C-236 | 333.22/334.06 | | <0.5 | <0.5 | 10-20 | >50 |
| C-237 | 401.14/401.95 | | <0.5 | <0.5 | 10-20 | >50 |
| O/S-61 | 359.12/359.89 | | <1 | <1 | 20-50 | >50 |
| N-225 | 348.23/348.97 | | <1 | <0.05 | 1-2 | >50 |
| N-226 | 320.20/321.01 | | <0.1 | <0.1 | 10-20 | >200 |
| C-238 | 341.17/342.02 | | <0.2 | <0.5 | 20-50 | >100 |
| O/S-353 | 349.22/350.00 | | <2 | <0.5 | 20-50 | >50 |
| N-227 | 362.25/363.01 | | <0.01 | <0.01 | 0.5-1 | >200 |
| O/S-354 | 375.09/375.85 | | <0.5 | <0.5 | 20-50 | >200 |
| N-228 | 334.22/335.01 | | <0.05 | <0.1 | 2-5 | >50 |
| N-229 | 356.18/356.92 | | <0.1 | <0.1 | 5-10 | >50 |
| N-230 | 388.12/388.86 | <0.01 | <0.01 | <0.01 | 0.5-1 | >200 |
| C-239 | 347.24/348.01 | | <0.2 | <0.2 | 10-20 | >50 |
| N-231 | 342.17/342.95 | <0.1 | <0.05 | <0.05 | 10-20 | >200 |
| N-232 | 402.14/402.86 | | <0.01 | <0.01 | 1-2 | >1000 |
| N-233 | 348.23/348.98 | | <0.1 | <0.2 | 10-20 | >50 |
| C-240 | 409.09/409.85 | | <0.2 | <0.5 | 5-10 | >20 |
| O/S-355 | 343.15/343.98 | | <2 | <2 | 50-100 | >20 |
| C-241 | 361.25/362.04 | | <0.2 | <0.5 | 5-10 | >20 |
| C-242 | 355.19/356.02 | | <1 | <1 | 10-20 | >10 |
| C-243 | 421.09/421.85 | | <1 | <0.5 | 10-20 | >20 |

TABLE 3-continued

| Cmpd. No. | MW (theor./meas. [M + H]+) | SH-SY5Y/BSO IC$_{50}$ [μM] | Ht22/GLU [μM] | Pfa1/TAM IC$_{50}$ [μM] | TC$_{50}$ [μM] | Therapeutic Window (approx.. fold) |
|---|---|---|---|---|---|---|
| O/S-356 | 351.18/352.00 | | <2 | <2 | 20-50 | >20 |
| N-234 | 418.31/419.03 | | <0.1 | <0.1 | 5-10 | >50 |
| O/S-357 | 351.18/351.99 | | <0.5 | <0.5 | 10-20 | >20 |
| C-244 | 319.20/320.07 | | <1 | <1 | 10-20 | >10 |
| O/S-358 | 349.22/349.99 | | <2 | <2 | 10-20 | >5 |
| O/S-359 | 359.13/359.96 | | <5 | >5 | 50-100 | >5 |
| N-235 | 348.23/348.97 | | <0.05 | <0.05 | 1-2 | >20 |
| O/S-189 | 391.13/391.88 | | <5 | <5 | 50-100 | >20 |
| O/S-360 | 423.06/423.78 | | <2 | <2 | NT | NT |
| O/S-361 or O/S-362 | 341.13/341.90 | | <0.5 | <0.5 | 20-50 | >200 |
| O/S-361 and O/S-362 | 341.13/341.94 | | <0.5 | <0.5 | 20-50 | >100 |
| C-245 and C-246 | 333.22/334.07 | | <0.1 | <0.05 | 5-10 | >100 |
| C-247 or C-248 | 373.11/373.94 | | <0.5 | <0.5 | 10-20 | >20 |
| C-247 or C-248 | 373.11/373.88 | | <2 | <2 | 10-20 | >5 |
| O/S-363 | 355.14/355.93 | <2 | <5 | <2 | 10-20 | >5 |
| N-236 | 388.12/388.83 | | <0.05 | <0.1 | 2-5 | >50 |
| C-249 | 362.21/363.02 | <1 | <5 | <5 | 50-100 | >20 |
| C-250 or C-251 | 407.07/407.79 | <0.2 | <1 | <1 | 10-20 | >10 |
| C-250 or C-251 | 407.07/407.86 | <0.5 | <2 | <2 | 5-10 | >5 |
| C-252 | 319.20/320.05 | <0.2 | <1 | <1 | 10-20 | >10 |
| O/S-364 or O/S-365 | 375.09/375.87 | <0.1 | <1 | <1 | 10-20 | >10 |
| C-253 | 333.22/334.06 | <0.1 | <1 | <1 | 10-20 | >10 |
| N-237 or N-238 | 320.20/321.01 | <0.02 | <0.05 | <0.1 | 5-10 | >100 |
| N-239 | 354.16/354.92 | <0.05 | <0.2 | <1 | 5-10 | >10 |
| C-111 | 396.17/396.98 | <0.5 | <1 | <1 | 10-20 | >10 |
| N-240 | 320.20/321.01 | <0.1 | <0.5 | <0.5 | 10-20 | >50 |
| N-241 or N-242 | 374.11/374.85 | <0.05 | <0.05 | <0.05 | 0.2-0.5 | >10 |
| N-241 or N-242 | 374.11/374.85 | <0.02 | <0.05 | <0.1 | 1-2 | >10 |
| N-243 or N-244 | 374.17/374.92 | <0.01 | <0.05 | <0.1 | 1-2 | >20 |
| C-254 | 373.18/373.98 | <0.05 | <0.5 | <0.5 | 5-10 | >20 |
| N-245 or N-246 | 340.15/340.94 | <0.01 | <0.05 | <0.1 | 2-5 | >20 |
| C-255 | 381.20/381.96 | <0.05 | <0.2 | <0.2 | 5-10 | >50 |
| C-206 | 367.18/367.97 | <0.05 | <0.5 | <0.5 | 5-10 | >10 |
| O/S-366 | 387.14/387.92 | <0.05 | <0.1 | <0.1 | 20-50 | >200 |
| C-256 | 385.16/385.86 | <0.05 | <0.2 | <0.1 | 20-50 | >200 |
| C-257 | 320.20/321.01 | <0.1 | <0.5 | <0.2 | 2-5 | >20 |
| N-247 or N-248 | 334.22/334.99 | <0.05 | <0.05 | <0.1 | 2-5 | >50 |
| N-249 and N-250 | 320.20/321.01 | <0.05 | <0.1 | <0.1 | 2-5 | >50 |
| N-251 | 402.20/402.94 | <0.01 | <0.05 | <0.1 | 0.5-1 | >10 |
| N-252 and N-253 | 374.17/374.96 | <0.05 | <0.1 | <0.1 | 1-2 | >10 |
| N-254 and N-255 | 340.15/340.94 | <0.01 | <0.05 | <0.05 | 1-2 | >20 |
| C-258 | 339.15/339.91 | <0.05 | <0.5 | <0.2 | 10-20 | >50 |
| C-259 | 373.18/373.95 | <0.1 | <0.5 | <0.5 | 5-10 | >20 |
| N-256 | 334.22/334.99 | <0.05 | <0.5 | <0.5 | 10-20 | >20 |
| N-257 | 352.21/352.98 | <0.02 | <0.1 | <0.1 | 1-2 | >20 |
| O/S-367 | 337.16/337.96 | <0.2 | <0.5 | <1 | 20-50 | >20 |
| O/S-368 | 337.16/338.01 | <2 | <2 | <5 | 20-50 | >10 |
| N-258 | 442.03/442.69 | <0.02 | <0.05 | <0.1 | 0.1-0.2 | >2 |
| C-260 | 455.11/455.98 | <0.05 | <0.5 | <0.2 | 5-10 | >50 |
| C-261 | 387.19/388.03 | <0.05 | <0.5 | <0.5 | 10-20 | >20 |
| C-262 | 415.16/415.95 | <0.1 | <0.5 | <0.5 | 10-20 | >20 |
| C-263 | 319.20/320.03 | <0.05 | <0.5 | <0.5 | 10-20 | >20 |
| N-117 | 376.13/376.86 | <0.01 | <0.05 | <0.05 | 1-2 | >20 |
| N-259 | 376.13/376.86 | <0.01 | <0.05 | <0.05 | 1-2 | >50 |
| C-264 | 441.10/441.93 | <0.05 | <0.5 | <0.5 | 10-20 | >20 |
| O/S-369 | 351.18/351.94 | <0.05 | <0.2 | <0.1 | 10-20 | >100 |
| C-265 | 409.09/409.80 | <0.05 | <0.5 | <0.5 | 10-20 | >50 |
| N-260 | 442.09/442.77 | <0.02 | <0.05 | <0.02 | 0.5-1 | >20 |
| N-185 | 354.16/354.92 | <0.05 | <0.5 | <0.2 | 1-2 | >5 |

TABLE 3-continued

| Cmpd. No. | MW (theor./meas.) $[M + H]^+$ | SH-SY5Y/BSO $IC_{50}$ [μM] | Ht22/GLU [μM] | Pfa1/TAM $IC_{50}$ [μM] | $TC_{50}$ [μM] | Therapeutic Window (approx.. fold) |
|---|---|---|---|---|---|---|
| O/S-370 | 389.10/389.92 | <1 | <5 | <2 | 50-100 | >20 |
| N-261 | 474.37/475.06 | <0.02 | <0.2 | <0.1 | 2-5 | >20 |
| N-262 | 362.25/363.01 | <0.02 | <0.05 | <0.05 | 0.5-1 | >10 |
| C-266 | 355.19/356.01 | <0.1 | <0.5 | <0.5 | 10-20 | >20 |
| C-267 | 401.14/401.87 | <0.1 | <0.5 | <0.2 | 10-20 | >50 |

MW: molecular weight (theoretical/measured as $[M + H]^+$ using HPLC/MS), see Example A for details;
SY5Y/BSO: see Example B.1 for details;
Ht22/GLU: see Example B.2 for details;
Pfa1/TAM see Example B4 for details;
$TC_{50}$ and Therapeutic Window: see Example B.5 for details;
NT: not tested Example B.2

Inhibition of Glutamate-induced Non-apoptotic Cell Death by Compounds of the Present Invention As also shown in Table 2, the present inventors observed the surprising finding that compounds disclosed herein showed activity as inhibitors of another model of non-apoptotic cell death induced in cells of the mouse hippocampal cell line (Ht22) grown in-vitro.

Glutamate toxicity is conferred on cells from the mouse hippocampal cell line (Ht22) by inhibition of the cysteine/glutamate antiporter, System xc-, leading to impaired cysteine uptake and subsequent GSH depletion. This model is frequently used for mimicking glutathione depletion following oxidative stress in stroke, brain trauma and other neurodegenerative diseases and cellular conditions following ischemia (for example: van Leyen et al, J. Neurochem. 92:824-30 (2005)).

Compounds disclosed herein were evaluated for their ability to promote cell survival upon administration of a lethal dose of glutamate (GLU) to the cell-culture medium.

Briefly, Ht22 cells (ATCC) were propagated DMEM supplemented with 10% FBS/1% Penicillin-Streptomycin, and then seeded onto 96-well plates at a concentration of 2,000 cells/well in 100 μL of MEDIA, simultaneously with glutamate (Sigma Aldrich) to a final concentration of 5 mM, together with increasing concentrations of the compound to be tested (0.5 pM to 100 μM), and the plates incubated at 37° C./5% $CO_2$ for 72 hours. Compound dilutions were prepared from 10 mM stocks dissolved in DMSO and diluted in media. Cells treated with glutamate alone were used as negative control and alpha-tocopherol (Sigma Aldrich) was used as positive control. Compound concentrations were tested in triplicate. After incubation, cell survival was detected and quantified as described in Example B.1. $IC_{50}$ values in such assay obtained for certain compounds disclosed herein are shown in Table 2 and Table 3.

Example B.3

Specificity for Inhibition of Non-apoptotic Cell Death by Compounds of the Present Invention.

Figure 1B:
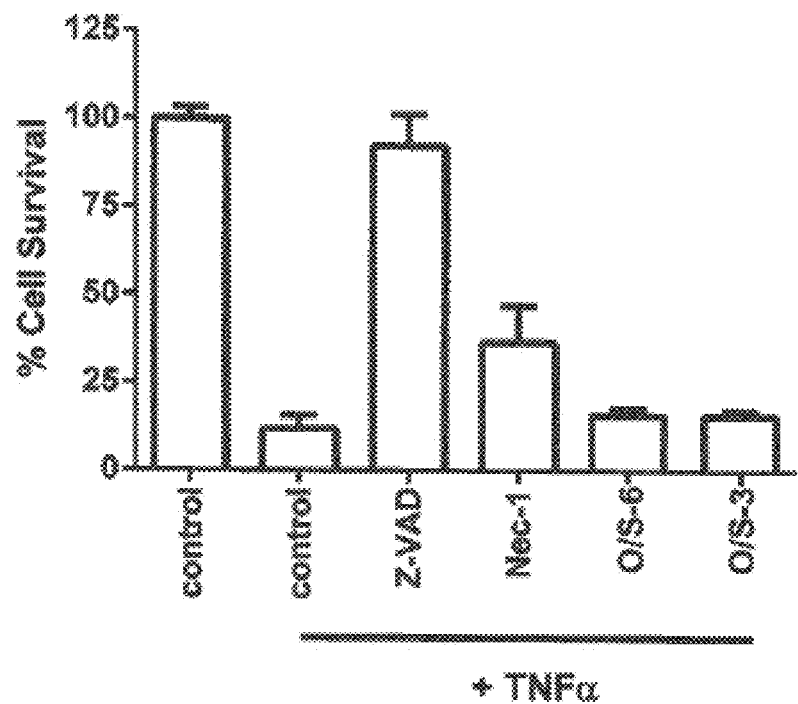
Figure 1C:
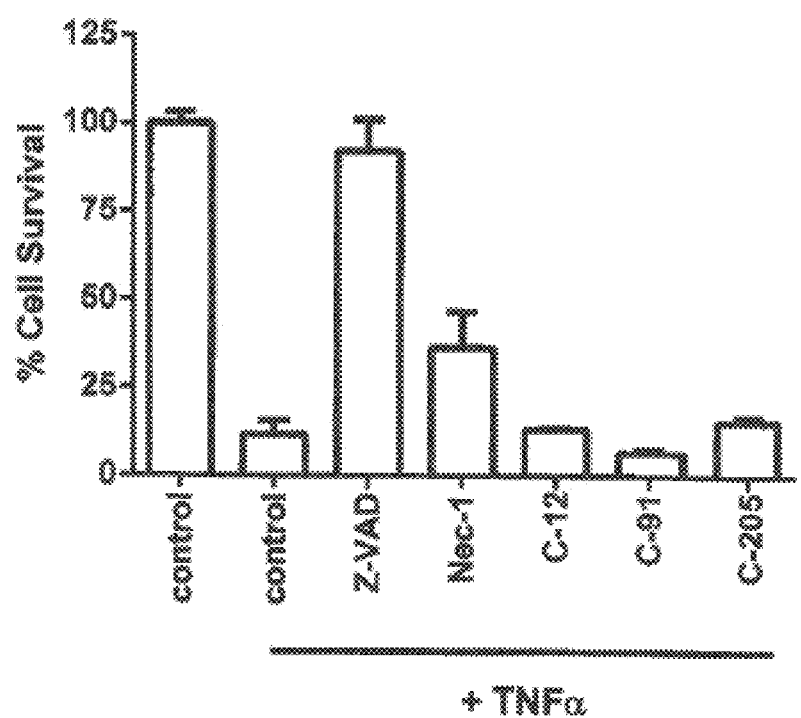

As shown in FIG. 1, the present inventors observed the surprising finding that compounds disclosed herein that showed activity as inhibitors of non-apoptotic cell death (as described above), did not appear to inhibit cell-death in an assays for classical apoptosis (for example: Alikhani et al., J. Cell Physiol. 201:341-8 (2004)).

Without being bound by theory, apoptosis (e.g., as assays in Example B.3) is believed to occur under or as a result of normal physiological conditions or events in a highly programmed manner as part of normal tissue homeostasis and cell turnover; while, conversely, non-apoptotic regulated cell death is thought to be triggered by abnormal physiological conditions or events such as external damaging stimuli and/or oxidative stress. Compounds that inhibit non-apoptotic regulated cell-death but do not appear to inhibit apoptotic cell-death may have preferred utility in the methods and applications of the present invention, as they may not interfere with the individual's innate cell-death mechanism and regulation, but preferentially only that caused by abnormal physiological conditions or events such as external damaging stimuli and/or oxidative stress.

Briefly, SH-SY5Y cells were propagated and seeded in 96-well plates, together with the compound to be tested (1 μM), generally as described in Example B.1, except they were seeded at 1,000 cell/well and instead of BSO, TNF-alpha (hivitrogen) was added to a final concentration of 10 mg/mL to induce apoptosis. The apoptosis and pan-caspase inhibitor Z-VAD-fmk (Enzo Life Science; final concentration 501 μM) and the necroptosis inhibitor Necrostatin-1 (Nec-1; Enzo Life Science; final concentration 5 μM) were used for comparison. Control wells were established with vehicle only (DMSO), with and without treatment with TNF-alpha to induce apoptosis. Cells were incubated, and cell survival was detected and quantified as described in Example B.1. Percentage cell survival after TNF-alpha-induced apoptosis for certain compounds disclosed herein are shown in FIG. 1. Surprisingly, those compounds tested appear to show more specificity than Nec-1 at known active concentrations.

Example B.4

Inhibition of Non-apoptotic Cell-death by Compounds Disclosed Herein Using a Recombinant Cell Line To combat high intracellular ROS levels, mammalian cells have evolved an intricate network of ROS scavenging in cells, in which the thioredoxin and glutathione (GSH) dependent systems prevail. Within the GSH system, glutathione peroxidase 4 (GPx4) is the most central player, as demonstrated by targeted knockout of the GPx4 gene in mice. GPx4 knockout causes early embryonic death at the same stage as mice lacking endogenous GSH synthesis, demonstrating that GPx4 is a key ROS controlling enzyme. A conditional GPx4 knockout mouse model, which allows experimental manipulation of endogenous ROS levels to mimic degenerative diseases (Seiler, A., et al, 2008; Cell Metab 8:237) was used to show that oxidative stress causes cell death by a specific signaling pathway entailing lipid peroxide generation and apoptosis-inducing-factor mediated cell death (Mannes et al, 2011; FASEB doi: 10.1096/0.10-177147). Knockout of GPx4 in neurons causes massive neurodegeneration in cortical, cerebellar and hippocampal neurons underscoring the high relevance of ROS-induced cell death signaling in the brain. Briefly, immortalised fibroblasts from these mice were made to contain tamoxifen-inducible CreERT2, which catalyzes the functional ablation of both copies of GPx4 and resulting in a complete knockout of GPx4, a massive ROS burst, and cell death in cell culture. These cells (Pfa1 cells) were used to characterize compounds of the present invention, whereby tamoxifen (TAM) was given on day 0 along with the compound under test, and 72 hours later cell survival was evaluated using AlamarBlue. Using a compound concentration range from 0.5 picomolar to 100 micrormolar and GraphPad Prism, the $IC_{50}$ of each tested compound was estimated. Such $IC_{50}$ values obtained for certain compounds disclosed herein are shown in Table 3.

Example B.5

Cellular Toxicity of Compounds of the Invention

An estimate of the toxicity for compounds of the invention was obtained by using the same assay as described in Example BA, but without the addition of TAM. Compounds were so tested over a concentration range from 100 nanomolar to 100 micromolar and the resulting $TC_{50}$ value estimated using GraphPad Prism. Such $TC_{50}$ values obtained for certain compounds disclosed herein, together with an approximate therapeutic window (estimated by dividing each $TC_{50}$ by the corresponding $IC_{50}$ determined from example B.4) are shown in Table 3.

Examples C

Activity in Animal Models of Conditions Disorders and Diseases

The in-vivo activity of compounds disclosed herein is demonstrated by one or more animal models including those described in more detail below.

Example C.1

Utility of Compounds Disclosed Herein for the Treatment of Liver-ischemic-reperfusion Injury Compounds disclosed herein are found to have surprising utility in the treatment of ischemia-reperfusion injury (IRI) of the liver, using an in-vivo murine model of such condition/disorder/disease.

Compounds of the invention that reduce IRI damage in the liver can be proposed as drug-candidates and have utility as medicines for limiting organ trauma upon transplantation and other diseases or conditions caused by ischemia-reperfusion and such utility can be tested in an in vivo model, for example, as described by Abe et al. (Free Radic. Biol. Med. 46: 1-7 (2009)).

Figure 2A:
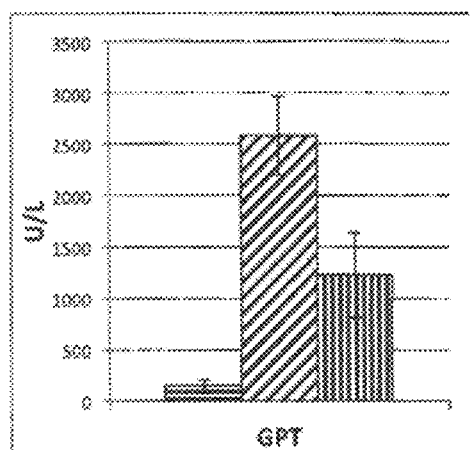
FIG. 2: Efficacy of a compound of the invention in an animal model of liver IRI. A significant reduction of the serum markers for liver cell damage, GPT (a) and GOT (b), compared to vehicle control, upon treatment of mice with compound N-2 ("Cmpd") of Table 1-N following IRI liver damage is shown. The "Sham" bar represents the data from control animals that were treated to the same protocol but without atraumatic clipping. Errors shown are SEM. Significant differences are seen between IRI+vehicle compared to IRI+Cmpd, as well as between IRI+vehicle compared to Sham+vehicle. No significant difference is seen between IRI+Cmpd and Sham+vehicle.
FIG. 2(c) shows a photograph representing a visual comparison between vehicle and compound-treated livers of mice from this study.
Figure 2B:
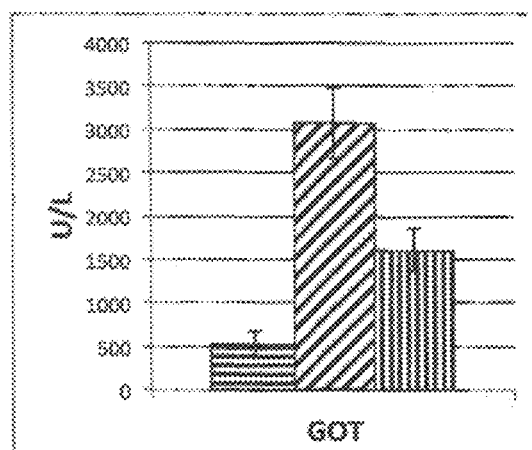
Figure 2C:
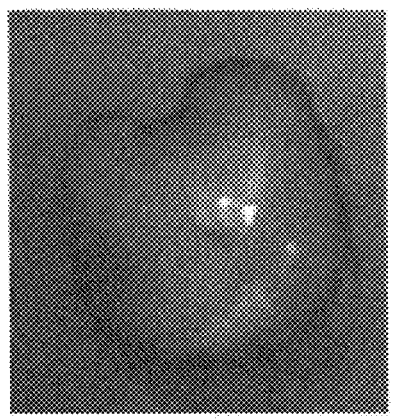
Figure 2C:
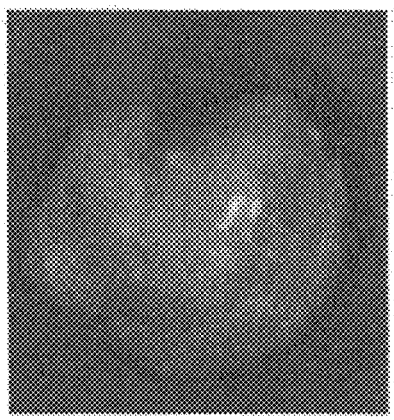

Briefly, to test such utility of compounds disclosed herein, ischemia is induced in the liver of 6-8 week old C57BL/6 mice (Charles River) by midline laparotomy whereby the blood supply to the left and median lobes of the liver is interrupted via atraumatic clipping for 90 rain, followed by reperfusion for a period of 24h. After reperfusion, but prior to final abdominal closure, animals are treated with a single i.p. dose of the compound to be tested (10 mg/Kg), or with vehicle (DMSO) as negative control. Markers to be investigated for IRI of liver include liver parameters from serum (ALT/GPT, AST/GOT, Bilirubin, Urea), histopathological analysis and rtPCR of inflammatory and non-apoptotic cell death markers (such as TNF-alpha and INF-gamma). FIGS. 2(a) and (b) show a significant reduction of the serum markers for liver cell damage, OPT and GOT, respectively (compared to vehicle control), upon treatment with a compound of the invention (N-2) of mice following IRI liver damage. The "Sham" bar represents the data from control animals that were treated to the same protocol but without atraumatic clipping. FIG. 2(c) shows a photograph representing a visual comparison between vehicle and compound-treated livers of mice from this study.

Example C.2

Utility of Compounds Disclosed Herein for the Treatment of Kidney-isehemic-reperfusion Injury Compounds disclosed herein are investigated for their utility in the treatment of ischemia-reperfusion injury (IRI) of the kidney, using an in-vivo murine model of such condition/disorder/disease.

Compounds of the invention that reduce IRI damage in the kidney can be proposed as drug-candidates and have utility as medicines for limiting organ trauma upon transplantation and other diseases or conditions caused by isehemia-reperfusion, and such utility can be tested in an in vivo model, for example, as described by Wu et al. (J. Clin. Invest. 117:2847-59 (2007)) and Linkermann et al. (Kidney Int. 81: 751-761 (2012)).

Figure 3:
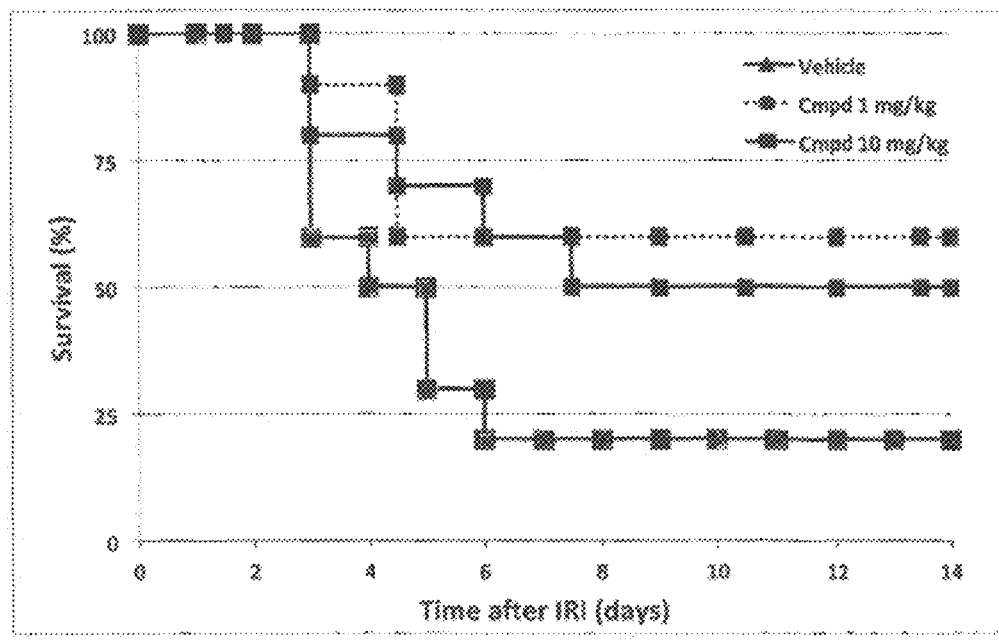
FIG. 3: Efficacy of a compound of the invention in an animal model of kidney IRI. Improved survival of mice suffering kidney-ischemic reperfusion injury (IRI), compared to vehicle control, after treatment with compound N-2 ("Cmpd") of Table 1-N at a dose of both 1 and 10 mg/kg was observed.

Briefly, to test such utility of compounds disclosed herein, ischemia is induced in the kidney of 6-8 week old C57BL/6 mice by interruption of the blood supply to the kidney via reversible clipping of the Arteria renalis for 30 min, followed by reperfusion for a period of 24 h. Mice are treated with compound (or vehicle control) generally as described in Example C.1 at 1 hour prior to and four hours after abdomal closure and once daily over a period of 14 days. Markers to be investigated for IRI of kidney include reduction of creatnine levels in the serum along with histopathological analysis. FIG. 3 shows an improvement of survival of mice suffering kidney-ischemic reperfision injury (compared to vehicle control) after treatment with a compound of the invention (N-2) at a dose of both 1 and 10 mg/kg.

Example C.3

Utility of Compounds Disclosed Herein for the Treatment of Paracetamol (APAP) Intoxication Compounds disclosed herein are investigated for their utility in the treatment of APAP intoxication, using an in-vivo murine model of such condition/disorder/disease.

Compounds of the invention that inhibit non-apoptotic regulated cell-death can be proposed as drug-candidates and have utility as medicines for limiting the effects of APA intoxication, and such utility can be tested in an in vivo model, for example, as described by Patterson et al. (Chem. Res. Toxicol. 2013, "Article ASAP Web publication", date 22 May 2013).

Briefly, to test such utility of compounds disclosed herein, groups of 6-8 week-old male C57BL/6 mice are given an i.p. injection of APAP (400 mg/kg) in saline, and at the same time or at a given time thereafter, compounds to be tested are administered (1 mg/Kg or 10 mg/Kg) by i.p. injection, or vehicle (DMSO) as control. Mice are sacrificed by $CO_2$ asphyxiation 6 h after the APAP dose, and to assess liver damage, livers are removed and washed in phosphate buffered saline, and portions of liver tissue are fixed in 10% buffered formalin or flash frozen at −80° C. The extent of non-apoptotic cell death is scored by haematoxylin and eosin staining. The extent of APAP-induced liver injury is determined by measuring aspartate aminotransferase (AST) and alanine aminotransferase (ALT) catalytic activities in serum. Reduced GSH levels in liver and liver mitochondria extracts are measured using a glutathione assay kit.

Example C.4

Utility of Compounds Disclosed Herein for the Treatment of Cisplatin Intoxication Compounds disclosed herein are investigated for their utility in the treatment of cisplatin intoxication, using an in-vivo murine model of such condition/disorder/disease.

Compounds of the invention that inhibit non-apoptotic regulated cell-death can be proposed as drug-candidates and have utility as medicines for limiting the effects of cisplatin intoxication, and such utility can be tested in an in vivo model, for example, as described by Tristao et al. (Ren. Fail. 34:373-7 (2012)).

Briefly, to test such utility of compounds disclosed herein, one day before single cisplatin treatment (25 mg/Kg i.p dissolved in 40% PEG), vehicle (DMSO) as control or compounds to be tested are administered (1 mg/Kg or 10 mg/Kg), e.g. injected i.p., in 6-8 week-old C57BL/6 male mice. Compound (or vehicle control) treatment is continued daily during an observation period of four to five days. Three days after cisplatin treatment, liver, spleen, and kidney samples are dissected for histopathological analysis. Blood samples are collected to determine blood urea nitrogen and plasma creatinine levels.

Example C.5

Utility of Compounds Disclosed Herein for the Treatment of Traumatic Brain Injury Compounds disclosed herein are investigated for their utility in the treatment of traumatic brain injury, using an in-vivo murine model of such condition/disorder/disease.

Non-apoptotic regulated cell death plays a major role in the pathogenesis of traumatic brain injury (TBI), and the utility of compounds of the invention as a medicine for such condition/disorder/disease can be investigated using an in-vivo murine model for example as described by You et al. (J. Cereb. Blood Flow Metab. 28:1564-73 (2008)), or Rauen et al. (J. Neurotrauma 30:1442-8 (2013)).

Figure 4:
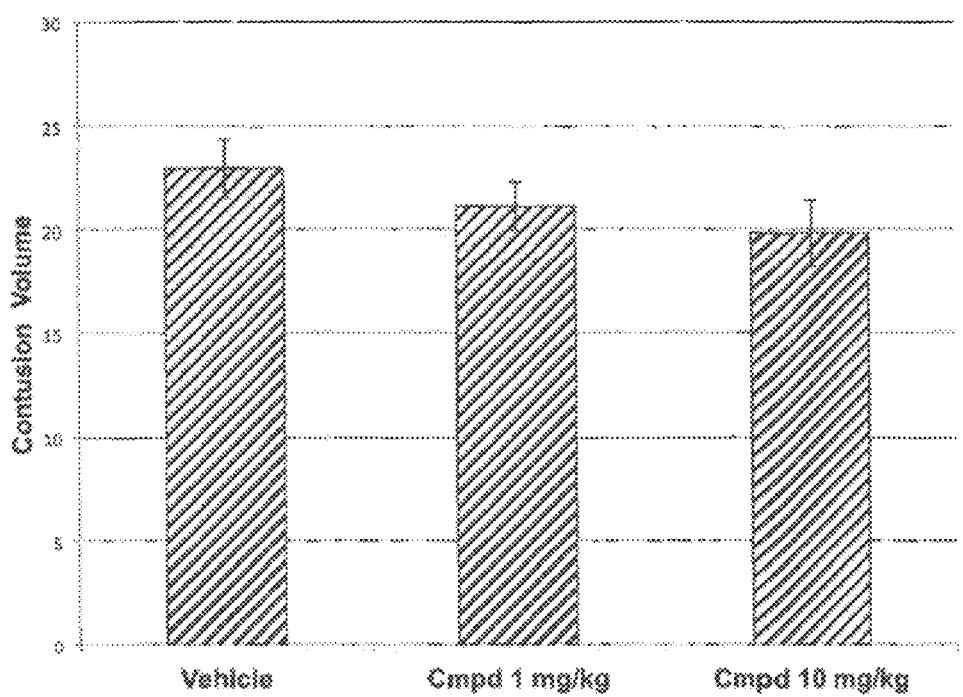
FIG. 4: Efficiency of a compound of the invention in an animal model of traumatic brain injury. A trend of a (non-significant) positive effect of treatment with compound N-2 ("Cmpd"), reducing the contusion volume in the brains of mice following traumatic brain injury (TBI) compared to vehicle control.

Briefly, to test such utility of compounds disclosed herein, male C57BL/6 mice are anesthetised prior to the induction of trauma. Core body temperature is maintained at 37° C. using a feedback-controlled heating pad connected to a rectal probe. To induce trauma, a craniotorny is prepared over the right parietal cortex. Controlled cortical impact (CCI) is delivered perpendicular to the surface of the brain with a custom-made CCI applicator for mice using the following parameters: 8 m/s velocity, 3 mm diameter, 1 mm brain displacement and 150 ms duration. Following CCI, the skull is closed by affixing the removed bone flap using veterinary-grade tissue glue (Vetbond, 3M, St. Paul, Minn.). Compounds are administered at 1 mgKg or 10 mg/Kg (dissolved in 40% PEG) 15 minutes after TBI induction and 40% PEG is included as vehicle control. The animals are recovered from anesthesia in an incubator heated to 33° C. Animals are sacrificed and the brain is removed 24 h after CCI and immediately frozen on crushed dry ice and stored at −80° C. Coronal sections (10 µm thick) are cut from rostral to caudal using a cryostat (CryoStar HM 560; Microm, Walldorf, Germany), and 1 in every 50 sections is prepared for further analysis. The sections are stained with cresyl violet for quantifying the area of contused brain, and contusion volume is calculated and the effect of the compounds tested observed following analysis of such data. FIG. 4 shows a trend of a (non-significant) positive effect of treatment with a compound of the invention (N-2), reducing the contusion volume in the brains of mice following TBI.

Example C.6

Utility of Compounds Disclosed Herein for the Treatment of Rheumatoid Arthritis (RA)

Compounds disclosed herein are investigated for their utility in the treatment of RA, using an in-vivo murine model of such condition/disorder/disease.

The collagen-induced arthritis (CIA) mouse model is the most commonly studied autoimmune model of rheumatoid arthritis, for example as described by Brand et al. (Nat. Protoc. 2:1269-75 (2007)), and can be used to study the utility of compounds of the invention to treat RA.

Briefly, to test such utility of compounds disclosed herein, RA is induced in this model by immunization with an emulsion of complete Freund's adjuvant and type II collagen as described in Brand et al. (2007). Compounds are administered daily by i.p. injections starting at day one. 40% PEG is used as vehicle control. Mice are monitored daily and disease progression is assessed using a scoring system.

Example C.7

Utility of Compounds Disclosed Herein for the Treatment of Multiple Sclerosis (MS)

Compounds disclosed herein are investigated for their utility in the treatment of MS, using an in-vivo murine model of such condition/disorder/disease.

Experimental autoimmune encephalomyelitis (EAE) is the most commonly used experimental model for the human inflammatory demyelinating disease, multiple sclerosis (MS), for example as described by Racke (Curr. Protoc. Neurosci. 9:unit 9.7 (2001)), and can be used to study the utility of compounds of the invention to treat MS.

Briefly, to test such utility of compounds disclosed herein, EAE is induced as described in Racke (2001). Compounds are administered daily by i.p. injections starting at day one. 40% PEG is used as vehicle control. Mice are monitored daily and disease progression is assessed using a scoring system.

Example C.8

Utility of Compounds Disclosed Herein for the Treatment of Lipopolysaccharide (LPS)-induced Endotoxic Shock Compounds disclosed herein are investigated for their utility in the treatment of LPS-induced endotoxic shock, using an in-vivo murine model of such condition/disorder/disease.

Compounds of the invention that inhibit non-apoptotic regulated cell-death can be proposed as drug-candidates and have utility as medicines for limiting the effects of LPS-induced endotoxic shock, and this utility can be investigated using an in-vivo murine model for example as described by Duprez et al. (Immunity 35:908-18 (2011)).

Briefly, to test such utility of compounds disclosed herein, endotoxic shock is induced by i.p. injection of LPS at a dose of 20 mg/kg of body weight in 6-8 week-old male C57BL/6 mice. Compounds to be tested are administered daily (1 mg/Kg or 10 mg/Kg) by i.p. injection, or vehicle (DMSO) as control, for a subsequent observation period of 4 days. Survival of mice is monitored by inspection twice daily for 5 days.

Example D

Selection and Development of Drug Candidates

In order to select the most appropriate compound to enter further experiments and to assess its suitability for use in a therapeutic/pharmaceutical composition for the treatment of one or more conditions, disorders and/or diseases, additional data are collected. Such data can include the in vitro inhibition of non-apoptotic cell-death, in particular inhibition of necroptosis or ferroptosis, as measured by $IC_{50}$, or from applicable in-vivo animal models of conditions, disorders and/or diseases. Furthermore, such experiments may also include the elucidation and/or determination of the target or mechanism of action of the subject compound or the target profile of the subject compound, and other characteristics of the subject compound, such as the binding affinity of the compound to the target(s) or the binding site of the compound on the target(s) and pharmacokinetic properties. Such experiments may also include molecular modelling of the drug-target interaction and the identification of metabolites formed after administration.

The compound that shows the most appropriate results for $IC_{50}$ for inhibition of non-apoptotic cell-death inhibition and/or in-vivo animal-model data, and/or other features, including absorption, distribution, metabolism, and excretion (ADME), pharmacokinetic and pharmacodynamic properties, may be chosen to enter further experiments. Such experiments may include, for example, therapeutic profiling and toxicology in animals, phase I clinical trials in humans and other clinical trails.

The invention claimed is:
1. A compound selected from the group consisting of a spiroquinoxaline derivative having the general formula (I)

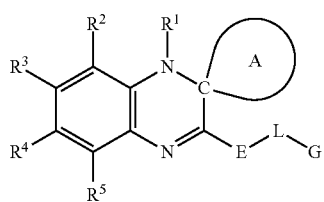

(I)

and solvates, salts, complexes, polymorphs, crystalline forms, racemic mixtures, diastereomers, enantiomers, tautomers, isotopically labeled forms, prodrugs, and combinations thereof,
wherein
E is —N($R^6$)—;
L is selected from the group consisting of $C_{1-10}$ alkylene, $C_{2-10}$ alkenylene, $C_{2-10}$ alkynylene, 1,1-$(CH_2)_a$-cyclopropylene-$(CH_2)_b$—, wherein each of a and b is independently selected from an integer between 0 and 3, and —$(CH_2)_m$—[Y—$(CH_2)_n]_o$—, wherein m is an integer between 1 and 6, n is an integer between 0 and 3, o is an integer between 1 and 3, wherein if n is 0 then o is 1; Y is independently selected from O, S, and —N($R^7$)—; and each of the $C_{1-10}$ alkylene, $C_{2-10}$ alk-enylene, $C_{2-10}$ alkynylene, 1,1-cyclopropylene, —$(CH_2)_m$—, and —$(CH_2)_n$— groups is optionally substituted with one or more independently selected $R^{30}$;
G is phenyl, optionally substituted with 1, 2, 3, 4 or 5 independently selected $R^8$;
ring A is a monocyclic 4- to 10-membered N-heterocycloalkylene or a monocyclic 4- to 10-membered O/S-heterocycloalkylene, wherein each of the N-heterocycloalkylene and O/S-heterocycloalkylene is optionally substituted with one or more independently selected $R^9$;
$R^1$ is H;
$R^2$, $R^3$, $R^4$, and $R^5$ are independently selected from the group consisting of —H, alkyl, alkenyl, alkynyl, aryl, heteroaryl, cycloalkyl, heterocyclyl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, aryl, heteroaryl, cycloalkyl, and heterocyclyl groups is optionally substituted with one or more independently selected $R^{30}$;
or $R^2$ and $R^3$ may join together with the atoms to which they are attached to form a ring which is optionally substituted with one or more independently selected $R^{30}$; $R^3$ and $R^4$ may join together with the atoms to which they are attached to form a ring which is optionally substituted with one or more independently selected $R^{30}$; and/or $R^4$ and $R^5$ may join together with the atoms to which they are attached to form a ring which is optionally substituted with one or more independently selected $R^{30}$;
$R^6$ is H;
$R^7$ is selected from the group consisting of —H, alkyl, alkenyl, alkynyl, cycloalkyl, aryl, heteroaryl, heterocyclyl, —$OR^{11}$, and —$NHR^{20}$, wherein each of the alkyl, alkenyl, alkynyl, cycloalkyl, aryl, heteroaryl, and heterocyclyl groups is optionally substituted with one or more independently selected $R^{30}$;
$R^8$ is, in each case, selected from the group consisting of alkyl, alkenyl, alkynyl, aryl, heteroaryl, cycloalkyl, heterocyclyl, halogen, —CN, azido, —$NO_2$, —$OR^{11}$, —$N(R^{12})(R^{13})$, —$N(R^{11})(OR^{11})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, aryl, heteroaryl, cycloalkyl, and heterocyclyl groups is optionally substituted with one or more independently selected $R^{30}$;
$R^9$ is, when substituting a hydrogen atom bound to a ring carbon atom, independently selected from the group consisting of alkyl, alkenyl, alkynyl, aryl, heteroaryl, cycloalkyl, heterocyclyl, halogen, —CN, azido, —$NO_2$, —$OR^{11}$, —$N(R^{12})(R^{13})$, —$S(O)_{0-2}R^{11}$, —$S(O)_{1-2}OR^{11}$, —$OS(O)_{1-2}R^{11}$, —$OS(O)_{1-2}OR^{11}$, —$S(O)_{1-2}N(R^{12})(R^{13})$, —$OS(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$XC(=X)R^{11}$, and —$XC(=X)XR^{11}$, wherein each of the alkyl, alkenyl, alkynyl, aryl, heteroaryl, cycloalkyl, and heterocyclyl groups is optionally substituted with one or more independently selected $R^{30}$, and/or any two $R^9$ which are bound to the same carbon atom of ring A may join together to form =X; or $R^9$ is, when substituting a hydrogen atom bound to a ring nitrogen atom, independently selected from the group consisting of alkyl, alkenyl, alkynyl, aryl, heteroaryl, cycloalkyl, heterocyclyl, —$OR^{11}$, —$N(R^{12})(R^{13})$, —$S(O)_{1-2}R^{11}$, —$S(O)_{1-2}OR^{11}$, —$S(O)_{1-2}N(R^{12})(R^{13})$, —$N(R^{11})S(O)_{1-2}R^{11}$, —$NR^{11}S(O)_{1-2}OR^{11}$, —$NR^{11}S(O)_{1-2}N(R^{12})(R^{13})$, —$C(=X)R^{11}$, —$C(=X)XR^{11}$, —$N(R^{14})C(=X)R^{11}$, and —$N(R^{14})C(=X)XR^{11}$, wherein each of the alkyl, alkenyl, alkynyl, aryl, heteroaryl, cycloalkyl, and heterocyclyl groups is optionally substituted with one or more independently selected $R^{30}$; or $R^9$ is, when bound to a ring sulfur atom of ring A, independently selected from the group consisting of alkyl, alkenyl, alkynyl, aryl, heteroaryl, cycloalkyl, heterocyclyl, —$OR^{11}$, and =O, wherein each of the alkyl, alkenyl, alkynyl, aryl, heteroaryl, cycloalkyl, and heterocyclyl groups is optionally substituted with one or more independently selected $R^{30}$;

X is independently selected from O, S, and $N(R^{14})$;

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —$N=CR^{15}R^{16}$, wherein each of the alkyl, alkenyl, alkynyl, cycloalkyl, aryl, heteroaryl, and heterocyclyl groups is optionally substituted with one or more independently selected $R^{30}$;

$R^{14}$ is independently selected from the group consisting of —H, alkyl, alkenyl, alkynyl, cycloalkyl, aryl, heteroaryl, heterocyclyl, and —$OR^{11}$, wherein each of the alkyl, alkenyl, alkynyl, cycloalkyl, aryl, heteroaryl, and heterocyclyl groups is optionally substituted with one or more independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more independently selected $R^{30}$, wherein each of the alkyl, alkenyl, alkynyl, cycloalkyl, aryl, heteroaryl, and heterocyclyl groups is optionally substituted with one or more independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$; and $R^{30}$ is a $1^{st}$ level substituent and is, in each case, independently selected from the group consisting of alkyl, alkenyl, alkynyl, aryl, heteroaryl, cycloalkyl, heterocyclyl, halogen, —CN, azido, —$NO_2$, —$OR^{71}$, —$N(R^{72})(R^{73})$, —$S(O)_{0-2}R^{71}$, —$S(O)_{1-2}OR^{71}$, —$OS(O)_{1-2}R^{71}$, —$OS(O)_{1-2}OR^{71}$, —$S(O)_{1-2}N(R^{72})(R^{73})$, —$OS(O)_{1-2}N(R^{72})(R^{73})$, —$N(R^{71})S(O)_{1-2}R^{71}$, —$NR^{71}S(O)_{1-2}OR^{71}$, —$NR^{71}S(O)_{1-2}N(R^{72})(R^{73})$, —$C(=X^1)R^{71}$, —$C(=X^1)X^1R^{71}$, —$X^1C(=X^1)R^{71}$, and —$X^1C(=X^1)X^1R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a $1^{st}$ level substituent is optionally substituted by one or more $2^{nd}$ level substituents, wherein said $2^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —$CF_3$, —CN, azido, —$NO_2$, —$OR^{81}$, —$N(R^{82})(R^{83})$, —$S(O)_{0-2}R^{81}$, —$S(O)_{1-2}OR^{81}$, —$OS(O)_{1-2}R^{81}$, —$OS(O)_{1-2}OR^{81}$, —$S(O)_{1-2}N(R^{82})(R^{83})$, —$OS(O)_{1-2}N(R^{82})(R^{83})$, —$N(R^{81})S(O)_{1-2}R^{81}$, —$NR^{81}S(O)_{1-2}OR^{81}$, —$NR^{81}S(O)_{1-2}N(R^{82})(R^{83})$, —$C(=X^2)R^{81}$, —$C(=X^2)X^2R^{81}$, —$X^2C(=X^2)R^{81}$, and —$X^2C(=X^2)X^2R^{81}$, and/or any two $2^{nd}$ level substituents which are bound to the same carbon atom of a cycloalkyl or heterocyclyl group being a $1^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups being a $2^{nd}$ level substituent is optionally substituted with one or more $3^{rd}$ level substituents, wherein said $3^{rd}$ level substituent is, in each case, independently selected from the group consisting of $C_{1-3}$ alkyl, halogen, —$CF_3$, —CN, azido, —$NO_2$, —OH, —$O(C_{1-3}$ alkyl), —$OCF_3$, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)OH, —C(=O)O($C_{1-3}$ alkyl), —C(=O)$NH_{2-z}(C_{1-3}$ alkyl)$_z$, —NHC(=O)($C_{1-3}$ alkyl), —NHC(=NH)$NH_{z-2}$ ($C_{1-3}$ alkyl)$_z$, and —$N(C_{1-3}$ alkyl)C(=NH)$NH_{2-z}$ ($C_{1-3}$ alkyl)$_z$, wherein z is 0, 1, or 2 and $C_{1-3}$ alkyl is methyl, ethyl, propyl or isopropyl, and/or any two $3^{rd}$ level substituents which are bound to the same carbon atom of a 3- to 14-membered cycloalkyl or heterocyclyl group being a $2^{nd}$ level substituent may join together to form =O, =S, =NH, or =$N(C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —$CF_3$, —CN, azido, —$NO_2$, —OH, —$O(C_{1-3}$ alkyl), —$OCF_3$, =O, —$S(C_{1-3}$ alkyl), —$NH_2$, —$NH(C_{1-3}$ alkyl), —$N(C_{1-3}$ alkyl)$_2$, —$NHS(O)_2(C_{1-3}$ alkyl), —$S(O)_2NH_{2-z}(C_{1-3}$ alkyl)$_z$, —C(=O)($C_{1-3}$ alkyl), —C(=O)OH, —C(=O)O($C_{1-3}$ alkyl), —C(=O)$NH_{2-z}(C_{1-3}$ alkyl)$_z$, —NHC(=O)($C_{1-3}$ alkyl), —NHC(=NH)$NH_{z-2}$ ($C_{1-3}$ alkyl)$_z$, and —$N(C_{1-3}$ alkyl)C(=NH)$NH_{2-z}(C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —$CF_3$, —CN, azido, —$NO_2$, —OH, —O($C_{1-3}$ alkyl), —$OCF_3$, =O, —S($C_{1-3}$ alkyl), —$NH_2$, —NH($C_{1-3}$ alkyl), —N($C_{1-3}$ alkyl)$_2$, —NHS(O)$_2$($C_{1-3}$ alkyl), —S(O)$_2NH_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and N($R^{84}$), wherein $R^{84}$ is —H or $C_{1-3}$ alkyl, with the proviso that (1) when $R^2$ to $R^5$ are each H, L is —$CH_2$—, and
(i) G is unsubstituted phenyl, then ring A is not

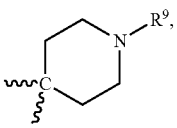
or wherein $R^9$ is —S(O)$_2$N(CH$_3$)$_2$, (cyclopropyl)sulfonyl, or (3-pyridinyl)sulfonyl, or $R^9$ is —C(O)Z, wherein Z is methyl, tert-butyl, methoxymethyl, 2-methoxyethyl, —CH$_2$NHC(O)CH$_3$, 2-methoxyethylamino, morpholin-4-ylmethyl, 2-furanylmethylamino, (2-methyl-1H-imidazol-1-yl)methyl, 2-furanyl, 3-furanyl, pyridin-2-yl, pyridin-3-yl, pyridin-4-yl, pyrazin-2-yl, 1-ethyl-1H-pyrazol-3-yl, or 1-ethyl-1H-pyrazol-5-yl;

(ii) G is unsubstituted phenyl, then ring A is not

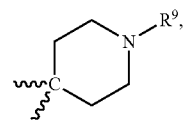

wherein $R^9$ is (1,3,5-trimethyl-1H-pyrazol-4-yl)sulfonyl or —C(O)Z, wherein Z is 2-methoxyethylamino, methoxycarbonylmethylamino, (2-trifluoromethylphenyl)amino, 5-chloro-1H-indol-2-yl, 4,5,6,7-tetrahydro-1H-indazol-3-yl, or 3-(2-thienyl)-1H-pyrazol-5-yl;

(iii) G is 2-chlorophenyl, 3-chlorophenyl, 4-chlorophenyl, 3-fluorophenyl, 4-fluorophenyl, 2-methylphenyl, 3-methylphenyl, 4-methylphenyl, 3-methoxyphenyl, or 4-methoxyphenyl, then ring A is not

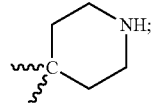

(iv) G is 3-methoxyphenyl, then ring A is not

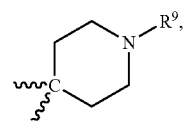

wherein $R^9$ is (3,5-dimethyl-1H-pyrazol-4-yl)sulfonyl;

(v) G is 4-fluorophenyl, then ring A is not

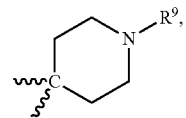

wherein $R^9$ is —C(O)Z, wherein Z is 6-methoxy-1H-indol-2-yl or 3,4-dimethoxyphenyl; or (vi) G is 4-chlorophenyl, then ring A is not

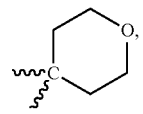

wherein $R^9$ is —C(O)Z, wherein Z is 1-methyl-2-(2-methyl-1H-imidazol-1-yl)ethyl;

(2) when ring A is

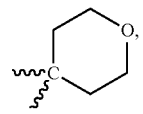

$R^2$ and $R^5$ are both H, L is —$CH_2$—, and
(i) $R^3$ and $R^4$ are both H, then G is not 3-methylphenyl, 3-methoxyphenyl, 4-chlorophenyl, or 4-fluorophenyl; or
(ii) $R^3$ and $R^4$ are both methyl, then G is not 4-fluorophenyl; and (3) when $R^2$ and $R^5$ are both H, L is —$CH_2$.

2. The compound of claim 1, wherein ring A contains 1 ring nitrogen atom and is 6-membered or 7-membered.

3. The compound of claim 1, wherein ring A is selected from the group consisting of piperidinylene, azepanylene (e.g., homopiperidinylene), azetidinylene, pyrrolidinylene, azocanylene, pyrazolidinylene, hexahydropyridazinylene, hexahydropyrimidinylene, diazepanylene (e.g., homopiperazinylene), diazocanylene, triazepanylene, and triazocanylene, each of which is optionally substituted with one or more independently selected $R^9$.

4. The compound of claim 1, wherein ring A is 4-, 5-, 6- or 7-membered.
5. The compound of claim 1 wherein the compound is selected from the group consisting of:
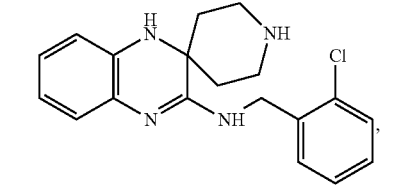
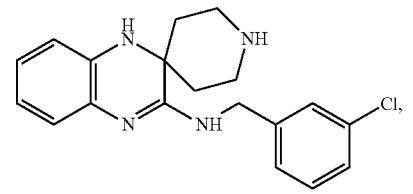
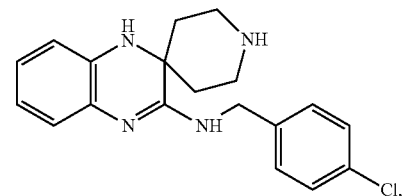
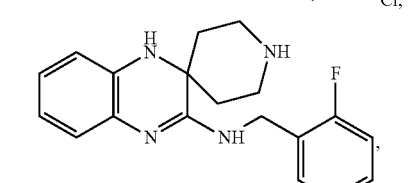
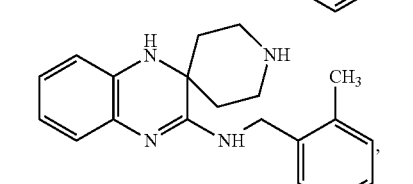
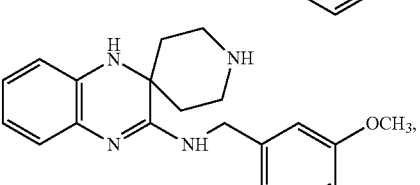
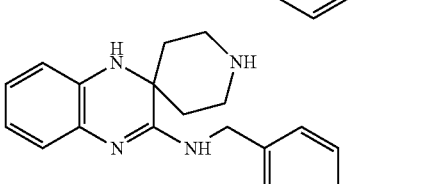
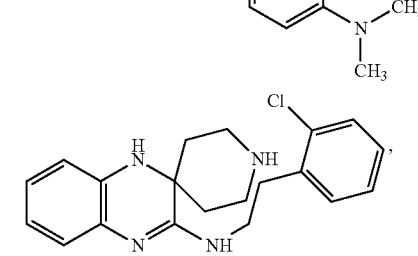
-continued
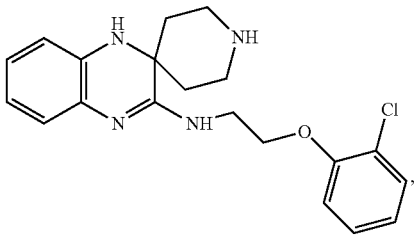
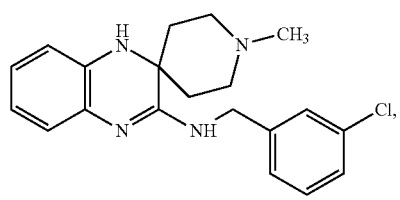
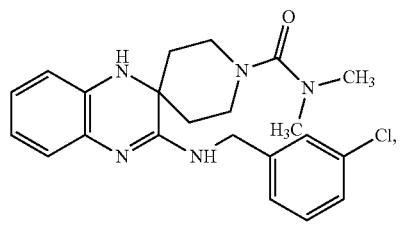
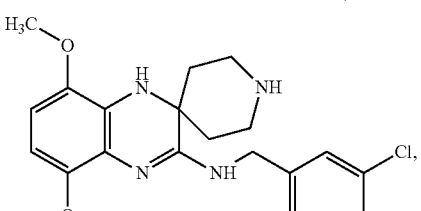
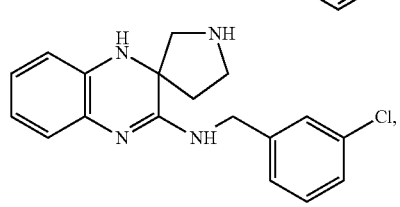

-continued
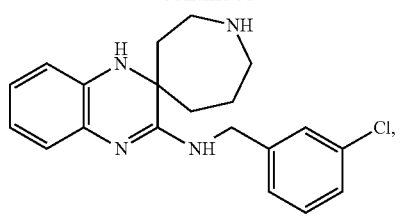
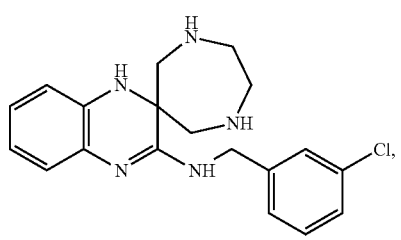
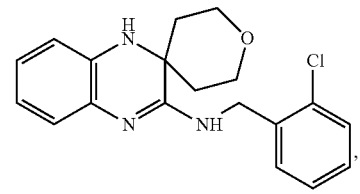
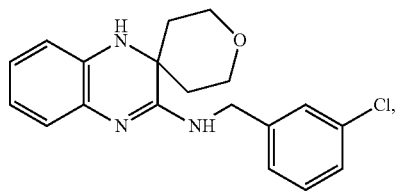
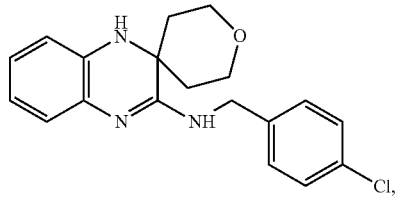
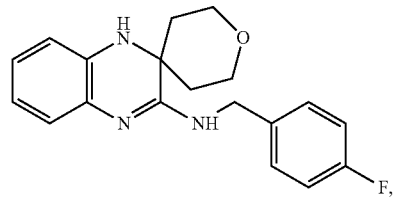
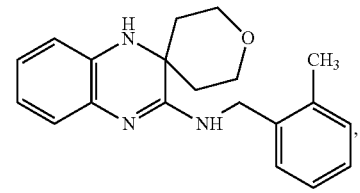
-continued
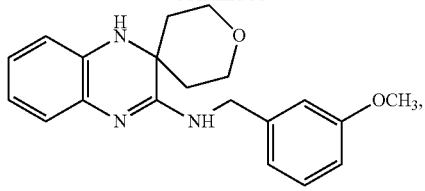
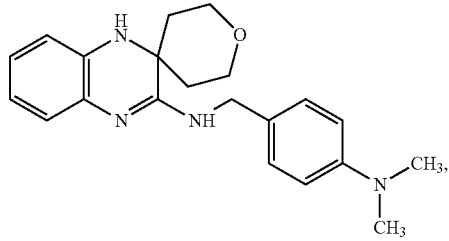
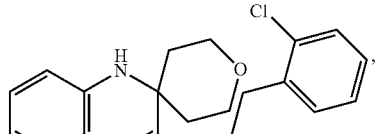
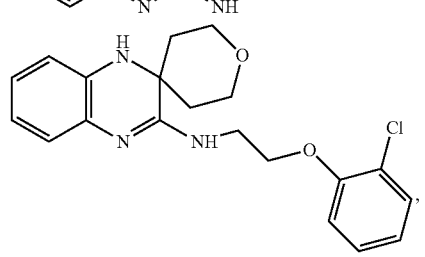
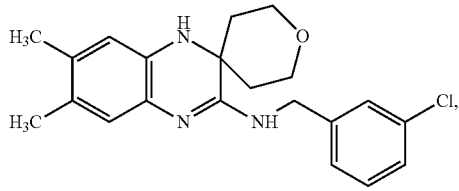
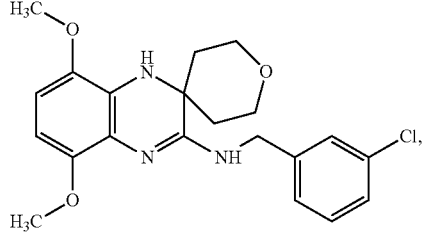
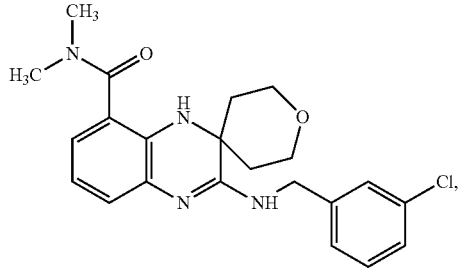
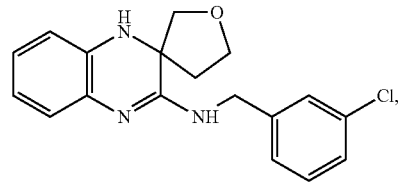

-continued

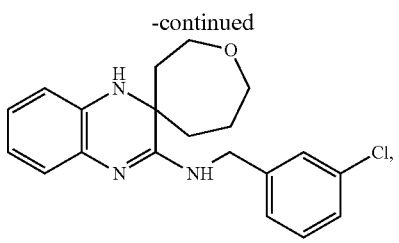

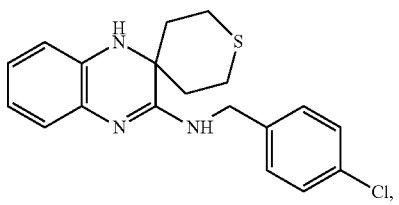

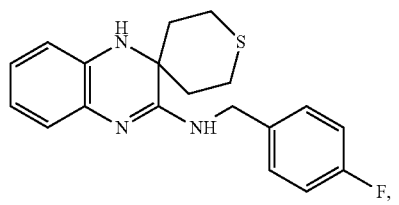

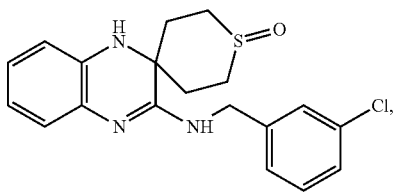

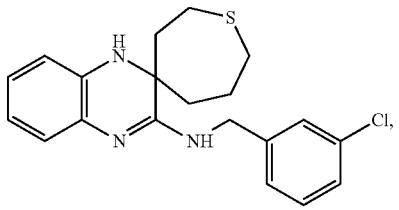

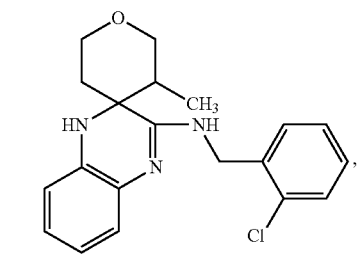

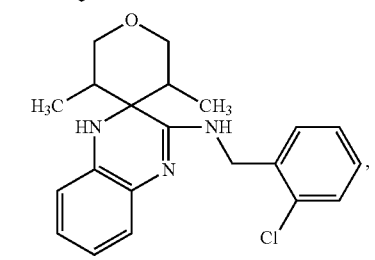

and solvates, salts, complexes, polymorphs, crystalline forms, racemic mixtures, diastereomers, enantiomers, tautomers, isotopically labeled forms, prodrugs, and combinations thereof.

6. The compound of claim 1 wherein the compound is selected from the group consisting of:

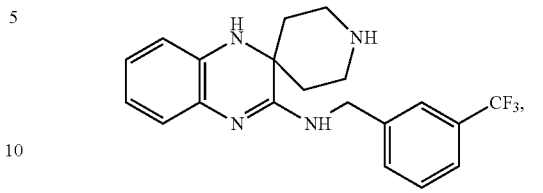

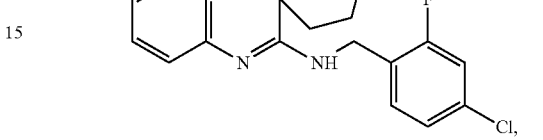

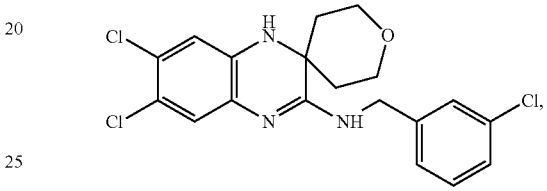

and solvates, salts, complexes, polymorphs, crystalline forms, racemic mixtures, diastereomers, enantiomers, tautomers, isotopically labeled forms, prodrugs, and combinations thereof.

7. The compound of claim 1, wherein the compound is selected from the group consisting of:

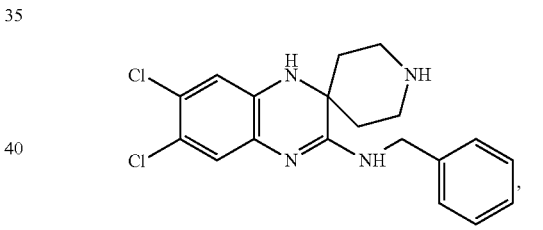

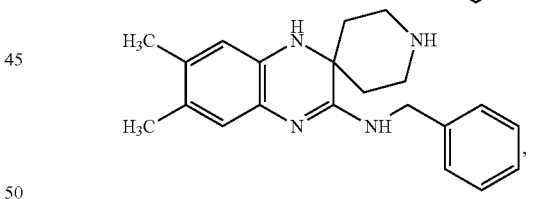

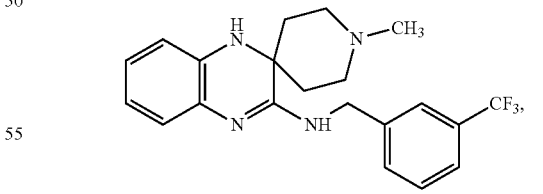

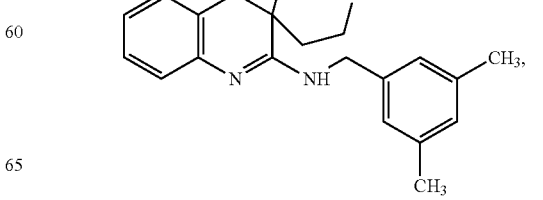

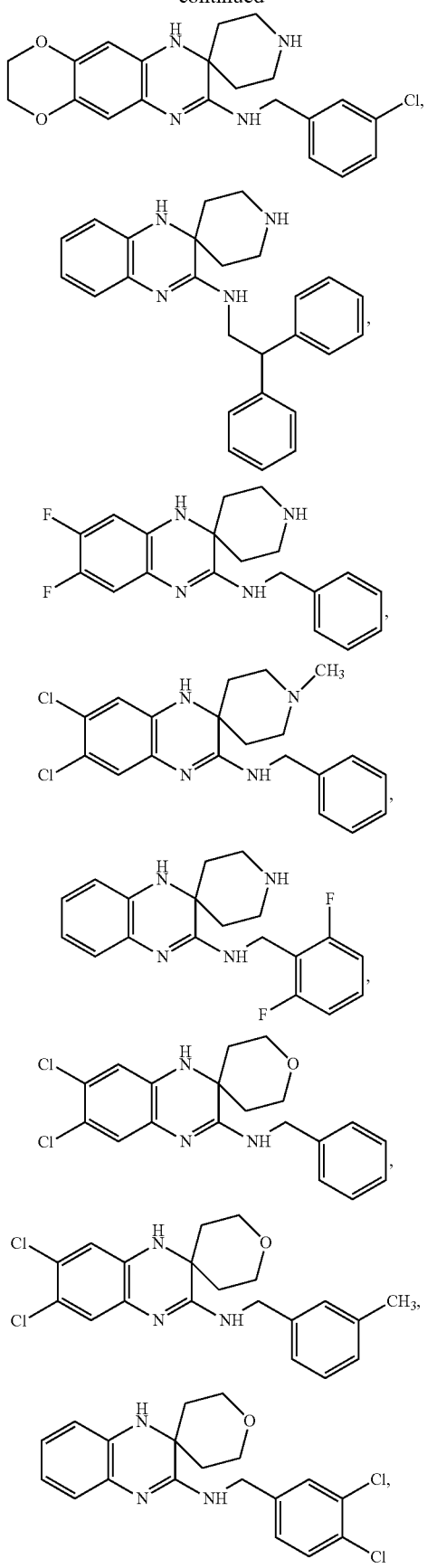

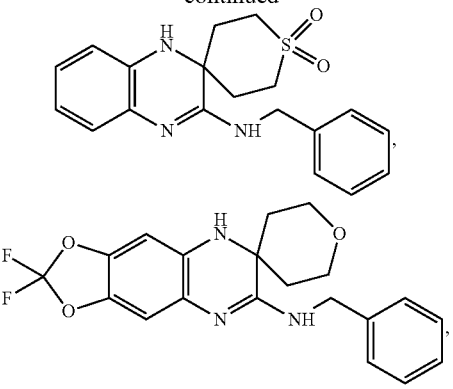

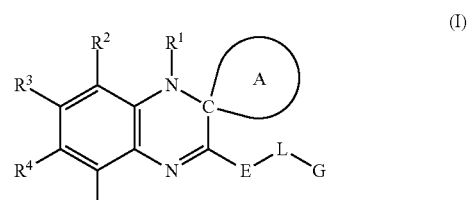

and solvates, salts, complexes, polymorphs, crystalline forms, racemic mixtures, diastereomers, enantiomers, tautomers, isotopically labeled forms, prodrugs, and combinations thereof.

8. The compound of claim 1, wherein $R^2$ and $R^5$ are each —H; $R^3$ is selected from the group consisting of —H, methyl, F, and Cl; and $R^4$ is selected from the group consisting of —H, methyl, F, and Cl.

9. The compound of claim 1, wherein G is selected from the group consisting of unsubstituted phenyl, 2-chlorophenyl, 3-chlorophenyl, 4-chlorophenyl, 3-methylphenyl, 3-(trifluoromethyl)phenyl, 2,6-difluorophenyl, 3,4-dichlorophenyl, 4-chloro-2-fluorophenyl, and 3,5-dimetylphenyl.

10. The compound of claims 1, wherein L is selected from the group consisting of methylene, 1,1-ethylene, 1,2-ethylene, trimethylene, tetramethylene, 2,4-butandiyl, and 2-phenyl-1,2-ethylene (—CH$_2$—CH(C$_6$H$_5$)—).

11. The compound of claim 1, wherein the ring nitrogen atom of ring A is unsubstituted or each $R^9$ substituting a hydrogen atom bound to a ring nitrogen atom is independently selected from the group consisting of $C_{1-12}$ alkyl (in particular methyl, n-octyl, or n-dodecyl) and —C(=O)R$^{11}$ (in particular —C(=O)CH$_3$ or —C(=O)(CH$_2$)$_6$CH$_3$).

12. A pharmaceutical composition comprising a pharmaceutically acceptable excipient and a compound selected from the group consisting of a spiroquinoxaline derivative having the general formula (I)

$$\text{(I)}$$

and solvates, salts, complexes, polymorphs, crystalline forms, racemic mixtures, diastereomers, enantiomers, tautomers, isotopically labeled forms, prodrugs, and combinations thereof,
wherein
E is —N(R$^6$)—;
L is selected from the group consisting of $C_{1-10}$ alkylene, $C_{2-10}$ alkenylene, $C_{2-10}$ alkynylene, 1,1-(CH$_2$)$_a$-cyclopropylene-(CH$_2$)$_b$—, wherein each of a and b is independently selected from an integer between 0 and 3, and —(CH$_2$)$_m$—[Y—(CH$_2$)$_n$]$_o$—, wherein m is an integer between 1 and 6, n is an integer between 0 and 3, o is an integer between 1 and 3, wherein if n is 0 then o is 1; Y is independently selected from O, S, and —N($R^7$)—; and each of the $C_{1-10}$ alkylene, $C_{2-10}$ alkenylene, $C_{2-10}$ alkynylene, 1,1-cyclopropylene, —(CH$_2$)$_m$—, and —(CH$_2$)$_n$— groups is optionally substituted with one or more independently selected $R^{30}$;

G is phenyl, optionally substituted with 1, 2, 3, 4 or 5 independently selected $R^8$;

ring A is a monocyclic 4- to 10-membered N-heterocloalkylene or a monocyclic 4- to 10-membered O/S-heterocycloalkylene, wherein each of the N-heterocycloalkylene and O/S-heterocycloalkylene is optionally substituted with one or more independently selected $R^9$;

$R^1$ is H;

$R^2$, $R^3$, $R^4$, and $R^5$ are independently selected from the group consisting of —H, alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more independently selected $R^{30}$;

or $R^2$ and $R^3$ may join together with the atoms to which they are attached to form a ring which is optionally substituted with one or more independently selected $R^{30}$; $R^3$ and $R^4$ may join together with the atoms to which they are attached to form a ring which is optionally substituted with one or more independently selected $R^{30}$; and/or $R^4$ and $R^5$ may join together with the atoms to which they are attached to form a ring which is optionally substituted with one or more independently selected $R^{30}$;

$R^6$ is H;

$R^7$ is selected from the group consisting of —H, alkyl, alkenyl, alkynyl, cycloalkyl, aryl, heteroaryl, heterocyclyl, —OR$^{11}$, and —NHR$^{20}$, wherein each of the alkyl, alkenyl, alkynyl, cycloalkyl, aryl, heteroaryl, and heterocyclyl groups is optionally substituted with one or more independently selected $R^{30}$;

$R^8$ is, in each case, selected from the group consisting of alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —N(R$^{11}$)(OR$^{11}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more independently selected $R^{30}$;

$R^9$ is, when substituting a hydrogen atom bound to a ring carbon atom, independently selected from the group consisting of alkyl, alkenyl, alkynyl, aryl, heteroaryl, cycloalkyl, heterocyclyl, halogen, —CN, azido, —NO$_2$, —OR$^{11}$, —N(R$^{12}$)(R$^{13}$), —S(O)$_{0-2}$R$^{11}$, —S(O)$_{1-2}$OR$^{11}$, —OS(O)$_{1-2}$R$^{11}$, —OS(O)$_{1-2}$OR$^{11}$, —S(O)$_{1-2}$N(R$^{12}$)(R$^{13}$), —OS(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —XC(=X)R$^{11}$, and —XC(=X)XR$^{11}$, wherein each of the alkyl, alkenyl, alkynyl, aryl, heteroaryl, cycloalkyl, and heterocyclyl groups is optionally substituted with one or more independently selected $R^{30}$, and/or any two $R^9$ which are bound to the same carbon atom of ring A may join together to form =X; or $R^9$ is, when substituting a hydrogen atom bound to a ring nitrogen atom, independently selected from the group consisting of alkyl, alkenyl, alkynyl, aryl, heteroaryl, cycloalkyl, heterocyclyl, —OR$^{11}$, —N(R$^{12}$)(R$^{13}$), —S(O)$_{1-2}$R$^{11}$, —S(O)$_{1-2}$OR$^{11}$, —S(O)$_{1-2}$N(R$^{12}$)(R$^{13}$), —N(R$^{11}$)S(O)$_{1-2}$R$^{11}$, —NR$^{11}$S(O)$_{1-2}$OR$^{11}$, —NR$^{11}$S(O)$_{1-2}$N(R$^{12}$)(R$^{13}$), —C(=X)R$^{11}$, —C(=X)XR$^{11}$, —N(R$^{14}$)C(=X)R$^{11}$, and —N(R$^{14}$)C(=X)XR$^{11}$, wherein each of the alkyl, alkenyl, alkynyl, aryl, heteroaryl, cycloalkyl, and heterocyclyl groups is optionally substituted with one or more independently selected $R^{30}$; or $R^9$ is, when bound to a ring sulfur atom of ring A, independently selected from the group consisting of alkyl, alkenyl, alkynyl, aryl, heteroaryl, cycloalkyl, heterocyclyl, —OR$^{11}$, and =O, wherein each of the alkyl, alkenyl, alkynyl, aryl, heteroaryl, cycloalkyl, and heterocyclyl groups is optionally substituted with one or more independently selected $R^{30}$;

X is independently selected from O, S, and N($R^{14}$);

$R^{11}$ is, in each case, selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$;

$R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=CR$^{15}$R$^{16}$, wherein each of the alkyl, alkenyl, alkynyl, cycloalkyl, aryl, heteroaryl, and heterocyclyl groups is optionally substituted with one or more independently selected $R^{30}$;

$R^{14}$ is independently selected from the group consisting of —H, alkyl, alkenyl, alkynyl, cycloalkyl, aryl, heteroaryl, heterocyclyl, and —OR$^{11}$, wherein each of the alkyl, alkenyl, alkynyl, cycloalkyl, aryl, heteroaryl, and heterocyclyl groups is optionally substituted with one or more independently selected $R^{30}$;

$R^{15}$ and $R^{16}$ are independently selected from the group consisting of —H, alkyl, alkenyl, alkynyl, cycloalkyl, aryl, heteroaryl, heterocyclyl, and —NH$_y$R$^{20}$$_{2-y}$, or $R^{15}$ and $R^{16}$ may join together with the atom to which they are attached to form a ring which is optionally substituted with one or more independently selected $R^{30}$, wherein each of the alkyl, alkenyl, alkynyl, cycloalkyl, aryl, heteroaryl, and heterocyclyl groups is optionally substituted with one or more independently selected $R^{30}$;

y is an integer from 0 to 2;

$R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more independently selected $R^{30}$; and $R^{30}$ is a 1$^{st}$ level substituent and is, in each case, independently selected from the group consisting of alkyl, alkenyl, alkynyl, aryl, heteroaryl, cycloalkyl, heterocyclyl, halogen, —CN, azido, —NO$_2$, —OR$^{71}$, —N(R$^{72}$)

($R^{73}$), —S(O)$_{0-2}$$R^{71}$, —S(O)$_{1-2}$O$R^{71}$, —OS(O)$_{1-2}$$R^{71}$, —OS(O)$_{1-2}$O$R^{71}$, —S(O)$_{1-2}$N($R^{72}$)($R^{73}$), —OS(O)$_{1-2}$N($R^{72}$)($R^{73}$), —N($R^{71}$)S(O)$_{1-2}$$R^{71}$, —N$R^{71}$S(O)$_{1-2}$O$R^{71}$, —N$R^{71}$S(O)$_{1-2}$N($R^{72}$)($R^{73}$), —C(=$X^1$)$R^{71}$, —C(=$X^1$)$X^1$$R^{71}$, —$X^1$C(=$X^1$)$R^{71}$, and —$X^1$C(=$X^1$)$X^1$$R^{71}$, and/or any two $R^{30}$ which are bound to the same carbon atom of a cycloalkyl or heterocyclyl group may join together to form =$X^1$, wherein each of the alkyl, alkenyl, alkynyl, aryl, heteroaryl, cycloalkyl, and heterocyclyl groups being a 1$^{st}$ level substituent is optionally substituted by one or more 2$^{nd}$ level substituents, wherein said 2$^{nd}$ level substituent is, in each case, independently selected from the group consisting of $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, azido, —NO$_2$, —O$R^{81}$, —N($R^{82}$)($R^{83}$), —S(O)$_{0-2}$$R^{81}$, —S(O)$_{1-2}$O$R^{81}$, —OS(O)$_{1-2}$$R^{81}$, —OS(O)$_{1-2}$O$R^{81}$, —S(O)$_{1-2}$N($R^{82}$)($R^{83}$), —OS(O)$_{1-2}$N($R^{82}$)($R^{83}$), —N($R^{81}$)S(O)$_{1-2}$$R^{81}$, —N$R^{81}$S(O)$_{1-2}$O$R^{81}$, —N$R^{81}$S(O)$_{1-2}$N($R^{82}$)($R^{83}$), —C(=$X^2$)$R^{81}$, —C(=$X^2$)$X^2$$R^{81}$, —$X^2$C(=$X^2$)$R^{81}$, and —$X^2$C(=$X^2$)$X^2$$R^{81}$, and/or any two 2$^{nd}$ level substituents which are bound to the same carbon atom of a cycloalkyl or heterocyclyl group being a 1$^{st}$ level substituent may join together to form =$X^2$, wherein each of the $C_{1-6}$ alkyl, $C_{2-6}$ alkenyl, $C_{2-6}$ alkynyl, 3- to 14-membered aryl, 3- to 14-membered heteroaryl, 3- to 14-membered cycloalkyl, 3- to 14-membered heterocyclyl groups being a 2$^{nd}$ level substituent is optionally substituted with one or more 3$^{rd}$ level substituents, wherein said 3$^{rd}$ level substituent is, in each case, independently selected from the group consisting of $C_{1-3}$ alkyl, halogen, —CF$_3$, —CN, azido, —NO$_2$, —OH, —O($C_{1-3}$ alkyl), —OCF$_3$, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl, and/or any two 3$^{rd}$ level substituents which are bound to the same carbon atom of a 3- to 14-membered cycloalkyl or heterocyclyl group being a 2$^{nd}$ level substituent may join together to form =O, =S, =NH, or =N($C_{1-3}$ alkyl);

wherein $R^{71}$, $R^{72}$, and $R^{73}$ are independently selected from the group consisting of —H, $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl, wherein each of the $C_{1-6}$ alkyl, $C_{2-6}$ alkenyl, $C_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of $C_{1-3}$ alkyl, halogen, —CF$_3$, —CN, azido, —NO$_2$, —OH, —O($C_{1-3}$ alkyl), —OCF$_3$, =O, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl;

$R^{81}$, $R^{82}$, and $R^{83}$ are independently selected from the group consisting of —H, $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl, wherein each of the $C_{1-4}$ alkyl, $C_{2-4}$ alkenyl, $C_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of $C_{1-3}$ alkyl, halogen, —CF$_3$, —CN, azido, —NO$_2$, —OH, —O($C_{1-3}$ alkyl), —OCF$_3$, =O, —S($C_{1-3}$ alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)($C_{1-3}$ alkyl), —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; and $X^1$ and $X^2$ are independently selected from O, S, and N($R^{84}$), wherein $R^{84}$ is —H or $C_{1-3}$ alkyl.

* * * * *